US012234460B2

(12) United States Patent
Bovijn et al.

(10) Patent No.: US 12,234,460 B2
(45) Date of Patent: Feb. 25, 2025

(54) METHODS OF TREATING DECREASED BONE MINERAL DENSITY WITH CLUSTER OF DIFFERENTIATION 109 (CD109) INHIBITORS

(71) Applicants: Regeneron Pharmaceuticals, Inc., Tarrytown, NY (US); The Royal Institution for the Advancement of Learning / McGill University, Montreal (CA)

(72) Inventors: Jonas Bovijn, Tarrytown, NY (US); Olukayode Sosina, Tarrytown, NY (US); Sirui Zhou, Montreal (CA); Luca Andrea Lotta, Tarrytown, NY (US); Aris Baras, Tarrytown, NY (US); John Brent Richards, Montreal (CA)

(73) Assignees: Regeneron Pharmaceuticals, Inc., Tarrytown, NY (US); The Royal Institution for the Advancement of Learning/McGill University, Montreal (CA)

( * ) Notice: Subject to any disclaimer, the term of this patent is extended or adjusted under 35 U.S.C. 154(b) by 0 days.

(21) Appl. No.: 18/392,181

(22) Filed: Dec. 21, 2023

(65) Prior Publication Data

US 2024/0200079 A1 Jun. 20, 2024

Related U.S. Application Data

(63) Continuation of application No. 17/816,084, filed on Jul. 29, 2022, now Pat. No. 11,891,607.

(60) Provisional application No. 63/230,707, filed on Aug. 7, 2021.

(51) Int. Cl.

| | |
|---|---|
| ***C12N 15/113*** | (2010.01) |
| ***A61K 31/4535*** | (2006.01) |
| ***A61K 31/565*** | (2006.01) |
| ***A61K 31/57*** | (2006.01) |
| ***A61K 31/663*** | (2006.01) |
| ***A61K 31/675*** | (2006.01) |
| ***A61K 38/23*** | (2006.01) |
| ***A61K 38/29*** | (2006.01) |
| ***C07K 16/28*** | (2006.01) |
| ***C12Q 1/6883*** | (2018.01) |

(52) U.S. Cl.

CPC ...... *C12N 15/1138* (2013.01); *A61K 31/4535* (2013.01); *A61K 31/565* (2013.01); *A61K 31/57* (2013.01); *A61K 31/663* (2013.01); *A61K 31/675* (2013.01); *A61K 38/23* (2013.01); *A61K 38/29* (2013.01); *C07K 16/2875* (2013.01); *C12Q 1/6883* (2013.01); *C12N 2310/11* (2013.01); *C12N 2310/14* (2013.01); *C12N 2310/531* (2013.01); *C12N 2320/30* (2013.01); *C12Q 2600/156* (2013.01)

(58) Field of Classification Search

None

See application file for complete search history.

(56) References Cited

PUBLICATIONS

Song et al., "CD109 regulates the inflammatory response and is required for the pathogenesis of rheumatoid arthritis", Annals of the Rheumatic Disease, 2019, 78(12), pp. 1632-1641.
Mundy, "Osteopenia", Disease-a-Month, 1987, 33(10), pp. 537-600.
Wang et al., "CD109 plays a role in osteoclastogensis", PLOS ONE, 2013, 8(4), pp. e61213.
International Search Report and Written Opinion mailed Nov. 10, 2022 for International Patent Application No. PCT/US2022/074307 (38120-3555).
Morris et al., "An atlas of genetic influences on osteoporosis in humans and mice", Nature Genet, 2019, 51, pp. 258-266.

*Primary Examiner* — Sean McGarry
(74) *Attorney, Agent, or Firm* — Armstrong Teasdale LLP

(57) ABSTRACT

The present disclosure provides methods of treating a subject having decreased bone mineral density or at risk of developing decreased bone mineral density, and methods of identifying subjects having an increased risk of developing decreased bone mineral density.

25 Claims, No Drawings

Specification includes a Sequence Listing.

SEQUENCE LISTING

```
Sequence total quantity: 58
SEQ ID NO: 1           moltype = DNA  length = 132532
FEATURE                Location/Qualifiers
source                 1..132532
                       mol_type = genomic DNA
                       organism = Homo sapiens
SEQUENCE: 1
atagttgcta tgaatttctc ctcacaagga tgggcctgtt tactcaccct gggcatcgtt  60
ggtagagcgc tagtgtaaac agcctgagga acccggtggg ccggggaagt gggcgcgctc  120
tgttctccgc ggccagctgg gacgccgggc caggtggggc cgcctgcgtt tagcaactgc  180
tttctcaccc cctggatttg cgatgtttgc cacagcagcg agaagcgcca ttgtaatggg  240
gatgggaggg gtggagcctc caagtcctgt ctcaatttag atctctcact ctgctgttag  300
gcgcgcccat ttcagattac taaactcgaa ttaagaggga aaaaaaatca gggaggaggt  360
ggcaagccac accccacggt gcccgcgaac ttccccggca gcggactgta gcccaggcag  420
acgccgtcga gatgcagggc ccaccgctcc tgaccgccgc ccacctcctc tgcgtgtgca  480
ccgccgcgct ggccgtggct cccgggtagg aacgtgggcg cgcggggggc gcgcgggcgc  540
gcgggcctgg gccgctctgc ggctctgggc cagggcttcg gggaggtggc ggctgctgtg  600
cagcagcggg tgggaaatgc cctcgcggct gcagtcccca gcctggtact ggcctggagg  660
tttgaccata tgtagcttca gcgtggctct ccatgggaca gttaactttc tccactcatg  720
aagttgttta agcgtctccc cggccataac aactttctga agagagtcat tttattttta  780
gtccacattg cctctgcctt ttgcttctca actttttgct cccagattgc gattcttctc  840
tcaaagacat gatatatttt ttctaaccaa gatgtctcaa ccttagcatt gccaaagtgt  900
ggcggagggg actgatgtat gggttcaggg gcagacatta taggaagaaa acaacagcac  960
ccaataatgg caagccccat tcattcctaa agatttctgt agttgagccc taacccctag  1020
ttatagcaga gaaagtgctg ctttagtgac ttcttttatg attcgctata cctggaattt  1080
tcaccagttg tagtttattt tcaaatggta tatttcaatc aatggtattg gttaaataat  1140
tttttaccct cgttgggcag ctactcaagg ataaaggttt gaataagaaa caggcaaaat  1200
cttagttaaa aaataacaac aacaacaaga aaataatcac gctgggataa ggtcctctgt  1260
aaaggagaag cttagagact tttgctttgc caataactcc attatgcccc ggtgcaagcc  1320
atttacatca tggttccttc tgtgcggttc gtggtttata aaatggaaat aataacacag  1380
gccttcctct agtagtgatg catgaattac tgcattaaaa ttgatttatg ggaattattg  1440
ttgtttcagt agcatttcaa ttcagttgcc aaatagagca gtgggcaatg ttaacggaaa  1500
caactgcaat tggcgcagta tggagtgcct atcgcactag gaaatctgag ggtcacaaaa  1560
gaaaggagat gtgaggataa gaaactttgt ttttcccttg ttgggaactc tttaggcctc  1620
ggtttctggt gacagcccca gggatcatca ggcccggagg aaatgtgact attggggtgg  1680
agcttctgga acactgccct tcacaggtga ctgtgaaggc ggagctgctc aagacagcat  1740
caaacctcac tgtctctgtc ctggaagcag aaggagtctt tgaaaaaggt aagataaaca  1800
gcataaagtc ttacccttct gcagtaataa ctggaatatg ttaataaggt catgtgttag  1860
gtagtatagc agagaaaccc caaatttgca gtatcttacc taatatactt ttaattctca  1920
```

-continued

```
ctcatgtaaa gtcctagatg gtgttcctgg atgctcttcc aagtgcagat tcagagaccc  1980
agtttccttc cattttgtgg ctccattatc atcacttggc tcccaagact gcaggggaag  2040
atcatggagt ttcttcatgg gagaagggga agaggatggg aagagcatat ggaaggtttt  2100
tatgggatag gcctagaaat agcttacatc actactgctc atattcacag gcaagggagg  2160
ctgggaagtg taggctaatg tgtgccccag aagaggaaat gggctagtct ctaacacaaa  2220
accatattta ttgagtgcaa agtattttac agaataggcc tgtaggaagg aaaggaaaag  2280
ctacacaata gttaaaatcc agttttatgg aatatttctt aagttttaaa gtaacaagag  2340
aaaaaaagaa aatagtgtga aagtgggagc catttgtagc agaaccaagt ttggttcttg  2400
tttcaagttt gggttctgac atggcccaag attaaattgg gccaatgaat gtcttctttt  2460
tcagtgctaa gggaaaaata attttgggag gaagaggtaa atacttaaat acttaaaaca  2520
tttttcatta aaatgaactt ttattgcatt tttttctttt tttagattct tataattatt  2580
tttagagaca agctctcacc atgttgccca ggctggtctc gaactcctaa gttcaagtga  2640
tccacccacc ttggcctccc aaagtgctgg gattacagtc ctaagctact gctcctggcc  2700
gagacataca tttttataat gttaagagtt atttaaaaaa aaaaatttaa ggcacgtaat  2760
gaagggtggt tggtattcat tacataagtg tttattctct acaagcgtag agaaatgaac  2820
accatcatga aatgaaataa aagtaaaagt ttatctgcat ctgtggttct ttccccactg  2880
gaagttcact gggtaggtat atttggaata ggagtcagga agagatggtg tgtgtagggg  2940
caagtcactt ttgtccctca tagaagcaat gtcagggaag tgggaggtct tatttccctg  3000
gaggggaagt ataggttagc ccttaagatc tgagtttgaa tcctggtact actttgctac  3060
tagttgtatg atcttaggta ggttacttaa ctgctttgag ccacagtttc cttgtctata  3120
aaatggaaat aatgaaactg atttcccagg gcagttataa agttaaaatc tgtatatagt  3180
acctcttagg catgcaataa acaacaattg ctaatattat tagtgtaata atactgcaga  3240
agaggatgca gaaagtccat ttccttttta catgggggca gacttcaact ttcgttattg  3300
gactatcatt tctgaaaatg aatgacccct gatcttatga tagtcgctaa agaaaatatt  3360
gaaatattaa atcacaggac ataatactta aggtagttcc acattcatta tttattcatt  3420
aagaatttat gagtgggaag agggagggta ttaaaaaacc acctattggg taccacactt  3480
atcacctgga tgatgaaata acatgtacac taaagcccta tgacaggcat tttacctata  3540
taacaaacct gcacgtgtat ccctgaaact aaaataaaag ttaaaaaaaa aagaatttat  3600
aatattggct ccactagtgt ggcagttttc ctgcaatgca gagatccaga atatatatgg  3660
atgtttttga taaatatttg agctttgctt ggacatttac atactctaat tctagaattt  3720
cacctgttag gtcttttctg tgatctctgt tatcagtctc tcttttttt tgcaacaaat  3780
agtacctaca ttggggtgca tgttgttgtg gcttggtttt cagctttatt cttagatctt  3840
cttttgggag aagggttcct tgtatgccca taggaaagtt caagtactca agactggggc  3900
gggcaaagct gtcctgggag cagaatggat ctgtgggaag gaaggaggga aaacgctgct  3960
tctttcatgg gctgttttg actctattga catagagttt cattgaaaat gccattgcta  4020
ggagcactct cctgtttcaa aggagaatgt tactgtatta tcagaggctg ggagttattg  4080
ttctcagagc agatgcttcc tgtaatgtga ggacttgagg atcaagacac ttctccctgc  4140
ttgtcttcac atcctttgct ttatctggct tctccagttg taacaatatg tagataaacc  4200
aggacttcta aatcaggggt ctggatcttc aagtatctgg atgtggattc atgttttgtt  4260
ttttctccat cacataaaca ccaaacacca acaaataaat accttttatt tttaagggac  4320
agagtctcac tctgttgccc aggccagagt gcagtggtga aatcatagct cactgcaact  4380
tggaattctt gggctcaagt gatcctgctg tctcagcctc ctgaatcagc tgggactaca  4440
ggcaagtgcc agcatgctag gtttaaaatt tttttttttt ttgtagagat ggggtcttgc  4500
tatgttgccc agactggtct tgaactcctg ggctcaagcg atcttcctgc ctcagcctcc  4560
cgaagtgctg ggattatggg tatgagcctg attgtttcat tttcctatga gccaccccca  4620
gccccccaac agaaggttgg ttttaataaa gatttatctt ctagtaaagt tgggtaaggc  4680
agtagactgt gtcttagtag cttatttcca gcagttttgg atttcttaga aatcctcagg  4740
atagggaggt gttttaccca aaccacaata gatttctggc tcaatttgtg ttggaaatag  4800
taataactaa attgttcaaa tggagaatgt atttaataaa ggtgaaaaag tatggcattt  4860
cttcagggaa gagttcattt gtttgtttga cagatatggg ggagatttta tttacatttc  4920
cacttttatg gccaggagtg taggttatat tactgttatt catttaaaaa tacattaatt  4980
ctacatttat tggggattga ttgtagtttt tttttttttt tttttttttt tttttgagac  5040
acagtctcac tctgtcaccc aggctggagt gcagtggtgc gatctcggct cactgcaacc  5100
tctgcctccc tggttcaagc gattctcctg cctcagcctt ccgagtaact gggactacag  5160
gcatgtgcca ccatgcctgg ctaatttttt gtatttttag tagagacgag gtttcactgt  5220
gttagccagg ttggtcttga actcctgacc tcgtgacctg cctgcctcgg cctcccaaag  5280
tgctaggatt ataggcgtga gccaccgtgc ccagcgatta tgggcttttt tttttttttt  5340
ggtgaataat agacctttag aaaaagtatt tctgctacac tttgcagagt tctgggaagg  5400
tgtatcaatg cctttctagt agtgagattc aaaagattgc ttgtcactgt taccactgtc  5460
actgcctcta ccactatcag catcattgcc atcagctcca tagtgattag aactatgttc  5520
ctaatcttat cttcctttgc ataaagagtt agttaaataa acataactgg caaaacgtag  5580
taaaagttca gcaggtaata attaccagag gaaagaagat ggcacagcta ttggcattta  5640
aaatcaagtc agattactgt tttgggtgga gagtgagtct gtccctttgt ctcttcccat  5700
attttttttc tctttcctta ctgtgaaagg agttccttgc caaatcaaga aaaaagaaat  5760
taagaacatt ttgagaactg tcctctcatc tgttaaggca tataaaataa tttaattttc  5820
gtgatgtcct tgaaaccata atttctgttt tattttccct tctcttgcta caatttgaca  5880
ttttcatttg taaactttca gtagttttcc tgaacaagag tcacttcaag taataaagaa  5940
tataaccttt ctccctcatt aatgaattca tcatcattag tttcatgtaa acctgattta  6000
agaaaaaatg ctagaggctg agtgcagtgg ctcacaaccg taatcccaga gcttgggagg  6060
ctgaggtggg aggattgctt gagcccagga gtttgagacc agcctggaca acacagtgaa  6120
attctatctc aaaaacaaaa acaaaagaac ccttaaaacc aaaaactccc aaaaacctaa  6180
actgaaaatg cctactgaaa ttttgggaac tctgcatggg cgtctccagg tgagtgcctg  6240
ctggtttggg ggcaccattt tttaaatgct gccaatccta cttccatctt cccattgagt  6300
tactggggtg gaatgtgctc tataaatgtg tctgtaactc gctttttctt tttgccctaa  6360
aatcctggag agttaatgga gtgttaacct tttttaaag atttttaaa aaatctattt  6420
tttcctttgt tgtctttctc acattgacta tgatatattt tattttccat cttggctcag  6480
taagggtggg aaatttttaa aaattgagat attagctgaa aaacttaaaa aatcatccaa  6540
tttggtttgg atggttttct ggtggaaaca aagctcctga acatgcattt catgcctcgt  6600
agataaaaat cagtcccatg gtctttatga aagtagatta attagtgtag tgtgtgggca  6660
```

-continued

```
gatctcccag agcaggtttt cacaggcagc tttgccaaca taactcagtc tgaacctgca  6720
gttatgttag aattattttt aaagggtgta ggcttttcat tcacacatcg tctttgttct  6780
tgtgtgtgat gtatattaac aggtaggtgg tacctgagaa taaaggacca cagcataatc  6840
acgatgtgcc tgggctctgg agcctggcta cctgggcaca ggtgctggcc attccactta  6900
gtggttgtgt ggctgtgggc agtcatgatc tcactaggct tcagtttcat catctgaaaa  6960
atagtggttt ctgccttata caattatatg gatattgtga ggattaaatg aggtaacata  7020
ttcaaggcac ttaacacaaa ggaattattc aagaaaatgg tagctattgt tactagaaga  7080
gagtagcaac agtttatgtc aaaggcaatt attaatcacc tattgtgaca atcttgaacc  7140
gggaactcta taaaagacac atccctagga ggggattgga agggatttaa catattaaat  7200
atccagtttc ctcatagtgc caaggacttt atgcactata tttaatttta acaacttgat  7260
gaagtagata ctcttgtctt cattttggag gtgaggaaat tgaggcaaag agagaagaat  7320
tagtttttct gagttaaccc agttagtaaa tggtgaagcc tgaatttgaa gttagttgta  7380
tctgaggtcc agagaccata aggttttcta ttgctgggaa gagagtgaag tatttttatt  7440
tccttgattt tgggatattg atgcaatgtt gcagttgtct tccactaaaa tcattttcac  7500
atttgcttgc agtagataga cctggatcta atgaaatcta atttgaatcg aaagaattac  7560
aaaatgaaat gccagctctc ctcttaattt actttcagcc tcatagagtt ttggagctgg  7620
aggggacctc aaagataagc aaattcaata gcctaatata tggctgggag actgaggtga  7680
ggcatgggat ctggggattt tcccaaggtc aaatcactta ttggtggcag agctggaaac  7740
agattgcagt ttcccaaatt tgcagtccag tgctatttcc agtatactct acgaaagttt  7800
cctaacatat ggagagctga gcttaagacc taagatatat ttacaaatgc tgattcttct  7860
gatatggaag aaaataaggc taactaagga gtttaaaaat gcttacttgc atactgtgaa  7920
agtttcttat tttagctcaa ggtggagttg ctctttatgc actatttgtt ctgtataagg  7980
ggtgggggct gggttagaag cttcatagac cttttaaaaa ctaaattctg ttgctttgtt  8040
tctcagagtc caaattgtat ttattaaaaa ggctgattca tggcctccct caagacatgg  8100
gtaagaatca agaatctcag ctgggtgtgg tggctcacgc ctataatccc agcactttgg  8160
gaagccaagg taggtggatc acttgaggcc agaagttcga gaccagcctg gccaacatgg  8220
tgaaaccccg tctctaccaa aaacacaaaa attagccagg tgtggtggtg ggcgcctata  8280
gtcccagtta cttgggaggc tgaggcagga gaatcgcttg aacccaggag gcagaggctg  8340
cagtgagatt gtaccagtgc actccagcct gggtgacaga gcaagactcc atctcaaaaa  8400
aaaaaaaaaa aagagaatct aacctttatg ttccaccatg accacaggtg attcttagtc  8460
acattagaat gagaacaact gccctttggt atctcacaaa ttgtactcga ccaaatactg  8520
gaaagctcga gggtgagtag catgcccctg caagcctgtg atgattcatg gcggcggagg  8580
gaaggctcct cgtggacttt catgtttgct tttaagcaac cctcaaccct aagcgctggt  8640
gttcattttc agccgcagag aaacatgact tggggtttga ttgtgaatca acgattgggt  8700
gaagttaaaa gtgaacacac tgattcttta aactccaagt taaacatgtg ctgctcctct  8760
tctagcactg gatgagtcac tgtcctagtg actcactgaa ggattgtggt ggaaatagaa  8820
aacagatccc ataagaattt gggctgggtt actgttgatc ctttatgtcc tgtgaagagg  8880
gctttataat gctgaaacta gttgtttccc cacagacatt tcttctcatt aatgtattat  8940
ttattgatta tttgctgtat gtgaaacatg aatgaatggg gagtggggaa taagagaaag  9000
gaaggcactg gaggacattc agaggtccca gaaggataat ataatattaa aagtgcagaa  9060
ggctagagga gtttttattt tttgtataaa aaatacaatg cggtttgtaa atagtgcttc  9120
ttgtatgtga gcctgtgcct ggtactatta tcttttactt ccagagctat acagatgtcc  9180
attcataaat gtcccacctc tgctgacata tttggccttt ggagggaaca gttacttcac  9240
gtactagaga cgggaagggt gtgccggagg aaagagctgc tggctggtgt ggcagttatg  9300
aaaaggagat aggggtttgt gtatatattt tctaaaaaga tgtttcattc tgctttggat  9360
atgagtttgg ggagacatcc aggtggagat gtccagcaga tagttttgaa attgcagctg  9420
gggagagaga tttaggcatt attttcatag aggcagacaa tattttgaag tcctggaaat  9480
acataagatg cacaagagag acagagctca tggaaagaac aagtcttttg agagaagctt  9540
ggaaagagga aaataagtta atgaagggaa aaagaccaga cacagtggct catgcctgta  9600
atcccagcaa cttgggaggc tgaggtgagc agatcgcttg agctcaagag tttgaaatca  9660
gcctggacaa catattggaa cctcatctct actaaaaata aaaaaaaggt agctggacgt  9720
ggtgacatgt gcttgtagtc ccagctactc aggaggctca ggcaggagga tttcttgagc  9780
tacagttata gtgccgttgt actctagcct gggtaacaaa gcatggccct gtctcaagaa  9840
aaagaaaaga aaagaaaaga aaagaaaaga atagaataga caacgagcaa tcagagaagg  9900
gtaaattgaa aatgtctcag aagccaaggg aagaagaagt tccaagaagg aaggtttaat  9960
agttaataat caattctctc aggtcagaga agaggaggac agaggaaaga acattggtga  10020
cgcttaagta aatggcttta agttgaatgt tggaagcaaa agcaaatttg agggaataaa  10080
tggatggtga aaaatataat caaaatttat tctttccaga agtttggtag ttgaaaggag  10140
agaggtggac ggtctctcaa aaggcacatt agaaaggtga aagtggttaa ggcaaaggag  10200
agggtggata attcctgggt tagaagtggt gagatcagta ttggggcaga ggcaagtgga  10260
ttatccttaa aaaaccctca tactttcttc tttgaagaaa gaaagaaata gaagagaatc  10320
attaaggaaa gaaatatttt gaggtatgaa attgagatga agaataaaat tgaaatacag  10380
ttttaggaaa acttatttac cgacttgtaa attgcacaga tctggccacc actttatagg  10440
aaatgggggt aaaagttaaa agtagtggca gaccagaatg agaaacacag gactggagat  10500
cttccctggt ggtgccctaa actgggtcac cgctggattg taggaaatta gaatacaggg  10560
gcaggaagtc atatttgtat ctgggagagc taacacaggg aggagagaga agaggaaagg  10620
gctgtttacg atgaagatat gcctcagttg aagctcgaga ggactgggtg gagttacttt  10680
attactgcca tggttgtcag tgaatttgta attcactctt agtgtgggcc aagatgacca  10740
aggtgcaatg ataaaacttg tctaggagga ttaaagtgga tcttggtctt gctctatctc  10800
tttcactctt cacttacctc ggagaattct atgaggagac tttcttccgt tgcaaggctc  10860
agggtgaaat tggtcaaaga tttggtggag ggggtagcag taggtaggta gatgacaggt  10920
ctataggttg ttagttctga agaaacgatt cataaattaa aatccgaaaa ccagactggt  10980
aaagagcttg gaaataaatg aagaggaaaa tttttaaaga acacctagta gctccctttt  11040
ggcagggctg tgttaggaat ttacatttat gaaaatatag ctggcagaaa tgatttagta  11100
ttacaaactt aagtttcact gcaatatatg ttaaagctcc tcaggaatat agataagaca  11160
gggaatttat tattctgagc aattcaaatt tattcagcac caaattgcct atggcacaat  11220
gctgggtgac ataaatattt ggtgaccaca tgaggttcct gtgcctgtgc tcttcgcagg  11280
gaagcagagt aggcttcatt tgatgtgtcc tcccacgttg attatagagg cttgttcggg  11340
tgccgtgttg acagtttcaa agtcaagcgt gggtttactg gactagagaa ctggatgaat  11400
```

-continued

```
tagctgtgtc tgccatggcc atgggagttg gggagtgtgg tatgaatgct gcgaaggatt  11460
ctgtagccca tccataaact ttatttatgg atcagttgaa gaggaatggt ctaagaggaa  11520
cggttatcta cgtagctaca taggggcttg aggtagtaac aacatggata agagagaaca  11580
gacgaaagag tgggtgtatc caaatagtaa atgagagtgg agtaagctac agaggaggaa  11640
caaggaggga agggatatga ggttatgttt gcactactgt tttggaagga atagctgggt  11700
ctgtcctgca ctgtttggga ggcacagtgg gttagaatgg gtgctcagga accacactga  11760
aattgaaccc tagcatcacc taatagtagt acccacctcg tagcattgtt gagaggatta  11820
aatgagataa tacttaagag ctgtatcatc caatatggta gctactaacc acatgtggtt  11880
tttgagcact tgaaatgtgg ctcatacaaa ttgagatgtg ccaggagtat aaaatacata  11940
atggattttg aatacttagt tccaagaaat gcaataaaac ttatgatttt aaaataatga  12000
tttcatgttc aatgttaata ttttggacat attgagttaa ataaaatatg ttattaaaag  12060
taatgtcacc caattttttc ttttttggc acataaaaga cacctaattt aataaatatt  12120
agttattatt ttctctttta ttatgcagtt aagaactttg atttaaaatt gttatcttta  12180
tatatatata tatatatata tatatatata tatatatata tatatttatt atactttatg  12240
tcctagggta catgtgcaca acatgcaggt ttgttacata tgtatacatg tgccatgttg  12300
gtgtgctgca cccattaacg cgtcacttac attaggtgta tctcctaata ctatcccttc  12360
ccccttcccc catcccacga caggccccgg tgtgtgatgt tccccgtcct gtgtccaagt  12420
gttctcattg ttcaattccc acctatgagt gagaacatgc ggtgtttggt tttttgtcct  12480
tgcgatagtt tgctgagaat gatggtttcc agcttcatcc atgtccctac aaaggacatg  12540
aactcatcat tttttatggc tgcattgtat tccatggtgt atatgtgcca caatttctta  12600
atccagtctg ttgttgttgg acatttgggt tggttccaag tctttgctat tgtgaataat  12660
gcctcaataa acatacgtgt gcatgtgtct ttatagcagc atgatttata gtcctttggg  12720
tatataccca gtaatgggat ggctgggtca aatggtattt ctagttatag atccctgagg  12780
aatcaccacc ctgtcttcca caatggttga actagtttac agtcccacca acagtgtaaa  12840
agtgttccta tttctccaca tcctctccag tacctgttgt ttcctgactt tttaatgatc  12900
gccattctaa ctggtgtgag atggtatctc attgtggttt tgatttgcat ttctctgatg  12960
gccagtgatg atgagcattt ttccatgtgt tttttggctg cacaaatgtc ttcttttgag  13020
aagtgtgtgt tcatatcctt tgcccacttg ttgatggggt tgtttgtttt ttttcttgta  13080
aatttgtttg acttctttgt agattctgga tattagccct ttgtcagatg agtaggttgc  13140
aaaaatgttc tcccattctg taggctgcct gttcactctg atggtagttt cttttgctgt  13200
gcagaagctc tttagtttaa ttagatccca tttgtcaatt ttggcttttg ttgctattgc  13260
ttttggtgtt ttagacatga agtccttccc catgcctgtg tcctgaatgg tattgcctag  13320
gttttcttct agggttttta tggttttagg tctaacattt aagtctttaa tccatcttga  13380
attaattttt gtataaggtg taaggaaggg atccagtttc agctttctac atatggctag  13440
ccagttttcc cagcaccatt tattaaatag ggaatccttt ccccatttct tgtttgtgtc  13500
aggtttgtca aagatcagat agttgtagat gtgtggcatt atttctgagg gctctattgt  13560
gttccattgg tctatatctc tgttttggta ccagtaccat gctgttttgg ttactgtagc  13620
ctcgtagtat agtttgaagt caggtagcat gatgcctcca gctttgttct tttggcttag  13680
gattgacttg gcaatgtgag ttgtttttttg gttccgtatg aactttaaag tagtttttc  13740
cagttctgtg aagaaagtca ttggtagctt gatggggatg gcattgaatc tataaattac  13800
cttgggcagt atggccattt tcctgatacc aaagcctggc agagacacaa caaaaaaaga  13860
gaattttagg ccaatatccc tgatgaacat cgatgcaaaa atcttcaata aaataccggc  13920
aaaccaaatc cagcagcaca tcaaaaagct tatccaccat gatcaagtgg gcttcatccc  13980
tgggatgcaa ggctggttca acatatgaaa atcaataaac gtaatccagc atataaacag  14040
aaccaaagac aaaaaccaca tgattatctc aacagatgca gaaaaggcct ttgacaaaat  14100
tcaacagcgc ttcatgctaa aaactctcaa taaattaggt attgatggga catatctaaa  14160
aataataaga gctattcatg acaaacccac agccaatatc atactgaatg ggcaaaaact  14220
ggaagcattc cctttgaaaa ctggcacaag acagggatgt cctctctcac cactcctatt  14280
caacatagtg ttggaggttc tggctagggc aatcaggcag gagaaagaaa taaaaggtat  14340
tcaattagga aaagaggaag tcaaattgtc cctgtttgta gatgacatga ttgtatatct  14400
agaaaacccc attgtctcag cccaaaatct ccttaagctg ataagcaact tcagcaaagt  14460
ctcaggatac aaaatcaatg tgcaaaaatc accagcattc ttatacacca ataacagaca  14520
aacagagagc caaatcatga gtgaactccc attcacaatt gcttcaaaga gaataaaata  14580
cctaggaatc caacttacaa gggatgtgaa ggacctcttc aaggagaact acaaaccact  14640
gctcaacgaa ataaaggagg acacaaacaa atggaagaac attccatgct catgggtagg  14700
aagaatcaat atcttgaaaa tggccatact gcccaatttt ttctattttt tttttagtgc  14760
acatctttaa aacatttatc acaatgcttg gtacatagaa gacaccgagg gaatgttaac  14820
tatgttgtac ctggtgtttc tcagtatcag atattaatac tgatgcctga ccacaagcct  14880
gtggcatgag tccaagtctc cctgctgatg actcattttg gcttaggtag atcttcaccc  14940
ttatccctta tcccttgagg aagaagaaaa tctccctaaa gagagccaca ggggtcggca  15000
aaatttctgt aaagggccag atgttaagca tgtaggtttt gccaaccttc aggtctttat  15060
tacagctgct caactctgcc tttatagctc ggaagcagct gtagacggtt cataaacaaa  15120
agagcatggt tgtgtaccag cagaacttta tttatggatg ctgaaatttt gagttcatat  15180
aatttttact tatcatgaaa tattcttctt cttttgatat tccccccagc tatttagaaa  15240
tgcaaaccca ttcttagttc atgaactgta caaaaaacag gcgtgggcca gactggatct  15300
gtaggctgtg gattgctgac cctgccatta aaaatgccct gtacatttag cagccaagaa  15360
ccttgcttga ctctgggttt ttcatttgta cttaacctaa catttgcttt atagtgtacc  15420
attttattta ttttactttt agtaggtttg tgtttgacct gctttttttt ttactcaatg  15480
tttgtgttta acctgctttt ttttagacaa tggaacaaaa ctttgtttat gaaactcaaa  15540
tttattaaga tatttgtaag caaagggaaa taagagagaa aaatataaaa ggagtatgta  15600
agggaccaaa ggagattttt tgtttggttt tgttctgctc agaatacttg tgttttctgt  15660
gtagactgaa tttacccaat agtttttttg ccttaaagtg acattaaact gtgaagcaga  15720
aacattgtat ttttaaaatc gtactttaag tttttttttt ttttttttgag acggagtctc  15780
gctctgtcgc ccaggctgga gtgcagtggc gggatctcgg ctcactgcaa gctccgcctc  15840
ccgggttcac gccattctcc tgcctcagcc tcccaagtag ctgggactac aggcgcccgc  15900
cactacgccc ggctaatttt ttttttgtat ttttagtaga gacggggttt caccgtttta  15960
gccgggatgg tctcgatctc ttgacctcgt gatccgcccg cctcggcctc ccaaagtgct  16020
gggattacag gcgtgagcca ccgcgcccgg cctaagtttt taaaatattt tatttttata  16080
gatttagggg gtacatgtgc agttttctta catggatatt ttgggtagtg gtggagtctg  16140
```

-continued

```
ggcttttagt ataaacatca gccaaatagt gtatgttgta tccattaagt catttcttat  16200
cccttacctc cctgccatat gaatctccaa tgtctattat ttcactctct aaaaaatatt  16260
gtattttata caaaaattag ccgggtatgg tggcgcatgc ctctaatccc agctactggg  16320
gggctgaggc aggaggattg cttgaacctg gaaagcggag gttgtagtga gccgagatca  16380
tgccactgca ctccagcctg ggcaacgaag cgagactccg tctcaaaaaa aaaaaaattg  16440
tattttaaag ttttgttttc catgaatttg tggggggaaa acccttattt cttaccttat  16500
ctgttgatca aagaaactgc tgaagaatga ggaaaaaaat ttagtaactt gataaagaga  16560
tcaaaatttt cagctaaaaa agtgataata aatttattat tgcataagac tgagtagcaa  16620
aaggctgcca aaaataatta agcagcaaac actaagtcag gcatatatat atatctagtg  16680
gaaaatccac tttttttttc atagagagta tttctgtacc tagttggatt tccggttaca  16740
cactactcct tcccttcaat gattttccaa agttatttgg tgaggacaga tgtcagaaga  16800
ggcagcatat aatggtatta cagagtatgt ttaaaaagtt aaggaaaggt tagtttttgt  16860
gtatgcttat tacacaattt aaaaatagct ttgactctat ttgtaaatca aatggccagt  16920
tctcaggctg tgccaaatgc gaagccttca aacaaggttt cttctgagtt gcttaagcag  16980
ccctgggaag gagaaagcat ctgaaagggt tttcagattg attgtctctg gttatacaca  17040
gaaatgattg gagttttata aagttatcta taaaaacact aagaagaacc ttacataaca  17100
gagtgtgtct ttagttagtg atttaaaaga gtgccatact gggtttcaag aggtggtgac  17160
catttcccgt gtctgaatgg agcctcgcca aaagggagaa aaatgttcac aacagtttgc  17220
aaatactatc tatttaattc tcaacctagc aacagcagag aaagagatta ttattcctct  17280
ctcatctatg ctgcccccac tctcctcccc gctgcccccg attttatgtt ttggttgtgt  17340
aaattattgc taaatgaata gaactttcaa ataagtccta tgctaggact tcataagtgc  17400
ctaggaaatt ccaagctgta tttgtaaatt taaagggaag atcagcagaa aaaaatgtca  17460
agtacttaaa atcgactttt tattaaggac gcatgagacc agtgagtagg ccttagattg  17520
gatgtgtcca catatcctct gagtcgctcc ctggatccag caagaaatag ggtgggtgg  17580
gacatctttg tccctacacc atagcgttgg ggaagagtct ttgtattttg tatttttatt  17640
tttttttaa tagagatggg gtcacacgat gttgcccagg ctggtcttga actccttgcc  17700
tcaagggatc cttctgcctc agccctccca aagtgctggt attataggcg tgagctgcca  17760
cacctggcct gggtaggact tctgtttcta gctctgtatc tttcttgcat ctgtgaacag  17820
ataaggtcat gtgtctgagc agtaggaccc aggcatgcag ttgaactgct cgtccaactt  17880
ctctctggtg agagaattcc tcaaagattt gacttcattc agagctgcat taaaaacaaa  17940
agacaaaaca aaaaacactt ctactatgaa atgagatttc ctgcacttca aatctgttta  18000
gcttgttttg aagtgccaga atgcttggcc tccaattagt caatctccga gagcctcatt  18060
tggattgtag actcccaact gttttttac tttctccttg ctgatgtcat tggataaaaa  18120
taaattacca cccctccccc gtcgttcttc atctttgtaa atttgctgcc ggtgggtggt  18180
agctggtatc agaccagggc aggaaggaag cacattgctt cctccagtta tggagctagc  18240
ataatagtca acccctgatg atttatctta atacaatgaa aaataagtaa ctctcaataa  18300
tggagggtgc tggtttgttg gggcgaagct cactgcagtt tgtttctatt ttattccaat  18360
gtgggacatt gtggtggatg ctgtgtttta gggcccagat cgctctttag ggatgaagga  18420
ctttttcccg aaagctgcta ggagtgttgt gcccgactgc cttcagagcc agttgtctct  18480
gatgatcgta tcagctagag aattgccttg cccatggtgg cctccctcct ggggatggcc  18540
tgtattatgt gactgattga cgtggggtat gaaggtctgg ccctttcgcc ccagttcagg  18600
acaactctca ctggccctga ctgcttctga gctgccctgg tggatgcctc tttggagcct  18660
gcattgcagc cccactgctc tctcccctag tgcagtttcc ccctttccct tctgcaggtg  18720
ctgatccacc gaatactcct tagtaaacct cctgcattgt aattaccgtc tcagagttgg  18780
ctactgttta actttccttt gaagaggaat gtttcagatc ttggaatcaa cttcaaacat  18840
gtcaaaactg tgtagtgtga agaattgaca tgagttggga aagtctttcg tttttatatc  18900
cttttcagag ttcttgtatg acacaaaata ttttagagtt agctccgcta ctgcagtgct  18960
tggagtataa ctctaagttt cttctaagag aaacttcatg gaagaagaat ccacaggttt  19020
tggtgagtga taaacttaga gttgaggaga gaaaagagtt caagatgatt gagattttga  19080
acatccatga ttgaggaagt ggtgatagca acatatacaa acaggctata caggcagtgg  19140
aacttttact ataatcaaag atatgtataa tgaaaacaat ggtgaggcac aaggctgggt  19200
ccagtggctc acgcctgtaa tcccagcact ttgggaggct gaggcgggca gatcacttga  19260
ggtcaggagt tcgagaccag cctggccaac atggcacaac cctgtctcta ctaaaaacac  19320
aaaaaattag ccagctgtga tggtgcttgc ctgtagtccc agctacatgg gaggctgagg  19380
catgagaatc tcttgaaccc gggaggtgga ggttgcagtg agctgagatc gtgccactgc  19440
actccagcct gggtgacaga gcaagactct gtctcaaaaa caaacaaaaa accagtgatg  19500
aggcacggtg actcacatct gtaatcctag ggccttggga agtcaaggtg ggaggatcac  19560
tcgagcctag gagtttgaga gcagcctggg caacataatg agcccccatt tctacaaaaa  19620
agtaaaaaaa attagccagg catggtggcc tgtgcttgta gtcctagtta ctggggaggc  19680
tgaggcagga agatcgcttg agtccaggag tttggggtgg cagtgagcta tgattgcacc  19740
actgtactcc agcctgggtg acagagtgag accctgtctc caaaaaaaaa aaaaaaaaag  19800
gtatgtataa taaaaccaac tatacaactg attctttttt taatttttaa ttgttgtgga  19860
tacatagaag atgtatatat ttacagggta catgagatac tttgaaacag gcatgcaatg  19920
tcaacaacca catcatagta actggggtat ccgttccctc aagcatttgt cctttgtgtt  19980
acaaacaatc cagttatact attttagtta tttaaaaatg tacaatcaaa ttgttattga  20040
ctacagtcct cctgttgtgc tatcaaatac taggtcttat tcatttttct aactattttt  20100
tgtgcccatt aaccatcctc acttgctccc taacccttca ctactctccc tagcctctgg  20160
taaccatcct tctacactct tatctccatt attagttaaa ttgttttaat ttttagctac  20220
cacaaataag tgagaacatg caaagtttgt ctttctgtgt ttgggttatt tcacttaaca  20280
taatgacctt cagttccatc catgttgttg caaatgacag gatctcattc atttttatgg  20340
ctgagtagta cttaattgtg tacatgtacc acattttctt tatccattca tttgttgatg  20400
gacacttagg ttgcttccaa atcttagcta ttatgaacag tggtgtaaca aacatgggag  20460
tgcagatagc tctttgatat actgatttcc tttcttttgg gtatatactc agcagtggga  20520
ttgctagatt gtatggtagc tctattttta gttttatgag gaacctccaa actgttctcc  20580
atagtggttg tgctaatttt catttccatc aacagtgtat gagggttccc tttcctccac  20640
atcctcatca gcatttgtta ctgcctgtct tttggataaa agccatttta actggggcga  20700
gatgatatct cattgtagtt ttgatttgca tttctctaat gatcaatggt gttgagaggg  20760
ccttttcata tacctgtttg ccatttgtat gtcttctttc gagaaatgtc tattcagatc  20820
gttttcccat ttttaattgg attattagat tttttcctgt agagttattt gagttcctta  20880
```

-continued

```
tgtgttttgg ttattaatcc cttgtgagat gagtagttac aaagattttc tctcattctg  20940
agttgtatct tcattttgtt gattgtttcc tttattgcgc agaagctttt taacttgacg  21000
tgatcccatt tgtcgatttt tgctttggtt gcctgtgctt gtgggatatt gctcaagaaa  21060
tctttgccca gttcagtgtc ctggagagtc cctccaaagt tttcttttag tagtttcaca  21120
gttttaggtt ttaggtttaa gtctttaatc cattttgatt tgattttagt gtatggtgag  21180
agacagggtc tagtttcatt cttctgcata tgtacatcca gatttcctag caccatttat  21240
tgaagagact atcttttcct caatatatgt tcttggcacc tttgtcaaaa atgagttcac  21300
tgtaggtgta tggatttgtt tctggcttct ctattgtgtt ccattggtcg tgtgtctgtt  21360
tttatgccaa tatcatactg ttttggttac tatagctctg tagcataatt tgaagtcagg  21420
taatgtgatt cctccttttt ttttttcttt ctcagtatgg ctttggctat tctgggtctt  21480
tggtggttcc ataaaaattt taggattttt tttctatttc tgtgaagaat gccattggta  21540
ttttgataga gattgcatta aatctataga ttgctttagg cagcatggac attttaacaa  21600
tattgataat ttcaatccgt gaacatggaa tatcttttca tttttttggt gtcatcttca  21660
attttttttca tcagtgtttt atacttttca ttgtacagat tttcacttc tttgatcaag  21720
ttaatgcctg ggtatttaac tttatttgct gctattgtaa atgggattac tttcttgatt  21780
tctttttcag attgttcact gctggcatat agaaattcta ctgattcttt tttttttttt  21840
tttttttttt tttgagatgg agtctcgctc tgtcacccag gctggagtgc agtggcgcaa  21900
tctcggctca ctgcaaactc cgcctcccgg gttcagggca ttctcctacc tcagacttcc  21960
aagtagctgg gactacaggc gcctgcaacc acgcccggct aattttttgt atttttagta  22020
gagacggggt ttcaccgtgt taaccaggac ggtctcgatc tcctgacctc gtgatccgcc  22080
cacctcggcc tcccaaagtg ctgggattac aggcgtgagc caccgcgcct ggcttctact  22140
gattcttgta tgttgatttt gtatcctgca actagactga gtttatcagt tctaatcgtg  22200
ttttggtggc atctttaggt ttttccaaat ataagatcat attggctggg cgtggtgact  22260
catgcctgta atcccagcac tttgggaggt ggaggagggc cagatcactt gagcctggga  22320
gtctgagacc agcctgggca acatagggag accctgtgtc tatttatctt taaaaagtaa  22380
attaattaaa aatattatat catctgcgaa caaaaataat ttgacttctt ccttccaat  22440
ttgcctgccc ttcatttctt tctcttgtct gattgcccta gctaggactt ccagtactat  22500
gttgagtaac agtggtgaaa gtgggcattc ttgtcgtctt cctgatctta gaggaaaggc  22560
tttcagtttt tccccattta gtatcatact agctgtgggt ctgtcatata tggctttttt  22620
tatgttgagg tgtgttcctt ctatatgcag ttttttttgag ggtttttatc atgaagaggt  22680
gctgaatttt atcaaatttt tttaaattat caattgaaat gatcatgtag tttttgccct  22740
tcattctgtt gatatgatgt atcacattga ttgatgtgca tacaactttt ttttttttta  22800
tattcagagt cagtgcagag cagtggttta gagctcaggc ccatgagtca ggtggttagg  22860
gtcagaagct tggccccact actttttgtc tgtgtgaccc tgggaaagtc atttcacatg  22920
tctatgtctc agtgttctca tttgtaaaat aagggtaata atacttaata gtattgttgt  22980
gagctttaaa ctcaatgtat gtaatgcttt agaacactct gtaagtggta tgtactatta  23040
ttattatttt attcatataa ctaaaaaatt gtattctgtc tgatctgttg gttgtttcat  23100
tgttgctaaa cacaaattta agtcttctat ccccgtgacc agttctgtcc aatacaagta  23160
taagtcaact acataagtta ttggcaattt tctagtagcc gcactaaaaa agaaagagaa  23220
acaggtgaaa ttaattgtaa taatatattt tatttaaccc aataatttac aagtattatt  23280
agttcagcat ttaatcacta taaaattatt gacatgacat tttacatttt tttggttgta  23340
agtctcagaa atatggggtg tattttacac ttgctgctta tttcagtggc tcaatagcca  23400
catgtattta gaggctcctg tatgtgactg agcagcttta aagagttgct agttaatctt  23460
gctcatttct gaagtgttcc agtcaactgt tgctgtgaaa taagccgccc ccagatttag  23520
tagattaaaa caacaatggt ttattatttc tcacaattct catttagcct atacatgcta  23580
gattgatgat tattgccatt atttttgtga tagttgtgaa ttccatgata gtttttgaat  23640
tccacgattc cttctacatt tattagttgg aattctgtgg taaggaataa ctctttcttc  23700
tctttcactc agtcatatat ttaattgtac atcagcatga actcatagat tcttgttgta  23760
ttcagtaggt tgtaacccat tatttatttt attattcaag tgatctgacc ataatatttt  23820
aaattaagaa aacaccctct ccacacatgc tcaggtacct gatgagatca gaacaaattc  23880
tgctacatgg atggtattct caattccatc ccccaacacc cccgtattgc aatgtttaaa  23940
tgtttcagcc caaatatttc acagggtctg cttgcagagc cccatgcttc tcttcaacaa  24000
atgtttttac aggacaaaat ttgtccagta aattgtctct atttatggtt cctttgaaag  24060
ttttaccaag tttacttgct gaaatatcct agggcttttc aatttcactt caattcagta  24120
tagaatataa taagtctttc ccattaaaag taagcttaat gaacagaagt ttcttcctac  24180
aaggtaagat actcccaaag tataactggt gtatatccaa agatatgaaa tcagtatgtt  24240
gaagagatag ctgcaccccc acatccactg cagcattatt cccaatatct aagatatgga  24300
atcgatgtca gtgtccatca atggataaat ggataaagaa agtgtggtat atatacgtaa  24360
tggaacacta ttcagccatt ttttttaaca aaaaaaatgt aaaaagaagg aggtcttgtc  24420
attttcagtg acatggatga acttggagga cattatgtta agtgaaataa gccaagcaca  24480
gaaaaacaaa tattgcatga tctcacttat atgtggaagg taaaaaaaga tgaactcata  24540
gaaacaaagg gtaaaatggc agttaccaga agtgaaagga atggggagat gttggtcaat  24600
agacacaaaa tttcagttat acgggaggaa taatttcaag agatctagtg tacagcatgg  24660
tgactatggt taatatcaac atattgtata cttaaaaatt gcttagagta gattttaatt  24720
gttcctttcc acaagtagtt atgtgaggta aggcacatgt taaatagtgt ggtttagcca  24780
ttccataagt tatacctcat tccataaggt atacatctat catctatatg tcgcatacca  24840
taaatatatt caattattac ttgtcaatta aaaaaagaat aaaacatttt cagagttaat  24900
ttatgtgcac attaaaccca tcctagaata atattttgct aaccaaaaaa agatccagga  24960
caaatgctaa atcaggatgc tggaataaca gcgtcaactg ggataatcct ggtgaggcct  25020
catcttgtcc aaagaccccc ttttgattgg gccaggcctc ctggctactg ctgtctttct  25080
ggctgtggtc tttgctcacc cagctctttg gtttggtaga ctcaggttga tctccactgc  25140
tttgcatttg ctgctctttt gcctgtaaca ttgtacccct ccttgctcat atggctaatt  25200
tctccatatc ctacaacctt agacactggc atcgttttct ctaggtgcct tcccttcatc  25260
cctccaatgt gctccttgtc ctacctgtac tatgtatatc tgttccacga tacttccttc  25320
ttcacctttt tgaaacacca tgttcaatat cctgttattt aagagtcttg ctctttgctt  25380
cctatgataa cagttattag aggaactgat ctgtgctagg tggtaagtga tggtgatgaa  25440
ttacttatct gttcctgaaa acatacttgt atttcatgga ggcccactgg ggtggtagtc  25500
ttcaaagtga gtgtgcacac gtctaagagt atatgagacc atttataagg atggaagtag  25560
aaaatgtagt aatttttatt tctttttttt ttttttttga gacagtatct ccctctgtag  25620
```

-continued

```
cccaggctgg agtgcagtgg cacgatcttg gctcgctgca agctctgcct cctgggttca  25680
caccattctc ctgcctcagc ctcccgagta gctaggacta caggcgcctg ccaccacacc  25740
cggctaattt ttggtatttt tagtagagat ggggtttcac catgttagcc aggatggtct  25800
caatctcctg acctcatgat ccacccgcct cggcctccca aagtgctggg attacaggca  25860
tgagccaccc acgcccggcc agtaattttt atttctatta ttttattaag caaagctaag  25920
aagttaaagt gtttctcttt ttctttttat tgatttattt atttattttt gagacagagt  25980
cttgctctgt tgcccaggct gtagtgcagt gatgtgatct cagctcactg caacctccac  26040
ctcctgggtt caagcaatcc tccttcctca gcttcccaag tagctgggac tacaggcgtg  26100
ccactatgcc tggctaattt ttgtagtttt tagtggagat ggggttttgc catgttggcc  26160
aggctggtct ctaactcctg acttcaggtg ttctgtctgc ctcagtctcc caaagtgctg  26220
ggattatagg tgtgagccac tgtgcctggc tataaagttt ttctaatgtt taatattttg  26280
gttgagaaaa tacatgtata taattttata aatctaattt gacattggta aggtatacta  26340
agtattttta ttgatggagt actctatcat aaaaatttga agactacgtc tataggggca  26400
tatgacatcc tcaatggaaa actcttcaag ctttttgaca ctataatagc taacatattt  26460
caagtgtttt ctatgtgtca cgcactgttc tatatgcttt acaggtatca acatacgtat  26520
tccttataac cacctcatga gattgatatg attattagca tcctcatctt atggatgaaa  26580
aaaattgagc tagagaatca ggtaatttgt tcaaggacag ggccagtaca tatcaaattc  26640
ttgatgtggt ctgattccag atgctgctag cttaacccct gctgtgtact gtgctgtgct  26700
ctggtgcctc tgctctcaca tgatagaccc atttggcttc ctggaggaga gggaccacat  26760
ctgtcttgca cattgtgcta gtttttacgg ggcctattat ttccttctct ctctttaaaa  26820
tcatcttttg ctccatttta tttcccaagg gcctgccatc ttcgatagga actttggaca  26880
agttctcttt tatttttaac atgaaaccat ttttcccctt gaaataaatg gatctgatga  26940
gaaattggca tgagtttaat tagcagtcct atgtatagaa actttacacg aaaaaagtct  27000
gcatcacccc agtactcacg agtcagttat gagtcccagc tcacccctga catgactaat  27060
gccttccttt cttcctttat cacgagggta tgaggacaag aaataaacct cagactactt  27120
ctgtacagcg tgtgaagtgt cccgcaagca cgtataacct taaaatagca acaagggcag  27180
cagcaacaac gacaacaaaa atgataatgg caaagagaag cagaacctaa tgtttttttgg  27240
gtttgcccac tgataccctt ttaatcctga tttttaattg tttggcacaa agatatgtaa  27300
taatttcttg ggtcttctgg gcatttaaat gtcattttgg tttcaccaaa tgtatttatg  27360
attccaccta cacatgtaag agtattggga gagttttgga aggtttgtat tctatcatca  27420
tattcaaatt gtgctaactc tgttttcttt cctgttttcc ttgtaggctc ttttaagaca  27480
cttactcttc catcagtaag tatccattta aaaaatttgg tttcagaaat atattgtatc  27540
agtgaactaa ataaattaat attttattgg attttatgtc aattcacaca tttcacgttt  27600
catgtaagtt tggcttgagt ttagttcagc cttcagatta tttatgaata atattatttc  27660
aaggagattg attatgaggc tcttcaaact cttggcagag attttcctct tgtaaaatag  27720
aagacttcac tgaaggaaac tggcctggac tattagcaca gaaatctgga ctggtcataa  27780
aaaggaacga gaccatgtcc tttgcaggaa catggatgga gctggaggcc attatcttta  27840
gcaaactaaa ataggaacag aaaactaaac accacatgtt ctcacttata agtgggagct  27900
gaatgatgag aacacatgga cacatagagg ggaacaacac acactggggc ctactggagg  27960
gtagagggag ggaggaggga gaggagcagg aaaaatagct aatgggttct aggtttagca  28020
actgggtgat gaaataatct gtgcgacaac ccccatgaca caagtttacc tatgtaacaa  28080
acctgcactt gtacccctga acttaaaata aaagttaaaa aaaaacaagg catctgggct  28140
ggtttgctcc tgcttctgtc gtaatgagcc ttctagtgtg gaactctgct cctcagtttc  28200
cttgtgcttg aaaagagcag tgccatgctg agacatacta gaacttgagg caaaaggaaa  28260
aatcagtaat attgaccctg tctttgttta aaacttcgac ttctttgttt ataatttttt  28320
gcattaattt tgatatttta aaatattgta ttaaaatatt attttcttga ttgctaaatt  28380
ttttggtacc cccttaaatt ttgcacctta gacaagtgcc tcactcacct caccatagcc  28440
ctggccttgg aaaagagaat gaagatacca tctttatctc acagcatgtc ctggagtgaa  28500
atgagatgtg gaagtgttgt agcacttgct atagaaatgg aaaggagtta ttattttgtt  28560
gagagattca taaaacctta ttattaaatg tttgtggatg aatcttccta tagctttgat  28620
ttggaagttt atactttcat tactatgctt tgttttgggg ctttacatgc ttaatgtaca  28680
gtatagtaaa ccacagcatc caacatcagg tgcagtttga tatatgtact tttctgagaa  28740
cagaggacta atgacttagg ccctgacaca ctgtatacct gattagtatc agcattacct  28800
cataagccag gttcgctcat taccttaaat tttttttttt ttttttttga gacaggtctt  28860
ggtctgttgc ccgggctgga gttcagtggc acaatcatgg ctcactgcag cctcaatctc  28920
ccaggttcaa gcaatcttct cacctcagcc tcccgactac tggcatgtgc caccatgcct  28980
ggctgatttt ttattttttg tagaaacagg tttccctatg ttgcccaggc ttgtctcaaa  29040
ctcctgggcc caagcatccc tcctgccttg gtcccccaaa gtgctgggat tacaggagtg  29100
aaccaccatg cctggcccac ttagtacctt ttgaaagtta cttgtcaagt acattcagaa  29160
accacattta ttttgggggg ttcatagaga atattatact ctcaaacaat actttataaa  29220
aattacttag tatgctatat ctattctgtt tgttacatat tatatttgta ctttctttcc  29280
taagaaatat actgctgcta ataatagaaa gtggaagaaa aaaggcataa gcaggcagaa  29340
gtgggggaaa aaaaccctgc aatctttgtg gcaataaaac attagattgc attaaaataa  29400
cctaaaacat tagatactgg ccccagtgcc tgggcgcaga actttgttga aagggtattc  29460
cagtggtaag atgaaaataa atcctgtgtc gtatatttgc cctatagcag aaggagggtg  29520
gggtttaagc tcaggaatca cagcctaaag cacaataatt gtctggtttc ctcaaaggag  29580
tttgcagttt cacataccgg aagtgtagaa aggctgaaag gagaaggcgg ggcaagggca  29640
tgagagtttc tttcaatgat actagtataa actgtacgtg tctgagctaa tattaactag  29700
aaatttgtct actacacttc tttttttttt tttttttttt tgagacagag tttctctctt  29760
gttgcccagg ctggagagca gtggcgcgat ctcggctcac tgcaacctcc gtttcccgga  29820
ttcaagagat tctcctgcct cagcctcccg agtagctggg attacaggca tgcaccacca  29880
tgcccagcta attttttttt gtatttttag tagggacaga gtttcgccat gttggtctgg  29940
ctggtcttga acttccaacc tcaagtaatc cgcctgcctc ggcctcccaa agtcctggga  30000
ttacaggcgc aagccactgc gcccagccta ctatacttct tttaagtctt aagtatatga  30060
aatactaact ctgacatcca gtatttgtct ttaatattat gtcatttcaa ttgtatataa  30120
atatagctat tatctattga aagctttatt agagattata ttttggagtg tatctctttt  30180
tagtaaagca cagtatgaaa gacttagaaa taaagtgtat ggacaaattt gataatgctt  30240
gacaaaaaaa gaaggctctg cattttaatg agttttcaat taaagcagaa ccaactttct  30300
ttttccccag tgagaacata cctgtgaata gaaccacctt ttaaagtgca cttgcattct  30360
```

-continued gacacttgta agtgtaatat tttaaattat ttttcaggtc tttatggctt tttagtgtaa 30420
aatataaata tttcaagaat gtgttaacac aaatgtgttt tttatttctg atttactcat 30480
tgtacttcaa gacactaaaa taacccccaa tatgaagtaa ataaaaaaca taaattgaga 30540
caatataaat attgttttgt acacaatatg gcagaaaaac ttcttttgtt ctctttgtca 30600
aatgaaggag tggttttatt tgattagaaa tgtttttaat gtgtaagtat aattactaat 30660
atatttttaa tggaaactat catcttagat ttctcaattt tattttgaaa aattgtctcc 30720
gttatgtttg gtaactggca ttattcctga agtatatgag gataaatact attgtgttgt 30780
ctcagtttcc ttacagcagt gaatctttca gagaaggtga aatggcttta gacagcccag 30840
attagaataa gtaatcctta tttattgtct agcaagaatg tttttgaatg tgcttacctt 30900
atgtatccta ggcagagagc tatcatctcc tcagagagtt tgcatttatg tatacacgaa 30960
atagatgtgc ctaagtgaga gtcaacatag ccaatccaga ggctgattga tattctgttg 31020
gtcaaagctt tgggatattg tcaattccca gactcttgtc ctgctttcag acagcctctc 31080
actgtgggaa ctgcaccttc ctccagccct gtgccctctg gtcaaggagt ccaaaatctc 31140
tgtgggtaaa taattgactc ctgtttaaga gccatggaag tcacttatca aggaacagct 31200
tttttcccc ctttccccca ccaatttcgg gaacctttt cagtaactgt ggccccaaga 31260
cggcagaagg caatttacca gtaaagatgc aggagcttct gttacctcat agtgtccact 31320
ctgctgtggg caggttataa cccactccag atctggcaca gagagagaaa cttttataaa 31380
aattgcttaa agtcaataat cttttcttca gtctcattat gcgcccccat tgttaaccat 31440
ggagcaccga ggtctgcatt gacaccacaa gactctggag caccacccag agtacgtggt 31500
gacaccccga gacatgtggt gatgccccat gcttcataca ggcacccagg tctaatgatt 31560
caccaaggcc catattgtca tctctgggtg gcttgccctg ggactaacac tgagtctttg 31620
aggatcccaa attacctaaa ttttatatat ggcaaggtgg ggtttttaac ggggaaaagt 31680
taaaaaagca aattagttaa ggtaacccaa aggaacagga agatagtcag taatgtttcc 31740
cctgagtcag tgtcagctcc ctgaaggagg atagagtagg aggtagaata aaatgttttc 31800
gggcatattt gcatttattt taattctctg accctttagg ctgcttgtgg ttaataggct 31860
tctttagctc taggcctctg tgtcattaat ttgacatcag tcttcaatct agcatctgtt 31920
ctggggcctc tgtgccacta aaaatgataa acatatcaaa tcaggaagag caatcccatc 31980
aaatatattt ttaaacatga aatatttaga aatcgatgcc atttataagc atataatatt 32040
ctggttcctg gtgtatatat tttcttgttt atagtattag gaaatctgat tcaaagagtc 32100
tgaggactga agtatcactt gagaaaatag aatttaagat tgcaagttcc aggctagact 32160
ctgctctacc agggcacagg tctttggttc atgttgtatc ccaagtacct agggcgtcct 32220
ggtacacaaa gggtgctcaa taaatacttc tttaggctgg gcgcagtggc tcacatgtat 32280
aatcccatca ctttgggagg ccgaggtggg tggatcactt gagttcagga attcgaaacc 32340
agcctggcca acatggtaaa accttttctc tactaaaaat acaaaaatta gctaggcatg 32400
gtggcgcaca cctgtagtcc cagctacttg ggaggctgag gcaggagaat cgcttgaacc 32460
caagaggtgg ggttgagatt gggccactgc actccagcct gggcaacaga gcaagagttc 32520
gtctcaaaac aaaacaaaac aaaacaaaac acttctttat tgaataaaag caaaaattga 32580
caccagaagt catttgaagg tgacatactg attgttttc ctaacatttt attattaact 32640
tttcaaatat acaaaaaact tgaaaatgtt tcataatgaa cactcctata cttgccactt 32700
agggtctacc attaacattt tactatactt gctctatcat acatctatcc atctacccat 32760
ctttctatcc atccattagt tcatcttatt tttaaatgta tttccaagta aattgcagac 32820
atcaatactc ttctccctaa atattgctgc tgaccatttt attgttgaca gtggtttctt 32880
gcactttctt catattctta accacattga tagcattctg atgtctgcta ttattggaaa 32940
atcccctttg agctatctgt agacaaaact tatttgcaaa aatgagtcag gatatagttt 33000
cgggacctca gttttaatat gaaaatcaac taaaagtcaa gcatgctagt tatctattgc 33060
taagtaactc taaaactttg cttcaaacaa taataaatta aacttttatt acttctcaca 33120
gtctttgtgg gtgaagaatt gggaacaata tggttgggca tttctgattt ggagtctcac 33180
gaggttgcaa tcaagatatc agctagggct gcagtcatct gaaggcttca tcagggctaa 33240
cacattctgt gaggcagctc attcactagg ctgacacgtg gttgttggtg gttggtggga 33300
ggccctggtt cctcccaatg tgggcctctc cacagacttc tttagtgtcc ttaccacacc 33360
actctggctt cctccagagt gagtgatcca agcgagaaag agagacaaca gggaagaagg 33420
tattcttttt ctgacatagc ctaattctag gatttggaag gaaatcacta agtctgggga 33480
attaggcttc accttttgaa gggactaaag tcagagaatt tttggacata ttttaaaatt 33540
accacatcaa agtgtgtgtg tgtgtgtgtg tgtgtagtgt gtgtgtctga aatgatttta 33600
ataagaatat ccacctgagg gattgttgtg aattaaaatg atatagtgca ggtaaactgc 33660
tcagtatggc tctggtctgc taatgctaga aggtaggact tctattgtta ttattattat 33720
tattattatt attattatta ttattattat tttgagacaa attctcgctc tgttgcccag 33780
gctggagtgc agtggcacga tctcggctca ctgcaacctc catgttcaag cgattctcct 33840
gcctcagcct cccggagtag ctgggactac aggcgcatgc caccacacct gggtgatttt 33900
tgtagtttta gtagagatgg ggtttcacca tgttggccag gctggtctca aactcctgac 33960
ctcaggtgat ctgcctgcct tggtctccca aagtgctggg attacaggtg tgagttaacg 34020
tgcctgggaa ggatttctgt tattaatagt agtagtagaa gtagcagcat catcatccct 34080
accaagacta tgacacatat gcgcaagatg cattaggaga atgcatctca gaaaacaggt 34140
tgagagaata tagcaagaaa caaattttgt gcagaagagc ctttcatcag ctgactgcct 34200
caaatagggt gagcgtggaa aagaaggttg aaggatgtta gatattctga cctgcaataa 34260
ctgttaggga ggatgaattt gcacttggaa taggaaatgg caaggtgact cctgctgagg 34320
gagagcagtg ggctatgtgt cccccattcc aggagccctg tgatgtaact ggagagcaaa 34380
ctgcaggaag ttaaaagagg gaaaacaaat taactctgat gcctgggagg ggcaaatttt 34440
caacatcgca gttactttg ataatactgt gtatttactt tttttattct aacttgcaat 34500
taaaacattt ttgaggtaaa ataatgagac cttgatgtgt gatctctttt tccccccagc 34560
tacctctgaa cagtgcagat gagatttatg agctacgtgt aaccggacgt acccaggatg 34620
agattttatt ctctaatagt acccgcttat catttgagac caagagaata tctgtcttca 34680
ttcaaacaga caaggcctta tacaagccaa agcaagaagt gaagtttcgc attgttacac 34740
tcttctcaga ttttaagcct tacaaaacct ctttaaacat tctcattaag gtaagtgcca 34800
gacagaaatg aagcaaggaa ttctagccat cttactaaac ccctctggga agttctgctt 34860
gtgttactga cactggaata ttttagaatt cacctaagat aagcttccct cccaacatgg 34920
aactcctcta ataggaaaga aggtggtgca tgcactgggt taagagctca gcctctagag 34980
tcaacctgct tgagttccag gcctggggtc ttcattgatt tatacagttg tcaaacattt 35040
attaaacttc tgtgttccag gcacagcgat agggcagtga acagaagaga ttaagtccct 35100

-continued

```
gctgacactg agtttatttt tcagtgggta gtaggagaca gacataataa ataaacatac  35160
aaatatatat ttataaaggg acagatatgt atgtatttgt gtgtgtgtat gagagagaaa  35220
aagggagtga gagacagaga gtttgtgttt gctattttct ttctttcttt tttttttttg  35280
agatggagtt tcactcttgt tgcccaggct ggagtgcaat ggcacgatct tggctcactg  35340
caacctccgc ctccttggtt caagcgattc tcctgcctca gcctcctgag tagctgggat  35400
tataggcatg tgccaccacg tctgcctaaa tttgaatttt tagtagagac ggggtttcac  35460
catgttggtc aggctgacct cgtgatccac ccacctcagc ctcccaaaga tgctgggatt  35520
ataggcgtga gccactgcgc ccagcatgtt tgttgctttc tctagggttg tctgggaaga  35580
ctgatttgag cagagagcca aaggcagtaa aagaaaataa gcccatacag agggggaagc  35640
acatggaaag gccctgaggg ggagcttgtt tggcgcattg gaggaacaac aagctggcag  35700
tgtgctggag ccccggggcg aggggacagg tgctaggaca tgaggtccta tacaagtagg  35760
tgggttaggg tggggctcat gcagggcctt attggccatg atagggactt tgaaacttat  35820
gctaagtgaa gtgagaattc actggagaat tctgaggcaa gacttgatgt aatctaactt  35880
aacatcttaa aaggatcact gtcagctcta agaagaatag atgctagatg ctagctgtgt  35940
gatcctgggt aaatttatta accttctaga acctcagttt ccttatctag aaaatatgta  36000
ataataaaac ctcaaaaggt ttttatgagg cttaagtgag ataattcaag taaaccattt  36060
agaactgtgt ctggcacata gtacatgctc actaaacgtt agccattatt attattttag  36120
gaacccettt tgaaaggtag tagttttgtc tctgctgctt aatactctga tgatttggag  36180
gcactgtggt tagcacactg agtgctttcc tgtgagaatc aagttgaaga caactgagat  36240
ccagctgggc ctggttttct gtatttaaac ggagaagaac actggacatt tgatcattac  36300
ttggaaatag ggtgactaac atcccagtct gcctgggatg cctctgattt taaaactgaa  36360
aagtctctgg tcctgggaac ctccttagtc tcaggacatt ggttactcca gatattctaa  36420
tgaataacat agtgtggaag gtaaagtagg cctttttagtt tggtatcttc ctattcttag  36480
tttatttgtt gttataaatt aaaacaacaa aacccaatca aataaacatg tatacattta  36540
actttgagcc aagatatatt tgtagccagt atcacatttg ttgccatggt gttcaatgca  36600
tattgcttga attgaactag cattatttca gagtttgcct ttggtatgta atggaatgtt  36660
tataaagcag gttgacatag tgaatagtat ttctaaattc atgtcacccc cctgagcaga  36720
gttgaactga ctccattcat accatctttc atcatttatc cacatatatg gagagcttac  36780
tgtatgtcag aaaggatgtg tacaatagat ggtttaataa atgtctggct atctctgggt  36840
gtttacattc aatgcttcct tctactgcag gcaaataaaa gttagcactg cataaattgc  36900
ctgttctaga catcaaccca gaactaaccc tgctggttct ggataattag tctgtgcatt  36960
ttcatagttc tgcctgtcta ctctgctcta gtatcttcct ttgaatcttt gatttgcaga  37020
ttctttgggc tcttctgtgc agtttgggac ttagcagacc acgtttggct ttctggaaag  37080
ggctcagaga gactttcctc ttattagctc tggtactgat atgactctct tggccagggg  37140
aggggagttt aaactaaaat tctacctgga acccaaagtg ttttggaact atgagtgagg  37200
ggtggccatg ctcctgtctc tgtacctggg aagtgatgct caaatgtgga cttaggtcta  37260
gctgccttcc tccttgtaac ttgcagaggc caggtgggag cagtaatgtg aactctttca  37320
gctgaaaaca gacatttggg ccaggtttac aagtctatga tattttctac atctttcagt  37380
gtggaataat tggtgtcttg gcaaaacttt tcagaacaaa ttgggactta gcctgaactg  37440
gagcccctga ctgagacagt tgtactcctt ggcacagcac cacctgcagg ctgatgtgga  37500
gaagtgcacc tgagagttaa cggggcccat cttgcccagc tagaaatggc tgcaggatgt  37560
agctaagata ctgactgtca cagcaccttc agggtgttca ttgttgttct tggggactgc  37620
aggccatctt tgggtgttat tcattttgca tgccccaata actggtcttc tcaggaggga  37680
aaggagcttc gaggcctttt ggcagtagaa aaaacataac ctatgtctcc cacgcttctg  37740
gcctcctcta gccaatttgg cctgacacaa tggaattgag tgcctctgac actgcgatgg  37800
cagctggcat ggctggcttc tgctctgacc tctccatcca gaagttgttg gtgctagtac  37860
gggtgaatga tcttgtaggg gaacaggtgt tattggcttg gggtatatc ctgttattgt  37920
gccctgacac tcagttttgg agcagtggtg gctaactcag aacctgaccg ctggccaggt  37980
gaagaagcta ccttatttga gtgatttgaa ttctctaatt ctacaggctg gacagacatg  38040
ttattcacac ataatccaga aatagtcctc acagacatat tctccagcca gggagcttac  38100
tgcttgagac aatcaggtac tgtgtgctgt gttgaggcat ctcagagatc cagagcgatc  38160
taaaggtgac tcgaagggca tgtggggcca ctattccagg atctctggcc tgcagctttt  38220
ctggctgtga cgggggtatt gctcatactg tacatggctg tgtcgtagca gcagatggcc  38280
gcatgcaaat gctgggctcc gctgtgacat caccatgctt ggctggttca aatcctgatg  38340
tgtcttgtag acttctggtg tttctgcatt ctctccctct gccttattgg taacagttag  38400
acctaggtcc aagacaggct tgggaaagca gaggaattat ctcattctcc cccaaccctc  38460
cagatccccc aggtacaaag ccatcaatga ggtcagttca gacttcattg tccaggagaa  38520
atgtatgccc tcactaccat aatgtttcag tagaatatgg acattccatt ttcctacact  38580
tcaggtaaca ccaagaatta ttgttattat tatttttatc tttgtcagac tgacagaaga  38640
aacacaatat tgttttcatt tgtatttcct taattactag acagcatata tttattggct  38700
atttgtattt cttcctttgt tcctgagcct ttgaacttca tagccctccc atgcgtcatg  38760
ctgtggcagg cacagtaggg ccaactgccc attacaatgc ctggcccagg agtttaccaa  38820
ggatacagtg acctgcttgt tcttgacttg cttttggtct ctggttttca caattggttt  38880
ctggcttatt agactgcttt ctgcacagtt ctcagcattg tacttacccc taactgtcat  38940
atctccactc tgggagagag gtttcttctg ttctaataac tggccccact cactacttct  39000
aggcaaagtt tagaggataa gtctaaggga aaatattcaa cccctgctct cagtcacagt  39060
ctagttggga ataataaaat atagattttt ggcaaaataa aatatgtaaa ataaacatat  39120
tttactgcct ttaacaaaaa tatgtattca agagagataa actccagata tactagggac  39180
tttccaggaa gaagtcacct ctgcctattg gaggcatgta taggaggcaa gaaactgaaa  39240
ctgatttcac cagtggacaa ggaagggagg gatttccatg cagcagttgc agagacctac  39300
atgcatgggc tttttgggaa taaactgcaa acaaatccgt atgtttggag gaagatgagc  39360
ctagaaatgt agatggagta gtattagtaa gggccttgta aactaggcaa aggagtgtag  39420
acttcctgta ggcaaacaaa agccatgggt acctagtggt ctagtataat catcatatac  39480
tataattagg gactataaaa agtgtatagc cactgctttt tatatgccag ggactgtgcc  39540
aagtatttca accactgtaa ctcattctca gatttgcgtt tcagatggat cacactgttg  39600
gcagtgggga agatgtattg tagagggcaa gactagaggg ggaagattag ttgcattagt  39660
tagaaaatag gacatggtgg ctggatgtga ggatggaaag aaggagacaa attagagata  39720
tattaaccta acaaagttaa aatgtcagga aatgtgagag aggaatctag gatgactgct  39780
ggaatggctt ggataaatgt tgcatgaagg gattgttgtt tgggaggtta taggaagaat  39840
```

```
gaagtgtttt ccatgtatat ccgtgattaa acatctctct aatatgcttt tgttgagtta  39900
aaaggcagac atgagtttgg attctgaatt tcatcatgca ctggtgctgt aatattgagt  39960
catgccagtc acttgaatgc gtacctccct ctccaggcat cagttttctc aactataaag  40020
tgaggataac catgtcctaa aggagaattg taatgattag agataaggca gagtgcctga  40080
cacatattgg gcctttaata aatggggcct gttatctcta cagttaaatt ttcttttaac  40140
actactacca ccaccgccgc caccaggggt ttggtgacgt acatgttgta gtgtttcatg  40200
tagaaggaaa tagggtgcca ggaattaaaa ggtggagcag aatcaagatg aacttgggag  40260
aaatatgaga aaagaataaa ctttgatttg tcttctttag aaatatagag cctacgtttt  40320
ccaaaatgtt catgcagcat tcatccaagc cattccagca gtcatcctag attcctctct  40380
cacatttcca gacctttttaa ctttgttagg ttaatatatc tctaatgtgt ctccttcttt  40440
ccatcctcac atcctgccat ccagccatat ttgtgccgta ttttggagta aagttctgga  40500
cctgggtggg aatgctgcaa ggcattattc ctaacctgat aggatacaca tgcacatggg  40560
cagcctctac atacttacat gtctggtttt cattttagga ccccaaatca aatttgatcc  40620
aacagtggtt gtcacaacaa agtgatcttg gagtcatttc caaaactttt cagctatctt  40680
cccatccaat acttggtgac tggtctattc aagttcaagt gaatgtgagt ataaatatat  40740
tttttggggg gaatgttaaa gtgatttaat taggtcaggt gggggaaaat ctccaaagtc  40800
atttatacaa tgaagagaaa aaaattaatg tgaacattta gacaatttaa acggtttatt  40860
tttaatttat gatgtttatc aagggtttat ttagctttca ttctaacata ttagaatttt  40920
cataactgtt gtctttttct atgatatgat gtttaaaggt taaaacattt tgacatttta  40980
gtacacaatg tttacttatt tgtttcatgc attattttaa aactaagtaa tgaacacata  41040
gctattattt ggcaaatttt atgccttaga ataatgactc ctaatgagtg attagattaa  41100
cctactttta tctttgtttt aagaaacagt gacttaaata gctacaccga ctgctattcc  41160
ccaatccttt ttccctagct tctacaccta ttgcctttac ttgctgccaa cttgtatagc  41220
tctgaaatct aaatggaggg cattaaatgg catataaatc taaatggggg gcattcattg  41280
gaatgaatga gacataaaca caatgggatg gaaacaattt taaaaagcaa tgagacttaa  41340
ctgttttatg tgatataaat tggtcattta gtatataaca tgtaaacctt tatatttttc  41400
tatatttatg tgacatataa acatataaga tataatcaac tttttctgta tctaaagggg  41460
aagatatgta atatgaaatg catgaaattg tagcttattc taagcattgt tgctgagcct  41520
tgagtaggtg ggactcgtgt gtgaattgac ctgtatgaat gagaacagtg ctggaggcac  41580
aatggactct caatatttgc ttcatggcca ccctgcatct ttatgggtgt ttgtatgatg  41640
tgtttaccaa tattattctt tttaaggtag cagaagctct accgaatgaa tgtatgatgt  41700
ggttttaaag aacatttgag gcaatattat gaaaggggct catactgtta gagaacaatg  41760
taatgcataa ccattaaagt catggacaat tttcagtgag gtctttgctt atttccttac  41820
ttataacagt gtaataataa ccactgttat aaatggcagc ctagagcagg atgtgatgag  41880
ttctagggga agtggaattc tttatatctg agcttgtaga gaaagtggaa agagtaggca  41940
tttgtgaaac ttagaaaata gggaaaaatt tgtgtgggag tagggaaaat ggaagagaac  42000
gttatgtgtc tggggatttg ggagaagttg atgttactgg agcatgtgga gaatgatggc  42060
ggtgtagatt aggaagcacg ttgtgagttt aaagtagttt gaatattatt ttcagttccc  42120
acttaaattc ttaagaatca cttttttttgg tccatccatc catcgatcct tctatccacc  42180
cacccaccca ccaacccagt atgtgttaag gactttatgg ctgtgatgaa tacaaagaag  42240
gtaaacatat gacctccatt ttcaaaggtc attgtcatgg tgacatgaac aatatgataa  42300
aaattaaatg acataagggg gacagacaaa cacagggcag tgcaatagca gaggaattgt  42360
aaggtgttca gtccagcttg gtgataaaga gggtttattg ttagcacaag cactgatgtt  42420
ttggggccag ctgctccttc tgtctcccat ggtctgctct gttctccttt cactcttctg  42480
ccaacctttg aggtgttctt cagttcttct gattccatta gcttagctaa ataaccatca  42540
tgcccagaat ctttaaagca agcctctgca caggtggctg gcagcctgtg ggtgggccgc  42600
cctgggtcaa ggtgtccatt tttggtccat tcagatgcca cctatgcaca atgaccagca  42660
agagcagttt tagctggata acaggcgctg agggattaat ttgttcattg aatggtggac  42720
agaataagta ccagaagaga gggggataga atagcagagg gagactttgc agaagatgtg  42780
agattatact ttgaaagatt tataggattt atcatgttgt ggtttgtgga cttggcttgt  42840
catattgctt ttatagaaaa caaatgctct taaggaaatt taggtgctta aaaaatgaaa  42900
agcatttgca ggatctggcc cttgcccaac ttttcagtct tgtaaagtgc cgcccttcct  42960
cttgaactct atgctttaga catcttatgt cccttaagtt tcttaaactc accgatctgt  43020
ctcattctag agcctttcat catgctgttc cctctgctga gaatgttttt tcttccttat  43080
tctcgctact tgcttttaac ctgcagccat tctctaaagt ggcctggctg ttccagacat  43140
tcccatagta ctgtgtgctt cccttaattc attcatctca cttttaatta gtggtccatg  43200
atagacagta gcctttgtaa agctggtgac cttctggtct tgctcacctc tctattcctg  43260
ggaccaagtt cagtgctttt gcatgtaagt agaaagcagt attttcttaa aacgaatgtg  43320
tgaaaactat atagcaataa tttgtcttga accaaatgca attttccctt ttgtatattc  43380
tataaagcat ctttatcttt ttgaagacaa gtatactgat caggtacttg tcatttgagg  43440
tatgttaatt tgaggcattc agctaagaaa aaataagccc cttaaaaaaa agagcccttt  43500
tagaaccacc aggggtcagt ataaccaagg aaatgttatg agaagcaact gtggccttgg  43560
tctctggctt ttgtttttct ttgactactg cgcagcatta aaggactgta tatttcttgt  43620
tattaaaccc cttttctttt agtagtgaat aataacatag aggaaatgta tttattattt  43680
aaatagccca ccattagaga ctatattttt acttttcggt ggcagtcacc attctcaata  43740
taaaactcag ggaaggaaaa tatttatttt caagaaagta ttggctgggc gtggtggctc  43800
acacctgtaa tcccagcact ttgggaagcc gaggcgggcg gatcacgagg tcaggagacc  43860
gagaccatct tggctaatac agtgaaaccc cgtctctact aaaaatacga aaaattagct  43920
gggtgtggtg gcgggcgcct gtagtcccag ctactcggga ggctgaggca ggagaatggc  43980
gtgaacctgg gaggcggagc ttgcagtgag ccaagatcat gccaccgctc tccagcctgg  44040
gcgacagagt gatactctgg ctaaaaaaaa aggaagtatt ttttaaattt tttaatttgt  44100
aagagacagg gttgtcgtct gtcactcagg ctagagtgaa gtggcacaat catagttcac  44160
tgcagcctcg aactcctggg ctcaagtgat cctcctgcct cagcctcctg agtagcaggg  44220
actacaggta tgtgccacta cgcctgccta gttaaaaaat tttttttttcc ttttcataga  44280
gacagggtct tgttatgttg cccaggctga tcttgagctc ctggactcaa gcaatccttc  44340
tgccttggcc tcacaaagtg ctgggattac atgtgtgagc catcatacac agcctttggg  44400
agagttttga aattccattt tgtctgtaga aaaaatatgg aatgatatga gtattcccac  44460
tgatggacaa tctctttaag aattaccgga gttatcagag ctttgatttg taatgactat  44520
acaggtaatc agaaagtggt attcttcagt taccctttgt cctaggtcag gaaaaggatc  44580
```

-continued

```
ctttaagtaa aacatacttg acggctcctt ggcatttctc cacttgtatt aataacatgt  44640
ttgtttgtag agtaagagtg aataagtcct ttatgatacc gtgttaacct ttctggatta  44700
atctaaattg tttgcccttc aagtattgta ttgcttttca ccttcaaggt tttttatgat  44760
agtaatggtg agtaattatt ttggtctagt atgatttcta gttttctttt ctttctttct  44820
tttttttttt tttcgagaca gagtctcgct cttttgccca ggccgtggtg tgatctcggc  44880
tcactgaaac ctccacatcc caggttcaag cgattctcct gcctcagcct cctgagtagc  44940
tgggattaca ggcatgcacc accatgccca gctaattttt gtatttttag tagagacggt  45000
ttcatcatgt tggccagggt ggtcttgaac tccagacctc aagtgatgca ccctactcgg  45060
cctcccaaag tgctgggatt acaggcatga gccactgtgc ctggccaaga aaggaaacaa  45120
atgttttggg ggattagtta agtgatttgc ccaatgtccc acaacttacc aaactaggat  45180
tagaactcag gccttttgac accaaatcca aggttctctc taccctgcca ccttggtttt  45240
ccatcttatg ttttatctct gtcattgttc agcatatgat ggtgggacat cataagttct  45300
caatatatac atagactttt tttttttta caatgctagt ttaatcaaat tgcaaagaaa  45360
ctcttgatga ttataatgtt taagacctct taaaatcagt aaagtttagt aagagccctg  45420
gctctttttg tgctacttat acgtgtgctt aattgacaca catattctag tgtgaatagt  45480
tctttgctac tttggggatt gtacttcttc tcttgagaat gtgaccaagt cttctacttc  45540
tgccatactt tgattgccct gctcttttc atcatttctt tgtctagagc accaagccct  45600
cctctcagag ggcagaggta tattttagct gtaacatctt ttcatagaag tgtgttttat  45660
agggccgtta tactttaggt acattataag ttgagtgtgg gaatatgttc tgatttaata  45720
attgacttga aaatacacct taggaagata atgtgtttta aaagttagac attcctttat  45780
tttcatttct ttgcaatata gttctctagg taccttatct ctaggtatgt tatctcttga  45840
ttggtgttga cagttttctc aaataattgc acatggtttt tttgttttgt tttgttttgt  45900
tttttgagaa agagtctcac tctgttgacc agtctggagt gcagtgtgca atctcagctc  45960
attgcaacct ccacctccca ggttgaagtg attttcctgc ctcagcctcc tgagtagctg  46020
ggattacagg tgtgcaccat catgttcagc taatttttgt atttttagta gagatggggt  46080
ttcaccatgt tggtcaggct gggctcgaac tcctgacctc aggtgattca cttgccttgg  46140
gtttccaaag tgctaggatt acaggcatga gccactgtgc ctggcctgca aatggttttt  46200
ccctccattt tttattttct gtagtaaaat acacataacg taaaatttgc cattgtaacc  46260
atttttaagt gtacagttca gtggtattaa gtacattaat attgttgtgc attcatcacc  46320
accatccatc tctgtaactc ttttcatctt gcaaaactga aaatctacac ctattaaaca  46380
ataactctcc attccctccc accccccagc ccctggcagc cactgtacat tctatctctg  46440
tggtgttgat tagtcttata tcagcagaat catacaggat ctctttttga gactggcttt  46500
tttctcttag cataatgtta ttatggctca cccatgttgt agcatatatc agaattttct  46560
ctcttttaaa ggctgaataa tattccattg tgtgaatata ccacatttgg ttgcgaatgt  46620
ttttgcatct atgatttaaa aattatattc gaggttatta gaaggtgatt ttaggggttc  46680
tttaaaagaa aggctaatgt tggtgtctga gaaccaggct tctgggagcc aggaggcatc  46740
tggccagagc agtgcagcct gcagcccaga gctccaggtc tttgcgtgac ccacgcactg  46800
gtgctcatgt tcctccaaga gcccgaaaga agagcctgag tcactgagag attcctggtc  46860
atttgatgac ggcagccctg tgctgtcttt cctcattgtc agatggaagt ctcttcttct  46920
ttctagagtg gcttaggcat ttgagtttac cataatggcc acctgaggct gcagctggtt  46980
ctgaaacatc agtgtgccac agaatcaatg gactgggagc ttgtttaaag atgcatagtc  47040
caggtcccac ccccagatca caatttacta attttggcat gggagctagg agtttgaatt  47100
ttaaataagc actcaaggaa attctactag ttttttgaac cacattttga gaagtgctca  47160
taaatgcccg cagctaggca tctttagaat ccatcttttc cattgagagg cagtgttggg  47220
cagtgttggg cagtcaacaa ggtatggaac tggggacagg ccatctgatt tattctttga  47280
attcctcagc agtgctactt tctgctattt actttacctt tttaggtaat cagctcagta  47340
gagctcccca gcaccttaga catactaagt cagaatttct gggacaatgt atatccttta  47400
caacagcttc tctgatgctt cagatgcaca gccagcttgg gaaccactga acttgataat  47460
catcttttct atctgtcact aactacaatt tcgtaaccgt tgtctcaatc ttaagccatt  47520
gttagaggtg gggaacaaga aatagcaagc agaaaactca acagggttaa ggcttgaagt  47580
cactcttctg gagccctgta taatgaaacg ggttatcaaa ttattatgta actcagaagc  47640
aatctgcatt gagttatttc tttgcatcta acagttatat ctagtttctc ttgagttact  47700
tgttttttct agattaggtg agggttgcca acaccttact gctttttata acctttcagg  47760
atattcctta ttttttctgg acttgttgtc cagcctctgc ctgggtcagc ttgctgcttc  47820
tgttaagtat ctctggagcc gtttttcttt tgcaaaagag cacatctttg tttggacagt  47880
tcttgtccct aaagcactct accaggagca tctgcttaac ccgcctggct tgtgacgaca  47940
acttaacaga aagcatggag caaaactttg acaggtcaga aaacagtggc attctctctg  48000
aaatgtggtt gtggcttcca aaatactttc actagtcttt gcttataaga agaatgcttt  48060
gtttgggaag gatctcaaac tcttacttcc ttgttcagtg agaaagggag ggaggagatg  48120
gttttagaat attgatttct tagagcatta tctggcagag ctcagcactt tctcctccat  48180
tcttccaaag gccccgataa acacctctag aatagcattt attaatcagt gtagcgttat  48240
tttcgttttt taaaaactgt ggtaagatat atatgtaaaa tttaccattt taacaattta  48300
aaagttaagt agcatcaggt gcattcacat tgtggtgcaa ccatctgcca ccatccatct  48360
ccagaaccta ttattatctt cagatattta aaaaaatgtc tgcctcattt cttaaactgt  48420
gaactccttg aagacaggaa ttctatttta ttaattttca tatttgttct gtctaatata  48480
atatctgacc tgttatggga actcattcat gcttgtggga tgaaagaatg agtgaataga  48540
gcttcttcta gatgattgct gttattatcc tttgtgatgt tctttgactt ctagtctcac  48600
tctgctatat catcttgcaa cttagtagaa atatctttgt atattttcat tttgagaata  48660
tatatggttg ctgtatttga tgaacctgtg agctaatgga aaacaggact tttggattaa  48720
tgccctggac tttctcattt tgaaaattaa aaaaaatctc aggcaagagc tgaatattct  48780
agtttgttat aaagtctaaa atagacttat aattttggtg ccatattatt cttgtgtctt  48840
tattcagcca tttgatctgc tagtgccagt cctttggcag tgtgcatttt aatttctagg  48900
ccccatatgc aaattttcat gaggagttct ttgttttgtt ctttctctac agaagccacc  48960
ctaggaggac ccctcctttc aaatgtgtct tctgtacccc tctctgaaga gacatgtttt  49020
tggcatcagt tagaaaactt tggggccaga ctttaggatg ttgtgttcat caatgaaatg  49080
gagggtctga gtatgtagca tcatcagtac ataggatagg gactcagtgc tatagatgat  49140
cttagaggtc gcctagatcc atctccccac tttatggagg aagaatctga gataagtgac  49200
gtgacctggt taggctcaca cagtgtgttg tgggagggtc aggactagca actagtttac  49260
tcatactttc agttctgtaa aattaaatta tttaatatgt gcagcaattg ctgttttatt  49320
```

-continued

```
tatttattta tttttgagac agagtcttgc tctgtcaccc aggctggagt gcagtggtgc  49380
tgtctcagct tactgcaact tctgcctccc aggttcaagt gattctcctg ccttagcctc  49440
ctgagtagct gggatttaca ggcatgtgcc accatgggcc tggctaattt ttgtattttt  49500
agtagagaca gggtttcacc atgttggcca ggctggtctt gaactcttga cctcaggtga  49560
tccgcccgcc ctggcctccc aaagtgctgg gattacaggc atgagtcatc atgcctggcc  49620
agcaattgct gttttaatat ggcctccttt taaggttgaa tttagatgtc aacagggctt  49680
gctgtatgca ttggtggaga agatacctac ttcttttata tgacttgtgg atgccacggg  49740
atcaccttgt ttgcacgttg gattgttccc aacgtgtccc agattctgac cacagcagcc  49800
atgtgtttag attgaagatt tgagtccagc atgtaggtta cttggttcat ctatttaata  49860
tccattaata tactattaag gattaggctg ctgtcacctc acagcctcta taaccttggt  49920
catatgaggc ttacaaagat taattttttg ttgtttgttt ttgagacaga gtctcgctgt  49980
gtcacccagg ctggagtgca gtggcacaat cttggcttac tgtaacctcc gcctcccagg  50040
ttcaagcgat tcacctgcct cagcctcccg agtaactggg attacaggca tccaccacca  50100
cgcctggcta aatttttgta tttttagtag agacaaggtt tcgccacatt ggccaggctg  50160
gtcttgaact tctgacctca agtgatccgc ctgcctctgc cttccaaagg gctgggatta  50220
taggcataag ccactgtgct cagccaagaa gattaatttt aaaaataact gtttaccttt  50280
aggtagattc acagaaagtt gcgaagatag cacaaagcgg ccctatatta tcttaacgca  50340
gtgcacccag tggttatatc ttatgttatt atagtacaat ataaaaagca agaatttgac  50400
gtttgtgtgg tatgtgtgta tggttctgta tgatgcttta ttttcagtgg catagaggga  50460
gttttggaaa atgataactc actgggctct gaccagtggt ggcagccctg ggtgaggggg  50520
aagggggcac tgaaatgagt accaagtccc tgggtggagt gaggaaaggg agaaagagca  50580
agaaatggag ttattttccc tcaagggtaa ctttcctatt cagtacaaac ctgtagctat  50640
gctgctgctt ttgctccctt gcttgagata ggtgcccaag aaaggtggtc atgttacatg  50700
tctttaaaaa ccatagttcc ttctactttg agtaggaaca gagagggtta aatgggtgat  50760
ttttgtttat tgtttgtttt taaagagaat atgtttctag ttagtacttt tttttttca   50820
acaccaagga aacaagtttg tcccttgtac tgcataatgt atttgtactg cagatggtaa  50880
cactgtttta ggagtatgaa tgtgcttgtg atccctggat acctggccac tattctgcta  50940
actggaggct tgtatggtct atgtcttggt cattggttag atccattatt cccaagtcct  51000
gtcactatga gtgactgtca ggtatagacc agcttcagtt cttcaggtgt ttagttccag  51060
ccttgataag aaccagaata tttgtaatcc tttctaatga gagaagggat ccaggaacaa  51120
aactgtctcc tggggaggtt ctgattcctc cctcctcaca ctcagtagat tatcttcctt  51180
tccacttcac agagaacaca gtcatcagat gggaatttct ttcacttttt ctgccagatt  51240
tgcatgtgtt gcctgtgccc atctcatgct tattctcttc tttttagagg aaaggtccta  51300
ttcttcacat ctaagaccaa tatcccgatt tctgccttgg cttctttctt cctctacttt  51360
gtcagaaaac ttgcagtgtt gacagtctct ttcttctcag tcttcaaact ggatctcttt  51420
ctgtcttaga tctttttata aaatctaata tgtttaattc tttctcattg aaaaaacaaa  51480
aaatatagag aagtactgta ctttaactct acttcctctt cagtgacttc acattcccat  51540
tctagccagt cttctaaaaa aaaatgtctg atctctctgc ctccatttc ccaactcact   51600
ccagtttgac tgagatttct ttctacttgt ttggattctt cttcttggtc actttcgtca  51660
tttactctct attacatatt ggcacattgc aagtttggtt ttaagtttct ttcatttctc  51720
actctaggga agttcacccg aaggcatggt ttcagtttcc atctatacac caatgactct  51780
caaattggcc tctctgagag aacctatacc tctgagttct agacctttaa aactatctac  51840
ctttaaaact atcaacatct gtatttggat gtttcaaagc accccaaact cttcatgtcc  51900
agtatcattc ttaacaatct ttccccacca cacctggctc ctctgcagca tttcctacct  51960
tatttaattc tctatccatt cggctgtgca ggctggtaac cttagagttc ttgacacctc  52020
atgctgcctg accacccata ttcaggcctt catcaattcc cacagctttt tcccttaaat  52080
aaatatattt ctttctttct ttttttttt tcctaccctg agacagagtc ttgctctgtc   52140
acccaggcaa tctcagctca ctgcaacctc cacctcccga gttcaagtga tcttcctgcc  52200
tccatctccc gagtagctgg gagtacaggc gtgtgccacc atgcccggct aatttttgta  52260
tttttgtag agatggggtt tcaccatgtt gcccaggctg gtctctaact ccttagctca   52320
agtgatctgc ctgcctcaac cttaaatata tttcaaatcc acctacttct ctatttccac  52380
ctctccctcc tttgtccaag ccactattat attgttccta gatattacag tgtctcttaa  52440
tctctctgca tttggttttt ttccccttg caaccaatta tctacacagc agtaaaaata   52500
atctcaacat tagctggatc atgttattcc ccagcttaaa actgtccaaa gactttccac  52560
tggcctcaga acaaaattca gatgttttac catggcctac acagggtctt acctgatctg  52620
actctgtttt tcccatctca tctccagatt tcataactct ctgtaaatgt taattcacag  52680
cttttatcat aatttgtaat acatactcac atatgtggtt atttgataaa tatccttctt  52740
tccactagat cagaaggtcc atgcggggtt gtattcccat tacacctgcc actcaggcgc  52800
aatgaatatc tcttgaagga atggatgaat gaatgcattt gttgtgtttg ggcctcagcc  52860
ctggtaattc tgattcagta gctctggggt aggaactgga cacctctatt tattaaaccc  52920
accacagctg attctgatgc tgagtttggg ttgaacccca tagagaaata tgttgcaact  52980
acagtttaga ccacaggtgt ttagactcta aacaggaaag ggaaggaaag gatgatgtaa  53040
atgttaataa acattttctc tcattttgca aaccctattg actctgtcat tcctctaagt  53100
aggacagtgt acatcagctg acacttttac aggatgatat ttccattgtg atttcttttt  53160
tatttttaag ctctcccaat tttatggtaa aaataaaaga ggggaaaaat agggtattac  53220
atgattgcta ttacgtaggc aataggttta ggcatagtca ggttagtagg gatcggaata  53280
aagctaaaaa tatgaagctt ttgtgttgta tgcgagggtg ggaagaaaca ccagtcagta  53340
cacatctaaa ggtgacaaga cacagacctg gctttcaagg agcttacaat cagaaaagct  53400
tcgtgtaaca aatgcaaaga gcattagatt aggagtccta agacctgggt actgtgctct  53460
agttaagtga tggtgggcat ggcatttcag ctgtgggtct ccgtttcctc agctgtaaaa  53520
taaggggttt ggatcaaggg atttttaagg atcttcacaa ctttacaagt ccaagatagg  53580
gctggagggg actgtaggat ttggatggga agtggtgggc tctgagctgg ctgacagggc  53640
tgtggggctg ggagcaggca ctggctggca tggagggctt gtagagagta gtagttgaag  53700
agaaaggtgg ggaagtttgt gggccgagct gtggaggata ttggctatca ggctgaaatt  53760
ttgtatttca ttttgtagac aacaggcagc tctaaaaact tttgtgtatt ttactttgaa  53820
tttcaatcag tgatgcaaat ttcaatatag gacttctgag gacaaaggaa acaaaatgtg  53880
tgtgaatggg tctctcaaat tataaaagtt ataggatcat accttcataa ttttcctctg  53940
gttataaaag taatgcatga gtaaggtaaa aacatccaaa catgatagtg tagaaagtat  54000
gacaccctta tggtaaactt ccaaacaaac aaaaatcatc agtatgtgtt gtcttcttat  54060
```

-continued

```
tgctttagta gaaagtttct atgtaaaagt atgacatgat taaagttgta ttttaggaag  54120
atcactttgg tggcagcatg tagggtgatt agagggagag aaactaaagt ccaggagact  54180
accagggggt tagtattatt gtttaacaaa tatacgaata ccttcaatgt tagcttataa  54240
tcgaatacct tcagtgttag taagttcaaa ggtaatgggg gactgcggta agagagcaga  54300
aaaaattaaa gaggaatgga tgaattcaag agacacttaa aggcagaatc attaggatta  54360
gtgactggat ttcgattgga gcagagaaga aagaggagca aaaggtacct gggaatttca  54420
agttgggtct ttgggagaat cacccatatc agttctaggg aagttaggga tggaagctca  54480
gtttgggtga gtggtatgag ctagatgtat ttggactgag ccatcagaaa tcacatttag  54540
gagcaaagca gagaagccat ccaaagcaat agagaaagaa cagccagttt tgggaagaga  54600
aaagcaagca agttcaggca cagagcagag ggcaagagat tcagagagag tggctttcca  54660
ggtgctgcag aggcctcaaa gggagtgagg cctgagaaag gtgacaggcg gttagaggaa  54720
agcaacctgg cataccgagc atcttctggg gtcagtgaaa tgggagaggc agaatcgaga  54780
tttcaagagc aataaagcgc ataaatagct atacataaca tagctatgta atgtagggta  54840
atgtatataa tagtctacaa cttctgttcc taagaaggag agaattaata tgattatctg  54900
gtggaggcag cagcaatata atttcattta tgttatggta ttcctattct tacttaacat  54960
attcatgccc agttatttat gtgtaactgt gaggttgaac atttattact tgacaggtga  55020
agtaaaaaag cacattattt ttgtgccatt ttgtcctgtt ctttgggacg aattcttccc  55080
tactccttgg ataaaatgta gggaaaatct catcattttt atggttactc tttggtaaca  55140
aaaggtcctg tcatgttcgg ttactttcat atacacagtc tacattcagt aattaatatg  55200
tccagtctaa taaaataaaa tgctcccttc tccagctcgg gtcttctttg gtctggatgc  55260
ctgcctccaa ctcactaggc tgcctttgac tcctccagac tgaattgggt ggaggaaaga  55320
gaagtgaggg gtaacaaaat tctcatctga tgtataagga tgagtcatgt gaacttgcta  55380
atatttgtcc tgcaaaaatg tcaatttaat atggttcaat gtaatactgt tgtcatctgc  55440
atgagacctg tctgggctaa gacggcattt aaaactacat ttttcctttt tagaactcct  55500
ttctgtattc ctaggaggac ccttaagatt gtggggaggt ctttcatcca aagtaccctg  55560
gatgcttttg aatctgtctc ctccaaatgg cagctcataa ctccatcttt agctgctggg  55620
catctagatc acacacctca gcttccctct tctgagggct tgccttattc ctactaaggc  55680
tgttttgatc aggatagaaa acagttccat gctgacttgc tcttttggca tatctagttg  55740
agggaaaatg ctcatgcttt ctctgatcct gaacattcag gagatgcaga ccactcctag  55800
catagcacac tcttagctcc actgccagca caaatattat accctttaga gttttcaggt  55860
gtgtcaacag cctgctcact gacagcttga ggatgctccc agggacacat acctagttgt  55920
ctgcattgtc tatggaagcc cgtttcccta ggcttgaaat gagggccaag caactctacc  55980
tgatgcccca gggtggggtg agtgccactc ctagctcatc gaaagctctc tcctgaaatt  56040
cccttctagt tttattttta tcttgacctt tccaccttgg tgatgggtta agagttacaa  56100
aaccagtttt tggaaacctc ctttacaggt cctgcatcct tcacctgtgg aaggtggaca  56160
tagttgacat ctattgtctt gggggctaaa cgcaaaactg agtctgaaat agttcccttt  56220
taacctcccg ttatgtgcag atttaacaaa ttcagtgcct ttcttaaagt aaaaggtaca  56280
tccagacact ggagagtagt gctaaaacaa actattaggg aattgaaatg accataaaag  56340
aacataatga acaaacagaa ataatccaac cagcacctta gttttgattc tggcattgct  56400
ttttactcca gaagcaagag ttgaaagaaa ctgacctgca ttttaaaata tattttttaa  56460
tggtcatgta atatgctata tttcttcaaa tctgttaaaa atagaaactc aagagttgga  56520
tggcatcatg gttagggaag aaaaattctg taactggaat agatggttgt agtaattcac  56580
atgtctcaat ttgtattcta gtcataacat acttcttaaa agggtggtaa aaataatgtg  56640
ttttctcttt cccacttcat ttgtctaatt tctgtaacat acaccctcac aatgaattat  56700
tgactcaggg acaagaggta gagaaattac agaggttgct aagaatacct gctgactctt  56760
attttctact tctgctttag aagttgttta gaaaatctaa tcaaggccgt cttacatcca  56820
gtagaaacag agagtttcta ctggatgtgc tttggagcag gtttttaaga gagagctttc  56880
cccatggaag agtgaccata ttggggaaag aagagctcag gagacatgag ttatgcttct  56940
cttgcctggg gaggtgtttg cttaaaagac atgctgccca agtatttaag ccttcaggtt  57000
agggtctttt ttccagttgt tggcagagtg aatgagcatg aactgtattt gatgaactac  57060
agttaacaca aatactcatt ttgaagcaga taaaattatt ttgaaagtga aggaaaattg  57120
tttcataaga gaaacttgta cttcctacga aaagactgtg tttttttgct ccatgttttt  57180
agtaaagttt agtcaaattt agtttagttc acctagaacg aacactgaac aatttggaaa  57240
tacattttat tcctttttt aaactagagg ttagcaaacc ctggcagaaa aaccaaatgt  57300
agcctgacac ctgtttttgt gaataaagat ttattggaac atagtcgtgc tcgtttgttt  57360
acaaattgtg tctggctaca tttgcattgc aacagcattg ttaagtagtt gggacagaga  57420
ccatatggcc tgcaaagcct aaaatattta ctatcccact ctttacagga aaagtttgca  57480
gatccctgtt ctagattaat gaaagtactc agtatcagtg tttttgtggt tatatatggc  57540
ataaatggct attaattctc tgaattatta ttaattttaa atatttcagt atcttttgta  57600
cttgattata tatctcatta aaataattga attaattctg aaaattggta tggtctgttt  57660
gcctaatgga caatacactg gacattacaa aactaatttc tgcttttcaa atcccttgga  57720
cagtaaaata atttatttct tgatttgcat tttaccacat atgagcacct tgggaagaca  57780
ttgtgtagta gaaagcatac tgtcagcacc cacttccaaa atgttttcta gatttattgg  57840
aacaatttaa aatgtcagtg aaaagaagta cttttcttcc tttgtgttct tcatttttct  57900
atgatggctg gatgcattca ctccttgggg cattcatgtt ccttccttaa agggcagagt  57960
taaggttact ctgtgggtca tttgcctctt cagggttgtt tgatccttct caagagaaga  58020
ttattttaat gtattgcagg agatgctgcc tgataactga ggctgatctg ttgagcactg  58080
taggaaccag actggggaca agaattgact catttattca tttatactta tgtttattca  58140
acaaacgttg aaggcatgct ttactaggtt ctgtgctctc aaggatttca tagtctctta  58200
caggagatgg acacaaagca aatgattatc atatactgtg ttaggcaaga tgattgagtt  58260
atagtcagga tattatagga gagaaggggc atctaatcca ccatggggag agggcaatca  58320
agaaaagcta tttgaaagag gctaaatcca gatcaataaa tccaggacat tctgtcagaa  58380
attcagatgg agatgtctgg caggtggatt tgagtctcaa tctgggatag agataaggat  58440
ttaggtgtct ttattctagg aatggcagtt aaaaccctga gagctgatga gagcctgaag  58500
agtgggaaga gggctcagca tgggaaaggc caacatttaa ggatcagaaa gagatgcata  58560
aaggaaacaa ggaaggggtc agagagataa ttaggaatac caagagaaca aaagacaatg  58620
gtgtttagag actgagtgag gggaaggaga cggtcaatgg aaagatggaa aatccaggat  58680
tgatcaggga ctggcaatgt aggaggcaga ggggagatgg aattcatttc aaatattcta  58740
atgtaaacta cttatgtgtt aaacaaatga tgacctaaaa cttagtttca ggctgttgtt  58800
```

-continued

```
taaagtaggc tcaaataagt aagttgattt cctatatttg taaaagctaa taatttttat  58860
ttaatcaaac acacatttat tgagcactta ttttgtacta ggtgctataa caggttggca  58920
ccctaaggga taaactatgc gggatataaa aatgatcaaa aagtgaagta gtaatattta  58980
agctaagccc tggaaaatgg ggagggatgg aagtacatat aagtcaagaa taggcaagag  59040
ttagagcaaa aacacagtgc atgaaacccc aggacactgt cagtcttgaa ttattgttct  59100
tgactatgtc tgtctccacc actagactct ctaatgctga ggactgtgat ttatagagcc  59160
tcacatggtg ttttgcatgt tgtatttact caattaatgt ttgctatatg aatgaaactt  59220
gagaaacaga aacatcataa ttgttactta ttccatagtc ttgtctgtgc tggcctcagt  59280
aataaagcaa aaactaactt aaagactagc attcttatgt tcattagtaa aacaggtaat  59340
agataaatta ccttcttgat ttgacttttg agaatgacgt gttagaactt ataaatgaat  59400
caaatacgtg taatttataa tgttactata tgatatgaaa acaatttgag atagaagtca  59460
taaatatgaa gtttcttaag actttgatca aaacaacaaa atttctttga gattttcttt  59520
ttttaaaact tttatttttc aacaacagct aaccaaagat gggatcttct ttacatgaca  59580
atgttgaagc caattgatac acaatttatt tgttagcgtg ttagtggttc tatttgtttt  59640
atattttgaa gtgaactatg gccttctttt aggactgaaa aataacttcg tggtgtacag  59700
atattttaga ttaaccaagg gtacttgtta acaaaagcta ttatttttata gctgcatctc  59760
cgtgtttgat ttgataaatt tgggaattaa atttacaatg caaatttcat tagtggaatt  59820
acatagccaa tttggagagg ttctatttaa tgtgctacct tgatttagaa tgagcgattt  59880
agaaatatga agagttgact gggcatggtg tctcatgcct gtaatcctag gactttggga  59940
ggctgaggtg tgattgcttg agctcaggag tttgagacca gcctgggcaa catggcaaaa  60000
tcctgttcta cttaaaaaaa aaaaaaatta gctgggcata gtgacttgcc cctgtggtcc  60060
cagctagttg gtgggctgag gcaggagaat cgcttgagtc caggaggttg aggcttcagt  60120
gagctgtgtt tgtgccacta tactccagcc tgggtgacaa agtgagaccc tgtctgaaaa  60180
aacaaaaaca aaaacaaaag caacaaaaaa aggagaaata tgaagagtta gataaatgat  60240
acgataatag cccacgtttt cttgttgatt gtggaaaagg aaataattaa cagtatctat  60300
tataaccaca taggatgtat tgatttaaga attacagtag aaaataattc aaggaattgg  60360
aaaagtgagg catgttgttc tatgaagatt ttgcatcctt aattatttat aagtatttga  60420
gttatgtgta acttcatttt ctccattaat ttttgataat gatatccaaa acaaatctgc  60480
agttatttgt tagtttgacc tgtgttatct ttgcttcata aattcctcaa ttatctagtt  60540
taatctagtt cttatttcac aaatgatgga agtcagatta agcagtttgt ttaaatgacc  60600
cgcaatgaat tatagagata ggtcaccatt ttatgctaac gggttggcaa gaaaaattca  60660
tgaaatttta caggcttcat gttgcagttg tctacaaata cacttccata aatgaaaata  60720
aacaagtttg ttcattgcat cattataaat gtaatttaaa aattaatttt ctaaattgtt  60780
ttatgcaagt aagtaagcaa gcaaaataaa taagaactca tatactttcc tgtctttttt  60840
ttctcccctg cccaatagga ccagacatac tatcaatcat ttcaggtttc agaatatggt  60900
aagagttcct caatctattt tggaagaaaa aaacatttgt tactttcagc agagattaga  60960
gaaattttta agagatgtat tatttgaagt aaaaatctca atggagttaa aattctggtg  61020
tttttaaag gcctaaccat atttttttc ctttgtaaaa attctaaaat ctcattatac  61080
agaaaaaagt agaaaaaaat cacctatagt tgcattgtgc tagtcttttt cttatccaca  61140
acatgatttt tctattttc tactttgttg tgataaaaaa atatttaaag tgttgcactt  61200
aaaaatactt aacaaattct cttccatatt tttcatttga ttgacattgg taaagatggt  61260
ctgtttctca ggtaaatcct cttcttgcag gtgccatact tacaatatct gttagaaacc  61320
catagataaa aacagtggga cccatctatt ttgttggtga atggagagga atgagagatg  61380
agactgaaag cataggatct tagtattagt tataatttga atagttattt tgaggttgca  61440
catgcagttt ttcatttgat ttgagcttct tttttgagat tgggttttat ttaggcagta  61500
gaaattataa tatacaggta gtaatacctc aggctctgtg ggccatatgt ctctgttgtt  61560
actactcaat tttgccgtgg tagcatgaga gcagccaaag ataatatgta catgaatgtt  61620
gctgtggttc aataaacttt attttatggg catgaaaatt tgaatttcat ataattttca  61680
tatgtcatga aatattcttc ttcttttgat ttttttcaac cagttaaaaa ttgtaaaaaa  61740
tgttcttggt tcatgctggt catagtttgc tgaactctga tctgtaactg tgctctccag  61800
tagcggggcc acttgccatg tgtggctgtt gagcacttca aatgtggcta gtccagatgg  61860
agacagcaga tgtcaaagac ttagtacaag aaaaatgaaa gaaagaaaaa tagttcatta  61920
ataaccattt ttaaattttt attatttgtt gaaaagatac tattttagat atatagggtt  61980
aagtaaaata taaaaattaa tttcacctgc ttatttttac tttaaaaatt tgactactag  62040
aaatgaaaaa ttacacatat ggctcccatt ttatgtcttt tagacagccc tgatctagaa  62100
gaataagtca taggggacca acatttttat aggctatctt tatatcccat tgtgatggta  62160
tgctgggtgg ttgtatgttg ttgaatgagg tatagtggag gtggggaatt gattgcaaac  62220
ctatgatgtt tgaggaagag gcatttggat tttcttggtg gtgggggttg cgggggcggg  62280
gtcatagttg actcacgtga ctttttggtc tccctgtcct agactgatct agagtctagg  62340
agtgtcttgg tacattcagg gccattagcc ttgattggag ctgaaggtct gccctatatt  62400
gttgactatt tggctttttt gatacttctc ttatgttaat tgaatggtga ggtgccttgt  62460
tatgagagtg gcctgtttct ttggtcagag aactatagaa aaaaagtttt atcgactgta  62520
aagaaacaca catttttttac tctggtggag tgctttatat caattatagt attagtactt  62580
ataaaatagt ttataccttta attattatta ttatttttcg agacggagtc tcactgtgtc  62640
actcaggctg gagtgcagtg gcatgatctc gggtcactgc aaccactgcc tcctgggttc  62700
aagcgattct cctgcctcag cctcctgagt agctgggatt acaggcatgc accaccatgc  62760
ccaacaattt ttgtattttt agtagagata ggattcacca tgctggccag gctggtcttg  62820
aactcctgac ctcaggtgat ccacctgcct ctgcctcccg agttctagaa ttacaggcgt  62880
gagccactac tcccagcctc ataccttaat tatataaagc tgaccaaatt agggatttct  62940
agttttgggt gaaacaaagg gcttttcatc tgtcttaata tgtatttgga ttctaataaa  63000
tttaagttca aatagtacaa attattaact ccttcacaac aattttattt ttcattttat  63060
tcagtggaag atgatagtga agtagattct ttaaaagatt taccccttgct tcttcgtctc  63120
aaaaagaaaa aaagatttac ccttgctttt cttttccagt attaccaaaa tttgaagtga  63180
ctttgcagac accattatat tgttctatga attctaagca tttaaatggt accatcacgg  63240
caaagtaagt gtcattttttc ttttgatatg actcaaaacc attataaaac tgtgtgacca  63300
aaagctgatt gtatacttca gaatattagg gcaatttttg cttattaaaa taccttagtg  63360
gacagtaaat gactatttat aataaataat taagcatggg acagagctcc acatttcact  63420
gcatctatca ctctgcttgc aagccgaccc agtcttaaaa tatttcccat atttcttaga  63480
cttattaagg gatttatatt atagatagca ctgttttttt ttcagatgac atggacttga  63540
```

-continued

```
agccaccacg cctggctaat tttttttcct ttatagagat ggggtcttgc cattttctcc  63600
aggctggtct tgaactcctg gcctcacatg atactcctgc cttggtctcc taaagtgctg  63660
agactacagg catgttccac cactcctggg ctgatttgct ttttaaaaat tagtcaagct  63720
tttattttct gagtgattaa cttatcccaa atgcttcccg gttctatttg ggacaataat  63780
tgtatctttg tttcacaatt attataacca gcttggtgtt tggaaaacta aatctgcttc  63840
acattaaagt caaaattaaa aatttttatg tctgagagta ctttaaatta tatttggatt  63900
ttaaagatcc ttttactacc atgtgatata actctgttaa aatacaatat cctggcattc  63960
tagttttgct tttatttaat ctttagcacg atacaagtag agtcaggttt cgaagactct  64020
tgaatgagtg aatttgatgc tcaggttgct aaccagggtt tccactgact ttactgtttt  64080
tgtttggaag tgtggtgcat ttgaacttgg attttttttt ttttcttctt agtttggaat  64140
atgctatatt ttaagatttg cttttgagtt gagttgatcc agatgagggg ctgtttctgt  64200
gttcagttaa tggattcagg aagccgccgt ttactgctgt gatttataga ctgcaaagca  64260
aaattgactt ccatgtctgg ctcagcattt cacaatagag atagaagcaa cccaggaaat  64320
gtacttaaaa aaggcttttct gggccgggcg cagtggctca cgcctgtaat cccagcactt  64380
tgggaggccg aggcgggcgg gtcacaaggt caggagatcg agaccatctt ggctaacacg  64440
gtgaaacccc gtctctactg aaaatacaaa aaattagccg ggcgcggtgg cgggcgcctg  64500
tagtcccagc tactcgggag gctgaggcag gagaatggcg tgaacctggg aggcggagct  64560
tgcagtgagc cgagattgtg ccactgcagt ccggcctggg ctaaagagcg ggaccccgtc  64620
tcaaaaaaaa aaaaaaaaaa aaaaaaaaaa aagcctttct ggcagtaaaa tgtattgcct  64680
cttcttcaca tgaagagact ttcctataat gagagaggat aaaattaata catagaaaga  64740
aaagtagcag agaatatttg acttacgaag ctaagtttgg gccaggtgag gtggctcgtg  64800
cctataatcc cagcactttg gggggccaaa ctgggtggat cacttgaggt caggagtttg  64860
agaccagcct ggccaatatg gtgaaactcc atttctactg aaaatacaaa aattagctgg  64920
gtgtagtggc agacgcctat aatcccagct attcgggagg ctgaagcaga gaattgattg  64980
aacctgggag gcagaggttg cagtgaccct agatcgcacc actgcactcc agcctgggtg  65040
acagagcgag actctgtctc aaaaaataaa ataaaataaa attcgctgga cgtggtggtg  65100
tgcgcttgtc atcccagcta ctcaggaggc tgaggcagga gaatctcttg aacccctgag  65160
gtggaggttg cagtgagccg agatcatgcc actgcatcca gcctgggtga cagagtgaga  65220
ctgtgtctaa acacacacac acacacacac acacacacac acacacacac acacacacac  65280
acacacaaac ccagaaacta agtttggtac tacagatttt aaaaattatt cttattttaa  65340
attttttggc aaaaaatcaa tttttgacag ccatgagcac atttggtgct tcagaatcta  65400
tggtgtaata aaccttcctc gctaatattg gaacatgtag caatagacca tggtgattgc  65460
actatcagct gacatttaaa aatcttctaa agctgcgaag tttcgtgggc attcagttaa  65520
tgggccagtc cagatttcta ggagtgaaag atttatgtaa tctttaaaaa atctttggac  65580
aggaaactgt cacttccaat tatgatcagg tattttctgg agtctttcag atggtcagag  65640
gttgggcaga gtgtgtgtta agaactgttt taagctacta tagttaaaag tcttcccatt  65700
ttggaaactt aatttcaagg atcaccattt atttttttatt tatttattta tttttttgagt  65760
tggagtctca ctctgttgcc caggctggag tgcagtggca cgatcttggc tcactgcagc  65820
ctccacctcc tgggttcaaa cagttctctg cctcagcctc caagtagctg ggattacagg  65880
cacccaccac cacgcctggc taattttttt gcatttttag tagagatggg gtttcaccat  65940
cttggccagg ctggtcttga actcctgacc tcgtgatcca ccagcctcgg cctcccaaag  66000
tgctgggatt acaggcatga gccaccgtgc ccatccagga tcaccgttta ttaaagacat  66060
ttttgttggg tttagtttaa aaaattatag taggagtatg tttttaatgt aactttttttc  66120
tttttaaaat tttctctttt tagtgttttg ccatcccata atgtattttt ttttaattta  66180
tttattttga gacagagtct tgctgtcttg ctgtgttgtc caggctggag tgcagtgatg  66240
cgatctcggc tcactgcaac ctccacttcc tgggttcaag cagttctcct gcctcagcct  66300
ccaaagtagc tgggagtaca ggtgcctgcc accatgccca gctgattttt gtatttttag  66360
tagagacagg gtttcactat gttggccagg ctggtcttgc actcctgacc tcgtgatcca  66420
cccgcctcgg cctcccaaag tgctgggatt acaggcgtga gccaccgctc ccagcccaat  66480
gtaatttttt aaaatgttag attgctaatt gctaatgtat gctattgaaa gtagtatttt  66540
tattgtgttc tgacaatatc aagttgatac ataaaaagac tatgtttata attattcagg  66600
tatacatatg ggaagccagt gaaaggagac gtaacgctta cattttttacc tttatccttt  66660
tggggaaaga agaaaaatat tacaaaaaca tttaaggtaa cttttgcaga cactttataa  66720
cttgtgatgg gtaaaatatg tgtattttttc tagaaataag atttagtact gaattaacaa  66780
aaagttaagt gtaagaaaat caagagcttt ccagcattga acaaatgaga atttatgcaa  66840
ttatagcgat taaaatggta ccagagctat catattgttg tgacttagtt tgagttttat  66900
ttctaaaatt tgaattgcta aaatggtaaa taatactgaa cttttaaaca aaacagataa  66960
atggatctgc aaacttctct tttaatgatg aagagatgaa aaatgtaatg gattcttcaa  67020
atggactttc tgaatacctg gatctatctt cccctggacc agtagaaatt ttaaccacag  67080
tgacagaatc agttacaggt ttgtagactt taaagtggag gtaaaactat tcatgtgaca  67140
ctgctttatc atctttctta ttataactgg cactttcatt tgggagcatc attgactttc  67200
taaagatgct atttaatgtt gaaattgtta tgactgttag tctaagttgc aggatgattt  67260
tataaggggg accttatttt ctatgaaagt cactacttca accacatgtg atagctcttc  67320
ttaatttttt tttccatttc tactctttcc ccctgaaaac tacatggaaa ggcttacatt  67380
ttcagctggt aaccttcttc tttttaaaat cactgaaatc tcagctgttc ctagacagtt  67440
ttcactttta ataagaaaat aaagttgagt ttcttggacc tttctgttac tatttcaaca  67500
actttagcca atccctgaaa gagcaaaaga ctattctttc attggcctta atttgctgct  67560
gttgtacatg tcactgcggt agaatggcag caatggtgct tagaggggat ccatagagaa  67620
cataatagaa ctgtgtggtg cttgtagtgt caaagtcaat atgggaatga ggcttatgtg  67680
ccctgatatt tttaaccctt tttgcaatag gttagatgga gagatttggt ggatagaagc  67740
tttgggtgaa acattacttt tgctttctaa attgtgcaat ttccaaaaaa ggtatttcaa  67800
gaaatgtaag cactaatgtg ttcttcaagc aacatgatta catcattgag tttttttgatt  67860
atactactgt cttgaagcca tctctcaact tcacagccac tgtaagttgg tatatttatt  67920
tccagtccat agcagtaagt tcagcttaat gaaatagaat gggaaataat attttcaatg  67980
cttttctaaa aatttaagcc aaaaagtata taactttgtc tctttagaca tgtggggcat  68040
gtagatttgt ttccaaatga cctttgtcta ttttttctaa aaaagtagtt ttcaacaaca  68100
gtaaaaatat tttttgaaaa tgtatttttt tttacaagca atttaagtta gatgtggatt  68160
gctacactga agcttttatt aattaattga aataattaca tggtagtcaa aaatttcaat  68220
ttcaatttgg tttttataat gattaattgt agttctaaca aagatgttac attaaaaaat  68280
```

-continued

```
tatcaacaaa tctcattttt tggagataat gttgaattaa cacattaatt gtgtgaatgt  68340
tgacaatgag caaggcatgg tgttgggcag ggctatagag ccaagaaggg ctcagtccct  68400
accctcaggt tcacagtttt tgtgatggtg acaggaaaat atatacttaa ctataactca  68460
tggcagatta agattagtgt tacaaattaa tttctgtagg gatttaaagc aggggttgcc  68520
aaactttttc tgcaaagggc tagagagtaa atattttcag ctttgtggcc atgtggtctt  68580
tgtcacagct actcagccct gccattgtag tgtgaaagca gccatagcca atttataaat  68640
aagtgagagt ggaatgtgtt ccagtaaaac tttgtttaca aacatactgg attggcctat  68700
cagcttgcag tagttggctg atctctgatt taaagaaagg aggagtcagg cctggcgtgg  68760
tggctcatgc ctgtaatccc agcactttgg gaggccgagg caggcggatc acctgaggtt  68820
aggagttcga gaccagcctg accaacatgg agaaacccca tctccactaa aaacacaaaa  68880
aattaggcgg gcgtggtggc acatgcctgt aattccaact actcgggagg ctgaggcaga  68940
agaatcgctt gaacccggga ggcggaggtt gtggtgagtg gagattgcgc cattgcactc  69000
cagcctgggc aacaaaagtg gaactccatt tcaaaaaaaa aaaaaaaaac aactaaaacg  69060
acaaagaaag aatggagggg tcacttgttg aatgggtcgg tagacgtttc aggtagtttc  69120
tgatttcaat gatcttaatt taggcagttt gaaaaggtca gtttaaaaaa ttgaggctgc  69180
aaatggtaat ttctgaatga gtagagtgaa accatgggcg ttcagagggg gagagttggc  69240
tgtgggatag gcatggggt tactatggga tgctttatgg aagaggatgg tctaaactgt  69300
tttttaaaag attagttgtg ttttaaatgc ttgggcatgg gagtgggagg tggggagcaa  69360
gataagaagt gagacaagaa ggagaggtct ggctggcaat ttcggggtgc actcaggtag  69420
tgtttgaggg agactgctca ggctgtgtgc aggaggatgg ctgtagccca ggagtgaggg  69480
gatgggcagc cttgtggtgg tagctgtggg agtggagagg atggaagaga gaagcatagg  69540
actttggtgt tcattggatt tggggggtgg ggagagggag ggaaaattca gaaatgtaaa  69600
gtcttgcaaa atcctgatgt tagcgaaaat aggaaaatga catggttgct cattttagat  69660
atgtgaattc aaggtgtcca ggatatccaa gtagaaattt cctgcaggta actggaggtg  69720
ttgggcatga actccagaga agggcaagga tgggaatttt ggctttaggg tacaatcaca  69780
gagatgacaa gctaagcaat aggattgctg agaccttgga ggaagggaga agaacagatg  69840
tccaaaattc ccacatttag ggagaggaaa gaggaactga aaaggacact gagaggatgc  69900
agaaagagag gtaggaagtg aagggggtta ttttggagcc gcggaagtta agggaatcca  69960
taatattaac aagggagtaa tcagtgatgt tggatgcctc ctagagagag gccactgaat  70020
ctggatatta tagtgctacc aataattttt gagagttcaa tttcatgaga atactacaga  70080
cggaaactgt atttaatcgt acttaaatcc tttgtgtttt taagatgttt tgttttgacc  70140
attaggtgaa ggtaactcgt gctgatggca accaactgac tcttgaagaa agaagaaata  70200
atgtagtcat aacagtgaca cagagaaact atactgagta ctggagcgga tctaacagtg  70260
gaaatcagaa aatggaagct gttcagaaaa taaattatac tgtcccccaa agtggaactt  70320
ttaagattga attcccaatc ctggaggatt ccagtgagct acagttgaag gtgccgtctg  70380
tttcccatca ttgtgtcact gcaacaacac cattacagtt gtaatcttgt ggtaggcact  70440
caacctgtca gaactgaaag tacataggaa gtggacacat gtttctgttt cacaaaatgg  70500
aggagagtgg taaaagtaat ttaatgacag tggctgaagg ttagactaaa tttttccttg  70560
taagttcatt ttgaagagca cagtaaaata tagcaatgtg aagatatgat ggagaatttc  70620
ctcaaatccc cagtctagtg tttgaggtca gtcatttgaa attttatttt ggcaggaatt  70680
gaaatgaaag ataaatatat atacatatat atatatacac acatatatat gtatatgtat  70740
atgtgtgtgt gtatatatat atatatatat tcctttcctg tgttttaaag ctatcagttt  70800
ctttacagta taagctataa aatgatgaaa atccaatgtc tggtgaatgt atttttcttg  70860
cattaaaaaa aagtgaagat gaatttggtc tttaataatt gttcagcagg taacatcttt  70920
tctcaaggtg ttactaaaga tgaacattta cagctccttt ttcttttatt ataggcctat  70980
ttccttggta gtaaaagtag catggcagtt catagtctgt ttaagtctcc tagtaagaca  71040
tacatccaac taaaaacaag agatgaaaat ataaaggtaa tgcttacaat tcacttgaga  71100
attacaatat aattggacta tcttgctttt gatatgtaca tattaattaa ggttttttc  71160
taggtgggat cgccttttga gttggtggtt agtggcaaca aacgattgaa ggagttaagc  71220
tatatggtaa tctcttatag aatctaaatt tatgatctat tatagaatca tctttttatt  71280
cacttttaag ttctggggta catgtgcagg tttgttatat agctaaactc atgtcatggg  71340
ggtttgttgt acagattatt tcatcaccca ggtattaatc ctagtaccca ttagttattt  71400
ttcctgatcc tctccctcct cctaccctcc accctcccat aggacccagt gtcggttgtt  71460
cccctctatg tgtccatgtg ttctcatcat ttagtgtgca cttataagtg agaatatgtg  71520
gtatttggtt ttctgttcct gcattagttt gctaaggata gtggcctcca gctccatcca  71580
tcttcctgca aaggacatga ttttattctt ttttatagct gcatagtatt ccgtagtata  71640
tgtgcaccac gttttcttta tccagtccac ctttgatggg catttaggtt gagaatcatc  71700
ttaaatggtg tctaccttat atctacacta aacttattaa tttttataac tcagcctcat  71760
acctttttag cctgtcgttt taacattgca atcaaataaa aaaccttttt tatttcttca  71820
cctatgtttg catttccaat ttaaaataga taactaaacc ttgttttatg tttaaaattt  71880
aaatttctat ttgataagca atatatattc attatagaaa attatacaat gtaagaaaaa  71940
tgaaaaagaa aataaaaagt gctatccatg accatgtaat tttgctaatt cagctttccc  72000
aatggtgccc tgtattcctt gcaatcaaaa atagattctt gactatgaag ctactgttgc  72060
tccaatcagt attactttaa tcttaccatt ttcttttttct cagtgtatgc tctctgtgtt  72120
tgtcagagag gttttcctgc attccaaaag actttgaagc tggtttaatt caagaatttg  72180
tgtgtatgca tacaattatg attaatgtag cttcagatga gatcctacta ggtttggcaa  72240
taaattaaac ccatctactg ttcttttcag gtagtatcca ggggacagtt ggtggctgta  72300
ggaaaacaaa attcaacaat gttctcttta acaccagaaa attcttggac tccaaaagcc  72360
tgtgtaattg tgtattatat tgaagatgat ggggaaatta taagtgatgt tctaaaaatt  72420
cctgttcagc ttgtttttaa aaataaggta agatttaagg taatgatgtt taaaagaaaa  72480
ctttatatta gtgaagtctg agaaatgtaa tatttcttta gaaaagtatc attaagccaa  72540
actggttaga aatttatatt attctatttc tagaactatg gttaaacttt tcaatattta  72600
gcattacata tatattttca cttgtggagt tattggggat tgatagtcta tttgtaaact  72660
atggttctgg tctttaagac tttaactcag atcatgaagc tgtttcagaa tttttcaaat  72720
ggttgaatta atattgctca ggagtgaaat tccagtggta acatagaatt cgtgtggtgt  72780
tgatattgca gtgatataaa gggtgtggga aggagtgagg ccatctagga taatacgtag  72840
aagcagagct gggctttcat taatctattt aattagctgg aaactagccc agggcaactt  72900
ttcaatgagc ttgattaccc tgcatgtgag gatctgtgtg gagtctggtc tccaagtgca  72960
ccagtgcctt ttatagccta atgtgaccag cttgagtagg aaatcccttt ggaccccagc  73020
```

-continued

```
tctgaaaaga aacctgattg catcatctca tgtatataag aatgagccat tgctgtcact  73080
aacaactgct gccctctcca tcctcttatg taaaaaatta ttcctttaaa tagtgatttg  73140
cagagtatgg ttcttctatt tctttttcct ttatttgtta aaatatttga gaagtaacag  73200
tagtgatctg tactttcttt tttaaaattt gtatttattt attttttgag actaggttat  73260
aagactggct aatttttgta ttttcggtag agagagggtt ttgccatgtt gctcaggttg  73320
gtctctaact cctgggctca ggagatccac ctgcctcagc ctctcaaggt gccgggatta  73380
cagacatgag ccactgcgcc aggcctgtac tttagttttg ttgagaatta ttactctcac  73440
tttgattgtt aaaatataat acaaacttct atttttttag cttatgaaaa gagttcttaa  73500
aaagataaca ctgtgttttg ttagtggtag agcacaattt ttgacttcta gtgatcctag  73560
taattgcctg acaaaggtga attttaaagt agaagttatg gaggcttaaa catctcagaa  73620
agcaagacca ggttctaaag ctggttacag tgtaaaagat cacggacttt gaggaagcag  73680
agtatatgaa tagcatactt tcaagtaatt tcttagctat aagagaaagg aattagtttc  73740
agttccattt gcaactatat atctttctct tatttttatg tgataatcat cacatttata  73800
aagaaacaac ataattagaa atggaatatg tctaagcaag agaaagttag tgaatgttta  73860
ttaatgttca gtaatgacta tggaataaat aaatgagctg taggagcggc aagagattta  73920
ggtttagaaa tcatccacac agaagtgcaa gttgaagcca tggggctctg aggtacagag  73980
tatagagtga gaagtacaag gtctaagact gagtcttgaa catgctgctc cctctccccc  74040
atgctttagt gtgtaggtgg agaaagtaac ctacatacag tggtttgaga ggcatgtcag  74100
aaaaaaattg cactggacaa gttaaacagg taaggaaggc tttattcaag actattgcaa  74160
tggaagagag agatgataaa ctcaactctg ctgaaacaaa aggcagaaga gtttttaagc  74220
actggggtga actcatatga aagtgctgga ggacattgtt gggaggttgg tcaatgtgat  74280
taggtagtct gtgtttgcta attagtactt actgaagtta ggtttccacc ctcccacaga  74340
gaatgagatc aattgggact ctgtctttct tgatgattat acttcaaagg gatggctctg  74400
aggaccttga gaaagacatg cctgggttgt aaaactggcc agaggctggg aaaagattta  74460
catctcagag agttggagaa agaatttata attgcatgtt ttctaaaata aatgctctaa  74520
gaaaagggag ctcaggggct tatagttagg aagaagcctg tctttgtaaa gtcgagtcaa  74580
cttgagggga atgttaaggc cctctttgtc aggcattata atcattggca cagcagaatg  74640
ttgagataga gctagatgaa atgaaaattc ccagcagggg ccaggcactg tggctcacgc  74700
ctgtaatccc agcactttgg gaggccgagg caggcggatc acctgtggtc aggagttgga  74760
gaccagcctg gccaacatgg tgaaaccctg tctctactaa aaaagttaca aaaattagcc  74820
gggcatggtg gtgggcgcct gtaatcccag ctacttggga ggctgaggca ggagaatcac  74880
ttgaacccag gaggcaaagg ttgcagtgag ccgagattgt gccattgtac tctagcctgg  74940
gcaacaagag ggaaactcca tctcaaaaac aaaaaaagaa aatgcccagt aggcaggggc  75000
ctcatgacaa ggccatttgg ttcagcggtg atgcgatgac tgatgctctt tataaagtat  75060
tagtaggtcc aggaccatgc tttcctgagg gtaatggtga ggaagtttag aaggccatgg  75120
agacagagca tgagggcctg gactagtgtt tgctctaacc acccactccc ttggaaaggc  75180
caccccctcac cctcagtcca ggtggttcta tgagtccccg aggagctctc cttgccttca  75240
cttctgagct cacgtcacca acatgtaggc atctgcagtt tctttcctct ttcgtgtttc  75300
tcctttgtat actggccttc cccaggtatg ctagacactg ctgtcttcta ctcagcactg  75360
gctgggatct gaggggtggg agatggagaa agggaagaaa aaagatacag aattaaagaa  75420
taattcagat ttataccact gtgagaagtt ctatgacttg caaacactct gggcgtagtt  75480
tttttattcc tttccctaga gaagggttat gcatggtttt agaattatcc ctgagccaag  75540
gcaaatgtag aatctttgct atattttggg ccagtggtct gctattggca agaatatgct  75600
ttaaaaaagt gaaataagtt aatcctcctt tctctctttt ttagataaag ctatattgga  75660
gtaaagtgaa agctgaacca tctgagaaag tctctcttag gatctctgtg acacagcctg  75720
actccatagt tgggattgta gctgttgaca aaagtgtgaa tctgatgaat gcctctaatg  75780
atattacaat ggaaaatgtg agtttagcta ttttttcatt atgaaaatat gtattacaag  75840
agaaagagga aactttattg tactacttta aatatttaaa gaaaatttca ttagttcctt  75900
tgcatgtgta agtcaataat tagtaaagct tccaaataaa aagtaatctg tatcgtaatg  75960
gttatgttgg aaagaagctt atgtggttaa gtgtccttgc tctctttcat cagaattatc  76020
acctaaagtt agatgggagg aataaattct ggaggtctgt ggtacaacat ggtgactgta  76080
gttaatgata atgtaccata tacttgaaaa ttgctaaaag agtagatttg aaatgttctc  76140
accacaaaaa atgatcagta tgtagtatgc aaggtgatag atatgttaat tagcttaatc  76200
attccacagt atatacaaat atcaatatat cacattgtac tccataaata tatacaataa  76260
aaaatgccac ctatagtttt ccttcatttt catactacat tttaagacac tcaagaaagt  76320
actaggaaat tgacttgcat tattctgggt tacgttggat aagagagctt tagataattt  76380
ttgaagtgtg ttctattttg gttatacgta atggttataa ataattacag cacccattgt  76440
gccgggcatg gtggctcatg cctgtaatct cagcactttg ggaggccgag gtgggtggat  76500
cacgaggtca ggagatcgag accatcttgg ctaacatggt gaaaccccat ctctactaaa  76560
aatacaaaaa attagccggg cgcggtggcg ggcgcctgta gtcccagcta ctcgggaggc  76620
tgaggcagga gaatggcatg aatcccagga ggcggagctt gcagcgagca gaaatcgtgc  76680
cactgcactc cagcctgggt gacagagcaa gactctgtct caaaaaaaaa aaaaaaaaaa  76740
aaaaaaatta cagttcccat tgaatcagga atttgcagta tattgagggg gtgaaatcat  76800
gttactctgc agaaaactta caaaccaaga agtatatgaa catctagcat tgcataaatg  76860
aatcccatat tcattagtca tttgattttt atttatatgt ccttgatata ttcttgtgta  76920
ccattgtcag ttgtaaacta gattgtataa tttttgtcta ttaatggatt cagtagagtg  76980
attaacaata catcagaaag aaaactatat atagttgggt tgatttggtc attatattgt  77040
aaaatttagt ttacttcaga aaaattgtac attttcttca gtctacacaa ctattttttt  77100
caatcttttc tttttttga aacttttttt tttttttaca accagttggt cattttctc  77160
tctttgactt ttcctgagtt cacattagtt ttatgtctgt agatcttgca tttgatttaa  77220
ctgaatataa tagtatctgt tattttatag ctttctaaat atcttggtaa atatattatt  77280
tcattttttc ttccctacat atgtgtatgt ttgtgtgtgt gtacgtgtgt gtatacatac  77340
acatacacac acaccccatc tgatgtgctg cgcactctgt ctctatttac atttatatat  77400
gtgtgttata tatatattta caagtatatt tatatataca tataatatat gcatatttac  77460
attaaatttt ttcagatatt aagattgctt tctcagcttt cttttggttc atattttcct  77520
ggtgtatttt tacatttctt attttcaacc ttttgtaaat ttttaagtgt atcttttaaa  77580
tagcatatta ttatattttg cttttgtttt tcaatctaat ctaatagtca acatctttta  77640
ataagctttt atttaatcca cttataagta tggtaattct ttttctaatg gggacttttt  77700
ctgcttttct atattttaaa atttagattc tttttctgtg ggctagatta aatttgtttt  77760
```

```
ggtgatttag aagttatgcg ttctattttt gttactctgt tagttacaaa ctgtacccat  77820
attaatttat ccttgttggt ttctaaaggt tatcagtatt tgaatcttct agtatgctcc  77880
tattcctttt ggtctctacc tctgtctcct ccttctcctc ctaccctggc cagatcattt  77940
tgctcgtgta cagattttag ttccatgtta ccatagattg cctttcaatc tatgctgttc  78000
tttcattttt taattgtgga aatctgtgtt gattatttct tcctccccat tttatttttt  78060
ctctccttct gggacttttg tttttcagaa attggcactt ttacttcctc cttcacatct  78120
cttagttttt tgttttatgt tttctatctc tttgtctttt ctgtgtttct ctgggagagt  78180
tcttcagtca actcagctta gtgatcattc attagctgta ttttaatcta ctttaatctc  78240
tcatattgtg tcttttatgt cagctattat gtttttaata tctattattt ttcctttgtt  78300
tcttgttttt gttttatatt ctgatatttc ccattatctc cttgtgtata tttgctatgc  78360
gtattttaaa ttattgaatt gaacttttca gtaattttgt gtcacatgct atatgttgtt  78420
tagttggatg tcttacttct acagtattta tactctttgg aagtctagct gatttggcag  78480
attctctgat aatatctatt ggtgaaggct gagcataagg ttccaatctg tgtaagtcct  78540
atgacccctt cctgagggga gaggactagc ctcatggact agagaattac tcttgatcct  78600
ttctgctgct tgcctctatt cagtgtttca ctcttaaacc cttggggaaa agagcaccag  78660
taagagaagg tctcctgagg ttatgattca ccagccctga gggtttggag gaggaggaga  78720
ggaagagtga atgcttgagg gacatgggtc tgtctgcatg ttttcttcac tttcccacac  78780
tagaaaggca gaggtgctga cctggtatta tcttttggat acttgcacag gccgtctgag  78840
ctgctactgc tgttgatttt ggcagtgaag ttgccaggac tgtgtgtcct gaggctaccc  78900
cctggaggga aataagagca aagtttaaaa acctctcctc cagcctgttt tctgactatg  78960
tctgctgctg tgtctagctg ccttctgcct tagactgaag cgatgcactt tctcccaaga  79020
ccaattcaag atgtccacca ctcttcctgg ggtttctcca ctgtgcacgt taaagttttc  79080
tgcttgcttt tattgtttct ccagttggtt ctggaggagg gagtgaggat cctgtcatag  79140
tagactgttt tggcttcttt tttttttttg ttaaatttat atgtgttgtc aatagcctct  79200
tgaatgcctt ggaataattt cagtatgtgg atcttccagg aataattttt agacattagc  79260
cttcttttcg ttagcctatg ctgcagcttt gacagtgctt tgtttattga gccagtgaga  79320
acaggaagat ttctttatga gatagatgct gcttttgctt tttttaaaat aaattttatt  79380
gtgtatattt gaggttatgt gtatatatat atatgtatat atgtatatat gaggttattg  79440
tgtatacatg aggttatgga atacatatag gcagtatagt ggttactgta gtgaagcaaa  79500
tttacatatt tatcatttttg catagctaca tttttgtgac aaaagcagtt aaaatcgatt  79560
taatgaaaac tccaaatatc atacaattct attaactata tctctcatgt tgtagattat  79620
ataactgcat tttttcatcc cacatatctg ctattttgta tcccttgacc tctatattcc  79680
cattttcttc ttcctttccc cctcgcccct gtaaccatca tttgtttatc tatttattta  79740
tttaaacttt taagttcagg gatacatgtg caggtttgtt acataggcaa ccttgtgtca  79800
taggggtttg ttgtacagat tatttcatta ctcaggtatg aagtccagta cccattagtt  79860
atttttcatg atcctctccc tgctcccacc ctccaccctc tgacaatctc tactgtgtgt  79920
tgttcctctc tatgtgtcca tgtgttctca tcatttaact cccacttata agtgagaaca  79980
tgtggtattt ggtttctgt tcctgagtta gtttgctaag gataatgacc tccagctcca  80040
tccatgtacc tgcaaaggag atgatcttgt tctttatggc tgcctagtat tccatggtgt  80100
acatgtacca cattttcttt atccagtcta tcattgacgg acatttagtt tgattccatg  80160
tctttgcttt tgtgaatagt gctgcaatga acatatgcat gcatacatct ttataataga  80220
attatttata ttcctttgga tatataccca ataatgggat tgctagtatt gaaatggtgt  80280
ttctgtctta agtctttgag gaattgtcac attgtcttgt acaatggctg aattaattaa  80340
cactcctacc gacagtgtat aagtgttcct tttctctaca acctctccag catctgttat  80400
tttttgact tttaaatgat agctatccat tctgactggt gtgagatggt atctcattgt  80460
gtgtttttat tttattttat ttttttgaga caaagtctca ctctgttgct caggctggag  80520
tgcggtggtg tgatctcggc tcactgcaac ctctgcctcc caggttcaag taattctcct  80580
gcctcagcct cccgagtagc tgggactaca ggtgtcgcct ccacgcctgg ctaattttta  80640
aactttttta gtagagaagg ggtttcacca tattggcctg gctggtctca aactcctgac  80700
cttgtgatcc atctcccttg gcctcctaaa gtgctgggat tgcaggcgtg agccaccacg  80760
caagtggcct tttttttttt tttttttttt tttgacagag ccttgatctg tcacccaggc  80820
tggagtgcag tgatgtgatc ttggctcact gcaaccttca ccttctgggt tcaagcgatt  80880
ctcctgcctc agcctcccaa gtagctggga ttacaggcgt gagccaccat acccagctga  80940
tttttgtatt ttaatagaga cagggtttca ccatgttgga caggctggtt tcaaactcct  81000
gatctcaagt gatcctcctg ctttggcctc ccaaagtgct ggggttacag atgtgagcac  81060
tgtgcctggt ggcctcctta tggttctgat ttgcatttct ctaatgatca gtgatgttga  81120
gctttttctc atatgattgt aggcctcatg tatgcatgta tgacttcttt tgaaaagtgt  81180
ctgttcatat cctttgccca tttttttttt tttttttttt gagatggagt ttccccccttg  81240
ttgcccacgc tgcaacctcc acctcccggg ttcaagtgat tctcctgcct cagcctccca  81300
agtagctgga attacaggca tgtgccacca tgcttgctaa ttttgtattt tttagtagag  81360
atggggtttc ttcatgttgg tcagcctggt cttgaaaact cttgatctca ggtgatctgc  81420
ctaccttggc ctcccaaagt gctgggatta gaggcatgag ccactgtgcc tggccccttt  81480
gctggcttaa aaaaattttt tttttcttgt aaatttgttt aagttcctta tagatgctgg  81540
atattagatc tttgtcagat gcacagtttg caaaaatttt ctcccatttt gtaggttgtt  81600
tactgtgttg atagtttctt tcactgtgca gatctctttc atttaatttg atcccatttg  81660
tcaattttttg cttttgttgc aattgctttt gaaatcttg gctgttccta tgtcctgaat  81720
ggtattgcct aggttgtctt ccagggtttt tatagttttg ggttttacat ttaagttttt  81780
aatccatctt gcgttaattt ttgtatatga tgtaaggaag gggtccagtt tcagtcttct  81840
gcatatggct agccagctct cccagcacca tttattgaat aggaaatcct ttccccattg  81900
cttgtttttg tcagatttgt tgaagatcag atagttgtag atgtgcagtc ttatttctgg  81960
gttctctatt ctgttccatt ggtctatgtg tctgtttttg tgtgagtacc atgctgtttt  82020
ggttactata gccttgtagt acagtttgaa ctctggtagc atgatgcctc cagctttgtt  82080
ctttttgctt aggattgtct tggctatacg agctcttttt tggttccata tgaattttaa  82140
aatagttttc tctcgttctg tgaagaatgt agtagtttaa taggaatagc attgaataca  82200
taaattgctt tgggcagtat ggccatttta acaatattga ttcttcctat ccatgagcat  82260
gggatgtttt cccattggtt tgttcatcta tgatttcttt gagcagtggt ttgtagttct  82320
ccttgtagag atcttttacc tccctagtta gctgtgttct taagtatttt atctttctgt  82380
ggcagttgtg aatgggagtt tatttctgat ttggctctct gctgtgtgtt gttggtgtat  82440
aggaatgcta gtgattttca cacatcgagg ctttcctgaa gttgtttatc ggtttaagaa  82500
```

-continued

```
acttttgggc tgagactatg gggttttcta gatataggat tatgtcatct gcaaacaggg  82560
atagtttgac ttcctctctt cctatttgga tgccctttgt ttcatttttt ctttctttct  82620
tttgcctgat tgccctggcc agaacttcta gtactatgtt gaataggagc ggtgagagag  82680
ggcattcttg tcttgtgctg ataaccactg tttagatgct gcttcttgaa ttggtgtctg  82740
agcaagagcg gaagcaaatc ttcatgtatt tgtattttgt gacagagttg gagtcatgga  82800
actctagcct tttctctcca atatgcctgg ctctggctcc cttgtctact tgccagcttc  82860
ttgacacatt atgaattttt tttcttattt tattgttttc ttattggtgc ctgttctagt  82920
tgcttactgt ggatgcagcc atggttgttg ttagcattgc agaaatagtg gttgcaggtg  82980
tttaatttta tgctggaatg tgttttttc aacttagttt tttttgtgat ttttaattct  83040
gactttgtct taatttgtct ggttaatgta aatttttagg gagaagtatc aaaattatta  83100
cctaaaaagg tataatactt gatttttatt gaagttaaat atatataaaa taaaatttgc  83160
tatttttacc attttaagtg tttaattcag tgacattaat tacttcacaa tgttatatga  83220
ccatcaccaa tatttccaaa acattttcat ggctccagac agagactctg taatcattaa  83280
gcaataacta ctcatttccc cttccccaca gcccttggga acctctagtc tacttctgtc  83340
tttatgaatt tacctattct agatatttca catttatata atatttgccc ttttgtgtct  83400
ggcttatttc acttagcaca gtgttttcaa gattattcca tgttgtagca tgtatcagag  83460
cttcatttct tttttttttt ttgagacgga gtcttgctct gttacccagg ctggagtgca  83520
atagcgcgat cttggctcac tgcaacctcc gcctcccggg ttcaaaccat tctccttcct  83580
cagcctcccg agtagttggg actacaggcg cccaccacta cgcccagcta attttttgta  83640
tttttagtag agacggggtt tcactatgtt ggccaggctg gtctcaaact cctgacctca  83700
tgatccgccc gcctcggcct cccaaagtgc tgggattaca ggtgtgagcc accgcaccta  83760
gcctcagagc ttcatttctt tttacggctg aataatattg tgttgtgtat atataccaca  83820
ttttgtttat ccattttttct gctgatggac acaggttgtt tccacctttt tggctactgt  83880
aactattgct gcaatgaacg gtggcataca agtatctctt ggagttactg ttttcagtcc  83940
ttttgtgtat atacctagga gtggaattac tgggtcatat tctaattcta tgttaatttt  84000
ttgaggatct gacagtttta ctcttttagc ctgttttacc cactcttgct agcaatgagt  84060
actattctta aaaaaaaaag cattgctaat ggggtacatg caaatatctc atttttgaaa  84120
aaaccgtatc tcatggatgt tgtcatttgc attgctttga ttatcagtga ggctgaatat  84180
ttttctgctt attaataact tatatttcta cttttgtaaa ttgcctcttc agtttttttt  84240
ttttttgta aatttaggtc actgacattt tgcagagttt atattaatct ccaacaaagt  84300
taacctgttt atctctgcca aaagtgtggg tcatttttaa tgctgacctc tgcctgttgg  84360
tcttgtcaaa cagtaacatc taagttctcc ctggcagaac tcaagtccag acttcttagg  84420
aactctggat tgctgaacag agtaaaagta agtataagta agaaatgtaa ttttggctga  84480
ctgactgatg aacaaagcaa ttacatattc attactcctc aatttgtgtc attttcaaag  84540
ttgataaaca tgaaggctaa gtcttatcta agttacttgg aagaagtgtg gaaagttgtt  84600
atgaatccat tcattccgta tattttatct tctccttagg tggtccatga gttggaactt  84660
tataacacag gatattattt aggcatgttc atgaattctt ttgcagtctt tcaggtatgt  84720
tttgcttgct atattgaaaa gatattaata ttttttacta ttgcaaaccc tttcagaatt  84780
agtgatcatt ttgagatgtt aaccttttat taaatgtgtc actgaagcgc agtcttatgt  84840
aagtataatt tgaaatgaaa agataatcat ctttccagtt ttaaaagcaa atggaacaat  84900
tcaccattgg aaaagttaat ggaattgaca ttaaacaaat aatttttcct ttatgtatat  84960
gtatttccat ataaatatat tttatgtata tatataatat ataaatatat tttatgtata  85020
tatataatat ataaatatat tttatgtata tatataatat ataaatatat tttatatata  85080
tttccttgac tttgaaatgg ctcttatgca tgagtgtgtg tgtgtatgtg tgtgtgtgta  85140
agactgatgt gtgtatgtgt gtttgagaaa gatcaatgtg tatgtgcgtg tgtgtgtttg  85200
agagagatcg atatgtgtat gcgtgtgtgt gtgtgtttga gtgagaaaga tcgatgggca  85260
tgtgcgtgtg tgtgtttgag tgagaaaggt tgatgtgtgt gtgcgtgtgt gtgtgtgttt  85320
gagtgagaga cagaaaggtt gaatgtatgt gcatgtgtat acctaagctc tcaaaaatga  85380
gcacaagtga gtcaggagtt tgggagactg ccttgataat ttagtgagca tttaaacttg  85440
tgttttaaaa gaaaataaaa attattcttt ttaggaatgt ggactctggg tattgacaga  85500
tgcaaacctc acgaaggatt atattgatgg tgtttgtaag taatacatgg cgacatgctt  85560
gtatttgtct ttcacatgat attcaacatt acttatatag gtatggatat tttttagatg  85620
aacatagaga ttgtgatttt catttttttg ttctcttctc ccaaaatgtt tggagtttaa  85680
tgtacttaga agtacatctg ggccatgaca tggaacgttc atctgagctc ctgtctagat  85740
atttgaagtg aatgctttcc tttttctcta ggtaattctt tgaggtagtt atatttttgg  85800
acatactgga agctgctttt cttctgattt gtatcacaaa ctgtcctatt cttttggaat  85860
tatttaaaag gagcaacata tttttgaaat atttttgtac tccagctttt tgatgttcac  85920
ctagaaaata gcccagatgc catcatgcca taaagtattc tggtacacac acacacacac  85980
acacacagac acagacacac acacacacac agagacatag acacacacgc agacacacac  86040
acacacacac acccctcatc aatctgagtt cttcctgggc aggattatat ctgtacatcc  86100
tagtttcttg aattgccaaa tagagttggc tgccaagtaa taataagtgt gcttttagaa  86160
agacgtcata aaatgtttg actgaaggaa atgtataaat gtataaatta gaatggttaa  86220
ccttagaagg gattctcttt tctttcaggt taagttatac taacatcatc ttgaaaggct  86280
tctagaactg tcacagtttc tatccctgaa ttccctgttt ctgtcaggta ttctgttatt  86340
ccatgctaag cccccgggtc tctttgggct ggttcttgcc ccaacaggac acctgatcct  86400
ctgtcctgaa acttaaaaga taattttata gtcttgaaga tgttatgaag tcattatgat  86460
ctctctacat taaagacatg tggtacattt agctttcctc atataaccct ctatcctaga  86520
caatcttcca agcatgtttt tccatttttc agtctcagtt tttacccatc tttgttcttt  86580
tttacatatt gaatccttct tgatgcccac tgtaataccc attctattgc cagtaatact  86640
tactgtatcc tttacctttt ctgaaaacct tcttctacct tttcactgta acagaaggaa  86700
cctgatactc tcactggcac attatgtctc tggacacctc aagtgattga cattcatttt  86760
gtatgtggag tttacaattc attctctcca gtgactgttt ttctaactac tgtcaatgtt  86820
tatttataga tgacaatgca gaatatgctg agaggtttat ggaggaaaat gaaggacata  86880
ttgtagatat tcatgacttt tctttgggta gcagtccaca tgtccgaaag catttttccag  86940
agacttggat ttggctagac accaacatgg ggtaaaaatt tataaagttc tttgcccata  87000
catattttgt ttagtgtttg ttttaaataa gctttgcccg ctttctaatg tttaagtaca  87060
aacatagtgt aactaagaac taagtagacc aaaaggattt tttaggaaat gatatttatt  87120
gaatctaaat acagttttttg ataaagccac acataaatta tggcaggaag gtctcatcaa  87180
tgagaagata ggcctttttt tttttttta actgaagggt gattttgact tccttgaagt  87240
```

-continued

```
ctcatgattc ttgttgaaga aaaattgctg ggagtacatt tgttgtcaca ggatgggaag  87300
cactcatgat tacctcctgt gacccctggc agtgctgcta actgaaccct gctcctcaca  87360
aagcattccc aggagtcaca gggagaaggg gcatgggtgg tggaaagaat tcagcttggc  87420
tgataaaccc cgtaccacct ggcctgataa ttgagcaggt aaatcatgaa atccacatag  87480
tattttatag tcagctgttt aaagatactt gagttaacac atgagtgaaa tctcaaggaa  87540
acaaataaca gcattgacag ggatacagag aaaaacttct gcaaatttag agaaaaaatt  87600
ggagttaagt ttgaaaatgt gtatttatta tctataaaaa atttgtgaaa aaataatgtt  87660
tattctgaag atgtaaattt tgcaggaaga ttttattaga atatggatca atatgcagta  87720
ttatgacctt atgatgacct attctttgaa aagttgggat ttactgtttt atacttaaac  87780
cttttaaatg gttttaaatt cagatatgta aacaatagga aaaattgaaa ttcttccaaa  87840
aatagtttag attattttgg cttatttcaa aatgtatcag ttcttggttt tgtgatgttt  87900
atatttatta tcttgacttc agttacagga tttaccaaga atttgaagta actgtacctg  87960
attctatcac ttcttgggtg gctactggtt ttgtgatctc tgaggacctg ggtcttggac  88020
taacaactac tccagtggag gtattgtatt aaagagctgc ttatcagtat tacggtgaca  88080
ttaagctaat acagcgtcag ctcctcaatt tttttttaa atgactgctt ataatgttta  88140
tcacagttta gagattcctt ggctttgtct tttggttttt atctgtttta tatttaagaa  88200
tgtgagctat atatagctat ataaactgct aaatgtgcaa agtccgtatt aagatttggg  88260
tagaaaagtt tattattgac ctgaactaac catctccaaa ggccagaaga gagagaaaga  88320
aaaagagaga gagagaaaga ggagaggaga gagagagtga gtctttctat ttgtcctctt  88380
caagaatgaa cagaacttct caagatgttc cctagccaat attccatcat gtcttttggt  88440
caaattgcat catatattgt ttcctaagcc agtcactggc aggaggaata taatgaccat  88500
gagtggcctg aatttttctca tttgaaattg aaatgtaatt ttgatttaca aaataatcgt  88560
attcatgaaa aatacagtgt agattgaaaa atgctttggg tttatataga aattggaatt  88620
agattgtaag ctcaggccac tataaacaga caattcagca acatgaatgt ctgaagggac  88680
attcaagaat cattaggaac atggggcaat ttttcattgt ctggggctgt cctgagtatt  88740
gcagactgtc acccactaac tacctatagc accttcgagt catggtgaca atctaagaca  88800
ccttcacaaa tgtgcagata aactctagag ggagttactg ctgccagcaa aaccactggc  88860
ctaaactaac ccaggtttag ctttagatgc aggtgtgggg cttggccttt tctgtaggac  88920
ttggccaaca atatcagaat tgggtcactg aggaggaagc acatgtattc agatgtccca  88980
cacattttct catctgtatg taaaaataaa tcatatatat gttttagaaa taatttccaa  89040
tttcctcttt aaatttagtc aggaagcaca tgtattcaga tgtcccacac tagaacaggg  89100
gctgttggat ttggcagggc ttttaaagca gattggtgga gtcaatacag catgaaagaa  89160
gagcaaattg cttcgggatt agacaggctg ggttctagtt ctggctcctc tacttgccag  89220
caatatgaat ttgtactagt tacaaaaatc tcaaaaattt aattttcttt tctataaact  89280
aggagactaa cagtaacctt atggggttgt aataaccaaa caaaataatt tatgtgaagt  89340
gtttggttgc tataaggcac ttaataaagt atagcaatta ttatgttaag taacataaat  89400
caagtcaatt tgccgtcatt catttgtgat aagttgctgt ttgctttctg ttgatagcaa  89460
gttgacattt ctagctgaag ttaaaagctt cacaggtttt ataaagattg catttaattg  89520
cataaaatgt gaagaatttt gacctgaata aaaatatgta ctcgttgtgt tctttccagc  89580
tccaagcctt ccaaccattt ttcatttttt tgaatcttcc ctactctgtt atcagaggtg  89640
aagaatttgc tttggaaata actatattca attatttgaa agatgccact gaggtaatgt  89700
attcaagctt ttgttgatca tttacactac aggagaaaat cgaggtagca tgaagggatt  89760
gggttgtgta gtatctgggc atttgggatt ctaagcactt tatacatttc tgggaggctg  89820
aaaatagaca tgtcttgtca gtgatttctt ctgctaatta atgtctaagg atatcattag  89880
catgtctaca cattacctcc ttgaattttc agcataggtt ttcctctttt gccatgtaag  89940
ttccttattg tctctgaagc atgcctttct ctttcctgcc tccctgcatt ttcccctggt  90000
tttccccaca tctagaatgt gtggccactt ctcactgcca ctctgtgccc actgcagttt  90060
tgtttttttt tttttttga gacatggtct tgctctgttg cccaggctgg agtgcagtgg  90120
cgtgatctcg gctcactgca acttccacct cacaggttca agtgattctc ctgcctcagc  90180
ctccgagtag ctgggattac aagggtgcac caccacgccc agctaatttt tgtgtttttc  90240
atagagacag agtgttgcca tgttggccag gcgggtcttg atcaagtgat ctgcctgcct  90300
tggcctccca aagtactggc attacaggca tgagccactg cacccgactg ccattctgtt  90360
atgtttgtag cccccatgtt tatattttca aggattcact attggattca cgtaccttgt  90420
atctccttag ctagtcattt ccctgggagg caggaattag gttcactgtt tgtgttgtgc  90480
ccacagtatg ttaaccaagt gactgatttt tcttccccca gaataagtag agatacgtaa  90540
ttaactttat tacatggatg aaaatgacat gatatcttta ggcactttat atataatttt  90600
ttttaattta aattttaatt ttttaagctt tttattggca tatttggctg acaaagtggg  90660
aagtaaattt ttttaatttt ttaattttac tttttaaccc agttatcatg gtaccatgta  90720
acaagcaaaa gatctagagt ctaaaggcct ggattcaatg tttaatctac cacttaccag  90780
caaatgactt aattgtagtt tcctcatctg taaaatggaa atgataatta ttacacccac  90840
aaaagatacc ttgagaagca gatgaaaaca tcaatgggaa aataattcgt aaaatttaag  90900
gcctagataa atgctattat tgatgagact tgcaactttg ggataattta caaaagttta  90960
caaccaagat atgcttcagg actaatatct gagttgtact ttccttggaa taatttttta  91020
cagagacttc aataaattca ataacatttc atgctgtttt cttcaaattt ttctaatgag  91080
accagtatgt tccaggatga catagttaaa tcaagctagt agtaatatca atatatgaaa  91140
tagcctttct gtgcacatcc ttaccatcta atggcttcag atagtgagag aatttaaagt  91200
tagtgggagg actagaaatg gggctgaaga tcgccctttc cccatgtatc ttgaggttga  91260
ggggaaagca tagaaaagaa atgaagtttt tcctgatact ctttgatact ctccttggtc  91320
gaatctttgt ctcatctttt cgctagtctt gagcctcaca gatttgacag tacttaaact  91380
ggtgataaaa gagcacttta ctgaagagca tctattatac aaaagctttg atttattttt  91440
ttctttcagg ttaaggtaat cattgagaaa agtgacaaat ttgatattct aatgacttca  91500
aatgaaataa atgccacagg ccaccagcag acccttctgg ttcccagtga ggatggggca  91560
actgttcttt ttcccatcag gccaacacat ctgggagaaa ttcctatcac agtcacagct  91620
ctttcaccca ctgcttctga tgctgtcacc cagatgattt tagtaaaggt aaatatttga  91680
tgtctgaaag aagtgaaatg gaaatacgta attaaaaagg aagcagaagg tttttctct  91740
tggttaaatt tgttggcata tctagtaggt catcttcttt acccttctgg taatgcctaa  91800
tcactttcta atctgtatgt aaaaataaat catttagaaa taattgccaa tttcctcttt  91860
aaatttagtc aggaatgtga ctataaagac taacgtctct tttgcagtca tttacatcta  91920
cagactgtgt tacgttggga tcctattaaa acacggccaa gtcgatttgt agatttggaa  91980
```

-continued

```
ttttggaatt tttcagtgaa ggtaaaagag attttgtaga tttttttcag agaagacatt  92040
ctagacagaa agataatgag catagtggat aaacacttgt attctggggt gaggcaaccc  92100
tgtgtttgaa tctcagctct gccaagtgtg attttgaaca aggcatttaa tctccccctc  92160
tttggataat aataggaact acctcaaagg gttttttttcc ttacattttc atcttcttct  92220
ttgtcatttt caaggccagt ccatgagatg ccttatctaa tttaactaga acttactaac  92280
agatttgaag taagaataac aaaatggtac gcgctgtgtc atcagattta attcatttcc  92340
atggaaatgg tgcctattaa gtgtaaatcc tgtgaaaaac acgtttcagt taatgaaggg  92400
tactgtactt agtgagaaaa tctaaaagga aaaattaatc aaagttatgg taattttttg  92460
taatacagac taacaagaaa aactcattct gtgaaatgaa tgtattactt gtttaaataa  92520
aatatctaat ttaaagaaaa caaaataaga aatgataggt gcctatttag ccacacacaa  92580
acctcagaca caacaggtca gatgtttgtg ctcatatctg cgtatagttc tctgtaaaca  92640
tgtgagtaga gaccatgtta attgtgttca ttttttttcaa caggctgaag gaatagaaaa  92700
atcatattca caatccatct tattagactt gactgacaat aggctacaga gtaccctgaa  92760
aactttgagt ttctcatttc ctcctaatac agtgactggc agtgaaagag ttcagatcac  92820
tgcaattggt aagaatagag tatatcacca tctattggtt taattgtata tgatcatata  92880
tgttgttctt gtaattatag atgtattttc ttattgagtc ctaataagaa gagatggcaa  92940
aagtttttaa ttgggcccaa caactcatta taatatgaag gctagcaaat tatgtatcct  93000
aaaactgttc tcaatcttca atgtgcataa gaatcacctg ggagtcttgt ttaaaagcaa  93060
attctggttt agtaggtctg gagtggggcc tgggaatctg cttttctaac aagctcctag  93120
gtgttggtga tactctggct tgtagaccac actttgagta gcaaggcctc actatactgt  93180
ggctggaggg agggttcatt cctaagagca gagcttctgg cttctgtggc tctccaccac  93240
tggtgaatat cagaatcttc taaggagctc tgtaaataca gaaacatctg ggttctactc  93300
taaacctact aagtcagaat cacttgggct atggcttggt catgtatatc ttaaaaaact  93360
ttcacaagtg attctgataa ccaaaggttg agtactcctc cctagggcag ttctctgtgc  93420
aggatatgag taacctttac agtaggaagt tactcactga cttcggtcgc ctctcctagt  93480
tactttccat aacataatag tacttttcaa aaattggcaa tttataattg tataaattta  93540
tgggatacaa agtgatatta tggcttatga atgcaatgtg gaataactaa atcaagctgg  93600
ttgacgtagt catcacctca aatacttaac tgtttttttt tgtgggaaga acatttgaaa  93660
tttgctgtct gagcattttt ttttttgag gcggagtctc gctctgtcgc ccaggctgga  93720
gtgcagtggc gcgaacttgg ctcactgcaa gctctgcttc ccaggttcac gccattctcc  93780
tgccacagcc tcccgagtag ttgggactac aggcacccgc caccatgcct ggctaatttt  93840
ttttttttgt atttttagt agagatgggg tttcaccatg ttagccagga tggtctccat  93900
ctcctgactt catgatccac ccgcctcggc ctcccaaagt gctgggatta caggcgtgag  93960
ccaccgcgcc cggccttttt tttttttttt tcctttgatg gagtcttgct ctgtctccca  94020
ggctagagtg cagtggcagg atcttggctc actgcaacct ctgcctcttg ggttcaagc  94080
gagtctcctg cctcagcctc ctgagtagct ggaattacag gcacgtgcca ccacacccag  94140
ctagtttttg tagttttagt agagatgggc ttttgcagtg ttggccaggc tggtctcgaa  94200
cccctgaccc aaagtgctgg gattacaggt gtgagccatg gcactcagcc tttcttagca  94260
atttggaaat ttacaatact cttgttatta actatattta ccatgctaaa agtccttttt  94320
ttttttttga gatggagtct ttctctgtag cccaggctgg agtgcagtgg tgtgatctcg  94380
gtttactgca accaccgcct actgggttta agcagttctt ataccttggc ctcctatgaa  94440
gatgggacta caggtgtgtg ccaccatgcc cggctaattt tttatatttt cattagagac  94500
gggatttcac catgttggcc aggctggtct caaacccctc acctcaggtg atccacccac  94560
ctcagcctcc caaagtgcca ggattacagg catgagccat tgcgcccagc ctaaaagtac  94620
tttttaatta gacatagtgt ctacacaaat ggtgttatta atcagggttc tccagagaaa  94680
cagaaccaat aggagatact tacatataaa aggaggttta ttatgaggaa ttggctcatg  94740
caattatgga ggctgagaag tcccatgatc tgcttttgca agctggagac ccaggaaggc  94800
tggtagtact cactctgagt ccaaaggcct gtgaagcaga ggagctgatg atgtaaatcc  94860
cagtcctagg agaagatgag atgagatgtc tgagctcaag tagtgaggca ggaaaaaaag  94920
ggtgaattcc tccttcctca agcttttgtc tattcaggct gtcagtggat tggatggtgc  94980
ccacacacac tggggaggac aatctgctgg acccagtcca ccaattcaaa tgctaatgtc  95040
atctagaaac accctcacag acactcagaa gcaatgctta atctaggcac cccttggctc  95100
acttaagttg acacacaaaa ttaaccctca caaatggttt gtttatatag ttgtgcttta  95160
caaataactg aagaaaacat tttaattaat gacgtctaat agtttgttag gtctttaagg  95220
tgttaggacc taaaacactt ttttacagtt cttttatatt tcactggcag atgtaatgct  95280
tttttattat aacccaaaca accaatccat aggcagagga ctttatttgg aggcatatat  95340
atacatacat acatatatat atatatatat atatatatat atatatatat atacacacac  95400
acacatacat atatatatat atatatatat atatataatt tttttttgga agaggcaggg  95460
tttagctatg tttgccccag gctggacttg aacttcttga acttctgagc tcatgtagtc  95520
ctcctgcatc agccccttgc ataactggga ctacaggcat gcaccactgt gcctggccaa  95580
ttcttaaaag gaattaaata agctctctat ttaggggaat aaattctgct taagcatctc  95640
ccacagtgtt gggatgctgg gacatgcact acacatacat acacacacac acacgcacac  95700
atatacacag agggaaggag cctggctttt taaatatgta ccatcactcc ttacacagga  95760
acgattctgt ctgtcgtcat ggaaataccc cgaggcttaa tttttatgct tgatgtaaag  95820
aacggatttt caagttttat ttttacatgt tgttttaaag acctattttg tatcccagaa  95880
tgtacgaatt ttagcttgct tctttgaact ttgatagtct atgttcactt tgaatattaa  95940
acacatagcc tgcagtggta ataatataac ctctattttt ttctttgtat tcacatctaa  96000
aatttaagct atactggcac agcttcagtc tattcatatg aaacaggttc ttttcccttt  96060
tttttcatat tcattttta ggatcacatt ttcactaggt atttggactt ggcttggtat  96120
aagttttcaa aataaactac atagaaagat actcttatct atacagctta acaatggcag  96180
ggccaaaatt agaactcagc cttcatattt ctgaattttt gctactttcc ctgagttgtg  96240
gtgttaggat gtgggtagag ggtttttaaa gcatgtgttt tgtttaattt tagattacta  96300
actttgaatc cttttccgaa tccttttgat cctgagatta attgaaatac ttatatttgt  96360
tgttactaaa cagaacacat tggaaaacac tacaatcctc attgtttttt taaaaaatta  96420
tttctcaagt tcttgtggtg tattagtaag aaataagaat aaaattttgt ttgcgtgaag  96480
aatactacta ataaaatgtt tctttcctgt atgagtgatg gtgtcttact gatcaattct  96540
gtacattttt ttaaagattt ttaaaaaaat tattttttgc ctaatttatg ccacatgctt  96600
aactgagcta aaaatgtcct ctttcatcac atgacctaca agttcagtac cagagcattg  96660
ttattttttt gaccagtctt cctaaaagct tggtgtaaag ttccaactct gttccaagca  96720
```

-continued

```
gtggaataat gatattgctt caatgacaga ggtcttctgt actcagtgga agtctctttg  96780
ccaccagcag gtcgttgtta ctgagtattt actgaatgaa ctgcatgtct tgtgcttcca  96840
ggagatgttc ttggtccttc catcaatggc ttagcctcat tgattcggat gccttatggc  96900
tgtggtgaac agaacatgat aaattttgct ccaaatattt acattttgga ttatctgact  96960
aaaaagaaac aactgacaga taatttgaaa gaaaaagctc tttcatttat gaggcaaggt  97020
aagcatttta gagacctaca tttgttcgta gaaaaaaatt tgttttttc aggtagggtt  97080
cattctagac catatttcaa aatagatgga ttttgtctta ggtaagtgat gggctacacg  97140
gtgttgacat gtgcaggaag tgcaaacaat ggaaagctgt tacaattctt cctttagcta  97200
actattcact cactgctgct aagatgtttg ttagtaatgg cttaagagtt agtttctggt  97260
gggagggctt gtattatact aagggatctg aaatttaaaa ctctttaaaa atctagagga  97320
atactcattc attttattac acatttgtgg agtgtttctt agtgccagga tcagttttcg  97380
tgccaagaaa acagagggag ccagggcctc tcttcttaaa gaattcgctg ctcaatggag  97440
aagatggttt gtatgtaaac agacgcagtg ccgtgtggtg gggaccttct cagtgcattt  97500
aaaatgatga ggaggacctg ctggaccctg aggaaatgtc atgctagtga agactgtatc  97560
ttgacacctt gaaaggtgga aactgttcac aggcaccaga tcctttgttt tggcaacttg  97620
ttaataacag cagctaacat gagttgagtg tgcactgtgt ggcaggcagt gttctaaaca  97680
ctttacatct catacctcat tggaggctca ccattagtat tagcatgatc ctgtttttt  97740
gcagatgagg aagctgaggt gcagaaaagt tagctaactt gcccagggtc atatagtcat  97800
acagagcttg gatttggact ctgagcctat gctcttgaca tccataccta ggaggaaaca  97860
aagagatgtg agacacgttt gatgttaata gtaaagtaaa tttgattttc tgaaatactc  97920
caaaagctta ccaaagttac agtctcagtt ttgtatttcc ttattagtgg acctctagca  97980
caaactctct gtggctgagt ttttctctct gcacaatttg tatgatatat cccgtccatc  98040
aaattcatga ggattagaag ggttcacaca aactgattaa aaatgaggat tcactataat  98100
ctaagagaaa tatagttcaa cgctttccaa ctcctaattt ttttagtttt tgttttttta  98160
taacaaatgg attaaatgaa aagtaggggc aagctattaa ttgattgcta atttctccat  98220
aggagaatta gaaaactcag taaagacgcc attgtaatgt gagcttttct tccaggttcc  98280
attattgtgt agagaccttt ttattctaaa ataattctat gtaatgacag taataacaac  98340
taaatctgtt taaatgtttt atgcatgttt catttaattc tcacaaaaac tctaggagca  98400
ggtgtcctat tattatttcc attttataga tgaggaaatt gaggcacaga gaggttaaag  98460
aatttaccca tggtggtctg gttccaccgt ccaccttgtt cctcagaaca ctatgggata  98520
attctgattt gcagtgttct ctggtttttta gaagcaatgg gatatgatgg aaaggaccag  98580
gaatcgggac gggatgcttg agtatcacca ccgtgtaaga agtctcactg gaggttttga  98640
taaaatatta agggaggaac atggggtcct gtagagaagg aggcaccaaa ggttagaata  98700
tggggtgtca gattagactg aagtaagctg taaggtgttg ggtttaagta gatgagctgg  98760
agtcagtgtc tgaagatctc cctgggatag gatggcacag acaaaggctg aatgggagtc  98820
aaggggttgc gggtcaggaa caatgcagtg tatgagatca caaaccaagg gagaccagcg  98880
tttagaatca gggctgagtg tggcctgagt tctgatgtgg ggaaggacat agtggtatat  98940
tttcccttag attagggcca gaccatgcag acactatgac cggccctgaa atgcaccagg  99000
tggttaggtc ctctgggata tttgtagaga tccagcagtt ggaatttcct gtatagagtt  99060
gcccatgtaa aattatccct gtttatacac atttgtggat tggtcgtgtt ttaaatatat  99120
acgtacaaga ataacctttg tcaaatttta ttataattaa atttaagtgg taccaagtgg  99180
tctctgtggt atattgtgtg ccatgctaaa cacaaatgag atctttacac attggcataa  99240
tggctgtaat taaggagata agtaaaaatt atttgggatt gtcatgaatg aacgttgtac  99300
cttttgaaaa caagattcca atttgtattc aagatttagt ttttctggtt tgaagtagaa  99360
actacatagg aattagactg gtgctttata atttggcata cattctttgg gatagtttaa  99420
tacaataagg taaaatattt cagaaaatgc cacatataac tccatattta catatgcttt  99480
atgaactgta actctggcta atcaaatatt aatgctttaa acagaaagca taaattttac  99540
atagcttgaa acatgtaagc agtgaaaact cattccttaa aaataatttc agtgtgtgtc  99600
ctagatactt ttgctgtgga tcagcagcca tcctacaaaa tgaatggtcc aaatcctcag  99660
tatctgttgt tttcccaaag cagtgctagt ccctcaggtc agtcctggcc aggtaggtgg  99720
ccaaactgta gtttttcaaa gtaacccaga aagggtctct actgattgcc tgagatccct  99780
cctcacatct gttggttgtt agaaggtaca gtggccagag tgcaaaaaaa gcatcgttct  99840
ctaaatgcca agcagtcctc ccaagtgtta agaatgccga gcgctacagc tgtaagtagg  99900
cgagtttccc cttgggagga agtagatcag gggcatagca ctggctgtgg aggcagtcac  99960
acctgggctt gagtcctggc tcccaccttg gaacaggttc ttagtgtctc caaggcttgg  100020
ttttttttacc tggaagacag ggataataaa agaacccact tagtagggtt gtttttagga  100080
gtcagtgaga ataaaagaac ccacgtggta gggttgtttt gaggagtcag tgagatatgt  100140
cagcatttta ttcaacacgt agtaagtgca caacaaatat cagctatagt agaattagtt  100200
gcctctaact agggagttag aggttaatgt cagtgaataa atcctgtcca ttctccctct  100260
aaaaacctgt atgaaattct tctatttctc tccatcccac tgctaattgt tccattcaag  100320
catgattgct cactggacta ctccaatggc ttcctgacta gtctttttct gtgttccctc  100380
cccttcagta cattctccat ataatgtaaa agggatctta gaaaatgtca agatcctgtc  100440
acttgcttgc ttatgatcct gcagtgggct cccggcttca gcctacaggg tcctgggtga  100500
tctggcttgg cctccctcct tagcctcatc tggagctggc tgtatctgga acactctgag  100560
ctccatgctg cttcagggac atgatgcttt cccttccttc tcctggcatg ctttctccct  100620
aggtctttcc atggctgctc cttttcatca ttcagttgat gtttgcctca gagtggcctt  100680
ccctgaccac ttagtaactc caatttgtac tactccattt tatttcttca cttaacatta  100740
tttaaaatta tcctgtccat catctgtcct ggcatttaga gggggagctc tgtgacagtg  100800
gggaccatgt ttgaccttca ttgtatagct atgtgggcat ctcaataaat ccagaatggg  100860
cgaataactt attaccaata ttaacttttt tggactttag gtccatcatc ctaatgtgga  100920
tattgggtcc agaagatctc tgaagcgccc ccacagtgta gcatgatgat ctctgggcac  100980
taatgggtcg acctggcctt ggcattctct tagcagctaa gaaatgtgac cagtgatttc  101040
catgtgctac tctttttgct ggtgaagtgg ctggtgaaag tcagcacagt ggagctcccc  101100
aaaaatacat catctcacat gctgaactaa attatatttc aaagtagtgg acgaaagctt  101160
cttggtataa tgcttttcat tatgaaatca gtgtctcatt tcagagactc tcttttttct  101220
tttgccatca catttgccaa agtcctttaa atatactgta gttgttttta tttttaaga  101280
aattaaagtg gcttcagcgt gagtcatgat tatattattt aaatgtcatt tatgaacagc  101340
gcattgtttt acttaaatca tgcttggccc aggagttctg taacctaacc cattattttg  101400
ttggtcgaaa caacagctac atcattgaat gaagtgtctt tgctgtcaaa aaggaaaatg  101460
```

```
gaaccataac atgaaaactg tttttgataa ggactggaaa tccagaacct gttaattgaa  101520
gatttaaacc atttgttttc ctcagatatt taaatcacag tgcctgcagt tcaacttttt  101580
aaagtgagac tcaaaccaag tctaattgaa aacactatat ttcctccatt gaaataaaaa  101640
taagagaaag aaagcttcag aattcggatg ttgccattgg tcacaagtat ggctagtggc  101700
catagcttaa aaaactgtga tgttctcact ttccatttca tgtcatagaa agtaaacaaa  101760
ttcataatga tttcttttaa tacagagaat ttttttatc agcttattac cagagaaaat  101820
tcttgaaata gtcacaaata gccgacttta cttcctttat ttacatgtaa ttttgacacg  101880
aggtaaatca agtcaaacta tgtttagaat gttacttttt cattgtttgt gagcagtatt  101940
tttatcttta ttataataaa ttttgaaatt ttacattcat ggttatccca aagaaaattc  102000
ataacccaga acaggatgtg tcttatctgg ccctttatga agggctcatg ggtttttatc  102060
ttaagagcct ctggacttct tctgcatttc aattttcaga agtctatgaa agttctgagc  102120
atatgattac ttttcaaact caagagccat tcctaaaatg attaacttaa aggtgatact  102180
cttatttctt cataaacttt tggagagagc tatgtttttg cttttctcgt ctgttgtgat  102240
gcagagtctc caacttagat gactgcactg gaaggctgag ttgttgtatt aacaacaaac  102300
attatagacg agtcatcagt gtcctgtttt tttttttttc tttttttgt gatggagtct  102360
tgctctgtca tccagtctgg agtacagtgg tacgatcttg gctcactgca acctccgcct  102420
cccaggttca agcgattctc ctgcttcagc ctcccgagta gctgggacta caggtgtgtg  102480
ccaccacacc tggctaattt ttgtattttt agtagagacg ggactttgcc gtattagcca  102540
ggctggtttc aaactcctgt cctcaggtaa tccacccgcc ttggcctccc aaagtgctgg  102600
gattataggc atgagccact gtgcctggac ctgttttgtt tatgggatgg aaattaggcc  102660
tgatacactg ggacgatttg gaggacagtc gagggatcca caatgatgca tgctggttta  102720
agatgaggaa ggaaacctca caggacactc ccacaaggag acatacaagt tctctccagg  102780
ttgtgaattt ctcccttact tttccatggg agcagagctg gtggtttgga ttctcggtgt  102840
tatctaagcc tgctcaagaa attcactgca aaactggtga ttgtctgtgg cctcttctct  102900
gggctggctg cctctagtgg aagaatggtg ctagttgttg atattaatgg ggaatgttgg  102960
aggtcagcca cctgaggggt aatttccata agcactgatc tcatctccat gatctcatct  103020
ctgaccagtt tcacaatatc tcatacttgg aactgccgtt gttgatgtga tctgggggtg  103080
tggaggcaca tggtcctctc cttgaggttg gtctttctgt cacaaaagta cctcaaactt  103140
ttgtgtaggg attgagggcc tcaaacctat tttcttttt cttcttccct ctcctctcct  103200
tctcctctct tctttccttt tcctcttttt tcttaggttg aattcatagt taaactctgg  103260
ctatctggag aatttagtcc ttaattaaaa attgagggag aatgtcctgg actctcttgc  103320
tgatttcttt tgtgaacatt aattattttg cttctctgtg atccctggct gcctctgaaa  103380
aatgagataa tatactgcat ttttaaaggt tatgtgaaaa ctaaaacatg ataaaatgaa  103440
ctagagtagt gataatgcct atcatttaat tttttccact tttgtttatg ttttgaacat  103500
gtagaacatt aacatgcttc caaaagacaa acttattttg agacatatat tcaaaagagt  103560
gtctcttctt cccctttctt ttctccctac ctctcattgg taactatatc aggcggttct  103620
tgcattacta taaagaaata cccgagtctg ggtaatttat aaggaaagag gtttaattgg  103680
ctcatgattc tgcaggctgt gcaggaagca tagcgccggc atttcccct aggaaggtct  103740
caggaagctt acagttgtgg cagaaggtga actgggaaca ggcacatcac atggtgaaaa  103800
caaggacaag agagacagtg ttgtggggag gtgccacaca cttttaaatg accagatctt  103860
acagtaactc actcactatc tcaaggacag caccaagatc cagtcacctc ccactgggcc  103920
ttacctccaa cattgaggat tataattgaa catgagattt gtgtggggac aaatatacca  103980
gtaacctact tcattagttt ctagactatc ttttctctct ctccttttgc gaaaataaat  104040
gtatacatat atgttttctc atttcccccc gcaatttttt tttttttttt aaagacaggg  104100
tgtctccctt tgcccaggct gaagtgcagt ggcacaatca tggttcactg cagccttgac  104160
ttactgggct caggtgattc tcccacttca gccttctgaa caggtgggac tacaggcaca  104220
tgccaccatg ctaatttttt ttttgtattt ttgtagagac aggcttttgt catattgccc  104280
aggctggtct caaactccta ggctcaagtg atccactcgc cttggcctcc caaagtgctg  104340
aaccttggca ataggtgaac cttggcgcct cgcctcattt cccctttta ttacacagaa  104400
gatagtatat ctatatgtac tattttacac tttgcctttt tcacttaaca gtgtatccag  104460
gaaattactc tgcatcagtt gaccgagata ttcctcattc tttttttcac agctgcatag  104520
tactctgtca tgtgtgtgta ccatagttta ttcaatcagt ctccagtttt ggggcactaa  104580
gattgtttcc attatgttac aattacagat gatgctgtaa tgaataatct tctgcgtata  104640
tatttttgta ttgttggagg tgtgtcttca gggtagattc ctagaactgg gattactggg  104700
tcagagggta aagacattcc cctacatggt agttgtaacc ttctgaattc cctctagcag  104760
tggatcagtg ctggtttcca tacagctcac ccaacagaag gagtggtcag actttttgaat  104820
cttaatgcta atctgatggg agagaaatgg tatctcagtg taggtttaat ttgagtttct  104880
cctgttatga agttgaatgt gttttctata ttaagatttg tttttatatt tttgtctttt  104940
gtgacttatc tgttttgcct tttattcact tatttttata gggcttttta tcctttaccc  105000
taatttttaa aaagttcttt atatatgtat atacatgtaa gtaataacat ataaacatac  105060
ataaaaatta cataatattg atattagcta tttatccatc ttatatgttg caaatatggt  105120
cttaatttat ttgttaagcc ttgcttatag tgtgttttgc cttggaatag tttaaaaact  105180
ttaaaaaaat agtcaaatgc atcaattttt ttattttatt gcatctggtg cttagagagc  105240
cttcctctac acctatatta gagagtaatg cctattgttt gttgagagct ttccatgtaa  105300
aaggtactta ctgaagtctt ttcttctttt atcatgttta ataattggaa gagctctgtg  105360
atttactagg agacagtggc cttggagcca gtgagaagtt ggctaatgcc caacttcact  105420
ccctgttagc tgtgtgacca tgcacatggt atctgtatcc gctgagtttc agtctcatta  105480
tctgtgaaaa agggaataat aatagcatct atgtcagagg gtccttgtga gaattacctg  105540
agttaatcct gcaaaggact ttgaacagtt cctgacatct aatgagtgct gaatgaaagt  105600
tggctaatta ctgcaccgta ataattcaat tagaaacata aaggtataat ctaatgttcc  105660
cttcttcaaa ttaagcaaag ttttgtcatc actttaaatg tttatatttc ttttaccata  105720
agtcttaaat atcaccatga aacagagtat cttgttttct ttttttcttt atgcattttg  105780
ttttattgta acttaaatca gatacttaaa tctagggttt cttttggaaa gactcaggga  105840
gaagtttggg acttgaaggt gagaacacat taactgtaat ttcaaaccat taatgcttat  105900
gtttagttag tcaaatatga attttactta tagttctgga tgcttctaaa atatggtatt  105960
tataaagtca aatttgttta ttactgcagt ttactgggga aggatttcaa catttcacaa  106020
atgagtatgg ttgccaagct ttgccatgtc tgtgctgcaa agctcaggct gtgtgccctt  106080
acctgctaat agtggaattg tgtaattttt agaaggattt ttggctatca gagagtcatt  106140
gataatgcct tgagctggaa atgttcctgc taatggttgc ttttttagtg ataagttatt  106200
```

-continued

```
gctatcttaa ctttattttt agcaagttag tttattgtgg gttgtttggt gaatccttta  106260
gagtttggcc tatgttttct cacactggac tttgagatct gtatgcattg ctttgcaaat  106320
atgaaacatc tgctttttat ttgcaatcat ttatttgtaa ctatttgcaa atatgacaca  106380
tttgctttta ttaatgcaga tacgtgagcc ttaacccccct acctaattta cttctgtaat  106440
gatacttcat tgccaccact gagcatgtgt atatgtgtgt gtgtgtgtgt gtgtgtgtgt  106500
gtgtgtatat atatatatat attttttttt tttttttttt ttttagtgga aacatggaat  106560
tggtgggtag gcaggcaagt tggtttttttg gtttacctca gttggccatg gccccaaaat  106620
ttaagagcca ccgttttaga ttattttgca tttcctcctc tgtattgctg gtctaagaat  106680
agaaaatact tttattttct actttggcct taaacttaaa ttaatgatac cctacatagt  106740
atttttcttc tgtagcaaac agtgctagat gactaagcat tgaaacaatt ttgatgaaca  106800
ctagacagtt aaataaaagt ctgcctttaa tttgcttgct tttgaatggc tagaagcatc  106860
atctatgcca tagtgatctt ttaatttact ttaatttggg atatcacagg cttttttttt  106920
ttttttgag atggaatttt atttgctctt gttgcctagg ctggagtgca atgacgcaaa  106980
tctcggctca ctgcaacctc tgcttcctgg gttcaagcga ttctcctgcc tcagcctccc  107040
gagtagctgg gattacaggc atgtgccacc atgcccggct actttttgta tttttaatag  107100
agatggggtt tcaccatgtt ggtcaagctg gtctcgaagt cctgacttca ggcaatccac  107160
ctgcttcggc ctcccaaagc gctgggatta taggtgtgag ccactgcacc cggctgggat  107220
atcacagttt ttattttatg cattctgctt gaaaagtcct ggcattttaa atttccaaca  107280
gcacttaaaa tagaaagtac tcaatattag ctcttggttt gatttcttct ttccccctct  107340
ctgcccatat ttcctcaata tgaagtcata attagaaact ttcatccatt gcaagttaat  107400
gattactttg actatctgtc tatttttgtg tctaggttac cagagagaac ttctctatca  107460
gagggaagat ggctctttca gtgcttttgg gaattatgac ccttctggga gcacttggta  107520
agtgtttttg ccaactgaac aaatccgtgt catggaatgg gctttcacta ggtcacaata  107580
gccacgaaat tgacagatat atctctatat attatagact gggaggttgc tttttcctta  107640
gtctggcttt aaaaagagat tttcttttta aagtattatt ttcaaacatt aacaaatcaa  107700
atgtttttat ttagaaaaga taagttataa atcctctttt ttgtgtgtgt gtgtgtgtgg  107760
aagaaacaga aataaaaata ctttatgatg atggtgcagc tgataaaatc agttagaaat  107820
gccgggtgat tgtgacacag cttttttctt aatcttccat gactaataca agtgttgtgt  107880
tactgcggtc aatgtagttt aagtttgtgt gtgtgtgtgt gtgtgtgtaa aaaacaaaca  107940
ctgatggaat taagtatgaa cagccagttt cctccagact ggaatctcta tgtggctgat  108000
tttggatgat taatctctct tcttgtactt atcttcaatt tcctatttta ctcagaaaaa  108060
gattgactca ctgtatcaat caggatagac taggagtgct gtggtaacaa ccaacctact  108120
caatctaagc aattaacaat gaagggattt cttgttcatg ctgcctttcc attgtggtca  108180
gcagggggct ctgcagctgc caacgtgtcc acgtctccaa aaggaggctc caggtttgcc  108240
acagcccgga aagaggaggc tggagtctat agcactggca attagagact tcatcctgag  108300
tgtatcattt ctactcattt tatccttctc agagctggtc acatggctat gcctaacctc  108360
actggggcag gaaagtgaat tcctctgtgt aaccaaagta aaagagaact gtatattatt  108420
gaatatcagt aatgtttacc acatgaaact ttatataaca tgaaacagat ctgcttcaaa  108480
ttttctcttg gccttggcct gactcaggat atagaaccat aaatagaaag ctttcagtgt  108540
tgtattgctt gatgttcttt ttacctcagt atagtgtttt gtagcaggga ctggcaaact  108600
tttctgtaaa gggtcagatt gtaagtattt caggcatttt gggccacgta gagtctccgt  108660
tgcatgctct tccctcttcc tccctctcct ccctctttct ttcctgtctt tgtctttttc  108720
ttttccttct tttaaaaccc gctcttaggt ggtggtgttg gcaggtgggg gctgggttgg  108780
tgcacacata aacaggccct gggctgtatt tggcttgagg gccagatttg ggccaggcag  108840
atttggccca caggctgcag ttggctaact cccattctat aggagagaaa aatatcattt  108900
tccccacctg aagtactaca gtttgcttgt gaactatgta tgcattcttc acccacagct  108960
ttggggctga ctgaagcgtg ttggagctct tctttggtaa atatctagaa cagtccaaag  109020
atgaataacc ttggacaatt tatttaactc tcttggactg tcagattctc agtctacaaa  109080
ataatggagc tggattcaac agacacatta aaaaatgctc atcatcactg gccatcagag  109140
aaatgtaaat caaaaccaca atgagatacc atctcacacc agttagaatg gcgatcatta  109200
taaaggcagg aaacaacagg tgctggagaa gttgtggaga gataggaata cttttacact  109260
gttggtggga ccataaacta gttcaaccat tgtggaagac agtgtggtga ttcctcaagg  109320
atctagaact agaaatacca tttgacccag ctgtggggaa aagaaagaga gatcagattg  109380
ttaccgtgtc tgtgtagaaa gaagtagaca taggagactc cattttgttc tgtactaaga  109440
aaaattcttc tgccttgaga tgctgttaat ctgtaacctt acccccaacc ctgagctctc  109500
tgaaacatgt gctgtgtcaa ctcagggtta aagaattaag tgctgtgctt tagatatgca  109560
tacacataaa catctcaatg ccttaaagag cagtattgct gcccgcatgt cccacctcca  109620
gccctaaggc aggtttcccc tatctcagta gatggaacat acaatcggat tttataccga  109680
gacattccat tgcccaggga cgggcaggag acagatgcct tcctcttatc tcaactgcaa  109740
agaggtgttc cttctgctta tactaatcct cctcagcaca gaccctttac gggtgttggg  109800
ctgggggacg gtcaggtctt tcccttccca cgaggccaca tttcagacta tcacatgggg  109860
agaaaccttg gacaatacct ggctttccta ggcagaggtc cctgcagcct tccgcagtgt  109920
ttgtgtccct gggtacttga gattagggag tggtgatgac tcttaacgag catgctgcct  109980
tcaagcatct gtttaacaag gcacatctta cacagccctt aatccattta accctgagtt  110040
gacacagcac atgtttcaga gggcacgggg ttgggggtaa ggttacagat taacagcatc  110100
tcaaggcaga agaatttttc ttagtacaga acaaaatgga gtctcctatg tctacttctt  110160
tctacacaga cacagcaaca atctgatctc tctttctttt ccccacaccc agccatccca  110220
ttactgggta tatacccaaa ggattataaa tcatgctgct ataaagacac atgcacacgt  110280
atgtttattg cggcactatt cacaatagca aagacttgga accagcccaa atgtccatca  110340
atgatagact ggattaagaa aatgtggcac atatacacca tggaatacta tgcagccata  110400
aaaaaggatg agttcatgtc ctttgtaggg acatggatga agctggaaac catcattctc  110460
agcaaactat cgcaaggaca aaaaaccaaa caccacatgt tctcactcat aggtggaaat  110520
tgaacaatga gaacacttgg acacaggaag gggaacatta cacaccggga cctgttgtgg  110580
ggtgggggga tgggggaggg atagcattag gagacatacc taatgtaaat gacgcgttaa  110640
tgggtgcagc acaccaacat ggcacatgta cacatatgta acaaacctgc acgttgtgca  110700
catgtaccct agaacttaaa gtataataaa taaaaataaa ataaaataaa attaaattaa  110760
aaaatggagc tggattagat catttctaaa ttccttttca aatctgagat ttttgagtca  110820
acatggaatt tcttggccaa gcccaagtgg aaaccagttc tgcctgctag agagagttgc  110880
ttaccttgtc cctttgctct ttcttttttg atttttttct ttccttgttc catcttcagt  110940
```

gattccccct ttgatgaatc ttctgatggg ggaaaaagtg ttgttgtttt gcttgctcgg 111000
tgttatttgg tggaccttat aaagtgtatt ttatgtaatt tttttctctt ttcataaagg 111060
ttgtcagctt ttgttttaag atgtttcctt gaagccgatc cttacataga tattgatcag 111120
aatgtgttac acagaacata cacttggctt aaaggacatc agaaatccaa cggtgaattt 111180
tgggatccag gaagagtgat tcatagtgag cttcaaggtg gcaataaaag tccagtaaca 111240
cttacagcct atattgtaac ttctctcctg ggatatagaa agtatcaggt atttcgtatt 111300
taatttaata aatgatagat gggaaattca aggaaggtag gtcttaatgg gtcaaatatg 111360
tgtgtggaaa cttaacaagt tgcagcttta caacacatgt gaaatctgaa tttgagtact 111420
cttttgcttt gcatttgtgg ccatgttcca aaatctgaga ataaaacatt aacccactct 111480
ttcagaataa ctaagagaat tctaaaaatg ctttttaatg tatgtattgt acttgctatt 111540
ggtaagataa gtcaatacat gttttatcat tgaaaaagtt aatttctgag gggaaagaaa 111600
attatttaaa atttgacaat gtgttctagc aagtttagat tgcaaaggat tttttactta 111660
taaaacatca tggaacagtt acaatatctg ttaatttagt gctgagaaca cccatacccct 111720
gaaaagtgtg ttgaatgggc atggatgcct ggatgagaat gagtatgcgt ggaaaggtat 111780
gctgacgagc ttaagtttgc tccagagctg tcctggtgat tgatgccttt actgcttact 111840
gcctgctgca ttttatgaga tcaccaaagt cattctcttt attaggaccc ccactatttt 111900
cctattctac tagtaggcat gtagaagcta aacttttcct gaacttaggg ccgcactacc 111960
agagatcaaa tataagaaat atatttctca agcagtttgc tgttcttatc tgagtctgtg 112020
atactgagtg ggagaaacac tggcaaaagc tctacttttt tcttctaggg aatgacacct 112080
gtttacttat aaaaactgaa aaacagtatt attttcaaaa tgcatggcaa atctttaaat 112140
gtcaatgatc atggttgatt ttcattgcct agtacaaggt caggtacttc atagacactg 112200
aacttatttt ttaaatgcat gtttcaaagt actttttgtt tcagtatgtg gtaatgggtt 112260
actctgaata gtaaaaaaca tacttttttt cttccaagcc taacattgat gtgcaagagt 112320
ctatccattt tttggagtct gaattcagta gaggaatttc agacaattat actctagccc 112380
ttataactta tgcattgtca tcagtgggga gtcctaaagc gaaggaagct ttgaatatgc 112440
tgacttggag agcagaacaa gaaggtaatg tgctgggccc acttgaggtt gttatgcttt 112500
atgaaatata taacttacat gagaaaaatt tttagccagg tttgaaattg attacatctg 112560
catcttttgg tgaaaagtaa aacacataat gagatcagga tggcctgac atggccacaa 112620
tgcttctggt ctccccaggg tttttttaac agaatttcag ggctcagatg tctctttatt 112680
ttagatatgt gatgccctat gtcagttacc ctttgagtgt ctgataccat ttctggtttg 112740
gcagccttgt agtttgctaa gaccttgggt tctggagaga caggttaaat cctggttctg 112800
caacttacct ttatgaggtt cagttttccc aactgtaaag tggaaatggc acctatttta 112860
gagtggctgt gaggattaaa tgagataatg tgcaatgctg ctgcatagca aatgctcaaa 112920
aataggaact aaaatgctaa ttaaaagaaa tgtgaatacc aaaaaatgct gctagtaagt 112980
ggattatgtg tattttatat acaaagtgga cagggatcca ggtgtgtgtg tgtgtgtgtg 113040
tgtgtgtgtg tgtgtgtgtg taagaaagag agagatggaa gtgggtgggc agaaataaga 113100
taatgtccag tgattcaaat ttctgttaat tcaagaaggg ataattgtag aaagtgttta 113160
gaggcttctg agactgtaaa aaatattgta ttaacagtaa cttagattga atccttgtta 113220
cctattccaa agctggggac tagaagatta ttgcttagag gctgaagcag tctttgacat 113280
tttttcttct tgtctgcttg gctaagtggt agttatttaa tattccacct aagtgtagtc 113340
atcatctaaa tagtaatatt tgagagaggg caccaagtag gatggtcctc tggggactag 113400
agcagaatta tctctaggaa ggttgttgag ttagctgggg atcctaattt tttttcctgg 113460
gggcttgaac ctcaaactgt taacaccaac cttcagataa tgaaaatggg agagtccaga 113520
atattagagc tagttaatgg cagattccca gaataggatt cttttcaatg tgtcttaaaa 113580
tattttgggg atggcctggt cagataagta acgtgcatta tcttctgaaa tatattattt 113640
tttcctttta tttatagcta tttagtcttg agccaaatat agggaatttc tcataggaaa 113700
actattttca tcaaaacatc ctcaaatgta ggcaatggga aaaggatgaa aatttacaag 113760
tatataggtt gagcatccct aatccaaaaa tctgaaatcc aaaatgctcc aatgagcatt 113820
tcctttgagt atcatgtcag tgctcaaaaa gtttcagatt tttgagcatt tcagattttg 113880
gaatgtatgt atgctgtaaa tattccaaaa attcaaacaa aacagaaatt ggacacactt 113940
ctggccccaa gctttttgga taagatatac ttaacttgta atagtttaaa aaagcaacat 114000
ataggcacat gtatacatat gtatgtgtgt gtgtgtttgt gataaataaa tacatgtctg 114060
gcataaataa atacatgtat acaagtatat attttttatg ctagttaagt acaacttgga 114120
ccagagtagg aatatttaat ggtataaaat gtaattttc tggataattg atcagaatgt 114180
tattactttt ctcttgcagg tggcatgcaa ttctgggtgt catcagagtc caaactttct 114240
gactcctggc agccacgctc cctggatatt gaagttgcag cctatgcact gctctcacac 114300
ttcttacaat ttcagacttc tgagggaatc ccaattatga ggtggctaag caggcaaaga 114360
aatagcttgg gtggttttgc atctactcag gtgagagatg atagtttttt ccctttaaac 114420
tataatatat aatatagatt tatttattat atatatttta tatataatat atagtatata 114480
ttatataaat catatgttat atataaaaaa tatttttaaa agtatgtggt tgcatttttt 114540
ccttgatttc ataaaattac ttggcagttt caaagtttag taacttaagc aaaaggctaa 114600
attgattaat tttaattttt ttctcctcat tactatgaat ttcatgtctg atatttatat 114660
ggaataaatc agttccccat ctgccacttt tcatctgtgg taactgatat aagagtagat 114720
gttcagttcc atatagcaaa tattttctat tttcttttct tctttttgga aaggaaaaac 114780
tgaaactttt aatttactga taatatgatc atttatgagc aaaattcagt gggatctaca 114840
gaaatgctac taggattaac aagtgaattt agtaacattg tggtataaaa aaatcattgt 114900
acagaaatcc attgtatcta tatataagca atggaaatgc aaatcaaaat agcataacat 114960
gtgaactgtt tagggattaa tctgacaaaa atcaataaga tctatacact aaaaactata 115020
aaacatttca gcaaacattt tctgagcctc tcctgtactc taggccaagg acattcaaat 115080
atgaatcagg gagcattcca ctctgaagga aggtgtatga atatccagca acaaaatact 115140
actaaattta ctctttgaag accttgatat atacttatat gtacaaatgt ttttcttccc 115200
tcaacaggat accactgtgg ctttaaaggc tctgtctgaa tttgcagccc taatgaatac 115260
agaaaggaca aatatccaag tgaccgtgac ggggcctagc tcaccaagtc ctgtaaagtt 115320
tctgattgac acacacaacc gcttactcct tcagacagca gaggtgtggg caaggggcag 115380
ttatttaaaa atcagtgtag acaattcttt atgctggaat actgctttat ttgtaatctg 115440
ttgatttcaa caaagacttg tttccagagc tctgtagagt aatagggaga agtggtgccc 115500
ttctttggct gaatttgctg agctctggaa gggtggggaa ctttggaaag attggtggaa 115560
caggagaaaa cacgggcact gtaacattgg gaaaggaatg aacatagaaa cctgttgagt 115620
ttctattctt cataggcact gtgctagatt actttacgta tgctattgca tttacttctc 115680

-continued

```
aaagtaactc taagaagtaa gtacatctat ccccatcata catatgataa aactgaggct  115740
gagagaggtt aagtgacttg ctcaagatca tgttactagt aacagtagag ctaggatttg  115800
aactcatcat tccaaagacc atgttctttt cagctgctcc acatgtcttc ttaggagaat  115860
tgatagaacc ggtagtagaa ttcttacttt aactggaata aaagaatatg ctagttctta  115920
actttattcc cttgatcagt tttgtgggag gttaagtaca atggatgaag gtgataactt  115980
caattctgga aagtgatgaa gagtggtgat gataaaggaa aagaaagaat aaagttaggc  116040
acagtcatag acaatgtgtt attgtgttcc tgggagagcc aggggattag gccctgatta  116100
agggaggtca ggggagggag atgactttag tttcttgtct tttatgcttc agccccaaca  116160
ggaggacaga cttgtcagta gcactaatgt gccctcccat gggcagaggt gagggagctt  116220
ggggagtgtg cacttttcct ttcatcacct tgcttaccta tttgacccat agcttttgat  116280
atgtgagaca gtgcaaagct cttagtgctg tcagtgattg cttcttttcc taatgaggga  116340
taggactgat ctgttttgct acttggaagg atctagatat ggaaaattag cctcattcac  116400
tttttttcac cttgattcag cttgctgtgg tacagccaac ggcagttaat atttccgcaa  116460
atggttttgg atttgctatt tgtcaggtat gtaacgatgc ttattttttt aagttaaata  116520
tgacttttta taataattat ttggtttggg gctttattaa atcttagata acttgaatat  116580
aattcctaat gatttacatc tgtgacttaa gcaagatata tcactgtctt taataaaaag  116640
tattagagat gttgccagcc aatgagtaga gagcaattat atagattgat tttctgtttg  116700
aaaagtattt cttggagatt atttgctttt tgaagtgagg gttaatgtcc tccaatatga  116760
ttcctgataa caaatacatg ttttacttat aatttcttaa tattcatctg agaatataga  116820
agtcaacatg gtagaattat tgacttgagg ggaggaattg tgtcccttta atgtaaaatc  116880
ttatataata gtaaatataa caattaaagc ataattatgc tcaatcctct ggtacagaaa  116940
gaaaatataa agaaatctac atttttatag tgcagcagga gctacaataa aatggaagta  117000
gtatgaaaaa tactgaataa gataatcatc acactaaata gcacataaaa atattgagga  117060
ctttaagatc atctcattag aacccaaaga taatttgtga taggaccaaa aatggttgtg  117120
tgcttgggta gaaacaaacg accaaacaaa aacactgaaa cacttactga gaaagtaaaa  117180
aaatggctat tatggagaaa aagtactttt ttcaaaaacc agaacaacca ttctagtaga  117240
gagaacaggt atacttgctg agtagggcgg gtataccttg ctaagcaggt ataatttaga  117300
aacttccaaa taattctaag attattttgc attattctca gaatacagta aacatttttt  117360
aaaactaaag gaaaaatgat cacaatgaaa aggaatggta ttcagtgaaa aggtcagaaa  117420
gagaaagtaa acaatttatt tcgatcttta ctaacaaaga ccatgggaaa attctcattc  117480
tcaagctgtc ttgcaatcca agagtaaatc cagaagtaaa tatgctgtgt attctagata  117540
aaattgaaaa attatatgta cttaaatcac caagttggtt ggaattcatt tttgataaac  117600
caaatgtaga gaaattagtg aaaccaagtg attttttact tgaggcttga agcacacagg  117660
ggtaaatgtg gtacctgttg gtcagaatgt tcatcaatcc catgttggtc tcaaaatgca  117720
gaaaacaaaa ggaagggact agtaggcacc tctcatgagg gaggaaaaaa attacaaaga  117780
agttggtcac tcagaaatgg gtattgagat ttcttacagt tgatattttt ataagtgctc  117840
tggaacaagg aaggcaaaga aaactcatga gtttgcagta aatattaccc tcttttgggt  117900
aataaaatac taaactgttg gaaataaact gcaagatctt ttgaagttcc ctgagtgagc  117960
agttgagctt tattgccaaa tgtaaaccct aatacttagt tatggatggg cattaattat  118020
gacccaagag acagagtagt ccttgtttgt ttcctgatag cattggtctc taaagggaca  118080
attgcatgcc accgaaaggg gaatgatgga aataatagaa agcatttctc caattttatg  118140
ggactgttct tcagctgctt caggaatact ctataattta atcattatac tttaagaaag  118200
agttgacaaa tgtccaaagt aagataacca gaaggatcga gtggatgaag gattatatca  118260
gtttggattg tggcagaata agaagattgc aacttttaga tttgaaaaat gaaggcttag  118320
aggatttttt taagtatgca aatccatgag gggtattaga tgttagttct gaggggtgtg  118380
tgtgtatgtg tgtgcacgtg tgcatatgtg tatgtgtttt aggtataagt taaaagaaaa  118440
cacaacctta caaagcaaca gtaagcttta tgaaccttgt tataaaaaag gggatgaggt  118500
aaaacattta aatagattcc agtccatctg gagatgagat tggactagga agttttgagt  118560
acattcctaa gcttctgatt taggatccct ttgagaaaga cacgggtcct caggctctcc  118620
cagtgtgtct acggcacctt taacatcagt ggtgggtaca gagtagatgc tgagaaagac  118680
ccagttgact tgaaagctat catttatttt atcatctttg acaaacattg tatgaacaaa  118740
aataatcctc agcaatgttc aactaaggct cttcaatgtt ttagttttga tttatcctac  118800
tgagagtttt tgaagttcta gttagagaaa aatgactcca tttgggcaac aggccttaga  118860
aattagtgaa tgctgtcaag aaagtttttt cctcaaggga atgtttgccc tctttggcaa  118920
accagtatcc ccaaatatca cccatagtgt tttattgtac ttgttttgga atattactta  118980
acagttttct ccatttaaac ataattttat aaattttaat actatttgtt aatagtgata  119040
ctttgtgagc aagttaaatt aatttttttc tagtttgaag attaaaaatc ttactgggtc  119100
catccaaaga gaatcattac ctaatacagt atttagaagg caaaatgatg gaaatttatg  119160
tccaacttgt tatttatgct agtttatttt ttacagctca atgttgtata taatgtgaag  119220
gcttctgggt cttctagaag acgaagatct atccaaaatc aagaagcctt tgatttagat  119280
gttgctgtaa aagaaaataa agatgatctc aatcatgtgg atttgaatgt gtgtacaagg  119340
taagtgtctg cttaggtctc tcttcttttt ttcctttaaa aaatagactt gaaggtttaa  119400
ttatgtatag ttgtctatat caatctaaga gttatattga acaaagaatt cagttatgca  119460
ctacacttca gattacaaac tagaaatact actaattata ttcaagcatt tattagatgc  119520
atacaaaaat tatttacaag ttttccctgg acgtataaca catttgaata gaacagtgta  119580
tatataaatt aataaaactc aggtctaatt taggaaaact ttaaattaag tcaatcatat  119640
ttaatacttc aaaaatggtt atttcttgtt atgagttatt tttctgtaga aataattatt  119700
tcgggttcat attgaacctt aactgttagg catttaaccc aaaactttat gataacatgc  119760
aaattcaatc aagaggatag ttttttttta ggtacattga aaatattcca gtttaggagt  119820
ttctcatctt ggataattag acacttaaca gctgaagctt ctgggagtac tttttaagtt  119880
gactcttaaa ttgttctata tccaaagcat ctgagaatct tgttaataag gaaaaagggt  119940
tctacctcaa ccctaccgac ttcacagtaa gactgggaag ctgcagattt ttggtcattc  120000
cactgcacac aggagtttga gcacactcct tgtgaaagtt cttgaataga ggcttcactt  120060
ttttttcttt catgaatcta ttctcttaca tctgcattat ttggtattga gctgggactt  120120
aaagatgcac tggcattgag gagctgctgt ttgctcttct aaaatatccc atagtgtcct  120180
ggtttaactt agcttattgt tgggctagaa gtccctgatg tggtcctgag ctggcagatg  120240
ttcttcaagg tcatctctgg gtgttcatcc aggtggccag ccttcacagc tattgcctgg  120300
acccagtctc cgccattact gctactgtct gtctttatct ttggaccttc ttgttcatga  120360
ttttggggta aaatgtccca catttgtccc attcttcacc ttcttgggca ttttgggcca  120420
```

-continued

```
gcagcaaggg gatatcagaa tctctgtgtt ggcatccttt tcagctgaga aaaaagtagg  120480
actccaatta ttttttacga atcttccaat tggtctctgt tatagaataa caacttcaag  120540
ttattactat tattataaac aataacaacc tacagtaatt acaaacttat atgccaggca  120600
cggcaccaaa cacttttaca tgcatatcat ttaattctta caggaactct gtaaagtatg  120660
tgttattatt atccctgctt ttctcaaatt cctggcctca agtgatcctc ctgcgttggc  120720
ctcccaaagt gctgggctta caggcatgag ccactgtgcc ccacctattc ttgctttttct  120780
cattcattta tttattacct cagcaagtat tgcttgagtc tctactatgt gccaggcatg  120840
gtgtctgtgt gtcaggcgtg ggaatataat tgtaagccaa aaaagatgca agctctgcct  120900
tgtggaactt gctgtttgag gggatacag aaattaatgg aaacaatccc ctaagcaagc  120960
ctaaaattct aattttgaaa agggcaaaga agaagaccct catggagtta agagagggag  121020
atttttacct cttaagagac atcaagtgaa gaaacatgag aaaaatgagg tggggaacca  121080
gaattcagac tgtgaagagg cctcagcatt tataggggtt catgtaagga tgcaggattt  121140
ccagttttaa gcatcaggaa tcaggtggac aacagagttt gggtggtagg tagagcctga  121200
agaagggaaa tgttttcatg tgagggtagg ggttttataa aaaggattta aatgctgcta  121260
ctagttttct gagaaaaatc tggtatgaag gacaaataac atttaggtgt attttttcag  121320
cagcacatta taaaaagatt acttgatatt tcagacactt tattcctatc aacagggtcc  121380
aagaccttac ctcataccag gctttctgtg tggcatgata gtttaacaaa ttctgcccca  121440
ggcttggtag agagatcaga tcaaccaagg tacttttaat atgtactgaa agtataatct  121500
gcattgtgct tttaaatgtt taagcatatt gactgttttt ttctcatcta tatttttttc  121560
tcatatgcaa acacctccag tttcaatcca tttattagtt ctcaataaca tctattttgg  121620
ctcagtgcat tgccagcaga tggtttcagt tgcttcggat tgcagagcca gctgaagtca  121680
gcagttgtac tgtatggctt ttcaatcagt catgtttggc aggcatgggt tttctgctct  121740
aaaaagcaag atttttctaa cagcccttct ttcttttgcc atttaaaagg acaacaggta  121800
ctaacttaat gctatgattc ttttaaattg gaggcaaaca tctttccata atcacttagc  121860
tgggctcctt ctgctctaaa tgaaaagctc ttgccatcaa ttcattttat aaaaatattt  121920
atttccaagc agacaaaatg ttgttggtgc ccagatcctt tgatgctcac atcacgtaca  121980
acagggcgag agaaggatgc agtgtaataa aactttccaa ggcttgtaat tccctcacgg  122040
tggccaaaga aaacagaaaa tgttcttcaa gtatatggga gaacaaaggg atggcttctc  122100
cctactggtc tgatgtttct aaaatcagac gaataaaagg ttgctaagac cttggatggg  122160
acctatcact aagtggtcaa gtgatgcctc cttctcaggg cctggctttc agcttgcaag  122220
tttggtgctg tcaacttttg agaaaaggaa aagtgcaatt ctgtttggaa tcaccactag  122280
aaaatagagt tgtctgttga aaggatgtat attgtactgt cacagtttat aagcacaagc  122340
ctcttacatt gcaggcattg catactatct gtcagatgaa cacattgttg tatcattatt  122400
ccttatatgg ttaaaagttt caagattacc acacatgtaa gaaaatgata acctgtttta  122460
aaattctcta tagggaattt tatttgaact caaacagtgt ttggaataac atttggtggg  122520
tttgattttt gtatgaagat aatttgataa cagctatggg tttttcctga ggagttttca  122580
ttcatcctcc ctctttgatt tagcttttcg ggcccgggta ggagtggcat ggctcttatg  122640
gaagttaacc tattaagtgg ctttatggtg ccttcagaag caatttctct gagcgagaca  122700
gtgaagaaag tggaatatga tcatggaaaa ctcaacctct atttagattc tgtaagtagt  122760
aaaacataag gtaactgttg acaaagccac tgtgttttgt attcaggtgt ctaccttact  122820
ttaagtatgt tttctttaat tcattgttat ttcaactttt tgtgtccctg aatgagttta  122880
acatggcaac catatattta tctccattag aaagacataa gtataaaatc agtttagaga  122940
gttgctatta atgacgagcc tgatgaaggc cttcataact aaatctttat gtcatgccag  123000
atgtgaaata catagaaatt tccatagtat aattaaaaaa attcaaccca gatctgaatt  123060
tgagagcctg tctgcctcag ggagttgcct aggctggagt gcagtggtgc aatcgtagct  123120
cactgcaacc tccaactcct gggctcaagt gatcctccca ctgcaggctc ctgagtagct  123180
gggaccacag gtgcatgcca ccatgcctag ataatttcat gagaattttt tgtggagata  123240
gggtctcatt ttgttgccca ggctggtttt gaactcctga cttcaagtga tcttctggtc  123300
ttggcttctc aaagtgttgg gattacaggt gtgagccgcc atgcctggct ggaagacgaa  123360
agtcttaatt acacatttta aaattcttcc atgaagcttt taacaaacct taaaggggtt  123420
catattctta ccttgaaaaa ttaggtgcta aatcatggaa gactattctc agagatttga  123480
tcttgacata gaattgttac ataaccttcg tgtactcttt ccattgctga atgagtacta  123540
ctgattcaag aataaagtgc acacagtgtg tagggaaagg taagtgaaga attccagact  123600
ctacttggta tgtctcaaaa ctggtggtat gtaagtttat tcttttctta tagcatctat  123660
atgagcttca taggttgaac tgatattgag ttcatagtat tctaaggatt tcatattaca  123720
tgggtgggtt tgtatgtttc ttatttcagt tttgctaagt atgaatcaga aatatattgc  123780
tgaatatatg cttttaaaaa gatagttctt gaatggtctc atttgtttta gcacttcaaa  123840
accactttgg ttaaagccct gttaaaacta attcagtctc aatataatgt taaataacag  123900
tctctagatt cttttgctgt ttaggaatta tcttacatta agcactgctc aaaagccatt  123960
ggcctgattt ggaacttgaa aaacaaattt aaggttttag tttagttgtg taattggttt  124020
tggagtttgt cttctatctt tgatgctctt gttaatggtt attttaattt gagtgtccag  124080
tactctttga gtggtcagtt tgacttttca tttactacta ttggcaaata agggaatgtt  124140
tgaaggaatt tactaatttc tgattcttta atgagtgttg ttgccaaatt ggccaaatct  124200
gtctctcttg gagacagata ggctggcttt gtgtacccca tctcagtcat tggctgtgga  124260
gtacagcccc atcttagtta cctcacctac tgggtgacat ggcttgcatg agctgagggt  124320
gattcccagg agaaggaggc tgctgtgagc cattagtagt aactgggggt ggggtgcacc  124380
atctgagaca ggagatctag gtgcatgcac cctaaggctt gctgcttact taaccactct  124440
aattctcagt atcccattca gcaaaatgga actaagaaca atacctttttt gtaagcattg  124500
ttttacaagt taaataagat agttcatagg aagtacttac tgcagtatct gacatgtaga  124560
aatcctccct aagtgttagt ctctgtttcc taaaatgatg agaaaaaaga aatgtcttta  124620
cttaatcatg aacacacagt gtgccaaccc cttaagactc ttttgtattt ctcaaggtaa  124680
atgaaaccca gttttgtgtt aatattcctg ctgtgagaaa ctttaaagtt tcaaataccc  124740
aagatgcttc agtgtccata gtggattact atgagccaag taagtatgct ctggagttct  124800
taatacttta gaaattaagc caggcattca ttcatttatt ggaagtgacc acacattgga  124860
ttggttctgt ggcgagggca ggatttggta ggagaaagta caggaggcgg gggggcagga  124920
agtgagcatt ccatttcagt gaagactatt gataatttac aagggtcaca tgataggttt  124980
tagcatatga aatttaaaaa tgatatattt tttcataatg ttttagattt ttaactcaca  125040
attataaact ttacaaagaa aaattggcat atagagtcca gttatgtctc atttgcaagg  125100
tattgcttct attccaagca cccattccat ctgtttccag ctttaaaatg ggagttctta  125160
```

-continued

```
atgtggcaca tatacaccat ggaatactat gcagctataa aaaaggatga gttcatgtcc  125220
tttgtaggga catggatgaa gctggaaacc attctcagca aactatcgca aggacaaaaa  125280
accaaatgct gcatgttcgc actcataggt gggaattgac caatgagaac acttggacac  125340
agagagggga tcatcacata ccagggcctg tcatggggtt gggggaggag ggagggatag  125400
cattaggagt tatacctaat gtaaatgacg agttaacggg tgcagcacac caacatggca  125460
catgtataca tatgtaacaa acctgcacgt tgtgcacatg taccctagca cttaaagtat  125520
aataaaaaaa atgggagttc ttctaaaagt agagctacca tttgacccca caatcccgtt  125580
actggatata tacccaaagg acaataaatt gttctaccaa aaagccacct gcactcatat  125640
gtttatcaca gcactaattc acaatagcaa agacaggtca tcgacctagg tgcccatcaa  125700
ctgtgaattg gataaataaa atgtggtaga tgtacatcat ggaatactat acagccataa  125760
aaaagaacta aattatgtct tttgcagcaa catggatgca gctgaaggtc attattctaa  125820
gtgaattaat gaagaaacag aaaaccaaat atcacatgtt ctcacttata agtgggagct  125880
gaacattggg tacacatgga cataaaaatg ggaacagtag acactgggga cttcaaaagt  125940
ggggagggag agggggaata agggctgaaa cactctctat tgggtacaat gttcattatt  126000
tgggtgacag gatcaataga agcccaaacc tcagcatcac ataatatacc cttgtaacaa  126060
acttgtacat gtacccctga acagtaaata aataagtaac aaataataaa taaaatggga  126120
cttcttcagg agagaacatg aacagcatct gcaatgcagt agcatcggct ggagttagct  126180
gtttctttat tgagggagtc tggtgttttg ccgaaactta cacttgataa cagattttta  126240
aaagtgtgtc aagaaaaata tagcctgttt ggaaaataac ttgagcttct ttgattttac  126300
tggtaacttc ttatttgtat aaaatgatgg aaatttagga cgtaaaaata gagagctggt  126360
ctggagatgg cccaagttta ataggatgaa tccatgttca gtcagaggga ctttttgtat  126420
gtgatctctg gcctaatgtt tctaattgta atatgtctta ttttgaataa gcgcttgtgg  126480
tggctcagaa tcatcacaat gcatgagaag catgaacatt tttgtgtgtt aggtagttgt  126540
agataattac actttaaatg agatgaactt gttcccattg ttgttagtgt ttcatagagt  126600
attcaagact aaggtgtagc accagttctc tcctcatagt caacaagcca gttcctcttg  126660
tcttttgcct cctgttggca ctgaggaaga gggttcaccc aggttcttgt gggacatttg  126720
ggaaacactg gtgtggcact ttttttctag tggagggatg gaatacactg tggagaccca  126780
atgacagtaa ctagttgtcc aactttatta ctttacttag ttgcaaaatt ccccaattta  126840
tatttcttgg gtgcatgggg aacattttaa acatttaaga aacaaaaata attcagtcta  126900
tgcaaatttt tatggaaaac aacttactta tgaggaggcc attttaaaat gaaaatatgg  126960
gaaagatcag aataagctaa accttccaac ccattttaaa aaatctcaaa acacatttac  127020
gatatggaaa acagtctctg aaaaatcatg aataaatttg aaaatagaat atgtttttta  127080
aaaattataa aactcattta tgttttacag tgagttcact gtggtgttat aggtacttta  127140
agtagttttt gtcatgttcg cttttagata ctatatgctg agtgttttaa aacaaggtat  127200
tgcataggca gtcttccctt catatttatg tatttttta ctagagccca gggtaaatgc  127260
cccttttcag tagttctaat gattagaatt tgatttgagt gcatagagaa tgtcatccta  127320
aaataaactc ttgaggaggt taaacagtcc ttaactgaaa attctccctg atgcagtaag  127380
agattaaagt ggtgcttgtg attgcagtgt gcagctgcag tctatttgct ctcttttaat  127440
gctggccaac tgctggtggt agacagattg gactgagcgc attgtttctc tcttggattt  127500
ggttagtact ttggaccact cttggacatt tcagttgttt cttgtaaaga aaaataaaat  127560
taggttaaga atggaaaact cagaaaagtg tatcgaaatg ctcttatatt ttggcaaagt  127620
caatgtttct aaacaaggga gccgtgtgaa ctgatgtctg cttctttgaa cagggagaca  127680
ggcggtgaga agttacaact ctgaagtgaa gctgtcctcc tgtgaccttt gcagtgatgt  127740
ccagggctgc cgtccttgtg aggatggagc ttcaggctcc catcatcact cttcagtcat  127800
ttttattttc tgtttcaagc ttctgtactt tatggaactt tggctgtgat ttatttttaa  127860
aggactctgt gtaacactaa catttccagt agtcacatgt gattgttttg ttttcgtaga  127920
agaatactgc ttctatttg aaaaaagagt tttttttctt tctatggggt tgcagggatg  127980
gtgtacaaca ggtcctagca tgtatagctg catagatttc ttcacctgat ctttgtgtgg  128040
aagatcagaa tgaatgcagt tgtgtgtcta tattttcccc tctcaaaatc ttttagaatt  128100
tttttggagg tgtttgtttt ctccagaata aaggtattac tttagaatag gtattctcct  128160
cattttgtga aagaaatgaa cctagattct taagcattat tacacatcca tgtttgctta  128220
aagatggatt tccctgggaa tgggagaaaa cagccagcag gaggagcttc atctgttccc  128280
ttcccacctc caacctagcc ctactgccca ccccacccca acccacccca tgcccagtgg  128340
tctcagtaga tacttcttaa ctggaaattc tttcttttca gaatctaggt ggtgaatttt  128400
ttttaagtgg cacggtcttt ttctgcttga aatctgatca cacccccag ccattgccct  128460
ccctctcttt ttcctctgta gagaaatgtg aggggcagta catttactgt gcttttcaca  128520
ccatctcaga ggttgaggag catactgaaa attgccctgg ggggtgctgg gtgtgctgtc  128580
tccttcccac atcctcagcc ccacaccagc tctatttcag gggtgagagt cagagagcac  128640
tgcaatatgt gcttcatggg atttcgattc gaagatccta gaccagggag acactgtgag  128700
ccagggatac aacaaaatac taggtaagtc actgcagacc gacctccctg cagtttggga  128760
aagaagctgg gtttgtggag aatcagagca tcttgacatg actgctgacc taaagatccc  128820
tggcattggc cagggatcct gtggaacctc ttctagttca ggggtgtgag cattagactg  128880
ccagttgtct agtgacatct gatgcttgct gtgaactttt aagatccccg aatcctgagc  128940
acctcaatct ttaattgccc tgtattccga agggtaatat aatttatctg gatggaaatt  129000
ttaaagatga atcccccttt tttcttttct tctctctttt ctttccttct ccctttcttc  129060
tttgccttct aaatatactg aaatgattta gatatgtgtc aacaattaat gatcttttat  129120
tcaatctaag aaatggttta gtttttctct ttagctctat ggcatttcac tcaagtggac  129180
aggggaaaaa gtaattgcca tgggctccaa agaatttgct ttatgttttt agctatttaa  129240
aaataaatcc atcaaaaata aagtatgcaa atgtatcttt taaagttaat ttttaaaaat  129300
gctcttattt tagtgaattt tcagaaatta tagtggaatg gatgctcata tattgcttat  129360
ggatattttg gataccaaag taggaataac tgacattcag tattttaaag ctggcaaacc  129420
tgtacataga aaatagatcc ccagacagtg gtctatgaag agggcagtta agtatcaaat  129480
acttaatttt cttgcctttt tttcttaagt ggggaaaagt ttctagatct cttacacctc  129540
tgacacaatc tgttctaaaa caggcacttg taatgttggg gcctccttgt aaacgtgttt  129600
ttgcccttta ctctctggga gttctttaaa ggtgaaatca tcttacaaag aaattggggg  129660
agggtcttgg caaaggactt tcccctcctc tttcctggcc tgggaacctt atactgacaa  129720
tcaatacttt atattttaaa gtatataatt tatagttaac ttctagtgta atatattagg  129780
aaacactaga atggaaaggc cattggaaga caggttgtat cttttttaga ccatatttcc  129840
ttgtttaaaa actatcattt gaatactttt ttggtgaaga actccatgtt ttcaagttaa  129900
```

-continued

```
aggtcacctc gtaggccagg cgcagtggct catgcctgta atcccagcac tctgggaggc  129960
tgaggcgggt gaatcacaag gttaggagtt tgagaccagc ctggccaata tggtgaaacc  130020
ccgtccctac taaaaataca aaatttagcc aggcgtggtg gcatgcacct gtagtcccac  130080
ctactcggga ggctgaggca ggagaatcac ttgaacctga gagacagagg ttgcagtgag  130140
ccgagatcac gccactgcac tccagcctgg gggacagagt gagattctgt ctcaaaaaac  130200
aaaaaacaaa aaagtcacct tgtaactcat ctctttttat tgtaagttta ttaaaaatga  130260
agaggacaac aatgagaagg aacataaagg gttagctagc actgtctcct ggtgcatggg  130320
gctgtgcaga tgtcccggcc acttcttcct tcatacttcc cttagagaac ttgctctgct  130380
acaagcagtg ggcttggact aaaagtgatt aaaataccac aggcataagg agaaaaggag  130440
tatatgtagt agtaataatt actagtataa attattttct tcacatgcta tgagtaataa  130500
tattaaaaaa ctcattttac cattaagatt ccttatgctg aagctcttcc atttagaata  130560
ctgtcaatgt catttactgg tatgaactaa agtccccctt cttttccact cactgggaac  130620
cttagtaaaa caccagcata tcttacctct ctttctgact ggccgatgct tccagagact  130680
gaatgttggg aaaacctagt agccaaacaa ttctaggaca gaataacatt tttatatttg  130740
gttccaccat cttattacat ttagttatag ttttaaaaaa gaaattcaag cccattaaaa  130800
tatgtctggt caatgaaatg cttcctttta ttgtgttgtg ctattgtact ttgtttttca  130860
aaacattgta aaaatagtat ctttggttta gtattttgga ttatatatta taatctgagg  130920
agtgttttgc ttatgtagaa tccagatata tttctgttac ctaggagatg ttacttacat  130980
atgtaatact gtatcctgca cgtggaaata ttcagaattg tagatagcat aactctccct  131040
gctcctattc ttttgagcct aggtataatt tttttttttt ttttagaaaa agacatattt  131100
agctttaatt tctatttatg ctaaacatat ttataagtag tctgtcaata taataccaac  131160
tatttttatt tttacataat tcaattattt catttgacat gtctggcaga ctcaagacat  131220
taagtaaaaa attggaacta tgatttttct ttgtcatttt ttaaaaaaga attattttat  131280
taacctgctg gcatataatc tggagttctt ttcacaacct tacttttttct gatttgcttt  131340
attgaatgat tgaatactca tttctttcta aaaatatgtt gtaaattctc ccttggcaag  131400
atttctccct atgagggtag ttattatttg agtctgccaa gtggttacca tggggcaagg  131460
tgccatgatg tattcttggg tgcattggtt ttttgcgcat tgtaaattta agacacttat  131520
agtaagtgga ctcattcata gatgagtttc agaacctttt acgttctcgg tagaggcttc  131580
tgtcggacag gcagaagagt gtattcctca cttttttttt tgtcttcaaa ttccagtaag  131640
gcatagcact tttaagaaat tagaattttt ctatcatcta tgcaaatgat atttatgtta  131700
atattaaata tcttatgtta cactgggagt aatttgaggt gcaattattt ttattactac  131760
tttgaataga ggaccattat ccttctttct tcagaaaact aagaagtaag tgtaactttt  131820
aaagtaagta tatatcagtg agagtaggct tgttttacaa ctatttctag ccagtgagtt  131880
gtgttttcat gtctcatcaa aagacaatac cacattgcat cattttacaa aatatgttgt  131940
cattttcatt tcagttgtaa cataggaaaa tagatatttc ctagatgatt tctgagtttc  132000
ttactgcaaa gaacagttat aaattggtat acatgtgtct ctgtaatagg gataatattg  132060
atatatctgt tgctacatat ttaagaatca ttctatctta tgttgtcttg aggccaagat  132120
ttaccacgtt tgcccagtgt attgaattgg tggtagaagg tagttccatg ttccatttgt  132180
agatctttaa gattttatct ttgataactt taatagaatg tggctcagtt ctggtccttc  132240
aagcctgtat ggtttggatt ttcagtaggg gacagttgat gtggagtcaa tctctttggt  132300
acacaggaag ctttataaaa tttcattcac gaatctctta ttttgggaag ctgttttgca  132360
tatgagaaga acactgttga aataaggaac taaagcttta tatattgatc aaggtgattc  132420
tgaaagtttt aatttttaat gttgtaatgt tatgttattg ttaattgtac tttattatgt  132480
attcaataga aaatcatgat ttattaataa aagcttaaat tctcatctat tt          132532

SEQ ID NO: 2            moltype = RNA  length = 9401
FEATURE                 Location/Qualifiers
source                  1..9401
                        mol_type = mRNA
                        organism = Homo sapiens
SEQUENCE: 2
atagttgcta tgaatttctc ctcacaagga tgggcctgtt tactcaccct gggcatcgtt  60
ggtagagcgc tagtgtaaac agcctgagga acccggtggg ccggggaagt gggcgcgctc  120
tgttctccgc ggccagctgg gacgccgggc caggtggggc cgcctgcgtt tagcaactgc  180
tttctcaccc cctggatttg cgatgtttgc cacagcagcg agaagcgcca ttgtaatggg  240
gatgggaggg gtggagcctc caagtcctgt ctcaatttag atctctcact ctgctgttag  300
gcgcgcccat ttcagattac taaactcgaa ttaagaggga aaaaaaatca gggaggaggt  360
ggcaagccac accccacggt gcccgcgaac ttccccggca gcggactgta gcccaggcag  420
acgccgtcga gatgcagggc ccaccgctcc tgaccgccgc ccacctcctc tgcgtgtgca  480
ccgccgcgct ggccgtggct cccgggcctc ggtttctggt gacagcccca gggatcatca  540
ggcccggagg aaatgtgact attggggtgg agcttctgga acactgccct tcacaggtga  600
ctgtgaaggc ggagctgctc aagacagcat caaacctcac tgtctctgtc ctggaagcag  660
aaggagtctt tgaaaaaggc tcttttaaga cacttactct tccatcacta cctctgaaca  720
gtgcagatga gatttatgag ctacgtgtaa ccggacgtac ccaggatgag attttattct  780
ctaatagtac ccgcttatca tttgagacca agagaatatc tgtcttcatt caaacagaca  840
aggccttata caagccaaag caagaagtga agtttcgcat tgttacactc ttctcagatt  900
ttaagcctta caaaacctct ttaaacattc tcattaagga ccccaaatca aatttgatcc  960
aacagtggtt gtcacaacaa agtgatcttg gagtcatttc caaaactttt cagctatctt  1020
cccatccaat acttggtgac tggtctattc aagttcaagt gaatgaccag acatactatc  1080
aatcatttca ggtttcagaa tatgtattac caaaatttga agtgactttg cagacaccat  1140
tatattgttc tatgaattct aagcatttaa atggtaccat cacggcaaag tatacatatg  1200
ggaagccagt gaaaggagac gtaacgctta catttttacc tttatccttt tggggaaaga  1260
agaaaaatat tacaaaaaca tttaagataa atggatctgc aaacttctct tttaatgatg  1320
aagagatgaa aaatgtaatg gattcttcaa atggactttc tgaatacctg gatctatctt  1380
cccctggacc agtagaaatt ttaacccacag tgacagaatc agttacaggt atttcaagaa  1440
atgtaagcac taatgtgttc ttcaagcaac atgattacat cattgagttt tttgattata  1500
ctactgtctt gaagccatct ctcaacttca cagccactgt gaaggtaact cgtgctgatg  1560
gcaaccaact gactcttgaa gaaagaagaa ataatgtagt cataacagtg acacagagaa  1620
actatactga gtactggagc ggatctaaca gtggaaatca gaaaatggaa gctgttcaga  1680
```

-continued

```
aaataaatta tactgtcccc caaagtggaa cttttaagat tgaattccca atcctggagg  1740
attccagtga gctacagttg aaggcctatt tccttggtag taaaagtagc atggcagttc  1800
atagtctgtt taagtctcct agtaagacat acatccaact aaaaacaaga gatgaaaata  1860
taaaggtggg atcgcctttt gagttggtgg ttagtggcaa caaacgattg aaggagttaa  1920
gctatatggt agtatccagg ggacagttgg tggctgtagg aaaacaaaat tcaacaatgt  1980
tctctttaac accagaaaat tcttggactc caaaagcctg tgtaattgtg tattatattg  2040
aagatgatgg ggaaattata agtgatgttc taaaaattcc tgttcagctt gtttttaaaa  2100
ataagataaa gctatattgg agtaaagtga aagctgaacc atctgagaaa gtctctctta  2160
ggatctctgt gacacagcct gactccatag ttgggattgt agctgttgac aaaagtgtga  2220
atctgatgaa tgcctctaat gatattacaa tggaaaatgt ggtccatgag ttggaacttt  2280
ataacacagg atattattta ggcatgttca tgaattcttt tgcagtcttt caggaatgtg  2340
gactctgggt attgacagat gcaaacctca cgaaggatta tattgatggt gtttatgaca  2400
atgcagaata tgctgagagg tttatggagg aaaatgaagg acatattgta gatattcatg  2460
acttttcttt gggtagcagt ccacatgtcc gaaagcattt tccagagact tggatttggc  2520
tagacaccaa catgggttac aggatttacc aagaatttga agtaactgta cctgattcta  2580
tcacttcttg ggtggctact ggttttgtga tctctgagga cctgggtctt ggactaacaa  2640
ctactccagt ggagctccaa gccttccaac catttttcat tttttgaat cttccctact  2700
ctgttatcag aggtgaagaa tttgctttgg aaataactat attcaattat ttgaaagatg  2760
ccactgaggt taaggtaatc attgagaaaa gtgacaaatt tgatattcta atgacttcaa  2820
atgaaataaa tgccacaggc caccagcaga cccttctggt tcccagtgag gatggggcaa  2880
ctgttctttt tcccatcagg ccaacacatc tgggagaaat tcctatcaca gtcacagctc  2940
tttcacccac tgcttctgat gctgtcaccc agatgatttt agtaaaggct gaaggaatag  3000
aaaaatcata ttcacaatcc atcttattag acttgactga caataggcta cagagtaccc  3060
tgaaaacttt gagtttctca tttcctccta atacagtgac tggcagtgaa agagttcaga  3120
tcactgcaat tggagatgtt cttggtcctt ccatcaatgg cttagcctca ttgattcgga  3180
tgccttatgg ctgtggtgaa cagaacatga taaattttgc tccaaatatt tacattttgg  3240
attatctgac taaaaagaaa caactgacag ataatttgaa agaaaaagct ctttcattta  3300
tgaggcaagg ttaccagaga gaacttctct atcagaggga agatggctct ttcagtgctt  3360
ttgggaatta tgacccttct gggagcactt ggttgtcagc ttttgtttta agatgtttcc  3420
ttgaagccga tccttacata gatattgatc agaatgtgtt acacagaaca tacacttggc  3480
ttaaaggaca tcagaaatcc aacggtgaat tttgggatcc aggaagagtg attcatagtg  3540
agcttcaagg tggcaataaa agtccagtaa cacttacagc ctatattgta acttctctcc  3600
tgggatatag aaagtatcag cctaacattg atgtgcaaga gtctatccat tttttggagt  3660
ctgaattcag tagaggaatt tcagacaatt atactctagc ccttataact tatgcattgt  3720
catcagtggg gagtcctaaa gcgaaggaag ctttgaatat gctgacttgg agagcagaac  3780
aagaaggtgg catgcaattc tgggtgtcat cagagtccaa actttctgac tcctggcagc  3840
cacgctccct ggatattgaa gttgcagcct atgcactgct ctcacacttc ttacaatttc  3900
agacttctga gggaatccca attatgaggt ggctaagcag gcaaagaaat agcttgggtg  3960
gttttgcatc tactcaggat accactgtgg ctttaaaggc tctgtctgaa tttgcagccc  4020
taatgaatac agaaaggaca aatatccaag tgaccgtgac ggggcctagc tcaccaagtc  4080
ctcttgctgt ggtacagcca acggcagtta atatttccgc aaatggtttt ggatttgcta  4140
tttgtcagct caatgttgta tataatgtga aggcttctgg gtcttctaga agacgaagat  4200
ctatccaaaa tcaagaagcc tttgatttag atgttgctgt aaaagaaaat aaagatgatc  4260
tcaatcatgt ggatttgaat gtgtgtacaa gcttttcggg cccgggtagg agtggcatgg  4320
ctcttatgga agttaaccta ttaagtggct ttatggtgcc ttcagaagca atttctctga  4380
gcgagacagt gaagaaagtg gaatatgatc atggaaaact caacctctat ttagattctg  4440
taaatgaaac ccagttttgt gttaatattc ctgctgtgag aaactttaaa gtttcaaata  4500
cccaagatgc ttcagtgtcc atagtggatt actatgagcc aaggagacag gcggtgagaa  4560
gttacaactc tgaagtgaag ctgtcctcct gtgacctttg cagtgatgtc cagggctgcc  4620
gtccttgtga ggatggagct tcaggctccc atcatcactc ttcagtcatt tttattttct  4680
gtttcaagct tctgtacttt atggaacttt ggctgtgatt tatttttaaa ggactctgtg  4740
taacactaac atttccagta gtcacatgtg attgttttgt tttcgtagaa gaatactgct  4800
tctattttga aaaaagagtt ttttttcttt ctatggggtt gcagggatgg tgtacaacag  4860
gtcctagcat gtatagctgc atagatttct tcacctgatc tttgtgtgga agatcagaat  4920
gaatgcagtt gtgtgtctat attttcccct ctcaaaatct tttagaattt ttttggaggt  4980
gtttgttttc tccagaataa aggtattact ttagaatagg tattctcctc attttgtgaa  5040
agaaatgaac ctagattctt aagcattatt acacatccat gtttgcttaa agatggattt  5100
ccctgggaat gggagaaaac agccagcagg aggagcttca tctgttccct tcccacctcc  5160
aacctagccc tactgcccac cccaccccaa ccccaccccat gcccagtggt ctcagtagat  5220
acttcttaac tggaaattct ttcttttcag aatctaggtg gtgaattttt tttaagtggc  5280
acggtctttt tctgcttgaa atctgatcac accccccagc cattgccctc cctctctttt  5340
tcctctgtag agaaatgtga ggggcagtac atttactgtg cttttcacac catctcagag  5400
gttgaggagc atactgaaaa ttgccctggg gggtgctggg tgtgctgtct ccttccccaca  5460
tcctcagccc cacaccagct ctatttcagg ggtgagagtc agagagcact gcaatatgtg  5520
cttcatggga tttcgattcg aagatcctag accagggaga cactgtgagc cagggataca  5580
acaaaatact aggtaagtca ctgcagaccg acctccctgc agtttgggaa agaagctggg  5640
tttgtggaga atcagagcat cttgacatga ctgctgacct aaagatccct ggcattggcc  5700
agggatcctg tggaacctct tctagttcag gggtgtgagc attagactgc cagttgtcta  5760
gtgacatctg atgcttgctg tgaactttta agatccccga atcctgagca cctcaatctt  5820
taattgccct gtattccgaa gggtaatata atttatctgg atggaaattt taaagatgaa  5880
tccccctttt ttcttttctt ctctcttttc tttccttctc cctttcttct ttgccttcta  5940
aatatactga aatgatttag atatgtgtca acaattaatg atcttttatt caatctaaga  6000
aatggtttag tttttctctt tagctctatg gcatttcact caagtggaca ggggaaaaag  6060
taattgccat gggctccaaa gaatttgctt tatgttttta gctatttaaa aataaatcca  6120
tcaaaaataa agtatgcaaa tgtatctttt aaagttaatt tttaaaaatg ctcttatttt  6180
agtgaatttt cagaaattat agtggaatgg atgctcatat attgcttatg gatattttgg  6240
ataccaaagt aggaataact gacattcagt attttaaagc tggcaaacct gtacatagaa  6300
aatagatccc cagacagtgg tctatgaaga gggcagttaa gtatcaaata cttaattttc  6360
ttgccttttt ttcttaagtg gggaaaagtt tctagatctc ttacacctct gacacaatct  6420
```

-continued

```
gttctaaaac aggcacttgt aatgttgggg cctccttgta aacgtgtttt tgccctttac  6480
tctctgggag ttctttaaag gtgaaatcat cttacaaaga aattgggggga gggtcttggc  6540
aaaggacttt cccctcctct ttcctggcct gggaacctta tactgacaat caatacttta  6600
tattttaaag tatataattt atagttaact tctagtgtaa tatattagga aacactagaa  6660
tggaaaggcc attggaagac aggttgtatc ttttttagac catatttcct tgtttaaaaa  6720
ctatcatttg aatacttttt tggtgaagaa ctccatgttt tcaagttaaa ggtcacctcg  6780
taggccaggc gcagtggctc atgcctgtaa tcccagcact ctgggaggct gaggcgggtg  6840
aatcacaagg ttaggagttt gagaccagcc tggccaatat ggtgaaaccc cgtccctact  6900
aaaaatacaa aatttagcca ggcgtggtgg catgcacctg tagtcccacc tactcgggag  6960
gctgaggcag gagaatcact tgaacctgag agacagaggt tgcagtgagc cgagatcacg  7020
ccactgcact ccagcctggg ggacagagtg agattctgtc tcaaaaaaca aaaaacaaaa  7080
aagtcacctt gtaactcatc tctttttatt gtaagtttat taaaaatgaa gaggacaaca  7140
atgagaagga acataaaggg ttagctagca ctgtctcctg gtgcatgggg ctgtgcagat  7200
gtcccggcca cttcttcctt catacttccc ttagagaact tgctctgcta caagcagtgg  7260
gcttggacta aaagtgatta aaataccaca ggcataagga gaaaaggagt atatgtagta  7320
gtaataatta ctagtataaa ttattttctt cacatgctat gagtaataat attaaaaaac  7380
tcattttacc attaagattc cttatgctga agctcttcca tttagaatac tgtcaatgtc  7440
atttactggt atgaactaaa gtccccccttc ttttccactc actgggaacc ttagtaaaac  7500
accagcatat cttacctctc tttctgactg gccgatgctt ccagagactg aatgttggga  7560
aaacctagta gccaaacaat tctaggacag aataacattt ttatatttgg ttccaccatc  7620
ttattacatt tagttatagt tttaaaaaag aaattcaagc ccattaaaat atgtctggtc  7680
aatgaaatgc ttccttttat tgtgttgtgc tattgtactt tgtttttcaa aacattgtaa  7740
aaatagtatc tttggtttag tattttggat tatatattat aatctgagga gtgttttgct  7800
tatgtagaat ccagatatat ttctgttacc taggagatgt tacttacata tgtaatactg  7860
tatcctgcac gtggaaatat tcagaattgt agatagcata actctccctg ctcctattct  7920
tttgagccta ggtataattt tttttttttt tttagaaaaa gacatattta gctttaattt  7980
ctatttatgc taaacatatt tataagtagt ctgtcaatat aataccaact atttttattt  8040
ttacataatt caattatttc atttgacatg tctggcagac tcaagacatt aagtaaaaaa  8100
ttggaactat gatttttctt tgtcattttt taaaaaagaa ttattttatt aacctgctgg  8160
catataatct ggagttcttt tcacaacctt acttttctg atttgcttta ttgaatgatt  8220
gaatactcat ttctttctaa aaatatgttg taaattctcc cttggcaaga tttctcccta  8280
tgagggtagt tattatttga gtctgccaag tggttaccat ggggcaaggt gccatgatgt  8340
attcttgggt gcattggttt tttgcgcatt gtaaatttaa gacacttata gtaagtggac  8400
tcattcatag atgagtttca gaacctttta cgttctcggt agaggcttct gtcggacagg  8460
cagaagagtg tattcctcac tttttttttt gtcttcaaat tccagtaagg catagcactt  8520
ttaagaaatt agaatttttc tatcatctat gcaaatgata tttatgttaa tattaaatat  8580
cttatgttac actgggagta atttgaggtg caattatttt tattactact ttgaatagag  8640
gaccattatc cttctttctt cagaaaacta agaagtaagt gtaactttta aagtaagtat  8700
atatcagtga gagtaggctt gttttacaac tatttctagc cagtgagttg tgttttcatg  8760
tctcatcaaa agacaatacc acattgcatc attttacaaa atatgttgtc attttcattt  8820
cagttgtaac ataggaaaat agatatttcc tagatgattt ctgagtttct tactgcaaag  8880
aacagttata aattggtata catgtgtctc tgtaataggg ataatattga tatatctgtt  8940
gctacatatt taagaatcat tctatcttat gttgtcttga ggccaagatt taccacgttt  9000
gcccagtgta ttgaattggt ggtagaaggt agttccatgt tccatttgta gatctttaag  9060
attttatctt tgataacttt aatagaatgt ggctcagttc tggtccttca agcctgtatg  9120
gtttggattt tcagtagggg acagttgatg tggagtcaat ctctttggta cacaggaagc  9180
tttataaaat ttcattcacg aatctcttat tttgggaagc tgttttgcat atgagaagaa  9240
cactgttgaa ataaggaact aaagctttat atattgatca aggtgattct gaaagtttta  9300
atttttaatg ttgtaatgtt atgttattgt taattgtact ttattatgta ttcaatagaa  9360
aatcatgatt tattaataaa agcttaaatt ctcatctatt t                      9401

SEQ ID NO: 3           moltype = RNA  length = 9221
FEATURE                Location/Qualifiers
source                 1..9221
                       mol_type = mRNA
                       organism = Homo sapiens
SEQUENCE: 3
atagttgcta tgaatttctc ctcacaagga tgggcctgtt tactcaccct gggcatcgtt  60
ggtagagcgc tagtgtaaac agcctgagga acccggtggg ccggggaagt gggcgcgctc  120
tgttctccgc ggccagctgg gacgccgggc caggtggggc cgcctgcgtt tagcaactgc  180
tttctcaccc cctggatttg cgatgtttgc cacagcagcg agaagcgcca ttgtaatggg  240
gatgggaggg gtggagcctc caagtcctgt ctcaatttag atctctcact ctgctgttag  300
gcgcgcccat ttcagattac taaactcgaa ttaagaggga aaaaaaatca gggaggaggt  360
ggcaagccac accccacggt gcccgcgaac ttccccggca gcggactgta gcccaggcag  420
acgccgtcga gatgcagggc ccaccgctcc tgaccgccgc ccacctcctc tgcgtgtgca  480
ccgccgcgct ggccgtggct cccgggcctc ggtttctggt gacagcccca gggatcatca  540
ggcccggagg aaatgtgact attggggtgg agcttctgga acactgccct tcacaggtga  600
ctgtgaaggc ggagctgctc aagacagcat caaacctcac tgtctctgtc ctggaagcag  660
aaggagtctt tgaaaaaggc tcttttaaga cacttactct tccatcagac cccaaatcaa  720
atttgatcca acagtggttg tcacaacaaa gtgatcttgg agtcatttcc aaaacttttc  780
agctatcttc ccatccaata cttggtgact ggtctattca agttcaagtg aatgaccaga  840
catactatca atcatttcag gtttcagaat atgtattacc aaaatttgaa gtgactttgc  900
agacaccatt atattgttct atgaattcta agcatttaaa tggtaccatc acggcaaagt  960
atacatatgg gaagccagtg aaaggagacg taacgcttac atttttacct ttatcctttt  1020
ggggaaagaa gaaaaatatt acaaaaacat ttaagataaa tggatctgca aacttctctt  1080
ttaatgatga agagatgaaa aatgtaatgg attcttcaaa tggactttct gaatacctgg  1140
atctatcttc ccctggacca gtagaaattt taaccacagt gacagaatca gttacaggta  1200
tttcaagaaa tgtaagcact aatgtgttct tcaagcaaca tgattacatc attgagtttt  1260
ttgattatac tactgtcttg aagccatctc tcaacttcac agccactgtg aaggtaactc  1320
```

-continued

```
gtgctgatgg caaccaactg actcttgaag aaagaagaaa taatgtagtc ataacagtga  1380
cacagagaaa ctatactgag tactggagcg gatctaacag tggaaatcag aaaatggaag  1440
ctgttcagaa aataaattat actgtccccc aaagtggaac ttttaagatt gaattcccaa  1500
tcctggagga ttccagtgag ctacagttga aggcctattt ccttggtagt aaaagtagca  1560
tggcagttca tagtctgttt aagtctccta gtaagacata catccaacta aaaacaagag  1620
atgaaaatat aaaggtggga tcgccttttg agttggtggt tagtggcaac aaacgattga  1680
aggagttaag ctatatggta gtatccaggg gacagttggt ggctgtagga aaacaaaatt  1740
caacaatgtt ctctttaaca ccagaaaatt cttggactcc aaaagcctgt gtaattgtgt  1800
attatattga agatgatggg gaaattataa gtgatgttct aaaaattcct gttcagcttg  1860
tttttaaaaa taagataaag ctatattgga gtaaagtgaa agctgaacca tctgagaaag  1920
tctctcttag gatctctgtg acacagcctg actccatagt tgggattgta gctgttgaca  1980
aaagtgtgaa tctgatgaat gcctctaatg atattacaat ggaaaatgtg gtccatgagt  2040
tggaacttta taacacagga tattatttag gcatgttcat gaattctttt gcagtctttc  2100
aggaatgtgg actctgggta ttgacagatg caaacctcac gaaggattat attgatggtg  2160
tttatgacaa tgcagaatat gctgagaggt ttatggagga aaatgaagga catattgtag  2220
atattcatga cttttctttg ggtagcagtc cacatgtccg aaagcatttt ccagagactt  2280
ggatttggct agacaccaac atgggttaca ggatttacca agaatttgaa gtaactgtac  2340
ctgattctat cacttcttgg gtggctactg gttttgtgat ctctgaggac ctgggtcttg  2400
gactaacaac tactccagtg gagctccaag ccttccaacc atttttcatt tttttgaatc  2460
ttccctactc tgttatcaga ggtgaagaat ttgctttgga aataactata ttcaattatt  2520
tgaaagatgc cactgaggtt aaggtaatca ttgagaaaag tgacaaattt gatattctaa  2580
tgacttcaaa tgaaataaat gccacaggcc accagcagac ccttctggtt cccagtgagg  2640
atggggcaac tgttcttttt cccatcaggc caacacatct gggagaaatt cctatcacag  2700
tcacagctct ttcacccact gcttctgatg ctgtcaccca gatgatttta gtaaaggctg  2760
aaggaataga aaaatcatat tcacaatcca tcttattaga cttgactgac aataggctac  2820
agagtaccct gaaaactttg agtttctcat ttcctcctaa tacagtgact ggcagtgaaa  2880
gagttcagat cactgcaatt ggagatgttc ttggtccttc catcaatggc ttagcctcat  2940
tgattcggat gccttatggc tgtggtgaac agaacatgat aaattttgct ccaaatattt  3000
acattttgga ttatctgact aaaaagaaac aactgacaga taatttgaaa gaaaaagctc  3060
tttcatttat gaggcaaggt taccagagag aacttctcta tcagagggaa gatggctctt  3120
tcagtgcttt tgggaattat gacccttctg ggagcacttg gttgtcagct tttgttttaa  3180
gatgtttcct tgaagccgat ccttacatag atattgatca gaatgtgtta cacagaacat  3240
acacttggct taaaggacat cagaaatcca acggtgaatt ttgggatcca ggaagagtga  3300
ttcatagtga gcttcaaggt ggcaataaaa gtccagtaac acttacagcc tatattgtaa  3360
cttctctcct gggatataga aagtatcagc ctaacattga tgtgcaagag tctatccatt  3420
ttttggagtc tgaattcagt agaggaattt cagacaatta tactctagcc cttataactt  3480
atgcattgtc atcagtgggg agtcctaaag cgaaggaagc tttgaatatg ctgacttgga  3540
gagcagaaca agaaggtggc atgcaattct gggtgtcatc agagtccaaa ctttctgact  3600
cctggcagcc acgctccctg gatattgaag ttgcagccta tgcactgctc tcacacttct  3660
tacaatttca gacttctgag ggaatcccaa ttatgaggtg gctaagcagg caaagaaata  3720
gcttgggtgg ttttgcatct actcaggata ccactgtggc tttaaaggct ctgtctgaat  3780
ttgcagccct aatgaataca gaaaggacaa atatccaagt gaccgtgacg gggcctagct  3840
caccaagtcc tgtaaagttt ctgattgaca cacacaaccg cttactcctt cagacagcag  3900
agcttgctgt ggtacagcca acggcagtta atatttccgc aaatggtttt ggatttgcta  3960
tttgtcagct caatgttgta tataatgtga aggcttctgg gtcttctaga agacgaagat  4020
ctatccaaaa tcaagaagcc tttgatttag atgttgctgt aaaagaaaat aaagatgatc  4080
tcaatcatgt ggatttgaat gtgtgtacaa gcttttcggg cccgggtagg agtggcatgg  4140
ctcttatgga agttaaccta ttaagtggct ttatggtgcc ttcagaagca atttctctga  4200
gcgagacagt gaagaaagtg gaatatgatc atggaaaact caacctctat ttagattctg  4260
taaatgaaac ccagttttgt gttaatattc ctgctgtgag aaactttaaa gtttcaaata  4320
cccaagatgc ttcagtgtcc atagtggatt actatgagcc aaggagacag gcggtgagaa  4380
gttacaactc tgaagtgaag ctgtcctcct gtgacctttg cagtgatgtc cagggctgcc  4440
gtccttgtga ggatggagct tcaggctccc atcatcactc ttcagtcatt tttattttct  4500
gtttcaagct tctgtacttt atggaacttt ggctgtgatt tatttttaaa ggactctgtg  4560
taacactaac atttccagta gtcacatgtg attgttttgt tttcgtagaa gaatactgct  4620
tctattttga aaaaagagtt ttttttcttt ctatggggtt gcagggatgg tgtacaacag  4680
gtcctagcat gtatagctgc atagatttct tcacctgatc tttgtgtgga agatcagaat  4740
gaatgcagtt gtgtgtctat atttttcccct ctcaaaatct tttagaattt ttttggaggt  4800
gtttgttttc tccagaataa aggtattact ttagaatagg tattctcctc attttgtgaa  4860
agaaatgaac ctagattctt aagcattatt acacatccat gtttgcttaa agatggattt  4920
ccctgggaat gggagaaaac agccagcagg aggagcttca tctgttccct tcccacctcc  4980
aacctagccc tactgcccac cccaccccaa cccaccccat gcccagtggt ctcagtagat  5040
acttcttaac tggaaattct ttcttttcag aatctaggtg gtgaattttt tttaagtggc  5100
acggtctttt tctgcttgaa atctgatcac accccccagc cattgccctc cctctctttt  5160
tcctctgtag agaaatgtga ggggcagtac atttactgtg cttttcacac catctcagag  5220
gttgaggagc atactgaaaa ttgccctggg gggtgctggg tgtgctgtct ccttcccaca  5280
tcctcagccc cacaccagct ctatttcagg ggtgagagtc agagagcact gcaatatgtg  5340
cttcatggga tttcgattcg aagatcctag accagggaga cactgtgagc cagggataca  5400
acaaaatact aggtaagtca ctgcagaccg acctccctgc agtttgggaa agaagctggg  5460
tttgtggaga atcagagcat cttgacatga ctgctgacct aaagatccct ggcattggcc  5520
agggatcctg tggaacctct tctagttcag gggtgtgagc attagactgc cagttgtcta  5580
gtgacatctg atgcttgctg tgaactttta agatccccga atcctgagca cctcaatctt  5640
taattgccct gtattccgaa gggtaatata atttatctgg atggaaattt taaagatgaa  5700
tccccctttt ttcttttctt ctctcttttc tttccttctc cctttcttct ttgccttcta  5760
aatatactga aatgatttag atatgtgtca acaattaatg atcttttatt caatctaaga  5820
aatggtttag tttttctctt tagctctatg gcatttcact caagtggaca ggggaaaaag  5880
taattgccat gggctccaaa gaatttgctt tatgttttta gctatttaaa aataaatcca  5940
tcaaaaataa agtatgcaaa tgtatctttt aaagttaatt tttaaaaatg ctcttatttt  6000
agtgaatttt cagaaattat agtggaatgg atgctcatat attgcttatg gatattttgg  6060
```

```
ataccaaagt aggaataact gacattcagt attttaaagc tggcaaacct gtacatagaa  6120
aatagatccc cagacagtgg tctatgaaga gggcagttaa gtatcaaata cttaattttc  6180
ttgccttttt ttcttaagtg gggaaaagtt tctagatctc ttacacctct gacacaatct  6240
gttctaaaac aggcacttgt aatgttgggg cctccttgta aacgtgtttt tgccctttac  6300
tctctgggag ttctttaaag gtgaaatcat cttacaaaga aattggggga gggtcttggc  6360
aaaggacttt cccctcctct ttcctggcct gggaacctta tactgacaat caatacttta  6420
tattttaaag tatataattt atagttaact tctagtgtaa tatattagga aacactagaa  6480
tggaaaggcc attggaagac aggttgtatc ttttttagac catatttcct tgtttaaaaa  6540
ctatcatttg aatacttttt tggtgaagaa ctccatgttt tcaagttaaa ggtcacctcg  6600
taggccaggc gcagtggctc atgcctgtaa tcccagcact ctgggaggct gaggcgggtg  6660
aatcacaagg ttaggagttt gagaccagcc tggccaatat ggtgaaaccc cgtccctact  6720
aaaaatacaa aatttagcca ggcgtggtgg catgcacctg tagtcccacc tactcgggag  6780
gctgaggcag gagaatcact tgaacctgag agacagaggt tgcagtgagc cgagatcacg  6840
ccactgcact ccagcctggg ggacagagtg agattctgtc tcaaaaaaca aaaaacaaaa  6900
aagtcacctt gtaactcatc tctttttatt gtaagtttat taaaaatgaa gaggacaaca  6960
atgagaagga acataaaggg ttagctagca ctgtctcctg gtgcatgggg ctgtgcagat  7020
gtcccggcca cttcttcctt catacttccc ttagagaact tgctctgcta caagcagtgg  7080
gcttggacta aaagtgatta aaataccaca ggcataagga gaaaaggagt atatgtagta  7140
gtaataatta ctagtataaa ttattttctt cacatgctat gagtaataat attaaaaaac  7200
tcattttacc attaagattc cttatgctga agctcttcca tttagaatac tgtcaatgtc  7260
atttactggt atgaactaaa gtcccccttc ttttccactc actgggaacc ttagtaaaac  7320
accagcatat cttacctctc tttctgactg gccgatgctt ccagagactg aatgttggga  7380
aaacctagta gccaaacaat tctaggacag aataacattt ttatatttgg ttccaccatc  7440
ttattacatt tagttatagt tttaaaaaag aaattcaagc ccattaaaat atgtctggtc  7500
aatgaaatgc ttccttttat tgtgttgtgc tattgtactt tgtttttcaa aacattgtaa  7560
aaatagtatc tttggtttag tattttggat tatatattat aatctgagga gtgttttgct  7620
tatgtagaat ccagatatat ttctgttacc taggagatgt tacttacata tgtaatactg  7680
tatcctgcac gtggaaatat tcagaattgt agatagcata actctccctg ctcctattct  7740
tttgagccta ggtataattt ttttttttt tttagaaaaa gacatattta gctttaattt  7800
ctatttatgc taaacatatt tataagtagt ctgtcaatat aataccaact atttttattt  7860
ttacataatt caattatttc atttgacatg tctggcagac tcaagacatt aagtaaaaaa  7920
ttggaactat gatttttctt tgtcattttt taaaaaagaa ttatttttatt aacctgctgg  7980
catataatct ggagttcttt tcacaacctt actttttctg atttgcttta ttgaatgatt  8040
gaatactcat ttctttctaa aaatatgttg taaattctcc cttggcaaga tttctcccta  8100
tgagggtagt tattatttga gtctgccaag tggttaccat ggggcaaggt gccatgatgt  8160
attcttgggt gcattggttt tttgcgcatt gtaaatttaa gacacttata gtaagtggac  8220
tcattcatag atgagtttca gaacctttta cgttctcggt agaggcttct gtcggacagg  8280
cagaagagtg tattcctcac ttttttttt gtcttcaaat tccagtaagg catagcactt  8340
ttaagaaatt agaatttttc tatcatctat gcaaatgata tttatgttaa tattaaatat  8400
cttatgttac actgggagta atttgaggtg caattatttt tattactact ttgaatagag  8460
gaccattatc cttctttctt cagaaaacta agaagtaagt gtaactttta aagtaagtat  8520
atatcagtga gagtaggctt gttttacaac tatttctagc cagtgagttg tgttttcatg  8580
tctcatcaaa agacaatacc acattgcatc attttacaaa atatgttgtc attttcattt  8640
cagttgtaac ataggaaaat agatatttcc tagatgattt ctgagtttct tactgcaaag  8700
aacagttata aattggtata catgtgtctc tgtaataggg ataatattga tatatctgtt  8760
gctacatatt taagaatcat tctatcttat gttgtcttga ggccaagatt taccacgttt  8820
gcccagtgta ttgaattggt ggtagaaggt agttccatgt tccatttgta gatctttaag  8880
attttatctt tgataacttt aatagaatgt ggctcagttc tggtccttca agcctgtatg  8940
gtttggattt tcagtagggg acagttgatg tggagtcaat ctctttggta cacaggaagc  9000
tttataaaat ttcattcacg aatctcttat tttgggaagc tgttttgcat atgagaagaa  9060
cactgttgaa ataaggaact aaagctttat atattgatca aggtgattct gaaagtttta  9120
atttttaatg ttgtaatgtt atgttattgt taattgtact ttattatgta ttcaatagaa  9180
aatcatgatt tattaataaa agcttaaatt ctcatctatt t                    9221
```

```
SEQ ID NO: 4           moltype = RNA  length = 9031
FEATURE                Location/Qualifiers
source                 1..9031
                       mol_type = mRNA
                       organism = Homo sapiens
SEQUENCE: 4
agacgccgtc gagatgcagg gcccaccgct cctgaccgcc gcccacctcc tctgcgtgtg  60
caccgccgcg ctggccgtgg ctcccgggcc tcggtttctg gtgacagccc cagggatcat  120
caggcccgga ggaaatgtga ctattggggt ggagcttctg gaacactgcc cttcacaggt  180
gactgtgaag gcggagctgc tcaagacagc atcaaacctc actgtctctg tcctggaagc  240
agaaggagtc tttgaaaaag gctcttttaa gacacttact cttccatcac tacctctgaa  300
cagtgcagat gagatttatg agctacgtgt aaccggacgt acccaggatg agattttatt  360
ctctaatagt acccgcttat catttgagac caagagaata tctgtcttca ttcaaacaga  420
caaggcctta tacaagccaa agcaagaagt gaagtttcgc attgttacac tcttctcaga  480
ttttaagcct tacaaaacct ctttaaacat tctcattaag gaccccaaat caaatttgat  540
ccaacagtgg ttgtcacaac aaagtgatct tggagtcatt tccaaaactt ttcagctatc  600
ttcccatcca atacttggtg actggtctat tcaagttcaa gtgaatgacc agacatacta  660
tcaatcattt caggtttcag aatatgtatt accaaaattt gaagtgactt tgcagacacc  720
attatattgt tctatgaatt ctaagcattt aaatggtacc atcacggcaa agtatacata  780
tgggaagcca gtgaaaggag acgtaacgct tacattttta cctttatcct tttggggaaa  840
gaagaaaaat attacaaaaa catttaagat aaatggatct gcaaacttct cttttaatga  900
tgaagagatg aaaaatgtaa tggattcttc aaatggactt tctgaatacc tggatctatc  960
ttcccctgga ccagtagaaa ttttaaccac agtgacagaa tcagttacag gtatttcaag  1020
aaatgtaagc actaatgtgt tcttcaagca acatgattac atcattgagt tttttgatta  1080
tactactgtc ttgaagccat ctctcaactt cacagccact gtgaaggtaa ctcgtgctga  1140
```

-continued

```
tggcaaccaa ctgactcttg aagaaagaag aaataatgta gtcataacag tgacacagag  1200
aaactatact gagtactgga gcggatctaa cagtggaaat cagaaaatgg aagctgttca  1260
gaaaataaat tatactgtcc cccaaagtgg aacttttaag attgaattcc caatcctgga  1320
ggattccagt gagctacagt tgaaggccta tttccttggt agtaaaagta gcatggcagt  1380
tcatagtctg tttaagtctc ctagtaagac atacatccaa ctaaaaacaa gagatgaaaa  1440
tataaaggtg ggatcgcctt ttgagttggt ggttagtggc aacaaacgat tgaaggagtt  1500
aagctatatg gtagtatcca ggggacagtt ggtggctgta ggaaaacaaa attcaacaat  1560
gttctcttta acaccagaaa attcttggac tccaaaagcc tgtgtaattg tgtattatat  1620
tgaagatgat ggggaaatta taagtgatgt tctaaaaatt cctgttcagc ttgtttttaa  1680
aaataagata aagctatatt ggagtaaagt gaaagctgaa ccatctgaga aagtctctct  1740
taggatctct gtgacacagc ctgactccat agttgggatt gtagctgttg acaaaagtgt  1800
gaatctgatg aatgcctcta atgatattac aatggaaaat gtggtccatg agttggaact  1860
ttataacaca ggatattatt taggcatgtt catgaattct tttgcagtct ttcaggaatg  1920
tggactctgg gtattgacag atgcaaacct cacgaaggat tatattgatg gtgtttatga  1980
caatgcagaa tatgctgaga ggtttatgga ggaaaatgaa ggacatattg tagatattca  2040
tgacttttct ttgggtagca gtccacatgt ccgaaagcat tttccagaga cttggatttg  2100
gctagacacc aacatgggtt acaggattta ccaagaattt gaagtaactg tacctgattc  2160
tatcacttct tgggtggcta ctggttttgt gatctctgag gacctgggtc ttggactaac  2220
aactactcca gtggagctcc aagccttcca accatttttc attttttga atcttcccta  2280
ctctgttatc agaggtgaag aatttgcttt ggaaataact atattcaatt atttgaaaga  2340
tgccactgag gttaaggtaa tcattgagaa aagtgacaaa tttgatattc taatgacttc  2400
aaatgaaata aatgccacag gccaccagca gacccttctg gttcccagtg aggatggggc  2460
aactgttctt tttcccatca ggccaacaca tctgggagaa attcctatca cagtcacagc  2520
tctttcaccc actgcttctg atgctgtcac ccagatgatt ttagtaaagg ctgaaggaat  2580
agaaaaatca tattcacaat ccatcttatt agacttgact gacaataggc tacagagtac  2640
cctgaaaact ttgagtttct catttcctcc taatacagtg actggcagtg aaagagttca  2700
gatcactgca attggagatg ttcttggtcc ttccatcaat ggcttagcct cattgattcg  2760
gatgccttat ggctgtggtg aacagaacat gataaatttt gctccaaata tttacatttt  2820
ggattatctg actaaaaaga aacaactgac agataatttg aaagaaaaag ctctttcatt  2880
tatgaggcaa ggttaccaga gagaacttct ctatcagagg gaagatggct ctttcagtgc  2940
ttttgggaat tatgaccctt ctgggagcac ttggttgtca gcttttgttt taagatgttt  3000
ccttgaagcc gatccttaca tagatattga tcagaatgtg ttacacagaa catacacttg  3060
gcttaaagga catcagaaat ccaacggtga attttgggat ccaggaagag tgattcatag  3120
tgagcttcaa ggtggcaata aaagtccagt aacacttaca gcctatattg taacttctct  3180
cctgggatat agaaagtatc agcctaacat tgatgtgcaa gagtctatcc attttttgga  3240
gtctgaattc agtagaggaa tttcagacaa ttatactcta gcccttataa cttatgcatt  3300
gtcatcagtg gggagtccta aagcgaagga agctttgaat atgctgactt ggagagcaga  3360
acaagaaggt ggcatgcaat tctgggtgtc atcagagtcc aaactttctg actcctggca  3420
gccacgctcc ctggatattg aagttgcagc ctatgcactg ctctcacact tcttacaatt  3480
tcagacttct gagggaatcc caattatgag gtggctaagc aggcaaagaa atagcttggg  3540
tggttttgca tctactcagg ataccactgt ggctttaaag gctctgtctg aatttgcagc  3600
cctaatgaat acagaaagga caaatatcca agtgaccgtg acggggccta gctcaccaag  3660
tcctgtaaag tttctgattg acacacacaa ccgcttactc cttcagacag cagagcttgc  3720
tgtggtacag ccaacggcag ttaatatttc cgcaaatggt tttggatttg ctatttgtca  3780
gctcaatgtt gtatataatg tgaaggcttc tgggtcttct agaagacgaa gatctatcca  3840
aaatcaagaa gcctttgatt tagatgttgc tgtaaaagaa aataaagatg atctcaatca  3900
tgtggatttg aatgtgtgta caagcttttc gggcccgggt aggagtggca tggctcttat  3960
ggaagttaac ctattaagtg gctttatggt gccttcagaa gcaatttctc tgagcgagac  4020
agtgaagaaa gtggaatatg atcatggaaa actcaacctc tatttagatt ctgtaaatga  4080
aacccagttt tgtgttaata ttcctgctgt gagaaacttt aaagtttcaa atacccaaga  4140
tgcttcagtg tccatagtgg attactatga gccaaggaga caggcggtga gaagttacaa  4200
ctctgaagtg aagctgtcct cctgtgacct ttgcagtgat gtccagggct gccgtccttg  4260
tgaggatgga gcttcaggct cccatcatca ctcttcagtc atttttattt tctgtttcaa  4320
gcttctgtac tttatggaac tttggctgtg atttattttt aaaggactct gtgtaacact  4380
aacatttcca gtagtcacat gtgattgttt tgttttcgta gaagaatact gcttctattt  4440
tgaaaaaaga gtttttttc tttctatggg gttgcaggga tggtgtacaa caggtcctag  4500
catgtatagc tgcatagatt tcttcacctg atctttgtgt ggaagatcag aatgaatgca  4560
gttgtgtgtc tatattttcc cctctcaaaa tcttttagaa tttttttgga ggtgtttgtt  4620
ttctccagaa taaaggtatt actttagaat aggtattctc ctcattttgt gaaagaaatg  4680
aacctagatt cttaagcatt attacacatc catgtttgct taaagatgga tttccctggg  4740
aatgggagaa aacagccagc aggaggagct tcatctgttc ccttcccacc tccaacctag  4800
ccctactgcc caccccaccc caacccaccc catgcccagt ggtctcagta gatacttctt  4860
aactggaaat tctttctttt cagaatctag gtggtgaatt ttttttaagt ggcacggtct  4920
ttttctgctt gaaatctgat cacacccccc agccattgcc ctccctctct ttttcctctg  4980
tagagaaatg tgaggggcag tacatttact gtgcttttca caccatctca gaggttgagg  5040
agcatactga aaattgccct ggggggtgct gggtgtgctg tctccttccc acatcctcag  5100
ccccacacca gctctatttc aggggtgaga gtcagagagc actgcaatat gtgcttcatg  5160
ggatttcgat tcgaagatcc tagaccaggg agacactgtg agccagggat acaacaaaat  5220
actaggtaag tcactgcaga ccgacctccc tgcagtttgg gaaagaagct gggtttgtgg  5280
agaatcagag catcttgaca tgactgctga cctaaagatc cctggcattg gccagggatc  5340
ctgtggaacc tcttctagtt caggggtgtg agcattagac tgccagttgt ctagtgacat  5400
ctgatgcttg ctgtgaactt ttaagatccc cgaatcctga gcacctcaat ctttaattgc  5460
cctgtattcc gaagggtaat ataatttatc tggatggaaa ttttaaagat gaatccccct  5520
tttttctttt cttctctctt ttctttcctt ctccctttct tctttgcctt ctaaatatac  5580
tgaaatgatt tagatatgtg tcaacaatta atgatctttt attcaatcta agaaatggtt  5640
tagtttttct ctttagctct atggcatttc actcaagtgg acaggggaaa aagtaattgc  5700
catgggctcc aaagaatttg ctttatgttt ttagctattt aaaaataaat ccatcaaaaa  5760
taaagtatgc aaatgtatct tttaaagtta atttttaaaa atgctcttat tttagtgaat  5820
tttcagaaat tatagtggaa tggatgctca tatattgctt atggatattt tggataccaa  5880
```

```
agtaggaata actgacattc agtattttaa agctggcaaa cctgtacata gaaaatagat  5940
ccccagacag tggtctatga agagggcagt taagtatcaa atacttaatt ttcttgcctt  6000
tttttcttaa gtggggaaaa gtttctagat ctcttacacc tctgacacaa tctgttctaa  6060
aacaggcact tgtaatgttg gggcctcctt gtaaacgtgt ttttgccctt tactctctgg  6120
gagttcttta aaggtgaaat catcttacaa agaaattggg ggagggtctt ggcaaaggac  6180
tttcccctcc tctttcctgg cctgggaacc ttatactgac aatcaatact ttatatttta  6240
aagtatataa tttatagtta acttctagtg taatatatta ggaaacacta gaatggaaag  6300
gccattggaa gacaggttgt atcttttttta gaccatattt ccttgtttaa aaactatcat  6360
ttgaatactt ttttggtgaa gaactccatg ttttcaagtt aaaggtcacc tcgtaggcca  6420
ggcgcagtgg ctcatgcctg taatcccagc actctgggag gctgaggcgg gtgaatcaca  6480
aggttaggag tttgagacca gcctggccaa tatggtgaaa ccccgtccct actaaaaata  6540
caaaatttag ccaggcgtgg tggcatgcac ctgtagtccc acctactcgg gaggctgagg  6600
caggagaatc acttgaacct gagagacaga ggttgcagtg agccgagatc acgccactgc  6660
actccagcct gggggacaga gtgagattct gtctcaaaaa acaaaaaaca aaaaagtcac  6720
cttgtaactc atctcttttt attgtaagtt tattaaaaat gaagaggaca acaatgagaa  6780
ggaacataaa gggttagcta gcactgtctc ctggtgcatg gggctgtgca gatgtcccgg  6840
ccacttcttc cttcatactt cccttagaga acttgctctg ctacaagcag tgggcttgga  6900
ctaaaagtga ttaaaatacc acaggcataa ggagaaaagg agtatatgta gtagtaataa  6960
ttactagtat aaattatttt cttcacatgc tatgagtaat aatattaaaa aactcatttt  7020
accattaaga ttccttatgc tgaagctctt ccatttagaa tactgtcaat gtcatttact  7080
ggtatgaact aaagtccccc ttcttttcca ctcactggga accttagtaa aacaccagca  7140
tatcttacct ctctttctga ctggccgatg cttccagaga ctgaatgttg ggaaaaccta  7200
gtagccaaac aattctagga cagaataaca tttttatatt tggttccacc atcttattac  7260
atttagttat agttttaaaa aagaaattca agcccattaa aatatgtctg gtcaatgaaa  7320
tgcttccttt tattgtgttg tgctattgta ctttgttttt caaaacattg taaaaatagt  7380
atctttggtt tagtatttg gattatatat tataatctga ggagtgtttt gcttatgtag  7440
aatccagata tatttctgtt acctaggaga tgttacttac atatgtaata ctgtatcctg  7500
cacgtggaaa tattcagaat tgtagatagc ataactctcc ctgctcctat tcttttgagc  7560
ctaggtataa tttttttttt ttttttagaa aaagacatat ttagctttaa tttctattta  7620
tgctaaacat atttataagt agtctgtcaa tataatacca actattttta tttttacata  7680
attcaattat ttcatttgac atgtctggca gactcaagac attaagtaaa aaattggaac  7740
tatgattttt ctttgtcatt ttttaaaaaa gaattatttt attaacctgc tggcatataa  7800
tctggagttc ttttcacaac cttacttttt ctgatttgct ttattgaatg attgaatact  7860
catttctttc taaaaatatg ttgtaaattc tcccttggca agatttctcc ctatgagggt  7920
agttattatt tgagtctgcc aagtggttac catggggcaa ggtgccatga tgtattcttg  7980
ggtgcattgg ttttttgcgc attgtaaatt taagacactt atagtaagtg gactcattca  8040
tagatgagtt tcagaacctt ttacgttctc ggtagaggct tctgtcggac aggcagaaga  8100
gtgtattcct cacttttttt tttgtcttca aattccagta aggcatagca cttttaagaa  8160
attagaattt ttctatcatc tatgcaaatg atatttatgt taatattaaa tatcttatgt  8220
tacactggga gtaatttgag gtgcaattat ttttattact actttgaata gaggaccatt  8280
atccttcttt cttcagaaaa ctaagaagta agtgtaactt ttaaagtaag tatatatcag  8340
tgagagtagg cttgttttac aactatttct agccagtgag ttgtgtttc atgtctcatc  8400
aaaagacaat accacattgc atcattttac aaaatatgtt gtcattttca tttcagttgt  8460
aacataggaa aatagatatt tcctagatga tttctgagtt tcttactgca aagaacagtt  8520
ataaattggt atacatgtgt ctctgtaata gggataatat tgatatatct gttgctacat  8580
atttaagaat cattctatct tatgttgtct tgaggccaag atttaccacg tttgcccagt  8640
gtattgaatt ggtggtagaa ggtagttcca tgttccattt gtagatcttt aagattttat  8700
ctttgataac tttaatagaa tgtggctcag ttctggtcct tcaagcctgt atggtttgga  8760
ttttcagtag gggacagttg atgtggagtc aatctctttg gtacacagga agctttataa  8820
aatttcattc acgaatctct tattttggga agctgttttg catatgagaa gaacactgtt  8880
gaaataagga actaaagctt tatatattga tcaaggtgat tctgaaagtt ttaatttta  8940
atgttgtaat gttatgttat tgttaattgt actttattat gtattcaata gaaaatcatg  9000
atttattaat aaaagcttaa attctcatct a                                9031

SEQ ID NO: 5            moltype = RNA  length = 5883
FEATURE                 Location/Qualifiers
source                  1..5883
                        mol_type = mRNA
                        organism = Homo sapiens
SEQUENCE: 5
ctaaactcga attaagaggg aaaaaaaatc agggaggagg tggcaagcca caccccacgg  60
tgcccgcgaa cttccccggc agcggactgt agcccaggca gacgccgtcg agatgcaggg  120
cccaccgctc ctgaccgccg cccacctcct ctgcgtgtgc accgccgcgc tggccgtggc  180
tcccgggcct cggtttctgg tgacagcccc agggatcatc aggcccggag gaaatgtgac  240
tattggggtg gagcttctgg aacactgccc ttcacaggtg actgtgaagg cggagctgct  300
caagacagca tcaaacctca ctgtctctgt cctggaagca gaaggagtct ttgaaaaagg  360
ctcttttaag acacttactc ttccatcact acctctgaac agtgcagatg agatttatga  420
gctacgtgta accggacgta cccaggatga gattttattc tctaatagta cccgcttatc  480
atttgagacc aagagaatat ctgtcttcat tcaaacagac aaggccttat acaagccaaa  540
gcaagaagtg aagtttcgca ttgttacact cttctcagat tttaagcctt acaaaacctc  600
tttaaacatt ctcattaagg accccaaatc aaatttgatc caacagtggt tgtcacaaca  660
aagtgatctt ggagtcattt ccaaaacttt tcagctatct tcccatccaa tacttggtga  720
ctggtctatt caagttcaag tgaatgacca gacatattat caatcatttc aggtttcaga  780
atatgtatta ccaaaatttg aagtgacttt gcagacacca ttatattgtt ctatgaattc  840
taagcattta aatggtacca tcacggcaaa gtatacatat gggaagccag tgaaaggaga  900
cgtaacgctt acatttttac ctttatcctt ttggggaaag aagaaaaata ttacaaaaac  960
atttaagata aatggatctg caaacttctc ttttaatgat gaagagatga aaaatgtaat  1020
ggattcttca aatggacttt ctgaatacct ggatctatct tcccctggac cagtagaaat  1080
tttaaccaca gtgacagaat cagttacagg tatttcaaga aatgtaagca ctaatgtgtt  1140
```

-continued

```
cttcaagcaa catgattaca tcattgagtt ttttgattat actactgtct tgaagccatc  1200
tctcaacttc acagccactg tgaaggtaac tcgtgctgat ggcaaccaac tgactcttga  1260
agaaagaaga aataatgtag tcataacagt gacacagaga aactatactg agtactggag  1320
cggatctaac agtggaaatc agaaaatgga agctgttcag aaaataaatt atactgtccc  1380
ccaaagtgga acttttaaga ttgaattccc aatcctggag gattccagtg agctacagtt  1440
gaaggcctat ttccttggta gtaaaagtag catggcagtt catagtctgt ttaagtctcc  1500
tagtaagaca tacatccaac taaaaacaag agatgaaaat ataaaggtgg gatcgccttt  1560
tgagttggtg gttagtggca acaaacgatt gaaggagtta agctatatgg tagtatccag  1620
gggacagttg gtggctgtag gaaaacaaaa ttcaacaatg ttctctttaa caccagaaaa  1680
ttcttggact ccaaaagcct gtgtaattgt gtattatatt gaagatgatg gggaaattat  1740
aagtgatgtt ctaaaaattc ctgttcagct tgtttttaaa aataagataa agctatattg  1800
gagtaaagtg aaagctgaac catctgagaa agtctctctt aggatctctg tgacacagcc  1860
tgactccata gttgggattg tagctgttga caaaagtgtg aatctgatga atgcctctaa  1920
tgatattaca atggaaaatg tggtccatga gttggaactt tataacacag gatattattt  1980
aggcatgttc atgaattctt ttgcagtctt tcaggaatgt ggactctggg tattgacaga  2040
tgcaaacctc acgaaggatt atattgatgg tgtttatgac aatgcagaat atgctgagag  2100
gtttatggag gaaaatgaag gacatattgt agatattcat gacttttctt tgggtagcag  2160
tccacatgtc cgaaagcatt ttccagagac ttggatttgg ctagacacca acatgggtta  2220
caggatttac caagaatttg aagtaactgt acctgattct atcacttctt gggtggctac  2280
tggttttgtg atctctgagg acctgggtct tggactaaca actactccag tggagctcca  2340
agccttccaa ccattttca ttttttgaa tcttccctac tctgttatca gaggtgaaga  2400
atttgctttg gaaataacta tattcaatta tttgaaagat gccactgagg ttaaggtaat  2460
cattgagaaa agtgacaaat ttgatattct aatgacttca aatgaaataa atgccacagg  2520
ccaccagcag accccttctgg ttcccagtga ggatggggca actgttcttt ttcccatcag  2580
gccaacacat ctgggagaaa ttcctatcac agtcacagct ctttcaccca ctgcttctga  2640
tgctgtcacc cagatgattt tagtaaaggc tgaaggaata gaaaaatcat attcacaatc  2700
catcttatta gacttgactg acaataggct acagagtacc ctgaaaactt tgagtttctc  2760
atttcctcct aatacagtga ctggcagtga aagagttcag atcactgcaa ttggagatgt  2820
tcttggtcct tccatcaatg gcttagcctc attgattcgg atgccttatg gctgtggtga  2880
acagaacatg ataaatttg ctccaaatat ttacattttg gattatctga ctaaaaagaa  2940
acaactgaca gataatttga aagaaaaagc tctttcattt atgaggcaag gttaccagag  3000
agaacttctc tatcagaggg aagatggctc tttcagtgct tttgggaatt atgacccttc  3060
tgggagcact tggttgtcag cttttgtttt aagatgtttc cttgaagccg atccttacat  3120
agatattgat cagaatgtgt tacacagaac atacacttgg cttaaaggac atcagaaatc  3180
caacggtgaa ttttgggatc caggaagagt gattcatagt gagcttcaag gtggcaataa  3240
aagtccagta acacttacag cctatattgt aacttctctc ctgggatata gaaagtatca  3300
gcctaacatt gatgtgcaag agtctatcca ttttttggag tctgaattca gtagaggaat  3360
ttcagacaat tatactctag cccttataac ttatgcattg tcatcagtgg ggagtcctaa  3420
agcgaaggaa gctttgaata tgctgacttg gagagcagaa caagaaggtg gcatgcaatt  3480
ctgggtgtca tcagagtcca aactttctga ctcctggcag ccacgctccc tggatattga  3540
agttgcagcc tatgcactgc tctcacactt cttacaattt cagacttctg agggaatccc  3600
aattatgagg tggctaagca ggcaaagaaa tagcttgggt ggttttgcat ctactcagga  3660
taccactgtg gctttaaagg ctctgtctga atttgcagcc ctaatgaata cagaaaggac  3720
aaatatccaa gtgaccgtga cggggcctag ctcaccaagt cctgtaaagt ttctgattga  3780
cacacacaac cgcttactcc ttcagacagc agagcttgct gtggtacagc caatggcagt  3840
taatatttcc gcaaatggtt ttggatttgc tatttgtcag ctcaatgttg tatataatgt  3900
gaaggcttct gggtcttcta gaagacgaag atctatccaa aatcaagaag cctttgattt  3960
agatgttgct gtaaaagaaa ataaagatga tctcaatcat gtggatttga atgtgtgtac  4020
aagcttttcg ggcccgggta ggagtggcat ggctcttatg gaagttaacc tattaagtgg  4080
ctttatggtg ccttcagaag caatttctct gagcgagaca gtgaagaaag tggaatatga  4140
tcatggaaaa ctcaacctct atttagattc tgtaaatgaa acccagtttt gtgttaatat  4200
tcctgctgtg agaaacttta aagtttcaaa tacccaagat gcttcagtgt ccatagtgga  4260
ttactatgag ccaaggagac aggcggtgag aagttacaac tctgaagtga agctgtcctc  4320
ctgtgacctt tgcagtgatg tccagggctg ccgtccttgt gaggatggag cttcaggctc  4380
ccatcatcac tcttcagtca tttttatttt ctgtttcaag cttctgtact ttatggaact  4440
ttggctgtga tttattttta aaggactctg tgtaacacta acatttccag tagtcacatg  4500
tgattgtttt gttttcgtag aagaatactg cttctatttt gaaaaaagag tttttttct  4560
ttctatgggg ttgcagggat ggtgtacaac aggtcctagc atgtatagct gcatagattt  4620
cttcacctga tctttgtgtg gaagatcaga atgaatgcag ttgtgtgtct atattttccc  4680
ctcacaaaat cttttagaat tttttggag gtgtttgttt tctccagaat aaaggtatta  4740
ctttagaaat aggtattctc ctcattttgt gaaagaaatg aacctagatt cttaagcatt  4800
attacacatc catgtttgct taaagatgga tttccctggg aatgggagaa aacagccagc  4860
aggaggagct tcatctgttc ccttcccacc tccaacctag ccctactgcc caccccaccc  4920
caacccaccc catgcccagt ggtctcagta gatacttctt aactggaaat tctttctttt  4980
cagaatctag gtggtgaatt tttttaagt ggcacggtct ttttctgctt gaaatctgat  5040
cacacccccc agccattgcc ctccctctct ttttcctctg tagagaaatg tgaggggcag  5100
tacatttact gtgcttttca caccatctca gaggttgagg agcatactga aaattgccct  5160
ggggggtgct gggtgtgctg tctccttccc acatcctcag ccccacacca gctctatttc  5220
aggggtgaga gtcagagagc actgcaatat gtgcttcatg ggatttcgat tcgaagatcc  5280
tagaccaggg agacactgtg agccagggat acaacaaaat actaggtaag tcactgcaga  5340
ccgacctccc tgcagtttgg gaaagaagct gggtttgtgg agaatcagag catcttgaca  5400
tgactgctga cctaaagatc cctggcattg gccagggatc ctgtggaacc tcttctagtt  5460
caggggtgtg agcattagac tgccagttgt ctagtgacat ctgatgcttg ctgtgaactt  5520
ttaagatccc cgaatcctga gcacctcaat ctttaattgc cctgtattcc gaagggtaat  5580
ataatttatc tggatggaaa ttttaaagat gaatcccccct tttttctttt cttctctctt  5640
ttctttcctt ctccctttct tctttgcctt ctaaatatac tgaaatgatt tagatatgtg  5700
tcaacaatta atgatctttt attcaatcta agaaatggtt tagttttttct ctttagctct  5760
atggcatttc actcaagtgg acaggggaaa aagtaattgc catgggctcc aaagaatttg  5820
ctttatgttt ttagctattt aaaaataaat ccatcaaaaa taaagtatgc aaatgtatct  5880
```

```
ttt                                                                   5883

SEQ ID NO: 6            moltype = RNA  length = 4449
FEATURE                 Location/Qualifiers
source                  1..4449
                        mol_type = mRNA
                        organism = Homo sapiens
SEQUENCE: 6
aaaactcgaa ttaagaggga aagaaaatca gggaggaggt ggcaagccac accccacggt  60
gcccgcgaac ttccccggca gcggactgta gcccaggcag acgccgtcga gatgcagggc  120
ccaccgctcc tgaccgccgc ccacctcctc tgcgtgtgca ccgccgcgct ggccgtggct  180
cccgggcctc ggtttctggt gacagcccca gggatcatca ggcccggagg aaatgtgact  240
attggggtgg agcttctgga acactgccct tcacaggtga ctgtgaaggc ggagctgctc  300
aagacagcat caaacctcac tgtctctgtc ctggaagcag aaggagtctt tgaaaaaggc  360
tcttttaaga cacttactct tccatcacta cctctgaaca gtgcagatga gatttatgag  420
ctacgtgtaa ccggacgtac ccaggatgag attttattct ctaatagtac ccgcttatca  480
tttgagacca agagaatatc tgtcttcatt caaacagaca aggccttata caagccaaag  540
caagaagtga agtttcgcat tgttacactc ttctcagatt ttaagcctta caaaacctct  600
ttaaacattc tcattaagga ccccaaatca aatttgatcc aacagtggtt gtcacaacaa  660
agtgatcttg gagtcatttc caaaactttt cagctatctt cccatccaat acttggtgac  720
tggtctattc aagttcaagt gaatgaccag acatattatc aatcatttca ggtttcagaa  780
tatgtattac caaaatttga agtgactttg cagacaccat tatattgttc tatgaattct  840
aagcatttaa atggtaccat cacggcaaag tatacatatg ggaagccagt gaaaggagac  900
gtaacgctta catttttacc tttatccttt tggggaaaga agaaaaatat tacaaaaaca  960
tttaagataa atggatctgc aaacttctct tttaatgatg aagagatgaa aaatgtaatg  1020
gattcttcaa atggactttc tgaatacctg gatctatctt cccctggacc agtagaaatt  1080
ttaaccacag tgacagaatc agttacaggt atttcaagaa atgtaagcac taatgtgttc  1140
ttcaagcaac atgattacat cattgagttt tttgattata ctactgtctt gaagccatct  1200
ctcaacttca cagccactgt gaaggtaact cgtgctgatg gcaaccaact gactcttgaa  1260
gaaagaagaa ataatgtagt cataacagtg acacagagaa actatactga gtactggagc  1320
ggatctaaca gtggaaatca gaaaatggaa gctgttcaga aaataaatta tactgtcccc  1380
caaagtggaa cttttaagat tgaattccca atcctggagg attccagtga gctacagttg  1440
aaggcctatt tccttggtag taaaagtagc atggcagttc atagtctgtt taagtctcct  1500
agtaagacat acatccaact aaaaacaaga gatgaaaata taaaggtggg atcgcctttt  1560
gagttggtgg ttagtggcaa caaacgattg aaggagttaa gctatatggt agtatccagg  1620
ggacagttgg tggctgtagg aaaacaaaat tcaacaatgt tctctttaac accagaaaat  1680
tcttggactc caaaagcctg tgtaattgtg tattatattg aagatgatgg ggaaattata  1740
agtgatgttc taaaaattcc tgttcagctt gtttttaaaa ataagataaa gctatattgg  1800
agtaaagtga aagctgaacc atctgagaaa gtctctctta ggatctctgt gacacagcct  1860
gactccatag ttgggattgt agctgttgac aaaagtgtga atctgatgaa tgcctctaat  1920
gatattacaa tggaaaatgt ggtccatgag ttggaacttt ataacacagg atattattta  1980
ggcatgttca tgaattcttt tgcagtcttt caggaatgtg gactctgggt attgacagat  2040
gcaaacctca cgaaggatta tattgatggt gtttatgaca atgcagaata tgctgagagg  2100
tttatggagg aaaatgaagg acatattgta gatattcatg acttttcttt gggtagcagt  2160
ccacatgtcc gaaagcattt tccagagact tggatttggc tagacaccaa catgggttcc  2220
aggatttacc aagaatttga agtaactgta cctgattcta tcacttcttg ggtggctact  2280
ggttttgtga tctctgagga cctgggtctt ggactaacaa ctactccagt ggagctccaa  2340
gccttccaac catttttcat ttttttgaat cttccctact ctgttatcag aggtgaagaa  2400
tttgctttgg aaataactat attcaattat ttgaaagatg ccactgaggt taaggtaatc  2460
attgagaaaa gtgacgaatt tgatattcta atgacttcaa atgaaataaa tgccacaggc  2520
caccagcaga cccttctggt tcccagtgag gatggggcaa ctgttctttt tcccatcagg  2580
ccaacacatc tgggagaaat tcctatcaca gtcacagctc tttcacccac tgcttctgat  2640
gctgtcaccc agatgatttt agtaaaggct gaaggaatag aaaaatcata ttcacaatcc  2700
atcttattag acttgactga caataggcta cagagtaccc tgaaaacttt gagtttctca  2760
tttcctccta atacagtgac tggcagtgaa agagttcaga tcactgcaat tggagatgtt  2820
cttggtcctt ccatcaatgg cttagcctca ttgattcgga tgccttatgg ctgtggtgaa  2880
cagaacatga taaattttgc tccaaatatt tacattttgg attatctgac taaaaagaaa  2940
caactgacag ataatttgaa agaaaaagct ctttcattta tgaggcaagg ttaccagaga  3000
gaacttctct atcagaggga agatggctct ttcagtgctt ttgggaatta tgacccttct  3060
gggagcactt ggttgtcagc ttttgtttta agatgtttcc ttgaagccga tccttacata  3120
gatattgatc agaatgtgtt acacagaaca tacacttggc ttaaaggaca tcagaaatcc  3180
aacggtgaat tttgggatcc aggaagagtg attcatagtg agcttcaagg tggcaataaa  3240
agtccagtaa cacttacagc ctatattgta acttctctcc tgggatatag aaagtatcag  3300
cctaacattg atgtgcaaga gtctatccat tttttggagt ctgaattcag tagaggaatt  3360
tcagacaatt atactctagc ccttataact tatgcattgt catcagtggg gagtcctaaa  3420
gcgaaggaag ctttgaatat gctgacttgg agagcagaac aagaaggtgg catgcaattc  3480
tgggtgtcat cagagtccaa actttctgac tcctggcagc cacgctccct ggatattgaa  3540
gttgcagcct atgcactgct ctcacacttc ttacaatttc agacttctga gggaatccca  3600
attatgaggt ggctaagcag gcaaagaaat agcttgggtg gttttgcatc tactcaggat  3660
accactgtgg ctttaaaggc tctgtctgaa tttgcagccc taatgaatac agaaaggaca  3720
aatatccagg tgaccgtgac ggggcctagc tcaccaagtc ctgtaaagtt tctgattgac  3780
acacacaacc gcttactcct tcagacagca gagcttgctg tggtacagcc aacggcagtt  3840
aatatttccg caaatggttt tggatttgct atttgtcagc tcaatgttgt atataatgtg  3900
aaggcttctg ggtcttctag aagacgaaga tctatccaaa atcaagaagc ctttgattta  3960
gatgttgctg taaaagaaaa taaagatgat ctcaatcatg tggatttgaa tgtgtgtaca  4020
agcttttcgg gcccgggtag gagtggcatg gctcttatgg aagttaacct attaagtggc  4080
tttatggtgc cttcagaagc aatttctctg agcgagacag tgaagaaagt ggaatatgat  4140
catggaaaac tcaacctcta tttagattct gtaaatgaaa cccagttttg tgttaatatt  4200
cctgctgtga gaaactttaa agtttcaaat acccaagatg cttcagtgtc catagtggat  4260
```

-continued

```
tactatgagc caaggagaca ggcggtgaga agttacaact ctgaagtgaa gctgtcctcc  4320
tgtgaccttt gcagtgatgt ccagggctgc cgtccttgtg aggatggagc ttcaggctcc  4380
catcatcact cttcagtcat ttttatttc tgtttcaagc ttctgtactt tatggaactt  4440
tggctgtga                                                          4449

SEQ ID NO: 7            moltype = RNA  length = 2273
FEATURE                 Location/Qualifiers
source                  1..2273
                        mol_type = mRNA
                        organism = Homo sapiens
SEQUENCE: 7
acacacccca cggtgcccgc gaacttcccc ggcagcggac tgtagcccag gcagacgccg  60
tcgagatgca gggcccaccg ctcctgaccg ccgcccacct cctctgcgtg tgcaccgccg  120
cgctggccgt ggctcccggg cctcggtttc tggtgacagc cccagggatc atcaggcccg  180
gaggaaatgt gactattggg gtggagcttc tggaacactg cccttcacag gtgactgtga  240
aggcggagct gctcaagaca gcatcaaacc tcactgtctc tgtcctggaa gcagaaggag  300
tctttgaaaa aggctctttt aagacactta ctcttccatc actacctctg aacagtgcag  360
atgagattta tgagctacgt gtaaccggac gtacccagga tgagatttta ttctctaata  420
gtacccgctt atcatttgag accaagagaa tatctgtctt cattcaaaca gacaaggcct  480
tatacaagcc aaagcaagaa gtgaagtttc gcattgttac actcttctca gattttaagc  540
cttacaaaac ctctttaaac attctcatta aggaccccaa atcaaatttg atccaacagt  600
ggttgtcaca acaaagtgat cttggagtca tttccaaaac ttttcagcta tcttcccatc  660
caatacttgg tgactggtct attcaagttc aagtgaatga ccagacatac tatcaatcat  720
ttcaggtttc agaatatgta ttaccaaaat ttgaagtgac tttgcagaca ccattatatt  780
gttctatgaa ttctaagcat ttaaatggta ccatcacggc aaagtataca tatgggaagc  840
cagtgaaagg agacgtaacg cttacatttt tacctttatc cttttgggga aagaagaaaa  900
atattacaaa aacatttaag ataaatggat ctgcaaactt ctcttttaat gatgaagaga  960
tgaaaaatgt aatggattct tcaaatggac tttctgaata cctggatcta tcttcccctg  1020
gaccagtaga aattttaacc acagtgacag aatcagttac aggtatttca agaaatgtaa  1080
gcactaatgt gttcttcaag caacatgatt acatcattga gttttttgat tatactactg  1140
tcttgaagcc atctctcaac ttcacagcca ctgtgaaggt aactcgtgct gatggcaacc  1200
aactgactct tgaagaaaga agaaataatg tagtcataac agtgacacag agaaactata  1260
ctgagtactg gagcggatct aacagtggaa atcagaaaat ggaagctgtt cagaaaataa  1320
attatactgt cccccaaagt ggaactttta agattgaatt cccaatcctg gaggattcca  1380
gtgagctaca gttgaaggcc tatttccttg gtagtaaaag tagcatggca gttcatagtc  1440
tgtttaagtc tcctagtaag acatacatcc aactaaaaac aagagatgaa aatataaagg  1500
tgggatcgcc ttttgagttg gtggttagtg gcaacaaacg attgaaggag ttaagctata  1560
tggtagtatc caggggacag ttggtggctg taggaaaaca aaattcaaca atgttctctt  1620
taacaccaga aaattcttgg actccaaaag cctgtgtaat tgtgtattat attgaagatg  1680
atggggaaat tataagtgat gttctaaaaa ttcctgttca gcttgttttt aaaaataaga  1740
taaagctata ttggagtaaa gtgaaagctg aaccatctga gaaagtctct cttaggatct  1800
ctgtgacaca gcctgactcc atagttggga ttgtagctgt tgacaaaagt gtgaatctga  1860
tgaatgcctc taatgatatt acaatggaaa atgtggtcca tgagttggaa ctttataaca  1920
caggatatta tttaggcatg ttcatgaatt cttttgcagt ctttcaggaa tgtggactct  1980
gggtattgac agatgcaaac ctcacgaagg attatattga tggtgtttat gacaatctct  2040
ttggtacaca ggaagcttta taaaatttca ttcacgaatc tcttattttg ggaagctgtt  2100
ttgcatatga gaagaacact gttgaaataa ggaactaaag ctttatatat tgatcaaggt  2160
gattctgaaa gttttaattt ttaatgttgt aatgttatgt tattgttaat tgtactttat  2220
tatgtattca atagaaaatc atgatttatt aataaaagct taaattctca tct          2273

SEQ ID NO: 8            moltype = RNA  length = 4688
FEATURE                 Location/Qualifiers
source                  1..4688
                        mol_type = mRNA
                        organism = Homo sapiens
SEQUENCE: 8
gggactgtag cccaggcaga cgccgtcgag atgcagggcc caccgctcct gaccgccgcc  60
cacctcctct gcgtgtgcac cgccgcgctg gccgtggctc ccgggcctcg gtttctggtg  120
acagccccag ggatcatcag gcccggagga aatgtgacta ttggggtgga gcttctggaa  180
cactgccctt cacaggtgac tgtgaaggcg gagctgctca agacagcatc aaacctcact  240
gtctctgtcc tggaagcaga aggagtcttt gaaaaaggct cttttaagac acttactctt  300
ccatcactac ctctgaacag tgcagatgag atttatgagc tacgtgtaac cggacgtacc  360
caggatgaga ttttattctc taatagtacc cgcttatcat ttgagaccaa gagaatatct  420
gtcttcattc aaacagacaa ggccttatac aagccaaagc aagaagtgaa gtttcgcatt  480
gttacactct tctcagattt taagccttac aaaacctctt taaacattct cattaaggac  540
cccaaatcaa atttgatcca acagtggttg tcacaacaaa gtgatcttgg agtcatttcc  600
aaaacttttc agctatcttc ccatccaata cttggtgact ggtctattca agttcaagtg  660
aatgaccaga catattatca atcatttcag gtttcagaat atgtattacc aaaatttgaa  720
gtgactttgc agacaccatt atattgttct atgaattcta agcatttaaa tggtaccatc  780
acggcaaagt atacatatgg gaagccagtg aaaggagacg taacgcttac atttttacct  840
ttatcctttt ggggaaagaa gaaaaatatt acaaaaacat ttaagataaa tggatctgca  900
aacttctctt ttaatgatga agagatgaaa aatgtaatgg attcttcaaa tggactttct  960
gaatacctgg atctatcttc ccctggacca gtagaaattt taaccacagt gacagaatca  1020
gttacaggta tttcaagaaa tgtaagcact aatgtgttct tcaagcaaca tgattacatc  1080
attgagtttt ttgattatac cactgtcttg aagccatctc tcaacttcac agccactgtg  1140
aaggtaactc gtgctgatgg caaccaactg actcttgaag aaagaagaaa taatgtagtc  1200
ataacagtga cacagagaaa ctatactgag tactggagcg gatctaacag tggaaatcag  1260
aaaatggaag ctgttcagaa aataaattat actgtccccc aaagtggaac ttttaagatt  1320
gaattcccaa tcctggagga ttccagtgag ctacagttga aggcctattt ccttggtagt  1380
```

-continued

```
aaaagtagca tggcagttca tagtctgttt aagtctccta gtaagacata catccaacta  1440
aaaacaagag atgaaaatat aaaggtggga tcgccttttg agttggtggt tagtggcaac  1500
aaacgattga aggagttaag ctatatggta gtatccaggg gacagttggt ggctgtagga  1560
aaacaaaatt caacaatgtt ctctttaaca ccagaaaatt cttggactcc aaaagcctgt  1620
gtaattgtgt attatattga agatgatggg gaaattataa gtgatgttct aaaaattcct  1680
gttcagcttg tttttaaaaa taagataaag ctatattgga gtaaagtgaa agctgaacca  1740
tctgagaaag tctctcttag gatctctgtg acacagcctg actccatagt tgggattgta  1800
gctgttgaca aaagtgtgaa tctgatgaat gcctctaatg atattacaat ggaaaatgtg  1860
gtccatgagt tggaacttta taacacagga tattatttag gcatgttcat gaattctttt  1920
gcagtctttc aggaatgtgg actctgggta ttgacagatg caaacctcac gaaggattat  1980
attgatggtg tttatgacaa tgcagaatat gctgagaggt ttatggagga aaatgaagga  2040
catattgtag atattcatga cttttctttg ggtagcagtc cacatgtccg aaagcatttt  2100
ccagagactt ggatttggct agacaccaac atgggttcca ggatttacca agaatttgaa  2160
gtaactgtac ctgattctat cacttcttgg gtggctactg gttttgtgat ctctgaggac  2220
ctgggtcttg gactaacaac tactccagtg gagctccaag ccttccaacc atttttcatt  2280
tttttgaatc ttccctactc tgttatcaga ggtgaagaat ttgctttgga aataactata  2340
ttcaattatt tgaaagatgc cactgaggtt aaggtaatca ttgagaaaag tgacaaattt  2400
gatattctaa tgacttcaag tgaaataaat gccacaggcc accagcagac ccttctggtt  2460
cccagtgagg atggggcaac tgttcttttt cccatcaggc caacacatct gggagaaatt  2520
cctatcacag tcacagctct ttcacccact gcttctgatg ctatcaccca gatgatttta  2580
gtaaaggctg aaggaataga aaaatcatat tcacaatcca tcttattaga cttgactgac  2640
aataggctac agagtaccct gaaaactttg agtttctcat ttcctcctaa tacagtgact  2700
ggcagtgaaa gagttcagat cactgcaatt ggagatgttc ttggtccttc catcaatggc  2760
ttagcctcat tgattcggat gccttatggc tgtggtgaac agaacatgat aaattttgct  2820
ccaaatattt acattttgga ttatctgact aaaaagaaac aactgacaga taatttgaaa  2880
gaaaaagctc tttcatttat gaggcaaggt taccagagag aacttctcta tcagagggaa  2940
gatggctctt tcagtgcttt tgggaattat gacccttctg ggagcacttg gttgtcagct  3000
tttgttttaa gatgtttcct tgaagccgat ccttacatag atattgatca gaatgtgtta  3060
cacagaacat acacttggct taaaggacat cagaaatcca acggtgaatt ttgggatcca  3120
ggaagagtga ttcatagtga gcttcaaggt ggcaataaaa gtccagcaac acttacagcc  3180
tatattgtaa cttctctcct gggatataga aagtatcagc ctaacattga tgtgcaagag  3240
tctatccatt ttttggagtc tgaattcagt agaggaattt cagacaatta tactctagcc  3300
cttataactt atgcattgtc atcagtgggg agtcctaaag cgaaggaagc tttgaatatg  3360
ctgacttgga gagcagaaca agaaggtggc atgcaattct gggtgtcatc agagtccaaa  3420
ctttctgact cctggcagcc acgctccctg gatattgaag ttgcagccta tgcactgctc  3480
tcacacttct tacaatttca gacttctgag ggaatcccaa ttatgaggtg gctaagcagg  3540
caaagaaata gcttgggtgg ttttgcatct actcaggata ccactgtggc tttaaaggct  3600
ctgtctgaat ttgcagccct aatgaataca gaaaggacaa atatccaagt gaccgtgacg  3660
gggcctagct caccaagtcc tgtaaagttt ctgattgaca cacacaaccg cttactcctt  3720
cagacagcag agcttgctgt ggtacagcca atggcagtta atatttccgc aaatggtttt  3780
ggatttgcta tttgtcagct caatgttgta tataatgtga aggcttctgg gtcttctaga  3840
agacgaagat ctatccaaaa tcaagaagcc tttgatttag atgttgctgt aaaagaaaat  3900
aaagatgatc tcaatcatgt ggatttgaat gtgtgtacaa gcttttcggg cccgggtagg  3960
agtggcatgg ctcttatgga agttaaccta ttaagtggct ttatggtgcc ttcagaagca  4020
atttctctga gcgagacagt gaagaaagtg gaatatgatc atggaaaact caacctctat  4080
ttagattctg taaatgaaac ccagttttgt gttaatattc ctgctgtgag aaactttaaa  4140
gtttcaaata cccaagatgc ttcagtgtcc atagtggatt actatgagcc aaggagacag  4200
gcggtgagaa gttacaactc tgaagtgaag ctgtcctcct gtgacctttg cagtgatgtc  4260
cagggctgcc gtccttgtga ggatggagct tcaggctccc atcatcactc ttcagtcatt  4320
tttattttct gtttcaagct tctgtacttt atggaacttt ggctgtgatt tatttttaaa  4380
ggactctgtg taacactaac atttccagta gtcacatgtg attgttttgt tttcgtagaa  4440
gaatactgct tctattttga aaaaagagtt ttttttcttt ctatggggtt gcagggatgg  4500
tgtacaacag gtcctagcat gtatagctgc atagatttct tcacctgatc tttgtgtgga  4560
agatcagaat gaatgcagtt gtgtgtctat atttcccct ctcaaaatct tttagaattt  4620
ttttggaggt gtttgtttc tccagaataa aggtattact ttagaaaaca aaaaaaaaaa  4680
aaaaaaaa                                                           4688

SEQ ID NO: 9           moltype = RNA  length = 4369
FEATURE                Location/Qualifiers
source                 1..4369
                       mol_type = mRNA
                       organism = Homo sapiens
SEQUENCE: 9
tgtagcccag gcagacgccg tcgagatgca gggcccaccg ctcctgaccg ccgcccacct  60
cctctgcgtg tgcaccgccg cgctggccgt ggctcccggg cctcggtttc tggtgacagc  120
cccagggatc atcaggcccg gaggaaatgt gactattggg gtggagcttc tggaacactg  180
cccttcacag gtgactgtga aggcggagct gctcaagaca gcatcaaacc tcactgtctc  240
tgtcctggaa gcagaaggag tctttgaaaa aggctctttt aagacactta ctcttccatc  300
actacctctg aacagtgcag atgagattta tgagctacgt gtaaccggac gtacccagga  360
tgagatttta ttctctaata gtacccgctt atcatttgag accaagagaa tatctgtctt  420
cattcaaaca gacaaggcct tatacaagcc aaagcaagaa gtgaagtttc gcattgttac  480
actcttctca gattttaagc cttacaaaac ctctttaaac attctcatta aggaccccaa  540
atcaaatttg atccaacagt ggttgtcaca acaaagtgat cttggagtca tttccaaaac  600
ttttcagcta tcttcccatc caatacttgg tgactggtct attcaagttc aagtgaatga  660
ccagacatat tatcaatcat ttcaggtttc agaatatgta ttaccaaaat ttgaagtgac  720
tttgcagaca ccattatatt gttctatgaa ttctaagcat ttaaatggta ccatcacggc  780
aaagtataca tatgggaagc cagtgaaagg agacgtaacg cttacatttt tacctttatc  840
cttttgggga aagaagaaaa atattacaaa aacatttaag ataaatggat ctgcaaactt  900
ctcttttaat gatgaagaga tgaaaaatgt aatggattct tcaaatggac tttctgaata  960
```

-continued

```
cctggatcta tcttcccctg gaccagtaga aattttaacc acagtgacag aatcagttac  1020
aggtatttca agaaatgtaa gcactaatgt gttcttcaag caacatgatt acatcattga  1080
gttttttgat tatactactg tcttgaagcc atctctcaac ttcacagcca ctgtgaaggt  1140
aactcgtgct gatggcaacc aactgactct tgaagaaaga agaaataatg tagtcataac  1200
agtgacacag agaaactata ctgagtactg gagcggatct aacagtggaa atcagaaaat  1260
ggaagctgtt cagaaaataa attatactgt cccccaaagt ggaactttta agattgaatt  1320
cccaatcctg gaggattcca gtgagctaca gttgaaggcc tatttccttg gtagtaaaag  1380
tagcatggca gttcatagtc tgtttaagtc tcctagtaag acatacatcc aactaaaaac  1440
aagagatgaa aatataaagg tgggatcgcc ttttgagttg gtggttagtg gcaacaaacg  1500
attgaaggag ttaagctata tggtagtatc caggggacag ttggtggctg taggaaaaca  1560
aaattcaaca atgttctctt taacaccaga aaattcttgg actccaaaag cctgtgtaat  1620
tgtgtattat attgaagatg atggggaaat tataagtgat gttctaaaaa ttcctgttca  1680
gcttgttttt aaaaataaga taaagctata ttggagtaaa gtgaaagctg aaccatctga  1740
gaaagtctct cttaggatct ctgtgacaca gcctgactcc atagttggga ttgtagctgt  1800
tgacaaaagt gtgaatctga tgaatgcctc taatgatatt acaatggaaa atgtggtcca  1860
tgagttggaa ctttataaca caggatatta tttaggcatg ttcatgaatt cttttgcagt  1920
ctttcaggaa tgtggactct gggtattgac agatgcaaac ctcacgaagg attatattga  1980
tggtgtttat gacaatgcag aatatgctga gaggtttatg gaggaaaatg aaggacatat  2040
tgtagatatt catgactttt ctttgggtag cagtccacat gtccgaaagc attttccaga  2100
gacttggatt tggctagaca ccaacatggg ttccaggatt taccaagaat ttgaagtaac  2160
tgtacctgat tctatcactt cttgggtggc tactggtttt gtgatctctg aggacctggg  2220
tcttggacta acaactactc cagtggagct ccaagccttc caaccatttt tcattttttt  2280
gaatcttccc tactctgtta tcagaggtga agaatttgct ttggaaataa ctatattcaa  2340
ttatttgaaa gatgccactg aggttaaggt aatcattgag aaaagtgaca aatttgatat  2400
tctaatgact tcaagtgaaa taaatgccac aggccaccag cagacccttc tggttcccag  2460
tgaggatggg gcaactgttc tttttcccat caggccaaca catctgggag aaattcctat  2520
cacagtcaca gctctttcac ccactgcttc tgatgctatc acccagatga ttttagtaaa  2580
ggctgaagga atagaaaaat catattcaca atccatctta ttagacttga ctgacaatag  2640
gctacagagt accctgaaaa ctttgagttt ctcatttcct cctaatacag tgactggcag  2700
tgaaagagtt cagatcactg caattggaga tgttcttggt ccttccatca atggcttagc  2760
ctcattgatt cggatgcctt atggctgtgg tgaacagaac atgataaatt ttgctccaaa  2820
tatttacatt ttggattatc tgactaaaaa gaaacaactg acagataatt tgaaagaaaa  2880
agctctttca tttatgaggc aaggttacca gagagaactt ctctatcaga gggaagatgg  2940
ctctttcagt gcttttggga attatgaccc ttctgggagc acttggttgt cagcttttgt  3000
tttaagatgt ttccttgaag ccgatcctta catagatatt gatcagaatg tgttacacag  3060
aacatacact tggcttaaag gacatcagaa atccaacggt gaattttggg atccaggaag  3120
agtgattcat agtgagcttc aaggtggcaa taaaagtcca gtaacactta cagcctatat  3180
tgtaacttct ctcctgggat atagaaagta tcagcctaac attgatgtgc aagagtctat  3240
ccatttttttg gagtctgaat tcagtagagg aatttcagac aattatactc tagcccttat  3300
aacttatgca ttgtcatcag tggggagtcc taaagcgaag gaagctttga atatgctgac  3360
ttggagagca gaacaagaag gtggcatgca attctgggtg tcatcagagt ccaaactttc  3420
tgactcctgg cagccacgct ccctggatat tgaagttgca gcctatgcac tgctctcaca  3480
cttcttacaa tttcagactt ctgagggaat cccaattatg aggtggctaa gcaggcaaag  3540
aaatagcttg ggtggttttg catctactca ggataccact gtggctttaa aggctctgtc  3600
tgaatttgca gccctaatga atacagaaag gacaaatatc caagtgaccg tgacggggcc  3660
tagctcacca agtcctcttg ctgtggtaca gccaacggca gttaatattt ccgcaaatgg  3720
ttttggattt gctatttgtc agctcaatgt tgtatataat gtgaaggctt ctgggtcttc  3780
tagaagacga agatctatcc aaaatcaaga agcctttgat ttagatgttg ctgtaaaaga  3840
aaataaagat gatctcaatc atgtggattt gaatgtgtgt acaagctttt cgggcccggg  3900
taggagtggc atggctctta tggaagttaa cctattaagt ggctttatgg tgccttcaga  3960
agcaatttct ctgagcgaga cagtgaagaa agtggaatat gatcatggaa aactcaacct  4020
ctatttagat tctgtaaatg aaacccagtt ttgtgttaat attcctgctg tgagaaactt  4080
taaagtttca aatacccaag atgcttcagt gtccatagtg gattactatg agccaaggag  4140
acaggcggtg agaagttaca actctgaagt gaagctgtcc tcctgtgacc tttgcagtga  4200
tgtccagggc tgccgtcctt gtgaggatgg agcttcaggc tcccatcatc actcttcagt  4260
catttttatt ttctgtttca agcttctgta ctttatggaa ctttggctgt gatttatttt  4320
taaaggactc tgtgtaacac taacatttcc agtagtcaca tgtgattgt             4369

SEQ ID NO: 10          moltype = RNA  length = 4237
FEATURE                Location/Qualifiers
source                 1..4237
                       mol_type = mRNA
                       organism = Homo sapiens
SEQUENCE: 10
gaggcagacg ccgtcgagat gcagggccca ccgctcctga ccgccgccca cctcctctgc  60
gtgtgcaccg ccgcgctggc cgtggctccc gggcctcggt ttctggtgac agccccaggg  120
atcatcaggc ccggaggaaa tgtgactatt ggggtggagc ttctggaaca ctgcccttca  180
caggtgactg tgaaggcgga gctgctcaag acagcatcaa acctcactgt ctctgtcctg  240
gaagcagaag gagtctttga aaaaggctct tttaagacac ttactcttcc atcagacccc  300
aaatcaaatt tgatccaaca gtggttgtca caacaaagtg atcttggagt catttccaaa  360
acttttcagc tatcttccca tccaatactt ggtgactggt ctattcaagt tcaagtgaat  420
gaccagacat actatcaatc atttcaggtt tcagaatatg tattaccaaa atttgaagtg  480
actttgcaga caccattata ttgttctatg aattctaagc atttaaatgg taccatcacg  540
gcaaagtata catatgggaa gccagtgaaa ggagacgtaa cgcttacatt tttaccttta  600
tcctttttggg gaaagaagaa aaatattaca aaaacattta agataaatgg atctgcaaac  660
ttctctttta atgatgaaga gatgaaaaat gtaatggatt cttcaaatgg actttctgaa  720
tacctggatc tatcttcccc tggaccagta gaaattttaa ccacagtgac agaatcagtt  780
acaggtattt caagaaatgt aagcactaat gtgttcttca agcaacatga ttacatcatt  840
gagtttttttg attatactac tgtcttgaag ccatctctca acttcacagc cactgtgaag  900
```

-continued

```
gtaactcgtg ctgatggcaa ccaactgact cttgaagaaa gaagaaataa tgtagtcata  960
acagtgacac agagaaacta tactgagtac tggagcggat ctaacagtgg aaatcagaaa  1020
atggaagctg ttcagaaaat aaattatact gtcccccaaa gtggaacttt taagattgaa  1080
ttcccaatcc tggaggattc cagtgagcta cagttgaagg cctatttcct tggtagtaaa  1140
agtagcatgg cagttcatag tctgtttaag tctcctagta agacatacat ccaactaaaa  1200
acaagagatg aaaatataaa ggtgggatcg cctttttgagt tggtggttag tggcaacaaa  1260
cgattgaagg agttaagcta tatggtagta tccaggggac agttggtggc tgtaggaaaa  1320
caaaattcaa caatgttctc tttaacacca gaaaattctt ggactccaaa agcctgtgta  1380
attgtgtatt atattgaaga tgatggggaa attataagtg atgttctaaa aattcctgtt  1440
cagcttgttt ttaaaaataa gataaagcta tattggagta aagtgaaagc tgaaccatct  1500
gagaaagtct ctcttaggat ctctgtgaca cagcctgact ccatagttgg gattgtagct  1560
gttgacaaaa gtgtgaatct gatgaatgcc tctaatgata ttacaatgga aaatgtggtc  1620
catgagttgg aactttataa cacaggatat tatttaggca tgttcatgaa ttcttttgca  1680
gtctttcagg aatgtggact ctgggtattg acagatgcaa acctcacgaa ggattatatt  1740
gatggtgttt atgacaatgc agaatatgct gagaggttta tggaggaaaa tgaaggacat  1800
attgtagata ttcatgactt ttctttgggt agcagtccac atgtccgaaa gcattttcca  1860
gagacttgga tttggctaga caccaacatg ggttacagga tttaccaaga atttgaagta  1920
actgtacctg attctatcac ttcttgggtg gctactggtt ttgtgatctc tgaggacctg  1980
ggtcttggac taacaactac tccagtggag ctccaagcct tccaaccatt tttcattttt  2040
ttgaatcttc cctactctgt tatcagaggt gaagaatttg ctttggaaat aactatattc  2100
aattatttga aagatgccac tgaggttaag gtaatcattg agaaaagtga caaatttgat  2160
attctaatga cttcaaatga aataaatgcc acaggccacc agcagaccct tctggttccc  2220
agtgaggatg gggcaactgt tctttttccc atcaggccaa cacatctggg agaaattcct  2280
atcacagtca cagctctttc acccactgct tctgatgctg tcacccagat gattttagta  2340
aaggctgaag gaatagaaaa atcatattca caatccatct tattagactt gactgacaat  2400
aggctacaga gtaccctgaa aactttgagt ttctcatttc ctcctaatac agtgactggc  2460
agtgaaagag ttcagatcac tgcaattgga gatgttcttg gtccttccat caatggctta  2520
gcctcattga ttcggatgcc ttatggctgt ggtgaacaga acatgataaa ttttgctcca  2580
aatatttaca ttttggatta tctgactaaa aagaaacaac tgacagataa tttgaaagaa  2640
aaagctcttt catttatgag gcaaggttac cagagagaac ttctctatca gagggaagat  2700
ggctctttca gtgcttttgg gaattatgac ccttctggga gcacttggtt gtcagccttt  2760
gttttaagat gtttccttga agccgatcct tacatagata ttgatcagaa tgtgttacac  2820
agaacataca cttggcttaa aggacatcag aaatccaacg gtgaattttg ggatccagga  2880
agagtgattc atagtgagct tcaaggtggc aataaaagtc cagtaacact tacagcctat  2940
attgtaactt ctctcctggg atatagaaag tatcagccta acattgatgt gcaagagtct  3000
atccattttt tggagtctga attcagtaga ggaatttcag acaattatac tctagccctt  3060
ataacttatg cattgtcatc agtggggagt cctaaagcga aggaagcttt gaatatgctg  3120
acttggagag cagaacaaga aggtggcatg caattctggg tgtcatcaga gtccaaactt  3180
tctgactcct ggcagccacg ctccctggat attgaagttg cagcctatgc actgctctca  3240
cacttcttac aatttcagac ttctgaggga atcccaatta tgaggtggct aagcaggcaa  3300
agaaatagct tgggtggttt tgcatctact caggatacca ctgtggcttt aaaggctctg  3360
tctgaatttg cagccctaat gaatacagaa aggacaaata tccaagtgac cgtgacgggg  3420
cctagctcac caagtcctgt aaagtttctg attgacacac acaaccgctt actccttcag  3480
acagcagagc ttgctgtggt acagccaatg gcagttaata tttccgcaaa tggttttgga  3540
tttgctattt gtcagctcaa tgttgtatat aatgtgaagg cttctgggtc ttctagaaga  3600
cgaagatcta tccaaaatca agaagccttt tgatttagat gttgctgtaa aagaaaataa  3660
agatgatctc aatcatgtgg atttgaatgt gtgtacaagc ttttcgggcc cgggtaggag  3720
tggcatggct cttatggaag ttaacctatt aagtggcttt atggtgcctt cagaagcaat  3780
ttctctgagc gagacagtga agaaagtgga atatgatcat ggaaaactca acctctattt  3840
agattctgta aatgaaaccc agttttgtgt taatattcct gctgtgagaa actttaaagt  3900
ttcaaatacc caagatgctt cagtgtccat agtggattac tatgagccaa ggagacaggc  3960
ggtgagaagt tacaactctg aagtgaagct gtcctcctgt gacctttgca gtgatgtcca  4020
gggctgccgt ccttgtgagg atggagcttc aggctcccat catcactctt cagtcatttt  4080
tattttctgt ttcaagcttc tgtactttat ggaactttgg ctgtgattta tttttaaagg  4140
actctgtgta acactaacat ttccagtagt cacatgtgat tgttttgttt tcgtagaaga  4200
atactgcttc tattttgaaa aaaaaaaaaa aaaaaca                          4237
```

```
SEQ ID NO: 11          moltype = RNA  length = 4338
FEATURE                Location/Qualifiers
source                 1..4338
                       mol_type = mRNA
                       organism = Homo sapiens
SEQUENCE: 11
atgcagggcc caccgctcct gaccgccgcc cacctcctct gcgtgtgcac cgccgcgctg  60
gccgtggctc ccgggcctcg gtttctggtg acagccccag ggatcatcag gcccggagga  120
aatgtgacta ttggggtgga gcttctggaa cactgccctt cacaggtgac tgtgaaggcg  180
gagctgctca agacagcatc aaacctcact gtctctgtcc tggaagcaga aggagtcttt  240
gaaaaaggct cttttaagac acttactctt ccatcactac ctctgaacag tgcagatgag  300
atttatgagc tacgtgtaac cggacgtacc caggatgaga ttttattctc taatagtacc  360
cgcttatcat ttgagaccaa gagaatatct gtcttcattc aaacagacaa ggccttatac  420
aagccaaagc aagaagtgaa gtttcgcatt gttacactct tctcagattt taagccttac  480
aaaacctctt taaacattct cattaaggac cccaaatcaa atttgatcca acagtggttg  540
tcacaacaaa gtgatcttgg agtcatttcc aaaacttttc agctatcttc ccatccaata  600
cttggtgact ggtctattca agttcaagtg aatgaccaga catattatca atcatttcag  660
gtttcagaat atgtattacc aaaatttgaa gtgactttgc agacaccatt atattgttct  720
atgaattcta agcatttaaa tggtaccatc acggcaaagt atacatatgg gaagccagtg  780
aaaggagacg taacgcttac atttttacct ttatcctttt ggggaaagaa gaaaaatatt  840
acaaaaacat ttaagataaa tggatctgca aacttctctt ttaatgatga agagatgaaa  900
aatgtaatgg attcttcaaa tggactttct gaatacctgg atctatcttc ccctggacca  960
```

-continued

```
gtagaaattt taaccacagt gacagaatca gttacaggta tttcaagaaa tgtaagcact  1020
aatgtgttct tcaagcaaca tgattacatc attgagtttt ttgattatac tactgtcttg  1080
aagccatctc tcaacttcac agccactgtg aaggtaactc gtgctgatgg caaccaactg  1140
actcttgaag aaagaagaaa taatgtagtc ataacagtga cacagagaaa ctatactgag  1200
tactggagcg gatctaacag tggaaatcag aaaatggaag ctgttcagaa aataaattat  1260
actgtccccc aaagtggaac ttttaagatt gaattcccaa tcctggagga ttccagtgag  1320
ctacagttga aggcctattt ccttggtagt aaaagtagca tggcagttca tagtctgttt  1380
aagtctccta gtaagacata catccaacta aaaacaagag atgaaaatat aaaggtggga  1440
tcgccttttg agttggtggt tagtggcaac aaacgattga aggagttaag ctatatggta  1500
gtatccaggg gacagttggt ggctgtagga aaacaaaatt caacaatgtt ctctttaaca  1560
ccagaaaatt cttggactcc aaaagcctgt gtaattgtgt attatattga agatgatggg  1620
gaaattataa gtgatgttct aaaaattcct gttcagcttg tttttaaaaa taagataaag  1680
ctatattgga gtaaagtgaa agctgaacca tctgagaaag tctctcttag gatctctgtg  1740
acacagcctg actccatagt tgggattgta gctgttgaca aaagtgtgaa tctgatgaat  1800
gcctctaatg atattacaat ggaaaatgtg gtccatgagt tggaacttta taacacagga  1860
tattatttag gcatgttcat aaattctttt gcagtctttc aggaatgtgg actctgggta  1920
ttgacagatg caaacctcac gaaggattat attgatggtg tttatgacaa tgcagaatat  1980
gctgagaggt ttatggagga aaatgaagga catattgtag atattcatga cttttctttg  2040
ggtagcagtc cacatgtccg aaagcatttt ccagagactt ggatttggct agacaccaac  2100
atgggttcca ggatttacca agaatttgaa gtaactgtac ctgattctat cacttcttgg  2160
gtggctactg gttttgtgat ctctgaggac ctgggtcttg gactaacaac tactccagtg  2220
gagctccaag ccttccaacc atttttcatt tttttgaatc ttccctactc tgttatcaga  2280
ggtgaagaat ttgctttgga aataactata ttcaattatt tgaaagatgc cactgaggtt  2340
aaggtaatca ttgagaaaag tgacaaattt gatattctaa tgacttcaag tgaaataaat  2400
gccacaagcc accagcagac ccttctggtt cccagtgagg atggggcaac tgttcttttt  2460
cccatcaggc caacacatct gggagaaatt cctatcacag tcacagctct ttcacccact  2520
gcttctgatg ctatcaccca gatgatttta gtaaaggctg aaggaataga aaaatcatat  2580
tcacaatcca tcttattaga cttgactgac aataggctac agagtaccct gaaaactttg  2640
agtttctcat ttcctcctaa tacagtgact ggcagtgaaa gagttcagat cactgcaatt  2700
ggagatgttc ttggtccttc catcaatggc ttagcctcat tgattcggat gccttatggc  2760
tgtggtgaac agaacatgat aaattttgct ccaaatattt acattttgga ttatctgact  2820
aaaaagaaac aactgacaga taatttgaaa gaaaaagctc tttcatttat gaggcaaggt  2880
taccagagag aacttctcta tcagagggaa gatggctctt tcagtgcttt tgggaattat  2940
gacccttctg ggagcacttg gttgtcagct tttgttttaa gatgtttcct tgaagccgat  3000
ccttacatag atattgatca gaatgtgtta cacagaacat acacttggct taaaggacat  3060
cagaaatcca acggtgaatt ttgggatcca ggaagagtga ttcatagtga gcttcaaggt  3120
ggcaataaaa gtccagtaac acttacagcc tatattgtaa cttctctcct gggatataga  3180
aagtatcagc ctaacattga tgtgcaagag tctatccatt ttttggagtc tgaattcagt  3240
agaggaattt cagacaatta tactctagcc cttataactt atgcattgtc atcagtgggg  3300
agtcctaaag cgaaggaagc tttgaatatg ctgacttgga gagcagaaca agaaggtggc  3360
atgcaattct gggtgtcatc agagtccaaa ctttctgact cctggcagcc acgctccctg  3420
gatattgaag ttgcagccta tgcactgctc tcacacttct tacaatttca gacttctgag  3480
ggaatcccaa ttatgaggtg gctaagcagg caaagaaata gcttgggtgg ttttgcatct  3540
actcaggata ccactgtggc tttaaaggct ctgtctgaat ttgcagccct aatgaataca  3600
gaaaggacaa atatccaagt gaccgtgacg gggcctagct caccaagtcc tgtaaagttt  3660
ctgattgaca cacacaaccg cttactcctt cagacagcag agcttgctgt ggtacagcca  3720
acggcagtta atatttccgc aaatggtttt ggatttgcta tttgtcagct caatgttgta  3780
tataatgtga aggcttctgg gtcttctaga agacgaagat ctatccaaaa tcaagaagcc  3840
tttgatttag atgttgctgt aaaagaaaat aaagatgatc tcaatcatgt ggatttgaat  3900
gtgtgtacaa gcttttcggg cccgggtagg agtggcatgg ctcttatgga agttaaccta  3960
ttaagtggct ttatggtgcc ttcagaagca atttctctga gcgagacagt gaagaaagtg  4020
gaatatgatc atggaaaact caacctctat ttagattctg taaatgaaac ccagttttgt  4080
gttaatattc ctgctgtgag aaactttaaa gtttcaaata cccaagatgc ttcagtgtct  4140
atagtggatt actatgagcc aaggagacag gcggtgagaa gttacaactc tgaagtgaag  4200
ctgtcctcct gtgacctttg cagtgatgtc cagggctgcc gtccttgtga ggatggagct  4260
tcaggctccc atcatcactc ttcagtcatt tttattttct gtttcaagct tctgtacttt  4320
atggaacttt ggctgtga                                                4338
```

```
SEQ ID NO: 12          moltype = RNA  length = 2938
FEATURE                Location/Qualifiers
source                 1..2938
                       mol_type = mRNA
                       organism = Homo sapiens
SEQUENCE: 12
gttgacaaaa gtgtgaatct gatgaatgcc tctaatgata ttacaatgga aaatgtggtc  60
catgagttgg aactttataa cacaggatat tatttaggca tgttcatgaa ttcttttgca  120
gtctttcagg aatgtggact ctgggtattg acagatgcaa acctcacgaa ggattatatt  180
gatggtgttt atgacaatgc agaatatgct gagaggttta tggaggaaaa tgaaggacat  240
attgtagata ttcatgactt ttctttgggt agcagtccac atgtccgaaa gcatttccca  300
gagacttgga tttggctaga caccaacatg ggttccagga tttaccaaga atttgaagta  360
actgtacctg attctatcac ttcttgggtg gctactggtt ttgtgatctc tgaggacctg  420
ggtcttggac taacaactac tccagtggag ctccaagcct tccaaccatt tttcattttt  480
ttgaatcttc cctactctgt tatcagaggt gaagaatttg ctttggaaat aactatattc  540
aattatttga aagatgccac tgaggttaag gtaatcattg agaaaagtga caaatttgat  600
attctaatga cttcaagtga aataaatgcc acaggccacc agcagaccct tctggttccc  660
agtgaggatg gggcaactgt tctttttccc atcaggccaa cacatctggg agaaattcct  720
atcacagtca cagctctttc acccactgct tctgatgcta tcacccagat gattttagta  780
aaggctgaag gaatagaaaa atcatattca caatccatct tattagactt gactgacaat  840
aggctacaga gtaccctgaa aactttgagt ttctcatttc ctcctaatac agtgactggc  900
```

```
agtgaaagag ttcagatcac tgcaattgga gatgttcttg gtccttccat caatggctta  960
gcctcattga ttcggatgcc ttatggctgt ggtgaacaga acatgataaa ttttgctcca  1020
aatatttaca ttttggatta tctgactaaa aagaaacaac tgacagataa tttgaaagaa  1080
aaagctcttt catttatgag gcaaggttac cagagagaac ttctctatca gagggaagat  1140
ggctctttca gtgcttttgg gaattatgac ccttctggga gcacttggtt gtcagctttt  1200
gttttaagat gtttccttga agccgatcct tacatagata ttgatcagaa tgtgttacac  1260
agaacataca cttggcttaa aggacatcag aaatccaacg gtgaattttg ggatccagga  1320
agagtgattc atagtgagct tcaaggtggc aataaaagtc cagtaacact tacagcctat  1380
attgtaactt ctctcctggg atatagaaag tatcagccta acattgatgt gcaagagtct  1440
atccattttt tggagtctga attcagtaga ggaatttcag acaattatac tctagccctt  1500
ataacttatg cattgtcatc agtggggagt cctaaagcga aggaagcttt gaatatgctg  1560
acttggagag cagaacaaga aggtggcatg caattctggg tgtcatcaga gtccaaactt  1620
tctgactcct ggcagccacg ctccctggat attgaagttg cagcctatgc actgctctca  1680
cacttcttac aatttcagac ttctgaggga atcccaatta tgaggtggct aagcaggcaa  1740
agaaatagct tgggtggttt tgcatctact caggatacca ctgtggcttt aaaggctctg  1800
tctgaatttg cagccctaat gaatacagaa aggacaaata tccaagtgac cgtgacgggg  1860
cctagctcac caagtcctgt aaagtttctg attgacacac acaaccgctt actccttcag  1920
acagcagagc ttgctgtggt acagccaacg gcagttaata tttccgcaaa tggttttgga  1980
tttgctattt gtcagctcaa tgttgtatat aatgtgaagg cttctgggtc ttctagaaga  2040
cgaagatcta tccaaaatca agaagccttt gatttagatg ttgctgtaaa agaaaataaa  2100
gatgatctca atcatgtgga tttgaatgtg tgtacaagct tttcgggccc gggtaggagt  2160
ggcatggctc ttatggaagt taacctatta agtggcttta tggtgccttc agaagcaatt  2220
tctctgagcg agacagtgaa gaaagtggaa tatgatcatg gaaaactcaa cctctattta  2280
gattctgtaa atgaaaccca gttttgtgtt aatattcctg ctgtgagaaa ctttaaagtt  2340
tcaaataccc aagatgcttc agtgtccata gtggattact atgagccaag gagacaggcg  2400
gtgagaagtt acaactctga agtgaagctg tcctcctgtg acctttgcag tgatgtccag  2460
ggctgccgtc cttgtgagga tggagcttca ggctcccatc atcactcttc agtcattttt  2520
attttctgtt tcaagcttct gtactttatg gaactttggc tgtgatttat ttttaaagga  2580
ctctgtgtaa cactaacatt tccagtagtc acatgtgatt gttttgtttt cgtagaagaa  2640
tactgcttct attttgaaaa aagagttttt tttctttcta tggggttgca gggatggtgt  2700
acaacaggtc ctagcatgta tagctgcata gatttcttca cctgatcttt gtgtggaaga  2760
tcagaatgaa tgcagttgtg tgtctatatt ttcccctctc aaaatctttt agaatttttt  2820
tggaggtgtt tgttttctcc agaataaagg tattacttta gaataaaaaa aaaaaaaaaa  2880
aaaaaaaaaa aaaaaaaaaa aaaaaaaaaa aaaaaaaaaa aaaaaaaaaa aaaaaaaa    2938

SEQ ID NO: 13           moltype = RNA  length = 2843
FEATURE                 Location/Qualifiers
source                  1..2843
                        mol_type = mRNA
                        organism = Homo sapiens
SEQUENCE: 13
ctgatgaatg cctctaatga tattacaatg gaaaatgtgg tccatgagtt ggaactttat  60
aacacaggat attatttagg catgttcatg aattcttttg cagtctttca ggaatgtgga  120
ctctgggtat tgacagatgc aaacctcacg aaggattata ttgatggtgt ttatgacaat  180
gcagaatatg ctgagaggtt tatggaggaa aatgaaggac atattgtaga tattcatgac  240
ttttctttgg gtagcagtcc acatgtccga aagcattttc cagagacttg gatttggcta  300
gacaccaaca tgggttccag gatttaccaa gaatttgaag taactgtacc tgattctatc  360
acttcttggg tggctactgg ttttgtgatc tctgaggacc tgggtcttgg actaacaact  420
actccagtgg agctccaagc cttccaacca tttttcattt ttttgaatct tccctactct  480
gttatcagag gtgaagaatt tgctttggaa ataactatat tcaattattt gaaagatgcc  540
actgaggtta aggtaatcat tgagaaaagt gacaaatttg atattctaat gacttcaagt  600
gaaataaatg ccacaggcca ccagcagacc cttctggttc ccagtgagga tggggcaact  660
gttctttttc ccatcaggcc aacacatctg ggagaaattc ctatcacagt cacagctctt  720
tcacccactg cttctgatgc tatcacccag atgattttag taaaggctga aggaatagaa  780
aaatcatatt cacaatccat cttattagac ttgactgaca ataggctaca gagtaccctg  840
aaaactttga gtttctcatt tcctcctaat acagtgactg gcagtgaaag agttcagatc  900
actgcaattg gagatgttct tggtccttcc atcaatggct tagcctcatt gattcggatg  960
ccttatggct gtggtgaaca gaacatgata aattttgctc caaatattta cattttggat  1020
tatctgacta aaaagaaaca actgacagat aatttgaaag aaaaagctct ttcatttatg  1080
aggcaaggtt accagagaga acttctctat cagagggaag atggctcttt cagtgctttt  1140
gggaattatg acccttctgg gagcacttgg ttgtcagctt ttgttttaag atgtttcctt  1200
gaagccgatc cttacataga tattgatcag aatgtgttac acagaacata cacttggctt  1260
aaaggacatc agaaatccaa cggtgaattt tgggatccag gaagagtgat tcatagtgag  1320
cttcaaggtg gcaataaaag tccagtaaca cttacagcct atattgtaac ttctctcctg  1380
ggatatagaa agtatcagcc taacattgat gtgcaagagt ctatccattt tttggagtct  1440
gaattcagta gaggaatttc agacaattat actctagccc ttataactta tgcattgtca  1500
tcagtgggga gtcctaaagc gaaggaagct ttgaatatgc tgacttggag agcagaacaa  1560
gaaggtggca tgcaattctg ggtgtcatca gagtccaaac tttctgactc ctggcagcca  1620
cgctccctgg atattgaagt tgcagcctat gcactgctct cacacttctt acaatttcag  1680
acttctgagg gaatcccaat tatgaggtgg ctaagcaggc aaagaaatag cttgggtggt  1740
tttgcatcta ctcaggatac cactgtggct ttaaaggctc tgtctgaatt tgcagcccta  1800
atgaatacag aaaggacaaa tatccaagtg accgtgacgg ggcctagctc accaagtcct  1860
gtaaagtttc tgattgacac acacaaccgc ttactccttc agacagcaga gcttgctgtg  1920
gtacagccaa cggcagttaa tatttccgca aatggttttg gatttgctat ttgtcagctc  1980
aatgttgtat ataatgtgaa ggcttctggg tcttctagaa gacgaagatc tatccaaaat  2040
caagaagcct ttgatttaga tgttgctgta aaagaaaata aagatgatct caatcatgtg  2100
gatttgaatg tgtgtacaag cttttcgggc ccgggtagga gtggcatggc tcttatggaa  2160
gttaacctat taagtggctt tatggtgcct tcagaagcaa tttctctgag cgagacagtg  2220
aagaaagtgg aatatgatca tggaaaactc aacctctatt tagattctgt aaatgaaacc  2280
```

-continued

```
cagttttgtg ttaatattcc tgctgtgaga aactttaaag tttcaaatac ccaagatgct  2340
tcagtgtcca tagtggatta ctatgagcca aggagacagg cggtgagaag ttacaactct  2400
gaagtgaagc tgtcctcctg tgacctttgc agtgatgtcc agggctgccg tccttgtgag  2460
aatggagctt caggctccca tcatcactct tcagtcattt ttattttctg tttcaagctt  2520
ctgtacttta tggaactttg gctgtgattt atttttaaag gactctgtgt aacactaaca  2580
tttccagtag tcacatgtga ttgttttgtt ttcgtagaag aatactgctt ctattttgaa  2640
aaaagagttt tttttctttc tatggggttg cagggatggt gtacaacagg tcctagcatg  2700
tatagctgca tagatttctt cacctgatct ttgtgtggaa gatcagaatg aatgcagttg  2760
tgtgtctata ttttcccctc tcaaaatctt ttagaatttt tttggaggtg tttgttttct  2820
ccagaataaa ggtattactt tag                                          2843

SEQ ID NO: 14          moltype = RNA  length = 8800
FEATURE                Location/Qualifiers
source                 1..8800
                       mol_type = mRNA
                       organism = Homo sapiens
SEQUENCE: 14
agacgccgtc gagatgcagg gcccaccgct cctgaccgcc gcccacctcc tctgcgtgtg  60
caccgccgcg ctggccgtgg ctcccgggcc tcggtttctg gtgacagccc cagggatcat  120
caggcccgga ggaaatgtga ctattggggt ggagcttctg gaacactgcc cttcacaggt  180
gactgtgaag gcggagctgc tcaagacagc atcaaacctc actgtctctg tcctggaagc  240
agaaggagtc tttgaaaaag gctcttttaa gacacttact cttccatcag accccaaatc  300
aaatttgatc caacagtggt tgtcacaaca aagtgatctt ggagtcattt ccaaaacttt  360
tcagctatct tcccatccaa tacttggtga ctggtctatt caagttcaag tgaatgacca  420
gacatactat caatcatttc aggtttcaga atatgtatta ccaaaatttg aagtgacttt  480
gcagacacca ttatattgtt ctatgaattc taagcattta aatggtacca tcacggcaaa  540
gtatacatat gggaagccag tgaaaggaga cgtaacgctt acatttttac ctttatcctt  600
ttggggaaag aagaaaaata ttacaaaaac atttaagata aatggatctg caaacttctc  660
ttttaatgat gaagagatga aaaatgtaat ggattcttca aatggacttt ctgaatacct  720
ggatctatct tcccctggac cagtagaaat tttaaccaca gtgacagaat cagttacagg  780
tatttcaaga aatgtaagca ctaatgtgtt cttcaagcaa catgattaca tcattgagtt  840
ttttgattat actactgtct tgaagccatc tctcaacttc acagccactg tgaaggtaac  900
tcgtgctgat ggcaaccaac tgactcttga agaaagaaga aataatgtag tcataacagt  960
gacacagaga aactatactg agtactggag cggatctaac agtggaaatc agaaaatgga  1020
agctgttcag aaaataaatt atactgtccc ccaaagtgga acttttaaga ttgaattccc  1080
aatcctggag gattccagtg agctacagtt gaaggcctat ttccttggta gtaaaagtag  1140
catggcagtt catagtctgt ttaagtctcc tagtaagaca tacatccaac taaaaacaag  1200
agatgaaaat ataaaggtgg gatcgccttt tgagttggtg gttagtggca acaaacgatt  1260
gaaggagtta agctatatgg tagtatccag ggacagttgg gtggctgtag gaaaacaaaa  1320
ttcaacaatg ttctctttaa caccagaaaa ttcttggact ccaaaagcct gtgtaattgt  1380
gtattatatt gaagatgatg gggaaattat aagtgatgtt ctaaaaattc ctgttcagct  1440
tgtttttaaa aataagataa agctatattg gagtaaagtg aaagctgaac catctgagaa  1500
agtctctctt aggatctctg tgacacagcc tgactccata gttgggattg tagctgttga  1560
caaaagtgtg aatctgatga atgcctctaa tgatattaca atggaaaatg tggtccatga  1620
gttggaactt tataacacag gatattattt aggcatgttc atgaattctt ttgcagtctt  1680
tcaggaatgt ggactctggg tattgacaga tgcaaacctc acgaaggatt atattgatgg  1740
tgtttatgac aatgcagaat atgctgagag gtttatggag gaaaatgaag gacatattgt  1800
agatattcat gacttttctt tgggtagcag tccacatgtc cgaaagcatt ttccagagac  1860
ttggatttgg ctagacacca acatgggtta caggatttac caagaatttg aagtaactgt  1920
acctgattct atcacttctt gggtggctac tggttttgtg atctctgagg acctgggtct  1980
tggactaaca actactccag tggagctcca agccttccaa ccatttttca ttttttttgaa  2040
tcttccctac tctgttatca gaggtgaaga atttgctttg gaaataacta tattcaatta  2100
tttgaaagat gccactgagg ttaaggtaat cattgagaaa agtgacaaat ttgatattct  2160
aatgacttca aatgaaataa atgccacagg ccaccagcag acccttctgg ttcccagtga  2220
ggatggggca actgttcttt ttcccatcag gccaacacat ctgggagaaa ttcctatcac  2280
agtcacagct ctttcaccca ctgcttctga tgctgtcacc cagatgattt tagtaaaggc  2340
tgaaggaata gaaaaatcat attcacaatc catcttatta gacttgactg acaataggct  2400
acagagtacc ctgaaaactt tgagtttctc atttcctcct aatacagtga ctggcagtga  2460
aagagttcag atcactgcaa ttggagatgt tcttggtcct tccatcaatg gcttagcctc  2520
attgattcgg atgccttatg gctgtggtga acagaacatg ataaattttg ctccaaatat  2580
ttacatttg gattatctga ctaaaaagaa acaactgaca gataatttga aagaaaaagc  2640
tctttcattt atgaggcaag gttaccagag agaacttctc tatcagaggg aagatggctc  2700
tttcagtgct tttgggaatt atgacccttc tgggagcact tggttgtcag cttttgtttt  2760
aagatgtttc cttgaagccg atccttacat agatattgat cagaatgtgt tacacagaac  2820
atacacttgg cttaaaggac atcagaaatc caacggtgaa ttttgggatc caggaagagt  2880
gattcatagt gagcttcaag gtggcaataa aagtccagta acacttacag cctatattgt  2940
aacttctctc ctgggatata gaaagtatca gcctaacatt gatgtgcaag agtctatcca  3000
ttttttggag tctgaattca gtagaggaat ttcagacaat tatactctag cccttataac  3060
ttatgcattg tcatcagtgg ggagtcctaa agcgaaggaa gctttgaata tgctgacttg  3120
gagagcagaa caagaaggtg gcatgcaatt ctgggtgtca tcagagtcca aactttctga  3180
ctcctggcag ccacgctccc tggatattga agttgcagcc tatgcactgc tctcacactt  3240
cttacaattt cagacttctg agggaatccc aattatgagg tggctaagca ggcaaagaaa  3300
tagcttgggt ggttttgcat ctactcagga taccactgtg gctttaaagg ctctgtctga  3360
atttgcagcc ctaatgaata cagaaaggac aaatatccaa gtgaccgtga cggggcctag  3420
ctcaccaagt cctgtaaagt ttctgattga cacacacaac cgcttactcc ttcagacagc  3480
agagcttgct gtggtacagc caacggcagt taatatttcc gcaaatggtt ttggatttgc  3540
tatttgtcag ctcaatgttg tatataatgt gaaggcttct gggtcttcta gaagacgaag  3600
atctatccaa aatcaagaag cctttgattt agatgttgct gtaaaagaaa ataaagatga  3660
tctcaatcat gtggatttga atgtgtgtac aagcttttcg ggcccgggta ggagtggcat  3720
```

-continued

```
ggctcttatg gaagttaacc tattaagtgg ctttatggtg ccttcagaag caatttctct  3780
gagcgagaca gtgaagaaag tggaatatga tcatggaaaa ctcaacctct atttagattc  3840
tgtaaatgaa acccagtttt gtgttaatat tcctgctgtg agaaacttta aagtttcaaa  3900
tacccaagat gcttcagtgt ccatagtgga ttactatgag ccaaggagac aggcggtgag  3960
aagttacaac tctgaagtga agctgtcctc ctgtgacctt tgcagtgatg tccagggctg  4020
ccgtccttgt gaggatggag cttcaggctc ccatcatcac tcttcagtca tttttatttt  4080
ctgtttcaag cttctgtact ttatggaact ttggctgtga tttattttta aaggactctg  4140
tgtaacacta acatttccag tagtcacatg tgattgtttt gttttcgtag aagaatactg  4200
cttctatttt gaaaaaagag tttttttttct ttctatgggg ttgcagggat ggtgtacaac  4260
aggtcctagc atgtatagct gcatagattt cttcacctga tctttgtgtg gaagatcaga  4320
atgaatgcag ttgtgtgtct atattttccc ctctcaaaat cttttagaat ttttttggag  4380
gtgtttgttt tctccagaat aaaggtatta ctttagaata ggtattctcc tcattttgtg  4440
aaagaaatga acctagattc ttaagcatta ttacacatcc atgtttgctt aaagatggat  4500
ttccctggga atgggagaaa acagccagca ggaggagctt catctgttcc cttcccacct  4560
ccaacctagc cctactgccc accccacccc aacccacccc atgcccagtg gtctcagtag  4620
atacttctta actggaaatt ctttcttttc agaatctagg tggtgaattt tttttaagtg  4680
gcacggtctt tttctgcttg aaatctgatc acaccccccca gccattgccc tccctctctt  4740
tttcctctgt agagaaatgt gaggggcagt acatttactg tgcttttcac accatctcag  4800
aggttgagga gcatactgaa aattgccctg gggggtgctg ggtgtgctgt ctccttccca  4860
catcctcagc cccacaccag ctctatttca ggggtgagag tcagagagca ctgcaatatg  4920
tgcttcatgg gatttcgatt cgaagatcct agaccaggga gacactgtga gccagggata  4980
caacaaaata ctaggtaagt cactgcagac cgacctccct gcagtttggg aaagaagctg  5040
ggtttgtgga gaatcagagc atcttgacat gactgctgac ctaaagatcc ctggcattgg  5100
ccagggatcc tgtggaacct cttctagttc aggggtgtga gcattagact gccagttgtc  5160
tagtgacatc tgatgcttgc tgtgaacttt taagatcccc gaatcctgag cacctcaatc  5220
tttaattgcc ctgtattccg aagggtaata taatttatct ggatggaaat tttaaagatg  5280
aatccccctt ttttcttttc ttctctcttt tctttccttc tccctttctt ctttgccttc  5340
taaatatact gaaatgattt agatatgtgt caacaattaa tgatctttta ttcaatctaa  5400
gaaatggttt agtttttctc tttagctcta tggcatttca ctcaagtgga caggggaaaa  5460
agtaattgcc atgggctcca aagaatttgc tttatgtttt tagctattta aaaataaatc  5520
catcaaaaat aaagtatgca aatgtatctt ttaaagttaa tttttaaaaa tgctcttatt  5580
ttagtgaatt ttcagaaatt atagtggaat ggatgctcat atattgctta tggatatttt  5640
ggataccaaa gtaggaataa ctgacattca gtattttaaa gctggcaaac ctgtacatag  5700
aaaatagatc cccagacagt ggtctatgaa gagggcagtt aagtatcaaa tacttaattt  5760
tcttgccttt ttttcttaag tggggaaaag tttctagatc tcttacacct ctgacacaat  5820
ctgttctaaa acaggcactt gtaatgttgg ggcctccttg taaacgtgtt tttgcccttt  5880
actctctggg agttctttaa aggtgaaatc atcttacaaa gaaattgggg gagggtcttg  5940
gcaaaggact ttcccctcct ctttcctggc ctgggaacct tatactgaca atcaatactt  6000
tatattttaa agtatataat ttatagttaa cttctagtgt aatatattag gaaacactag  6060
aatggaaagg ccattggaag acaggttgta tctttttttag accatatttc cttgtttaaa  6120
aactatcatt tgaatacttt tttggtgaag aactccatgt tttcaagtta aaggtcacct  6180
cgtaggccag gcgcagtggc tcatgcctgt aatcccagca ctctgggagg ctgaggcggg  6240
tgaatcacaa ggttaggagt ttgagaccag cctggccaat atggtgaaac cccgtcccta  6300
ctaaaaatac aaaatttagc caggcgtggt ggcatgcacc tgtagtccca cctactcggg  6360
aggctgaggc aggagaatca cttgaacctg agagacagag gttgcagtga gccgagatca  6420
cgccactgca ctccagcctg ggggacagag tgagattctg tctcaaaaaa caaaaaacaa  6480
aaaagtcacc ttgtaactca tctcttttta ttgtaagttt attaaaaatg aagaggacaa  6540
caatgagaag gaacataaag ggttagctag cactgtctcc tggtgcatgg ggctgtgcag  6600
atgtcccggc cacttcttcc ttcatacttc ccttagagaa cttgctctgc tacaagcagt  6660
gggcttggac taaaagtgat taaaatacca caggcataag gagaaaagga gtatatgtag  6720
tagtaataat tactagtata aattattttc ttcacatgct atgagtaata atattaaaaa  6780
actcatttta ccattaagat tccttatgct gaagctcttc catttagaat actgtcaatg  6840
tcatttactg gtatgaacta aagtcccccct tcttttccac tcactgggaa ccttagtaaa  6900
acaccagcat atcttacctc tctttctgac tggccgatgc ttccagagac tgaatgttgg  6960
gaaaacctag tagccaaaca attctaggac agaataacat ttttatattt ggttccacca  7020
tcttattaca tttagttata gttttaaaaa agaaattcaa gcccattaaa atatgtctgg  7080
tcaatgaaat gcttcctttt attgtgttgt gctattgtac tttgtttttc aaaacattgt  7140
aaaaatagta tctttggttt agtattttgg attatatatt ataatctgag gagtgttttg  7200
cttatgtaga atccagatat atttctgtta cctaggagat gttacttaca tatgtaatac  7260
tgtatcctgc acgtggaaat attcagaatt gtagatagca taactctccc tgctcctatt  7320
cttttgagcc taggtataat tttttttttt tttttagaaa aagacatatt tagctttaat  7380
ttctatttat gctaaacata tttataagta gtctgtcaat ataataccaa ctatttttat  7440
ttttacataa ttcaattatt tcatttgaca tgtctggcag actcaagaca ttaagtaaaa  7500
aattggaact atgattttttc tttgtcattt tttaaaaaag aattatttta ttaacctgct  7560
ggcatataat ctggagttct tttcacaacc ttacttttttc tgatttgctt tattgaatga  7620
ttgaatactc atttctttct aaaaatatgt tgtaaattct ccccttggcaa gatttctccc  7680
tatgagggta gttattattt gagtctgcca agtggttacc atggggcaag gtgccatgat  7740
gtattcttgg gtgcattggt tttttgcgca ttgtaaattt aagacactta tagtaagtgg  7800
actcattcat agatgagttt cagaaccttt tacgttctcg gtagaggctt ctgtcggaca  7860
ggcagaagag tgtattcctc acttttttttt ttgtcttcaa attccagtaa ggcatagcac  7920
ttttaagaaa ttagaatttt tctatcatct atgcaaatga tatttatgtt aatattaaat  7980
atcttatgtt acactgggag taatttgagg tgcaattatt tttattacta ctttgaatag  8040
aggaccatta tccttctttc ttcagaaaac taagaagtaa gtgtaacttt taaagtaagt  8100
atatatcagt gagagtaggc ttgttttaca actatttcta gccagtgagt tgtgttttca  8160
tgtctcatca aaagacaata ccacattgca tcattttaca aaatatgttg tcattttcat  8220
ttcagttgta acataggaaa atagatattt cctagatgat ttctgagttt cttactgcaa  8280
agaacagtta taaattggta tacatgtgtc tctgtaatag ggataatatt gatatatctg  8340
ttgctacata tttaagaatc attctatctt atgttgtctt gaggccaaga tttaccacgt  8400
ttgcccagtg tattgaattg gtggtagaag gtagttccat gttccatttg tagatcttta  8460
```

```
agattttatc tttgataact ttaatagaat gtggctcagt tctggtcctt caagcctgta  8520
tggtttggat tttcagtagg ggacagttga tgtggagtca atctctttgg tacacaggaa  8580
gctttataaa atttcattca cgaatctctt attttgggaa gctgttttgc atatgagaag  8640
aacactgttg aaataaggaa ctaaagcttt atatattgat caaggtgatt ctgaaagttt  8700
taatttttaa tgttgtaatg ttatgttatt gttaattgta ctttattatg tattcaatag  8760
aaaatcatga tttattaata aaagcttaaa ttctcatcta                        8800

SEQ ID NO: 15          moltype = RNA  length = 8980
FEATURE                Location/Qualifiers
source                 1..8980
                       mol_type = mRNA
                       organism = Homo sapiens
SEQUENCE: 15
agacgccgtc gagatgcagg gcccaccgct cctgaccgcc gcccacctcc tctgcgtgtg  60
caccgccgcg ctggccgtgg ctcccgggcc tcggtttctg gtgacagccc cagggatcat  120
caggcccgga ggaaatgtga ctattggggt ggagcttctg gaacactgcc cttcacaggt  180
gactgtgaag gcggagctgc tcaagacagc atcaaacctc actgtctctg tcctggaagc  240
agaaggagtc tttgaaaaag gctcttttaa gacacttact cttccatcac tacctctgaa  300
cagtgcagat gagatttatg agctacgtgt aaccggacgt acccaggatg agattttatt  360
ctctaatagt acccgcttat catttgagac caagagaata tctgtcttca ttcaaacaga  420
caaggcctta tacaagccaa agcaagaagt gaagtttcgc attgttacac tcttctcaga  480
ttttaagcct tacaaaacct ctttaaacat tctcattaag gaccccaaat caaatttgat  540
ccaacagtgg ttgtcacaac aaagtgatct tggagtcatt tccaaaactt ttcagctatc  600
ttcccatcca atacttggtg actggtctat tcaagttcaa gtgaatgacc agacatacta  660
tcaatcattt caggtttcag aatatgtatt accaaaattt gaagtgactt tgcagacacc  720
attatattgt tctatgaatt ctaagcattt aaatggtacc atcacggcaa agtatacata  780
tgggaagcca gtgaaaggag acgtaacgct tacattttta cctttatcct tttggggaaa  840
gaagaaaaat attacaaaaa catttaagat aaatggatct gcaaacttct cttttaatga  900
tgaagagatg aaaaatgtaa tggattcttc aaatggactt tctgaatacc tggatctatc  960
ttcccctgga ccagtagaaa ttttaaccac agtgacagaa tcagttacag gtatttcaag  1020
aaatgtaagc actaatgtgt tcttcaagca acatgattac atcattgagt tttttgatta  1080
tactactgtc ttgaagccat ctctcaactt cacagccact gtgaaggtaa ctcgtgctga  1140
tggcaaccaa ctgactcttg aagaaagaag aaataatgta gtcataacag tgacacagag  1200
aaactatact gagtactgga gcggatctaa cagtggaaat cagaaaatgg aagctgttca  1260
gaaaataaat tatactgtcc cccaaagtgg aacttttaag attgaattcc caatcctgga  1320
ggattccagt gagctacagt tgaaggccta tttccttggt agtaaaagta gcatggcagt  1380
tcatagtctg tttaagtctc ctagtaagac atacatccaa ctaaaaacaa gagatgaaaa  1440
tataaaggtg ggatcgcctt ttgagttggt ggttagtggc aacaaacgat tgaaggagtt  1500
aagctatatg gtagtatcca ggggacagtt ggtggctgta ggaaaacaaa attcaacaat  1560
gttctcttta acaccagaaa attcttggac tccaaaagcc tgtgtaattg tgtattatat  1620
tgaagatgat ggggaaatta taagtgatgt tctaaaaatt cctgttcagc ttgtttttaa  1680
aaataagata aagctatatt ggagtaaagt gaaagctgaa ccatctgaga aagtctctct  1740
taggatctct gtgacacagc ctgactccat agttgggatt gtagctgttg acaaaagtgt  1800
gaatctgatg aatgcctcta atgatattac aatggaaaat gtggtccatg agttggaact  1860
ttataacaca ggatattatt taggcatgtt catgaattct tttgcagtct ttcaggaatg  1920
tggactctgg gtattgacag atgcaaacct cacgaaggat tatattgatg gtgtttatga  1980
caatgcagaa tatgctgaga ggtttatgga ggaaaatgaa ggacatattg tagatattca  2040
tgacttttct ttgggtagca gtccacatgt ccgaaagcat tttccagaga cttggatttg  2100
gctagacacc aacatgggtt acaggattta ccaagaattt gaagtaactg tacctgattc  2160
tatcacttct tgggtggcta ctggttttgt gatctctgag gacctgggtc ttggactaac  2220
aactactcca gtggagctcc aagccttcca accatttttc atttttttga atcttcccta  2280
ctctgttatc agaggtgaag aatttgcttt ggaaataact atattcaatt atttgaaaga  2340
tgccactgag gttaaggtaa tcattgagaa aagtgacaaa tttgatattc taatgacttc  2400
aaatgaaata aatgccacag gccaccagca gacccttctg gttcccagtg aggatggggc  2460
aactgttctt tttcccatca ggccaacaca tctgggagaa attcctatca cagtcacagc  2520
tctttcaccc actgcttctg atgctgtcac ccagatgatt ttagtaaagg ctgaaggaat  2580
agaaaaatca tattcacaat ccatcttatt agacttgact gacaataggc tacagagtac  2640
cctgaaaact ttgagtttct catttcctcc taatacagtg actggcagtg aaagagttca  2700
gatcactgca attggagatg ttcttggtcc ttccatcaat ggcttagcct cattgattcg  2760
gatgccttat ggctgtggtg aacagaacat gataaatttt gctccaaata tttacatttt  2820
ggattatctg actaaaaaga aacaactgac agataatttg aaagaaaaag ctctttcatt  2880
tatgaggcaa ggttaccaga gagaacttct ctatcagagg gaagatggct ctttcagtgc  2940
ttttgggaat tatgaccctt ctgggagcac ttggttgtca gcttttgttt taagatgttt  3000
ccttgaagcc gatccttaca tagatattga tcagaatgtg ttacacagaa catacacttg  3060
gcttaaagga catcagaaat ccaacggtga attttgggat ccaggaagag tgattcatag  3120
tgagcttcaa ggtggcaata aaagtccagt aacacttaca gcctatattg taacttctct  3180
cctgggatat agaaagtatc agcctaacat tgatgtgcaa gagtctatcc atttttttgga  3240
gtctgaattc agtagaggaa tttcagacaa ttatactcta gcccttataa cttatgcatt  3300
gtcatcagtg gggagtccta aagcgaagga agctttgaat atgctgactt ggagagcaga  3360
acaagaaggt ggcatgcaat tctgggtgtc atcagagtcc aaactttctg actcctggca  3420
gccacgctcc ctggatattg aagttgcagc ctatgcactg ctctcacact tcttacaatt  3480
tcagacttct gagggaatcc caattatgag gtggctaagc aggcaaagaa atagcttggg  3540
tggttttgca tctactcagg ataccactgt ggctttaaag gctctgtctg aatttgcagc  3600
cctaatgaat acagaaagga caaatatcca agtgaccgtg acggggccta gctcaccaag  3660
tcctcttgct gtggtacagc caacggcagt taatatttcc gcaaatggtt ttggatttgc  3720
tatttgtcag ctcaatgttg tatataatgt gaaggcttct gggtcttcta gaagacgaag  3780
atctatccaa aatcaagaag cctttgattt agatgttgct gtaaaagaaa ataaagatga  3840
tctcaatcat gtggatttga atgtgtgtac aagcttttcg ggcccgggta ggagtggcat  3900
ggctcttatg gaagttaacc tattaagtgg ctttatggtg ccttcagaag caatttctct  3960
```

-continued

```
gagcgagaca gtgaagaaag tggaatatga tcatggaaaa ctcaacctct atttagattc  4020
tgtaaatgaa acccagtttt gtgttaatat tcctgctgtg agaaacttta aagtttcaaa  4080
tacccaagat gcttcagtgt ccatagtgga ttactatgag ccaaggagac aggcggtgag  4140
aagttacaac tctgaagtga agctgtcctc ctgtgacctt tgcagtgatg tccagggctg  4200
ccgtccttgt gaggatggag cttcaggctc ccatcatcac tcttcagtca tttttatttt  4260
ctgtttcaag cttctgtact ttatggaact ttggctgtga tttattttta aaggactctg  4320
tgtaacacta acatttccag tagtcacatg tgattgtttt gttttcgtag aagaatactg  4380
cttctatttt gaaaaaagag tttttttttct ttctatgggg ttgcagggat ggtgtacaac  4440
aggtcctagc atgtatagct gcatagattt cttcacctga tctttgtgtg gaagatcaga  4500
atgaatgcag ttgtgtgtct atattttccc ctctcaaaat cttttagaat tttttggag   4560
gtgtttgttt tctccagaat aaaggtatta ctttagaata ggtattctcc tcattttgtg  4620
aaagaaatga acctagattc ttaagcatta ttacacatcc atgtttgctt aaagatggat  4680
ttccctggga atgggagaaa acagccagca ggaggagctt catctgttcc cttcccacct  4740
ccaacctagc cctactgccc accccacccc aacccacccc atgcccagtg gtctcagtag  4800
atacttctta actggaaatt ctttcttttc agaatctagg tggtgaattt tttttaagtg  4860
gcacggtctt tttctgcttg aaatctgatc acacccccca gccattgccc tccctctctt  4920
tttcctctgt agagaaatgt gaggggcagt acatttactg tgcttttcac accatctcag  4980
aggttgagga gcatactgaa aattgccctg gggggtgctg ggtgtgctgt ctccttccca  5040
catcctcagc cccacaccag ctctatttca ggggtgagag tcagagagca ctgcaatatg  5100
tgcttcatgg gatttcgatt cgaagatcct agaccaggga gacactgtga gccagggata  5160
caacaaaata ctaggtaagt cactgcagac cgacctccct gcagtttggg aaagaagctg  5220
ggtttgtgga gaatcagagc atcttgacat gactgctgac ctaaagatcc ctggcattgg  5280
ccagggatcc tgtggaacct cttctagttc aggggtgtga gcattagact gccagttgtc  5340
tagtgacatc tgatgcttgc tgtgaacttt taagatcccc gaatcctgag cacctcaatc  5400
tttaattgcc ctgtattccg aagggtaata taatttatct ggatggaaat tttaaagatg  5460
aatccccctt ttttcttttc ttctctcttt tctttccttc tccctttctt ctttgccttc  5520
taaatatact gaaatgattt agatatgtgt caacaattaa tgatctttta ttcaatctaa  5580
gaaatggttt agtttttctc tttagctcta tggcatttca ctcaagtgga caggggaaaa  5640
agtaattgcc atgggctcca aagaatttgc tttatgtttt tagctattta aaaataaatc  5700
catcaaaaat aaagtatgca aatgtatctt ttaaagttaa tttttaaaaa tgctcttatt  5760
ttagtgaatt ttcagaaatt atagtggaat ggatgctcat atattgctta tggatatttt  5820
ggataccaaa gtaggaataa ctgacattca gtattttaaa gctggcaaac ctgtacatag  5880
aaaatagatc cccagacagt ggtctatgaa gagggcagtt aagtatcaaa tacttaattt  5940
tcttgccttt ttttcttaag tggggaaaag tttctagatc tcttacacct ctgacacaat  6000
ctgttctaaa acaggcactt gtaatgttgg ggcctccttg taaacgtgtt tttgcccttt  6060
actctctggg agttctttaa aggtgaaatc atcttacaaa gaaattgggg gagggtcttg  6120
gcaaaggact ttcccctcct ctttcctggc ctgggaacct tatactgaca atcaatactt  6180
tatattttaa agtatataat ttatagttaa cttctagtgt aatatattag gaaacactag  6240
aatggaaagg ccattggaag acaggttgta tctttttttag accatatttc cttgtttaaa  6300
aactatcatt tgaatacttt tttggtgaag aactccatgt tttcaagtta aaggtcacct  6360
cgtaggccag gcgcagtggc tcatgcctgt aatcccagca ctctgggagg ctgaggcggg  6420
tgaatcacaa ggttaggagt ttgagaccag cctggccaat atggtgaaac cccgtcccta  6480
ctaaaaatac aaaatttagc caggcgtggt ggcatgcacc tgtagtccca cctactcggg  6540
aggctgaggc aggagaatca cttgaacctg agagacagag gttgcagtga gccgagatca  6600
cgccactgca ctccagcctg ggggacagag tgagattctg tctcaaaaaa caaaaaaacaa  6660
aaaagtcacc ttgtaactca tctcttttta ttgtaagttt attaaaaatg aagaggacaa  6720
caatgagaag gaacataaag ggttagctag cactgtctcc tggtgcatgg ggctgtgcag  6780
atgtcccggc cacttcttcc ttcatacttc ccttagagaa cttgctctgc tacaagcagt  6840
gggcttggac taaaagtgat taaaatacca caggcataag gagaaaagga gtatatgtag  6900
tagtaataat tactagtata aattattttc ttcacatgct atgagtaata atattaaaaa  6960
actcatttta ccattaagat tccttatgct gaagctcttc catttagaat actgtcaatg  7020
tcatttactg gtatgaacta aagtccccct tcttttccac tcactgggaa ccttagtaaa  7080
acaccagcat atcttacctc tctttctgac tggccgatgc ttccagagac tgaatgttgg  7140
gaaaacctag tagccaaaca attctaggac agaataacat ttttatattt ggttccacca  7200
tcttattaca tttagttata gttttaaaaa agaaattcaa gcccattaaa atatgtctgg  7260
tcaatgaaat gcttcctttt attgtgttgt gctattgtac tttgtttttc aaaacattgt  7320
aaaaatagta tctttggttt agtattttgg attatatatt ataatctgag gagtgttttg  7380
cttatgtaga atccagatat atttctgtta cctaggagat gttacttaca tatgtaatac  7440
tgtatcctgc acgtggaaat attcagaatt gtagatagca taactctccc tgctcctatt  7500
cttttgagcc taggtataat tttttttttt tttttagaaa aagacatatt tagctttaat  7560
ttctatttat gctaaacata tttataagta gtctgtcaat ataataccaa ctatttttat  7620
ttttacataa ttcaattatt tcatttgaca tgtctggcag actcaagaca ttaagtaaaa  7680
aattggaact atgattttc tttgtcattt tttaaaaaag aattatttta ttaacctgct  7740
ggcatataat ctggagttct tttcacaacc ttactttttc tgatttgctt tattgaatga  7800
ttgaatactc atttctttct aaaaatatgt tgtaaattct cccttggcaa gatttctccc  7860
tatgagggta gttattattt gagtctgcca agtggttacc atggggcaag gtgccatgat  7920
gtattcttgg gtgcattggt tttttgcgca ttgtaaattt aagacactta tagtaagtgg  7980
actcattcat agatgagttt cagaaccttt tacgttctcg gtagaggctt ctgtcggaca  8040
ggcagaagag tgtattcctc acttttttttt ttgtcttcaa attccagtaa ggcatagcac  8100
ttttaagaaa ttagaatttt tctatcatct atgcaaatga tatttatgtt aatattaaat  8160
atcttatgtt acactgggag taatttgagg tgcaattatt tttattacta ctttgaatag  8220
aggaccatta tccttctttc ttcagaaaac taagaagtaa gtgtaacttt taaagtaagt  8280
atatatcagt gagagtaggc ttgttttaca actatttcta gccagtgagt tgtgttttca  8340
tgtctcatca aaagacaata ccacattgca tcattttaca aaatatgttg tcattttcat  8400
ttcagttgta acataggaaa atagatattt cctagatgat ttctgagttt cttactgcaa  8460
agaacagtta taaattggta tacatgtgtc tctgtaatag ggataatatt gatatatctg  8520
ttgctacata tttaagaatc attctatctt atgttgtctt gaggccaaga tttaccacgt  8580
ttgcccagtg tattgaattg gtggtagaag gtagttccat gttccatttg tagatcttta  8640
agattttatc tttgataact ttaatagaat gtggctcagt tctggtcctt caagcctgta  8700
```

```
tggtttggat tttcagtagg ggacagttga tgtggagtca atctctttgg tacacaggaa  8760
gctttataaa atttcattca cgaatctctt attttgggaa gctgttttgc atatgagaag  8820
aacactgttg aaataaggaa ctaaagcttt atatattgat caaggtgatt ctgaaagttt  8880
taatttttaa tgttgtaatg ttatgttatt gttaattgta ctttattatg tattcaatag  8940
aaaatcatga tttattaata aaagcttaaa ttctcatcta                        8980

SEQ ID NO: 16          moltype = DNA  length = 9401
FEATURE                Location/Qualifiers
source                 1..9401
                       mol_type = genomic DNA
                       organism = Homo sapiens
SEQUENCE: 16
atagttgcta tgaatttctc ctcacaagga tgggcctgtt tactcaccct gggcatcgtt  60
ggtagagcgc tagtgtaaac agcctgagga acccggtggg ccggggaagt gggcgcgctc  120
tgttctccgc ggccagctgg gacgccgggc caggtggggc cgcctgcgtt tagcaactgc  180
tttctcaccc cctggatttg cgatgtttgc cacagcagcg agaagcgcca ttgtaatggg  240
gatgggaggg gtggagcctc caagtcctgt ctcaatttag atctctcact ctgctgttag  300
gcgcgcccat ttcagattac taaactcgaa ttaagaggga aaaaaaatca gggaggaggt  360
ggcaagccac accccacggt gcccgcgaac ttccccggca gcggactgta gcccaggcag  420
acgccgtcga gatgcagggc ccaccgctcc tgaccgccgc ccacctcctc tgcgtgtgca  480
ccgccgcgct ggccgtggct cccgggcctc ggtttctggt gacagcccca gggatcatca  540
ggcccggagg aaatgtgact attggggtgg agcttctgga acactgccct tcacaggtga  600
ctgtgaaggc ggagctgctc aagacagcat caaacctcac tgtctctgtc ctggaagcag  660
aaggagtctt tgaaaaaggc tcttttaaga cacttactct tccatcacta cctctgaaca  720
gtgcagatga gatttatgag ctacgtgtaa ccggacgtac ccaggatgag attttattct  780
ctaatagtac ccgcttatca tttgagacca agagaatatc tgtcttcatt caaacagaca  840
aggccttata caagccaaag caagaagtga agtttcgcat tgttacactc ttctcagatt  900
ttaagcctta caaaacctct ttaaacattc tcattaagga ccccaaatca aatttgatcc  960
aacagtggtt gtcacaacaa agtgatcttg gagtcatttc caaaactttt cagctatctt  1020
cccatccaat acttggtgac tggtctattc aagttcaagt gaatgaccag acatactatc  1080
aatcatttca ggtttcagaa tatgtattac caaaatttga agtgactttg cagacaccat  1140
tatattgttc tatgaattct aagcatttaa atggtaccat cacggcaaag tatacatatg  1200
ggaagccagt gaaaggagac gtaacgctta catttttacc tttatccttt tggggaaaga  1260
agaaaaatat tacaaaaaca tttaagataa atggatctgc aaacttctct tttaatgatg  1320
aagagatgaa aaatgtaatg gattcttcaa atggactttc tgaatacctg gatctatctt  1380
cccctggacc agtagaaatt ttaaccacag tgacagaatc agttacaggt atttcaagaa  1440
atgtaagcac taatgtgttc ttcaagcaac atgattacat cattgagttt tttgattata  1500
ctactgtctt gaagccatct ctcaacttca cagccactgt gaaggtaact cgtgctgatg  1560
gcaaccaact gactcttgaa gaaagaagaa ataatgtagt cataacagtg acacagagaa  1620
actatactga gtactggagc ggatctaaca gtggaaatca gaaaatggaa gctgttcaga  1680
aaataaatta tactgtcccc caaagtggaa cttttaagat tgaattccca atcctggagg  1740
attccagtga gctacagttg aaggcctatt tccttggtag taaaagtagc atggcagttc  1800
atagtctgtt taagtctcct agtaagacat acatccaact aaaaacaaga gatgaaaata  1860
taaaggtggg atcgcctttt gagttggtgg ttagtggcaa caaacgattg aaggagttaa  1920
gctatatggt agtatccagg ggacagttgg tggctgtagg aaaacaaaat tcaacaatgt  1980
tctctttaac accagaaaat tcttggactc caaaagcctg tgtaattgtg tattatattg  2040
aagatgatgg ggaaattata agtgatgttc taaaaattcc tgttcagctt gtttttaaaa  2100
ataagataaa gctatattgg agtaaagtga aagctgaacc atctgagaaa gtctctctta  2160
ggatctctgt gacacagcct gactccatag ttgggattgt agctgttgac aaaagtgtga  2220
atctgatgaa tgcctctaat gatattacaa tggaaaatgt ggtccatgag ttggaacttt  2280
ataacacagg atattattta ggcatgttca tgaattcttt tgcagtcttt caggaatgtg  2340
gactctgggt attgacagat gcaaacctca cgaaggatta tattgatggt gtttatgaca  2400
atgcagaata tgctgagagg tttatggagg aaaatgaagg acatattgta gatattcatg  2460
acttttcttt gggtagcagt ccacatgtcc gaaagcattt tccagagact tggatttggc  2520
tagacaccaa catgggttac aggatttacc aagaatttga agtaactgta cctgattcta  2580
tcacttcttg ggtggctact ggttttgtga tctctgagga cctgggtctt ggactaacaa  2640
ctactccagt ggagctccaa gccttccaac catttttcat tttttgaat cttccctact  2700
ctgttatcag aggtgaagaa tttgctttgg aaataactat attcaattat ttgaaagatg  2760
ccactgaggt taaggtaatc attgagaaaa gtgacaaatt tgatattcta atgacttcaa  2820
atgaaataaa tgccacaggc caccagcaga cccttctggt tcccagtgag gatggggcaa  2880
ctgttctttt tcccatcagg ccaacacatc tgggagaaat tcctatcaca gtcacagctc  2940
tttcacccac tgcttctgat gctgtcaccc agatgatttt agtaaaggct gaaggaatag  3000
aaaaatcata ttcacaatcc atcttattag acttgactga caataggcta cagagtaccc  3060
tgaaaacttt gagtttctca tttcctccta atacagtgac tggcagtgaa agagttcaga  3120
tcactgcaat tggagatgtt cttggtcctt ccatcaatgg cttagcctca ttgattcgga  3180
tgccttatgg ctgtggtgaa cagaacatga taaattttgc tccaaatatt tacattttgg  3240
attatctgac taaaaagaaa caactgacag ataatttgaa agaaaaagct ctttcattta  3300
tgaggcaagg ttaccagaga gaacttctct atcagaggga agatggctct ttcagtgctt  3360
ttgggaatta tgacccttct gggagcactt ggttgtcagc ttttgtttta agatgtttcc  3420
ttgaagccga tccttacata gatattgatc agaatgtgtt acacagaaca tacacttggc  3480
ttaaaggaca tcagaaatcc aacggtgaat tttgggatcc aggaagagtg attcatagtg  3540
agcttcaagg tggcaataaa agtccagtaa cacttacagc ctatattgta acttctctcc  3600
tgggatatag aaagtatcag cctaacattg atgtgcaaga gtctatccat tttttggagt  3660
ctgaattcag tagaggaatt tcagacaatt atactctagc ccttataact tatgcattgt  3720
catcagtggg gagtcctaaa gcgaaggaag ctttgaatat gctgacttgg agagcagaac  3780
aagaaggtgg catgcaattc tgggtgtcat cagagtccaa actttctgac tcctggcagc  3840
cacgctccct ggatattgaa gttgcagcct atgcactgct ctcacacttc ttacaatttc  3900
agacttctga gggaatccca attatgaggt ggctaagcag gcaaagaaat agcttgggtg  3960
gttttgcatc tactcaggat accactgtgg ctttaaaggc tctgtctgaa tttgcagccc  4020
```

-continued taatgaatac agaaaggaca aatatccaag tgaccgtgac ggggcctagc tcaccaagtc 4080
ctcttgctgt ggtacagcca acggcagtta atatttccgc aaatggtttt ggatttgcta 4140
tttgtcagct caatgttgta tataatgtga aggcttctgg gtcttctaga agacgaagat 4200
ctatccaaaa tcaagaagcc tttgatttag atgttgctgt aaaagaaaat aaagatgatc 4260
tcaatcatgt ggatttgaat gtgtgtacaa gcttttcggg cccgggtagg agtggcatgg 4320
ctcttatgga agttaaccta ttaagtggct ttatggtgcc ttcagaagca atttctctga 4380
gcgagacagt gaagaaagtg gaatatgatc atggaaaact caacctctat ttagattctg 4440
taaatgaaac ccagttttgt gttaatattc ctgctgtgag aaactttaaa gtttcaaata 4500
cccaagatgc ttcagtgtcc atagtggatt actatgagcc aaggagacag gcggtgagaa 4560
gttacaactc tgaagtgaag ctgtcctcct gtgacctttg cagtgatgtc cagggctgcc 4620
gtccttgtga ggatggagct tcaggctccc atcatcactc ttcagtcatt tttatttttct 4680
gtttcaagct tctgtacttt atggaacttt ggctgtgatt tatttttaaa ggactctgtg 4740
taacactaac atttccagta gtcacatgtg attgttttgt tttcgtagaa gaatactgct 4800
tctattttga aaaaagagtt tttttctttt ctatggggtt gcagggatgg tgtacaacag 4860
gtcctagcat gtatagctgc atagatttct tcacctgatc tttgtgtgga agatcagaat 4920
gaatgcagtt gtgtgtctat attttcccct ctcaaaatct tttagaattt ttttggaggt 4980
gtttgttttc tccagaataa aggtattact ttagaatagg tattctcctc attttgtgaa 5040
agaaatgaac ctagattctt aagcattatt acacatccat gtttgcttaa agatggattt 5100
ccctgggaat gggagaaaac agccagcagg aggagcttca tctgttccct tcccacctcc 5160
aacctagccc tactgcccac cccaccccaa ccccaccccat gcccagtggt ctcagtagat 5220
acttcttaac tggaaattct ttcttttcag aatctaggtg gtgaattttt tttaagtggc 5280
acggtctttt tctgcttgaa atctgatcac accccccagc cattgccctc cctctctttt 5340
tcctctgtag agaaatgtga ggggcagtac atttactgtg cttttcacac catctcagag 5400
gttgaggagc atactgaaaa ttgccctggg gggtgctggg tgtgctgtct ccttccccaca 5460
tcctcagccc cacaccagct ctatttcagg ggtgagagtc agagagcact gcaatatgtg 5520
cttcatggga tttcgattcg aagatcctag accagggaga cactgtgagc cagggataca 5580
acaaaatact aggtaagtca ctgcagaccg acctccctgc agtttgggaa agaagctggg 5640
tttgtggaga atcagagcat cttgacatga ctgctgacct aaagatccct ggcattggcc 5700
agggatcctg tggaacctct tctagttcag gggtgtgagc attagactgc cagttgtcta 5760
gtgacatctg atgcttgctg tgaactttta agatccccga atcctgagca cctcaatctt 5820
taattgccct gtattccgaa gggtaatata atttatctgg atggaaattt taaagatgaa 5880
tccccctttt ttcttttctt ctctcttttc tttccttctc cctttcttct ttgccttcta 5940
aatatactga aatgatttag atatgtgtca acaattaatg atcttttatt caatctaaga 6000
aatggtttag tttttctctt tagctctatg gcatttcact caagtggaca ggggaaaaag 6060
taattgccat gggctccaaa gaatttgctt tatgttttta gctatttaaa aataaatcca 6120
tcaaaaataa agtatgcaaa tgtatctttt aaagttaatt tttaaaaatg ctcttatttt 6180
agtgaatttt cagaaattat agtggaatgg atgctcatat attgcttatg gatattttgg 6240
ataccaaagt aggaataact gacattcagt attttaaagc tggcaaacct gtacatagaa 6300
aatagatccc cagacagtgg tctatgaaga gggcagttaa gtatcaaata cttaattttc 6360
ttgccttttt ttcttaagtg gggaaaagtt tctagatctc ttacacctct gacacaatct 6420
gttctaaaac aggcacttgt aatgttgggg cctccttgta aacgtgtttt tgccctttac 6480
tctctgggag ttctttaaag gtgaaatcat cttacaaaga aattgggggga gggtcttggc 6540
aaaggacttt cccctcctct ttcctggcct gggaacctta tactgacaat caatacttta 6600
tattttaaag tatataattt atagttaact tctagtgtaa tatattagga aacactagaa 6660
tggaaaggcc attggaagac aggttgtatc tttttagac catatttcct tgtttaaaaa 6720
ctatcatttg aatacttttt tggtgaagaa ctccatgttt tcaagttaaa ggtcacctcg 6780
taggccaggc gcagtggctc atgcctgtaa tcccagcact ctgggaggct gaggcgggtg 6840
aatcacaagg ttaggagttt gagaccagcc tggccaatat ggtgaaaccc cgtccctact 6900
aaaaatacaa aatttagcca ggcgtggtgg catgcacctg tagtcccacc tactcgggag 6960
gctgaggcag gagaatcact tgaacctgag agacagaggt tgcagtgagc cgagatcacg 7020
ccactgcact ccagcctggg ggacagagtg agattctgtc tcaaaaaaca aaaaacaaaa 7080
aagtcacctt gtaactcatc tctttttatt gtaagtttat taaaaatgaa gaggacaaca 7140
atgagaagga acataaaggg ttagctagca ctgtctcctg gtgcatgggg ctgtgcagat 7200
gtcccggcca cttcttcctt catacttccc ttagagaact tgctctgcta caagcagtgg 7260
gcttggacta aaagtgatta aaataccaca ggcataagga gaaaaggagt atatgtagta 7320
gtaataatta ctagtataaa ttattttctt cacatgctat gagtaataat attaaaaaac 7380
tcattttacc attaagattc cttatgctga agctcttcca tttagaatac tgtcaatgtc 7440
atttactggt atgaactaaa gtccccccttc ttttccactc actgggaacc ttagtaaaac 7500
accagcatat cttacctctc tttctgactg gccgatgctt ccagagactg aatgttggga 7560
aaacctagta gccaaacaat tctaggacag aataacattt ttatatttgg ttccaccatc 7620
ttattacatt tagttatagt tttaaaaaag aaattcaagc ccattaaaat atgtctggtc 7680
aatgaaatgc ttccttttat tgtgttgtgc tattgtactt tgtttttcaa aacattgtaa 7740
aaatagtatc tttggtttag tattttggat tatatattat aatctgagga gtgttttgct 7800
tatgtagaat ccagatatat ttctgttacc taggagatgt tacttacata tgtaatactg 7860
tatcctgcac gtggaaatat tcagaattgt agatagcata actctccctg ctcctattct 7920
tttgagccta ggtataattt ttttttttt tttagaaaaa gacatattta gctttaattt 7980
ctatttatgc taaacatatt tataagtagt ctgtcaatat aataccaact atttttattt 8040
ttacataatt caattatttc atttgacatg tctggcagac tcaagacatt aagtaaaaaa 8100
ttggaactat gatttttctt tgtcattttt taaaaaagaa ttatttttatt aacctgctgg 8160
catataatct ggagttcttt tcacaacctt actttttctg atttgcttta ttgaatgatt 8220
gaatactcat ttctttctaa aaatatgttg taaattctcc cttggcaaga tttctcccta 8280
tgagggtagt tattatttga gtctgccaag tggttaccat ggggcaaggt gccatgatgt 8340
attcttgggt gcattggttt tttgcgcatt gtaaatttaa gacacttata gtaagtggac 8400
tcattcatag atgagtttca gaacctttta cgttctcggt agaggcttct gtcggacagg 8460
cagaagagtg tattcctcac tttttttttt gtcttcaaat tccagtaagg catagcactt 8520
ttaagaaatt agaattttc tatcatctat gcaaatgata tttatgttaa tattaaatat 8580
cttatgttac actgggagta atttgaggtg caattatttt tattactact ttgaatagag 8640
gaccattatc cttctttctt cagaaaacta agaagtaagt gtaactttta aagtaagtat 8700
atatcagtga gagtaggctt gttttacaac tatttctagc cagtgagttg tgttttcatg 8760

-continued

```
tctcatcaaa agacaatacc acattgcatc attttacaaa atatgttgtc attttcattt  8820
cagttgtaac ataggaaaat agatatttcc tagatgattt ctgagtttct tactgcaaag  8880
aacagttata aattggtata catgtgtctc tgtaataggg ataatattga tatatctgtt  8940
gctacatatt taagaatcat tctatcttat gttgtcttga ggccaagatt taccacgttt  9000
gcccagtgta ttgaattggt ggtagaaggt agttccatgt tccatttgta gatctttaag  9060
attttatctt tgataacttt aatagaatgt ggctcagttc tggtccttca agcctgtatg  9120
gtttggattt tcagtagggg acagttgatg tggagtcaat ctctttggta cacaggaagc  9180
tttataaaat ttcattcacg aatctcttat tttgggaagc tgttttgcat atgagaagaa  9240
cactgttgaa ataaggaact aaagctttat atattgatca aggtgattct gaaagtttta  9300
atttttaatg ttgtaatgtt atgttattgt taattgtact ttattatgta ttcaatagaa  9360
aatcatgatt tattaataaa agcttaaatt ctcatctatt t                      9401

SEQ ID NO: 17          moltype = DNA  length = 9221
FEATURE                Location/Qualifiers
source                 1..9221
                       mol_type = genomic DNA
                       organism = Homo sapiens
SEQUENCE: 17
atagttgcta tgaatttctc ctcacaagga tgggcctgtt tactcaccct gggcatcgtt  60
ggtagagcgc tagtgtaaac agcctgagga acccggtggg ccggggaagt gggcgcgctc  120
tgttctccgc ggccagctgg gacgccgggc caggtggggc cgcctgcgtt tagcaactgc  180
tttctcaccc cctggatttg cgatgtttgc cacagcagcg agaagcgcca ttgtaatggg  240
gatgggaggg gtggagcctc caagtcctgt ctcaatttag atctctcact ctgctgttag  300
gcgcgcccat ttcagattac taaactcgaa ttaagaggga aaaaaaatca gggaggaggt  360
ggcaagccac accccacggt gcccgcgaac ttccccggca gcggactgta gcccaggcag  420
acgccgtcga gatgcagggc ccaccgctcc tgaccgccgc ccacctcctc tgcgtgtgca  480
ccgccgcgct ggccgtggct cccgggcctc ggtttctggt gacagcccca gggatcatca  540
ggcccggagg aaatgtgact attggggtgg agcttctgga acactgccct tcacaggtga  600
ctgtgaaggc ggagctgctc aagacagcat caaacctcac tgtctctgtc ctggaagcag  660
aaggagtctt tgaaaaaggc tcttttaaga cacttactct tccatcagac cccaaatcaa  720
atttgatcca acagtggttg tcacaacaaa gtgatcttgg agtcatttcc aaaacttttc  780
agctatcttc ccatccaata cttggtgact ggtctattca agttcaagtg aatgaccaga  840
catactatca atcatttcag gtttcagaat atgtattacc aaaatttgaa gtgactttgc  900
agacaccatt atattgttct atgaattcta agcatttaaa tggtaccatc acggcaaagt  960
atacatatgg gaagccagtg aaaggagacg taacgcttac atttttacct ttatcctttt  1020
ggggaaagaa gaaaaatatt acaaaaacat ttaagataaa tggatctgca aacttctctt  1080
ttaatgatga agagatgaaa aatgtaatgg attcttcaaa tggactttct gaatacctgg  1140
atctatcttc ccctggacca gtagaaattt taaccacagt gacagaatca gttacaggta  1200
tttcaagaaa tgtaagcact aatgtgttct tcaagcaaca tgattacatc attgagtttt  1260
ttgattatac tactgtcttg aagccatctc tcaacttcac agccactgtg aaggtaactc  1320
gtgctgatgg caaccaactg actcttgaag aaagaagaaa taatgtagtc ataacagtga  1380
cacagagaaa ctatactgag tactggagcg gatctaacag tggaaatcag aaaatggaag  1440
ctgttcagaa aataaattat actgtccccc aaagtggaac ttttaagatt gaattcccaa  1500
tcctggagga ttccagtgag ctacagttga aggcctattt ccttggtagt aaaagtagca  1560
tggcagttca tagtctgttt aagtctccta gtaagacata catccaacta aaaacaagag  1620
atgaaaatat aaaggtggga tcgccttttg agttggtggt tagtggcaac aaacgattga  1680
aggagttaag ctatatggta gtatccaggg gacagttggt ggctgtagga aaacaaaatt  1740
caacaatgtt ctctttaaca ccagaaaatt cttggactcc aaaagcctgt gtaattgtgt  1800
attatattga agatgatggg gaaattataa gtgatgttct aaaaattcct gttcagcttg  1860
tttttaaaaa taagataaag ctatattgga gtaaagtgaa agctgaacca tctgagaaag  1920
tctctcttag gatctctgtg acacagcctg actccatagt tgggattgta gctgttgaca  1980
aaagtgtgaa tctgatgaat gcctctaatg atattacaat ggaaaatgtg gtccatgagt  2040
tggaacttta taacacagga tattatttag gcatgttcat gaattctttt gcagtctttc  2100
aggaatgtgg actctgggta ttgacagatg caaacctcac gaaggattat attgatggtg  2160
tttatgacaa tgcagaatat gctgagaggt ttatggagga aaatgaagga catattgtag  2220
atattcatga cttttctttg ggtagcagtc cacatgtccg aaagcatttt ccagagactt  2280
ggatttggct agacaccaac atgggttaca ggatttacca agaatttgaa gtaactgtac  2340
ctgattctat cacttcttgg gtggctactg gttttgtgat ctctgaggac ctgggtcttg  2400
gactaacaac tactccagtg gagctccaag ccttccaacc atttttcatt tttttgaatc  2460
ttccctactc tgttatcaga ggtgaagaat ttgctttgga aataactata ttcaattatt  2520
tgaaagatgc cactgaggtt aaggtaatca ttgagaaaag tgacaaattt gatattctaa  2580
tgacttcaaa tgaaataaat gccacaggcc accagcagac ccttctggtt cccagtgagg  2640
atggggcaac tgttcttttt cccatcaggc caacacatct gggagaaatt cctatcacag  2700
tcacagctct ttcacccact gcttctgatg ctgtcaccca gatgatttta gtaaaggctg  2760
aaggaataga aaaatcatat tcacaatcca tcttattaga cttgactgac aataggctac  2820
agagtaccct gaaaactttg agtttctcat ttcctcctaa tacagtgact ggcagtgaaa  2880
gagttcagat cactgcaatt ggagatgttc ttggtccttc catcaatggc ttagcctcat  2940
tgattcggat gccttatggc tgtggtgaac agaacatgat aaattttgct ccaaatattt  3000
acattttgga ttatctgact aaaaagaaac aactgacaga taatttgaaa gaaaaagctc  3060
tttcatttat gaggcaaggt taccagagag aacttctcta tcagagggaa gatggctctt  3120
tcagtgcttt tgggaattat gacccttctg ggagcacttg gttgtcagct tttgttttaa  3180
gatgtttcct tgaagccgat ccttacatag atattgatca gaatgtgtta cacagaacat  3240
acacttggct taaaggacat cagaaatcca acggtgaatt ttgggatcca ggaagagtga  3300
ttcatagtga gcttcaaggt ggcaataaaa gtccagtaac acttacagcc tatattgtaa  3360
cttctctcct gggatataga aagtatcagc ctaacattga tgtgcaagag tctatccatt  3420
ttttggagtc tgaattcagt agaggaattt cagacaatta tactctagcc cttataactt  3480
atgcattgtc atcagtgggg agtcctaaag cgaaggaagc tttgaatatg ctgacttgga  3540
gagcagaaca agaaggtggc atgcaattct gggtgtcatc agagtccaaa ctttctgact  3600
cctggcagcc acgctccctg gatattgaag ttgcagccta tgcactgctc tcacacttct  3660
```

-continued tacaatttca gacttctgag ggaatcccaa ttatgaggtg gctaagcagg caaagaaata 3720
gcttgggtgg ttttgcatct actcaggata ccactgtggc tttaaaggct ctgtctgaat 3780
ttgcagccct aatgaataca gaaaggacaa atatccaagt gaccgtgacg gggcctagct 3840
caccaagtcc tgtaaagttt ctgattgaca cacacaaccg cttactcctt cagacagcag 3900
agcttgctgt ggtacagcca acggcagtta atatttccgc aaatggtttt ggatttgcta 3960
tttgtcagct caatgttgta tataatgtga aggcttctgg gtcttctaga agacgaagat 4020
ctatccaaaa tcaagaagcc tttgatttag atgttgctgt aaaagaaaat aaagatgatc 4080
tcaatcatgt ggatttgaat gtgtgtacaa gcttttcggg cccgggtagg agtggcatgg 4140
ctcttatgga agttaaccta ttaagtggct ttatggtgcc ttcagaagca atttctctga 4200
gcgagacagt gaagaaagtg gaatatgatc atggaaaact caacctctat ttagattctg 4260
taaatgaaac ccagttttgt gttaatattc ctgctgtgag aaactttaaa gtttcaaata 4320
cccaagatgc ttcagtgtcc atagtggatt actatgagcc aaggagacag gcggtgagaa 4380
gttacaactc tgaagtgaag ctgtcctcct gtgacctttg cagtgatgtc cagggctgcc 4440
gtccttgtga ggatggagct tcaggctccc atcatcactc ttcagtcatt tttatttttct 4500
gtttcaagct tctgtacttt atggaacttt ggctgtgatt tatttttaaa ggactctgtg 4560
taacactaac atttccagta gtcacatgtg attgttttgt tttcgtagaa gaatactgct 4620
tctattttga aaaaagagtt ttttttcttt ctatggggtt gcagggatgg tgtacaacag 4680
gtcctagcat gtatagctgc atagatttct tcacctgatc tttgtgtgga agatcagaat 4740
gaatgcagtt gtgtgtctat atttcccct ctcaaaatct tttagaattt ttttggaggt 4800
gtttgttttc tccagaataa aggtattact ttagaatagg tattctcctc attttgtgaa 4860
agaaatgaac ctagattctt aagcattatt acacatccat gtttgcttaa agatggattt 4920
ccctgggaat gggagaaaac agccagcagg aggagcttca tctgttccct tcccacctcc 4980
aacctagccc tactgcccac cccaccccaa ccccaccccat gcccagtggt ctcagtagat 5040
acttcttaac tggaaattct ttcttttcag aatctaggtg gtgaattttt tttaagtggc 5100
acggtctttt tctgcttgaa atctgatcac accccccagc cattgccctc cctctctttt 5160
tcctctgtag agaaatgtga ggggcagtac atttactgtg cttttcacac catctcagag 5220
gttgaggagc atactgaaaa ttgccctggg gggtgctggg tgtgctgtct ccttccccaca 5280
tcctcagccc cacaccagct ctatttcagg ggtgagagtc agagagcact gcaatatgtg 5340
cttcatggga tttcgattcg aagatcctag accagggaga cactgtgagc cagggataca 5400
acaaaatact aggtaagtca ctgcagaccg acctccctgc agtttgggaa agaagctggg 5460
tttgtggaga atcagagcat cttgacatga ctgctgacct aaagatccct ggcattggcc 5520
agggatcctg tggaacctct tctagttcag gggtgtgagc attagactgc cagttgtcta 5580
gtgacatctg atgcttgctg tgaactttta agatccccga atcctgagca cctcaatctt 5640
taattgccct gtattccgaa gggtaatata atttatctgg atggaaattt taaagatgaa 5700
tcccccttttt ttcttttctt ctctctttc tttccttctc cctttcttct ttgccttcta 5760
aatatactga aatgatttag atatgtgtca acaattaatg atcttttatt caatctaaga 5820
aatggtttag tttttctctt tagctctatg gcatttcact caagtggaca ggggaaaaag 5880
taattgccat gggctccaaa gaatttgctt tatgttttta gctatttaaa aataaatcca 5940
tcaaaaataa agtatgcaaa tgtatctttt aaagttaatt tttaaaaatg ctcttatttt 6000
agtgaatttt cagaaattat agtggaatgg atgctcatat attgcttatg gatattttgg 6060
ataccaaagt aggaataact gacattcagt attttaaagc tggcaaacct gtacatagaa 6120
aatagatccc cagacagtgg tctatgaaga gggcagttaa gtatcaaata cttaattttc 6180
ttgccttttt ttcttaagtg gggaaaagtt tctagatctc ttacacctct gacacaatct 6240
gttctaaaac aggcacttgt aatgttgggg cctccttgta aacgtgtttt tgccctttac 6300
tctctgggag ttctttaaag gtgaaatcat cttacaaaga aattgggggga gggtcttggc 6360
aaaggacttt cccctcctct ttcctggcct gggaacctta tactgacaat caatacttta 6420
tattttaaag tatataattt atagttaact tctagtgtaa tatattagga aacactagaa 6480
tggaaaggcc attggaagac aggttgtatc ttttttagac catatttcct tgtttaaaaa 6540
ctatcatttg aatacttttt tggtgaagaa ctccatgttt tcaagttaaa ggtcacctcg 6600
taggccaggc gcagtggctc atgcctgtaa tcccagcact ctgggaggct gaggcgggtg 6660
aatcacaagg ttaggagttt gagaccagcc tggccaatat ggtgaaaccc cgtccctact 6720
aaaaatacaa aatttagcca ggcgtggtgg catgcacctg tagtcccacc tactcgggag 6780
gctgaggcag gagaatcact tgaacctgag agacagaggt tgcagtgagc cgagatcacg 6840
ccactgcact ccagcctggg ggacagagtg agattctgtc tcaaaaaaca aaaaacaaaa 6900
aagtcacctt gtaactcatc tctttttatt gtaagtttat taaaaatgaa gaggacaaca 6960
atgagaagga acataaaggg ttagctagca ctgtctcctg gtgcatgggg ctgtgcagat 7020
gtcccggcca cttcttcctt catacttccc ttagagaact tgctctgcta caagcagtgg 7080
gcttggacta aaagtgatta aaataccaca ggcataagga gaaaaggagt atatgtagta 7140
gtaataatta ctagtataaa ttattttctt cacatgctat gagtaataat attaaaaaac 7200
tcattttacc attaagattc cttatgctga agctcttcca tttagaatac tgtcaatgtc 7260
atttactggt atgaactaaa gtccccccttc ttttccactc actgggaacc ttagtaaaac 7320
accagcatat cttacctctc tttctgactg gccgatgctt ccagagactg aatgttggga 7380
aaacctagta gccaaacaat tctaggacag aataacattt ttatatttgg ttccaccatc 7440
ttattacatt tagttatagt tttaaaaaag aaattcaagc ccattaaaat atgtctggtc 7500
aatgaaatgc ttccttttat tgtgttgtgc tattgtactt tgtttttcaa aacattgtaa 7560
aaatagtatc tttggtttag tattttggat tatatattat aatctgagga gtgttttgct 7620
tatgtagaat ccagatatat ttctgttacc taggagatgt tacttacata tgtaatactg 7680
tatcctgcac gtggaaatat tcagaattgt agatagcata actctccctg ctcctattct 7740
tttgagccta ggtataattt ttttttttt tttagaaaaa gacatattta gctttaattt 7800
ctatttatgc taaacatatt tataagtagt ctgtcaatat aataccaact atttttattt 7860
ttacataatt caattatttc atttgacatg tctggcagac tcaagacatt aagtaaaaaa 7920
ttggaactat gatttttctt tgtcattttt taaaaaagaa ttattttatt aacctgctgg 7980
catataatct ggagttcttt tcacaacctt actttttctg atttgcttta ttgaatgatt 8040
gaatactcat ttctttctaa aaatatgttg taaattctcc cttggcaaga tttctcccta 8100
tgagggtagt tattatttga gtctgccaag tggttaccat ggggcaaggt gccatgatgt 8160
attcttgggt gcattggttt tttgcgcatt gtaaatttaa gacacttata gtaagtggac 8220
tcattcatag atgagtttca gaacctttta cgttctcggt agaggcttct gtcggacagg 8280
cagaagagtg tattcctcac tttttttttt gtcttcaaat tccagtaagg catagcactt 8340
ttaagaaatt agaattttc tatcatctat gcaaatgata tttatgttaa tattaaatat 8400

-continued

```
cttatgttac actgggagta atttgaggtg caattatttt tattactact ttgaatagag  8460
gaccattatc cttctttctt cagaaaacta agaagtaagt gtaactttta aagtaagtat  8520
atatcagtga gagtaggctt gttttacaac tatttctagc cagtgagttg tgttttcatg  8580
tctcatcaaa agacaatacc acattgcatc attttacaaa atatgttgtc attttcattt  8640
cagttgtaac ataggaaaat agatatttcc tagatgattt ctgagtttct tactgcaaag  8700
aacagttata aattggtata catgtgtctc tgtaataggg ataatattga tatatctgtt  8760
gctacatatt taagaatcat tctatcttat gttgtcttga ggccaagatt taccacgttt  8820
gcccagtgta ttgaattggt ggtagaaggt agttccatgt tccatttgta gatctttaag  8880
attttatctt tgataacttt aatagaatgt ggctcagttc tggtccttca agcctgtatg  8940
gtttggattt tcagtagggg acagttgatg tggagtcaat ctctttggta cacaggaagc  9000
tttataaaat ttcattcacg aatctcttat tttgggaagc tgttttgcat atgagaagaa  9060
cactgttgaa ataaggaact aaagctttat atattgatca aggtgattct gaaagtttta  9120
atttttaatg ttgtaatgtt atgttattgt taattgtact ttattatgta ttcaatagaa  9180
aatcatgatt tattaataaa agcttaaatt ctcatctatt t                      9221

SEQ ID NO: 18          moltype = DNA  length = 9031
FEATURE                Location/Qualifiers
source                 1..9031
                       mol_type = genomic DNA
                       organism = Homo sapiens
SEQUENCE: 18
agacgccgtc gagatgcagg gcccaccgct cctgaccgcc gcccacctcc tctgcgtgtg  60
caccgccgcg ctggccgtgg ctcccgggcc tcggtttctg gtgacagccc cagggatcat  120
caggcccgga ggaaatgtga ctattggggt ggagcttctg gaacactgcc cttcacaggt  180
gactgtgaag gcggagctgc tcaagacagc atcaaacctc actgtctctg tcctggaagc  240
agaaggagtc tttgaaaaag gctcttttaa gacacttact cttccatcac tacctctgaa  300
cagtgcagat gagatttatg agctacgtgt aaccggacgt acccaggatg agattttatt  360
ctctaatagt acccgcttat catttgagac caagagaata tctgtcttca ttcaaacaga  420
caaggcctta tacaagccaa agcaagaagt gaagtttcgc attgttacac tcttctcaga  480
ttttaagcct tacaaaacct ctttaaacat tctcattaag gaccccaaat caaatttgat  540
ccaacagtgg ttgtcacaac aaagtgatct tggagtcatt tccaaaactt ttcagctatc  600
ttcccatcca atacttggtg actggtctat tcaagttcaa gtgaatgacc agacatacta  660
tcaatcattt caggtttcag aatatgtatt accaaaattt gaagtgactt tgcagacacc  720
attatattgt tctatgaatt ctaagcattt aaatggtacc atcacggcaa agtatacata  780
tgggaagcca gtgaaaggag acgtaacgct tacattttta cctttatcct tttggggaaa  840
gaagaaaaat attacaaaaa catttaagat aaatggatct gcaaacttct cttttaatga  900
tgaagagatg aaaaatgtaa tggattcttc aaatggactt tctgaatacc tggatctatc  960
ttcccctgga ccagtagaaa ttttaaccac agtgacagaa tcagttacag gtatttcaag  1020
aaatgtaagc actaatgtgt tcttcaagca acatgattac atcattgagt tttttgatta  1080
tactactgtc ttgaagccat ctctcaactt cacagccact gtgaaggtaa ctcgtgctga  1140
tggcaaccaa ctgactcttg aagaaaagag aaataatgta gtcataacag tgacacagag  1200
aaactatact gagtactgga gcggatctaa cagtggaaat cagaaaatgg aagctgttca  1260
gaaaataaat tatactgtcc cccaaagtgg aacttttaag attgaattcc caatcctgga  1320
ggattccagt gagctacagt tgaaggccta tttccttggt agtaaaagta gcatggcagt  1380
tcatagtctg tttaagtctc ctagtaagac atacatccaa ctaaaaacaa gagatgaaaa  1440
tataaaggtg ggatcgcctt ttgagttggt ggttagtggc aacaaacgat tgaaggagtt  1500
aagctatatg gtagtatcca ggggacagtt ggtggctgta ggaaaacaaa attcaacaat  1560
gttctcttta acaccagaaa attcttggac tccaaaagcc tgtgtaattg tgtattatat  1620
tgaagatgat ggggaaatta taagtgatgt tctaaaaatt cctgttcagc ttgtttttaa  1680
aaataagata aagctatatt ggagtaaagt gaaagctgaa ccatctgaga aagtctctct  1740
taggatctct gtgacacagc ctgactccat agttgggatt gtagctgttg acaaaagtgt  1800
gaatctgatg aatgcctcta atgatattac aatggaaaat gtggtccatg agttggaact  1860
ttataacaca ggatattatt taggcatgtt catgaattct tttgcagtct ttcaggaatg  1920
tggactctgg gtattgacag atgcaaacct cacgaaggat tatattgatg gtgtttatga  1980
caatgcagaa tatgctgaga ggtttatgga ggaaaatgaa ggacatattg tagatattca  2040
tgacttttct ttgggtagca gtccacatgt ccgaaagcat tttccagaga cttggatttg  2100
gctagacacc aacatgggtt acaggattta ccaagaattt gaagtaactg tacctgattc  2160
tatcacttct tgggtggcta ctggttttgt gatctctgag gacctgggtc ttggactaac  2220
aactactcca gtggagctcc aagccttcca accatttttc attttttga atcttcccta  2280
ctctgttatc agaggtgaag aatttgcttt ggaaataact atattcaatt atttgaaaga  2340
tgccactgag gttaaggtaa tcattgagaa aagtgacaaa tttgatattc taatgacttc  2400
aaatgaaata aatgccacag gccaccagca gacccttctg gttcccagtg aggatgggc  2460
aactgttctt tttcccatca ggccaacaca tctgggagaa attcctatca cagtcacagc  2520
tctttcaccc actgcttctg atgctgtcac ccagatgatt ttagtaaagg ctgaaggaat  2580
agaaaaatca tattcacaat ccatcttatt agacttgact gacaataggc tacagagtac  2640
cctgaaaact ttgagtttct catttcctcc taatacagtg actggcagtg aaagagttca  2700
gatcactgca attggagatg ttcttggtcc ttccatcaat ggcttagcct cattgattcg  2760
gatgccttat ggctgtggtg aacagaacat gataaatttt gctccaaata tttacatttt  2820
ggattatctg actaaaaaga aacaactgac agataatttg aaagaaaaag ctctttcatt  2880
tatgaggcaa ggttaccaga gagaacttct ctatcagagg gaagatggct ctttcagtgc  2940
ttttgggaat tatgaccctt ctgggagcac ttggttgtca gcttttgttt taagatgttt  3000
ccttgaagcc gatccttaca tagatattga tcagaatgtg ttacacagaa catacacttg  3060
gcttaaagga catcagaaat ccaacggtga attttgggat ccaggaagag tgattcatag  3120
tgagcttcaa ggtggcaata aaagtccagt aacacttaca gcctatattg taacttctct  3180
cctgggatat agaaagtatc agcctaacat tgatgtgcaa gagtctatcc attttttgga  3240
gtctgaattc agtagaggaa tttcagacaa ttatactcta gcccttataa cttatgcatt  3300
gtcatcagtg gggagtccta aagcgaagga agctttgaat atgctgactt ggagagcaga  3360
acaagaaggt ggcatgcaat tctgggtgtc atcagagtcc aaactttctg actcctggca  3420
gccacgctcc ctggatattg aagttgcagc ctatgcactg ctctcacact tcttacaatt  3480
```

-continued

```
tcagacttct gagggaatcc caattatgag gtggctaagc aggcaaagaa atagcttggg  3540
tggttttgca tctactcagg ataccactgt ggctttaaag gctctgtctg aatttgcagc  3600
cctaatgaat acagaaagga caaatatcca agtgaccgtg acggggccta gctcaccaag  3660
tcctgtaaag tttctgattg acacacacaa ccgcttactc cttcagacag cagagcttgc  3720
tgtggtacag ccaacggcag ttaatatttc cgcaaatggt tttggatttg ctatttgtca  3780
gctcaatgtt gtatataatg tgaaggcttc tgggtcttct agaagacgaa gatctatcca  3840
aaatcaagaa gcctttgatt tagatgttgc tgtaaaagaa aataaagatg atctcaatca  3900
tgtggatttg aatgtgtgta caagcttttc gggcccgggt aggagtggca tggctcttat  3960
ggaagttaac ctattaagtg gctttatggt gccttcagaa gcaatttctc tgagcgagac  4020
agtgaagaaa gtggaatatg atcatggaaa actcaacctc tatttagatt ctgtaaatga  4080
aacccagttt tgtgttaata ttcctgctgt gagaaacttt aaagtttcaa atacccaaga  4140
tgcttcagtg tccatagtgg attactatga gccaaggaga caggcggtga gaagttacaa  4200
ctctgaagtg aagctgtcct cctgtgacct ttgcagtgat gtccagggct gccgtccttg  4260
tgaggatgga gcttcaggct cccatcatca ctcttcagtc atttttattt tctgtttcaa  4320
gcttctgtac tttatggaac tttggctgtg atttattttt aaaggactct gtgtaacact  4380
aacatttcca gtagtcacat gtgattgttt tgttttcgta gaagaatact gcttctattt  4440
tgaaaaaaga gttttttttc tttctatggg gttgcaggga tggtgtacaa caggtcctag  4500
catgtatagc tgcatagatt tcttcacctg atctttgtgt ggaagatcag aatgaatgca  4560
gttgtgtgtc tatattttcc cctctcaaaa tcttttagaa ttttttttgga ggtgtttgtt  4620
ttctccagaa taaaggtatt actttagaat aggtattctc ctcattttgt gaaagaaatg  4680
aacctagatt cttaagcatt attacacatc catgtttgct taaagatgga tttccctggg  4740
aatgggagaa aacagccagc aggaggagct tcatctgttc ccttcccacc tccaacctag  4800
ccctactgcc caccccaccc caacccaccc catgcccagt ggtctcagta gatacttctt  4860
aactggaaat tctttctttt cagaatctag gtggtgaatt ttttttaagt ggcacggtct  4920
ttttctgctt gaaatctgat cacacccccc agccattgcc ctccctctct ttttcctctg  4980
tagagaaatg tgaggggcag tacatttact gtgcttttca caccatctca gaggttgagg  5040
agcatactga aaattgccct gggggggtgct gggtgtgctg tctccttccc acatcctcag  5100
ccccacacca gctctatttc aggggtgaga gtcagagagc actgcaatat gtgcttcatg  5160
ggatttcgat tcgaagatcc tagaccaggg agacactgtg agccagggat acaacaaaat  5220
actaggtaag tcactgcaga ccgacctccc tgcagtttgg gaaagaagct gggtttgtgg  5280
agaatcagag catcttgaca tgactgctga cctaaagatc cctggcattg gccagggatc  5340
ctgtggaacc tcttctagtt caggggtgtg agcattagac tgccagttgt ctagtgacat  5400
ctgatgcttg ctgtgaactt ttaagatccc cgaatcctga gcacctcaat ctttaattgc  5460
cctgtattcc gaagggtaat ataatttatc tggatggaaa ttttaaagat gaatccccct  5520
tttttctttt cttctctctt ttctttcctt ctccctttct tctttgcctt ctaaatatac  5580
tgaaatgatt tagatatgtg tcaacaatta atgatctttt attcaatcta agaaatggtt  5640
tagtttttct ctttagctct atggcatttc actcaagtgg acaggggaaa aagtaattgc  5700
catgggctcc aaagaatttg ctttatgttt ttagctattt aaaaataaat ccatcaaaaa  5760
taaagtatgc aaatgtatct tttaaagtta atttttaaaa atgctcttat tttagtgaat  5820
tttcagaaat tatagtggaa tggatgctca tatattgctt atggatattt tggataccaa  5880
agtaggaata actgacattc agtattttaa agctggcaaa cctgtacata gaaaatagat  5940
ccccagacag tggtctatga agagggcagt taagtatcaa atacttaatt ttcttgcctt  6000
tttttcttaa gtggggaaaa gtttctagat ctcttacacc tctgacacaa tctgttctaa  6060
aacaggcact tgtaatgttg gggcctcctt gtaaacgtgt ttttgccctt tactctctgg  6120
gagttcttta aaggtgaaat catcttacaa agaaattggg ggagggtctt ggcaaaggac  6180
tttcccctcc tctttcctgg cctgggaacc ttatactgac aatcaatact ttatatttta  6240
aagtatataa tttatagtta acttctagtg taatatatta ggaaacacta gaatggaaag  6300
gccattggaa gacaggttgt atctttttta gaccatattt ccttgtttaa aaactatcat  6360
ttgaatactt ttttggtgaa gaactccatg ttttcaagtt aaaggtcacc tcgtaggcca  6420
ggcgcagtgg ctcatgcctg taatcccagc actctgggag gctgaggcgg gtgaatcaca  6480
aggttaggag tttgagacca gcctggccaa tatggtgaaa ccccgtccct actaaaaata  6540
caaaatttag ccaggcgtgg tggcatgcac ctgtagtccc acctactcgg gaggctgagg  6600
caggagaatc acttgaacct gagagacaga ggttgcagtg agccgagatc acgccactgc  6660
actccagcct gggggacaga gtgagattct gtctcaaaaa acaaaaaaca aaaaagtcac  6720
cttgtaactc atctcttttt attgtaagtt tattaaaaat gaagaggaca acaatgagaa  6780
ggaacataaa gggttagcta gcactgtctc ctggtgcatg gggctgtgca gatgtcccgg  6840
ccacttcttc cttcatactt cccttagaga acttgctctg ctacaagcag tgggcttgga  6900
ctaaaagtga ttaaaatacc acaggcataa ggagaaaagg agtatatgta gtagtaataa  6960
ttactagtat aaattatttt cttcacatgc tatgagtaat aatattaaaa aactcatttt  7020
accattaaga ttccttatgc tgaagctctt ccatttagaa tactgtcaat gtcatttact  7080
ggtatgaact aaagtccccc ttcttttcca ctcactggga accttagtaa aacaccagca  7140
tatcttacct ctctttctga ctggccgatg cttccagaga ctgaatgttg ggaaaaccta  7200
gtagccaaac aattctagga cagaataaca tttttatatt tggttccacc atcttattac  7260
atttagttat agttttaaaa aagaaattca agcccattaa aatatgtctg gtcaatgaaa  7320
tgcttccttt tattgtgttg tgctattgta ctttgttttt caaaacattg taaaaatagt  7380
atctttggtt tagtattttg gattatatat tataatctga ggagtgtttt gcttatgtag  7440
aatccagata tatttctgtt acctaggaga tgttacttac atatgtaata ctgtatcctg  7500
cacgtggaaa tattcagaat tgtagatagc ataactctcc ctgctcctat tcttttgagc  7560
ctaggtataa tttttttttt ttttttagaa aaagacatat ttagctttaa tttctattta  7620
tgctaaacat atttataagt agtctgtcaa tataatacca actattttta tttttacata  7680
attcaattat ttcatttgac atgtctggca gactcaagac attaagtaaa aaattggaac  7740
tatgattttt ctttgtcatt ttttaaaaaa gaattatttt attaacctgc tggcatataa  7800
tctggagttc ttttcacaac cttacttttt ctgatttgct ttattgaatg attgaatact  7860
catttctttc taaaaatatg ttgtaaattc tcccttggca agatttctcc ctatgagggt  7920
agttattatt tgagtctgcc aagtggttac catggggcaa ggtgccatga tgtattcttg  7980
ggtgcattgg ttttttgcgc attgtaaatt taagacactt atagtaagtg gactcattca  8040
tagatgagtt tcagaacctt ttacgttctc ggtagaggct tctgtcggac aggcagaaga  8100
gtgtattcct cactttttttt tttgtcttca aattccagta aggcatagca cttttaagaa  8160
attagaattt ttctatcatc tatgcaaatg atatttatgt taatattaaa tatcttatgt  8220
```

```
tacactggga gtaatttgag gtgcaattat ttttattact actttgaata gaggaccatt  8280
atccttcttt cttcagaaaa ctaagaagta agtgtaactt ttaaagtaag tatatatcag  8340
tgagagtagg cttgttttac aactatttct agccagtgag ttgtgttttc atgtctcatc  8400
aaaagacaat accacattgc atcattttac aaaatatgtt gtcattttca tttcagttgt  8460
aacataggaa aatagatatt tcctagatga tttctgagtt tcttactgca aagaacagtt  8520
ataaattggt atacatgtgt ctctgtaata gggataatat tgatatatct gttgctacat  8580
atttaagaat cattctatct tatgttgtct tgaggccaag atttaccacg tttgcccagt  8640
gtattgaatt ggtggtagaa ggtagttcca tgttccattt gtagatcttt aagattttat  8700
ctttgataac tttaatagaa tgtggctcag ttctggtcct tcaagcctgt atggtttgga  8760
ttttcagtag gggacagttg atgtggagtc aatctctttg gtacacagga agctttataa  8820
aatttcattc acgaatctct tattttggga agctgttttg catatgagaa gaacactgtt  8880
gaaataagga actaaagctt tatatattga tcaaggtgat tctgaaagtt ttaattttta  8940
atgttgtaat gttatgttat tgttaattgt actttattat gtattcaata gaaaatcatg  9000
atttattaat aaaagcttaa attctcatct a                                 9031

SEQ ID NO: 19           moltype = DNA  length = 5883
FEATURE                 Location/Qualifiers
source                  1..5883
                        mol_type = genomic DNA
                        organism = Homo sapiens
SEQUENCE: 19
ctaaactcga attaagaggg aaaaaaaatc agggaggagg tggcaagcca caccccacgg  60
tgcccgcgaa cttccccggc agcggactgt agcccaggca gacgccgtcg agatgcaggg  120
cccaccgctc ctgaccgccg cccacctcct ctgcgtgtgc accgccgcgc tggccgtggc  180
tcccgggcct cggtttctgg tgacagcccc agggatcatc aggcccggag gaaatgtgac  240
tattggggtg gagcttctgg aacactgccc ttcacaggtg actgtgaagg cggagctgct  300
caagacagca tcaaacctca ctgtctctgt cctggaagca gaaggagtct ttgaaaaagg  360
ctcttttaag acacttactc ttccatcact acctctgaac agtgcagatg agatttatga  420
gctacgtgta accggacgta cccaggatga gattttattc tctaatagta cccgcttatc  480
atttgagacc aagagaatat ctgtcttcat tcaaacagac aaggccttat acaagccaaa  540
gcaagaagtg aagtttcgca ttgttacact cttctcagat tttaagcctt acaaaacctc  600
tttaaacatt ctcattaagg accccaaatc aaatttgatc caacagtggt tgtcacaaca  660
aagtgatctt ggagtcattt ccaaaacttt tcagctatct tcccatccaa tacttggtga  720
ctggtctatt caagttcaag tgaatgacca gacatattat caatcatttc aggtttcaga  780
atatgtatta ccaaaatttg aagtgacttt gcagacacca ttatattgtt ctatgaattc  840
taagcattta aatggtacca tcacggcaaa gtatacatat gggaagccag tgaaaggaga  900
cgtaacgctt acatttttac ctttatcctt ttggggaaag aagaaaaata ttacaaaaac  960
atttaagata aatggatctg caaacttctc ttttaatgat gaagagatga aaaatgtaat  1020
ggattcttca aatggacttt ctgaatacct ggatctatct tcccctggac cagtagaaat  1080
tttaaccaca gtgacagaat cagttacagg tatttcaaga aatgtaagca ctaatgtgtt  1140
cttcaagcaa catgattaca tcattgagtt ttttgattat actactgtct tgaagccatc  1200
tctcaacttc acagccactg tgaaggtaac tcgtgctgat ggcaaccaac tgactcttga  1260
agaaagaaga aataatgtag tcataacagt gacacagaga aactatactg agtactggag  1320
cggatctaac agtggaaatc agaaaatgga agctgttcag aaaataaatt atactgtccc  1380
ccaaagtgga acttttaaga ttgaattccc aatcctggag gattccagtg agctacagtt  1440
gaaggcctat ttccttggta gtaaaagtag catggcagtt catagtctgt ttaagtctcc  1500
tagtaagaca tacatccaac taaaaacaag agatgaaaat ataaaggtgg gatcgccttt  1560
tgagttggtg gttagtggca acaaacgatt gaaggagtta agctatatgg tagtatccag  1620
ggacagttgg gtggctgtag gaaaacaaaa ttcaacaatg ttctctttaa caccagaaaa  1680
ttcttggact ccaaaagcct gtgtaattgt gtattatatt gaagatgatg gggaaattat  1740
aagtgatgtt ctaaaaattc ctgttcagct tgtttttaaa aataagataa agctatattg  1800
gagtaaagtg aaagctgaac catctgagaa agtctctctt aggatctctg tgacacagcc  1860
tgactccata gttgggattg tagctgttga caaaagtgtg aatctgatga atgcctctaa  1920
tgatattaca atggaaaatg tggtccatga gttggaactt tataacacag gatattattt  1980
aggcatgttc atgaattctt ttgcagtctt tcaggaatgt ggactctggg tattgacaga  2040
tgcaaacctc acgaaggatt atattgatgg tgtttatgac aatgcagaat atgctgagag  2100
gtttatggag gaaaatgaag gacatattgt agatattcat gacttttctt tgggtagcag  2160
tccacatgtc cgaaagcatt ttccagagac ttggatttgg ctagacacca acatgggtta  2220
caggatttac caagaatttg aagtaactgt acctgattct atcacttctt gggtggctac  2280
tggttttgtg atctctgagg acctgggtct tggactaaca actactccag tggagctcca  2340
agccttccaa ccatttttca ttttttgaa tcttccctac tctgttatca gaggtgaaga  2400
atttgctttg gaaataacta tattcaatta tttgaaagat gccactgagg ttaaggtaat  2460
cattgagaaa agtgacaaat ttgatattct aatgacttca aatgaaataa atgccacagg  2520
ccaccagcag acccttctgg ttcccagtga ggatggggca actgttcttt ttcccatcag  2580
gccaacacat ctgggagaaa ttcctatcac agtcacagct ctttcaccca ctgcttctga  2640
tgctgtcacc cagatgattt tagtaaaggc tgaaggaata gaaaaatcat attcacaatc  2700
catcttatta gacttgactg acaataggct acagagtacc ctgaaaactt tgagtttctc  2760
atttcctcct aatacagtga ctggcagtga aagagttcag atcactgcaa ttggagatgt  2820
tcttggtcct tccatcaatg gcttagcctc attgattcgg atgccttatg gctgtggtga  2880
acagaacatg ataaatttg ctccaaatat ttacattttg gattatctga ctaaaaagaa  2940
acaactgaca gataatttga aagaaaaagc tctttcattt atgaggcaag gttaccagag  3000
agaacttctc tatcagaggg aagatggctc tttcagtgct tttgggaatt atgacccttc  3060
tgggagcact tggttgtcag cttttgtttt aagatgtttc cttgaagccg atccttacat  3120
agatattgat cagaatgtgt tacacagaac atacacttgg cttaaaggac atcagaaatc  3180
caacggtgaa ttttgggatc caggaagagt gattcatagt gagcttcaag gtggcaataa  3240
aagtccagta acacttacag cctatattgt aacttctctc ctgggatata gaaagtatca  3300
gcctaacatt gatgtgcaag agtctatcca ttttttggag tctgaattca gtagaggaat  3360
ttcagacaat tatactctag cccttataac ttatgcattg tcatcagtgg ggagtcctaa  3420
agcgaaggaa gctttgaata tgctgacttg gagagcagaa caagaaggtg gcatgcaatt  3480
```

```
ctgggtgtca tcagagtcca aactttctga ctcctggcag ccacgctccc tggatattga  3540
agttgcagcc tatgcactgc tctcacactt cttacaattt cagacttctg agggaatccc  3600
aattatgagg tggctaagca ggcaaagaaa tagcttgggt ggttttgcat ctactcagga  3660
taccactgtg gctttaaagg ctctgtctga atttgcagcc ctaatgaata cagaaaggac  3720
aaatatccaa gtgaccgtga cggggcctag ctcaccaagt cctgtaaagt ttctgattga  3780
cacacacaac cgcttactcc ttcagacagc agagcttgct gtggtacagc caatggcagt  3840
taatatttcc gcaaatggtt ttggatttgc tatttgtcag ctcaatgttg tatataatgt  3900
gaaggcttct gggtcttcta gaagacgaag atctatccaa aatcaagaag cctttgattt  3960
agatgttgct gtaaaagaaa ataaagatga tctcaatcat gtggatttga atgtgtgtac  4020
aagcttttcg ggcccgggta ggagtggcat ggctcttatg gaagttaacc tattaagtgg  4080
ctttatggtg ccttcagaag caatttctct gagcgagaca gtgaagaaag tggaatatga  4140
tcatggaaaa ctcaacctct atttagattc tgtaaatgaa acccagtttt gtgttaatat  4200
tcctgctgtg agaaacttta aagtttcaaa tacccaagat gcttcagtgt ccatagtgga  4260
ttactatgag ccaaggagac aggcggtgag aagttacaac tctgaagtga agctgtcctc  4320
ctgtgacctt tgcagtgatg tccagggctg ccgtccttgt gaggatggag cttcaggctc  4380
ccatcatcac tcttcagtca tttttatttt ctgtttcaag cttctgtact ttatggaact  4440
ttggctgtga tttattttta aaggactctg tgtaacacta acatttccag tagtcacatg  4500
tgattgtttt gttttcgtag aagaatactg cttctatttt gaaaaaaagag tttttttttct  4560
ttctatgggg ttgcagggat ggtgtacaac aggtcctagc atgtatagct gcatagattt  4620
cttcacctga tctttgtgtg gaagatcaga atgaatgcag ttgtgtgtct atattttccc  4680
ctcacaaaat cttttagaat ttttttggag gtgtttgttt tctccagaat aaaggtatta  4740
ctttagaaat aggtattctc ctcattttgt gaaagaaatg aacctagatt cttaagcatt  4800
attacacatc catgtttgct taaagatgga tttccctggg aatgggagaa aacagccagc  4860
aggaggagct tcatctgttc ccttcccacc tccaacctag ccctactgcc caccccaccc  4920
caacccaccc catgcccagt ggtctcagta gatacttctt aactggaaat tctttctttt  4980
cagaatctag gtggtgaatt ttttttaagt ggcacggtct ttttctgctt gaaatctgat  5040
cacacccccc agccattgcc ctccctctct ttttcctctg tagagaaatg tgaggggcag  5100
tacatttact gtgcttttca caccatctca gaggttgagg agcatactga aaattgccct  5160
ggggggtgct gggtgtgctg tctccttccc acatcctcag ccccacacca gctctatttc  5220
aggggtgaga gtcagagagc actgcaatat gtgcttcatg ggatttcgat tcgaagatcc  5280
tagaccaggg agacactgtg agccagggat acaacaaaat actaggtaag tcactgcaga  5340
ccgacctccc tgcagtttgg gaaagaagct gggtttgtgg agaatcagag catcttgaca  5400
tgactgctga cctaaagatc cctggcattg gccagggatc ctgtggaacc tcttctagtt  5460
caggggtgtg agcattagac tgccagttgt ctagtgacat ctgatgcttg ctgtgaactt  5520
ttaagatccc cgaatcctga gcacctcaat ctttaattgc cctgtattcc gaagggtaat  5580
ataatttatc tggatggaaa ttttaaagat gaatccccct tttttctttt cttctctctt  5640
ttctttcctt ctccctttct tctttgcctt ctaaatatac tgaaatgatt tagatatgtg  5700
tcaacaatta atgatctttt attcaatcta agaaatggtt tagtttttct ctttagctct  5760
atggcatttc actcaagtgg acaggggaaa aagtaattgc catgggctcc aaagaatttg  5820
ctttatgttt ttagctattt aaaaataaat ccatcaaaaa taaagtatgc aaatgtatct  5880
ttt                                                                5883

SEQ ID NO: 20          moltype = DNA  length = 4449
FEATURE                Location/Qualifiers
source                 1..4449
                       mol_type = genomic DNA
                       organism = Homo sapiens
SEQUENCE: 20
aaaactcgaa ttaagaggga aagaaaatca gggaggaggt ggcaagccac accccacggt  60
gcccgcgaac ttccccggca gcggactgta gcccaggcag acgccgtcga gatgcagggc  120
ccaccgctcc tgaccgccgc ccacctcctc tgcgtgtgca ccgccgcgct ggccgtggct  180
cccgggcctc ggtttctggt gacagcccca gggatcatca ggcccggagg aaatgtgact  240
attggggtgg agcttctgga acactgccct tcacaggtga ctgtgaaggc ggagctgctc  300
aagacagcat caaacctcac tgtctctgtc ctggaagcag aaggagtctt tgaaaaaggc  360
tcttttaaga cacttactct tccatcacta cctctgaaca gtgcagatga gatttatgag  420
ctacgtgtaa ccggacgtac ccaggatgag attttattct ctaatagtac ccgcttatca  480
tttgagacca agagaatatc tgtcttcatt caaacagaca aggccttata caagccaaag  540
caagaagtga agtttcgcat tgttacactc ttctcagatt ttaagcctta caaaacctct  600
ttaaacattc tcattaagga ccccaaatca aatttgatcc aacagtggtt gtcacaacaa  660
agtgatcttg gagtcatttc caaaactttt cagctatctt cccatccaat acttggtgac  720
tggtctattc aagttcaagt gaatgaccag acatattatc aatcatttca ggtttcagaa  780
tatgtattac caaaatttga agtgactttg cagacaccat tatattgttc tatgaattct  840
aagcatttaa atggtaccat cacggcaaag tatacatatg ggaagccagt gaaaggagac  900
gtaacgctta cattttacc tttatccttt tggggaaaga agaaaaatat tacaaaaaca  960
tttaagataa atggatctgc aaacttctct tttaatgatg aagagatgaa aaatgtaatg  1020
gattcttcaa atggactttc tgaatacctg gatctatctt cccctggacc agtagaaatt  1080
ttaaccacag tgacagaatc agttacaggt atttcaagaa atgtaagcac taatgtgttc  1140
ttcaagcaac atgattacat cattgagttt tttgattata ctactgtctt gaagccatct  1200
ctcaacttca cagccactgt gaaggtaact cgtgctgatg gcaaccaact gactcttgaa  1260
gaaagaagaa ataatgtagt cataacagtg acacagagaa actatactga gtactggagc  1320
ggatctaaca gtggaaatca gaaaatggaa gctgttcaga aaataaatta tactgtcccc  1380
caaagtggaa cttttaagat tgaattccca atcctggagg attccagtga gctacagttg  1440
aaggcctatt tccttggtag taaaagtagc atggcagttc atagtctgtt taagtctcct  1500
agtaagacat acatccaact aaaaacaaga gatgaaaata taaaggtggg atcgcctttt  1560
gagttggtgg ttagtggcaa caaacgattg aaggagttaa gctatatggt agtatccagg  1620
ggacagttgg tggctgtagg aaaacaaaat tcaacaatgt tctctttaac accagaaaat  1680
tcttggactc caaaagcctg tgtaattgtg tattatattg aagatgatgg ggaaattata  1740
agtgatgttc taaaaattcc tgttcagctt gtttttaaaa ataagataaa gctatattgg  1800
agtaaagtga aagctgaacc atctgagaaa gtctctctta ggatctctgt gacacagcct  1860
```

-continued

```
gactccatag ttgggattgt agctgttgac aaaagtgtga atctgatgaa tgcctctaat  1920
gatattacaa tggaaaatgt ggtccatgag ttggaacttt ataacacagg atattattta  1980
ggcatgttca tgaattcttt tgcagtcttt caggaatgtg gactctgggt attgacagat  2040
gcaaacctca cgaaggatta tattgatggt gtttatgaca atgcagaata tgctgagagg  2100
tttatggagg aaaatgaagg acatattgta gatattcatg acttttcttt gggtagcagt  2160
ccacatgtcc gaaagcattt tccagagact tggatttggc tagacaccaa catgggttcc  2220
aggatttacc aagaatttga agtaactgta cctgattcta tcacttcttg ggtggctact  2280
ggttttgtga tctctgagga cctgggtctt ggactaacaa ctactccagt ggagctccaa  2340
gccttccaac catttttcat ttttttgaat cttccctact ctgttatcag aggtgaagaa  2400
tttgctttgg aaataactat attcaattat ttgaaagatg ccactgaggt taaggtaatc  2460
attgagaaaa gtgacgaatt tgatattcta atgacttcaa atgaaataaa tgccacaggc  2520
caccagcaga cccttctggt tcccagtgag gatggggcaa ctgttctttt tcccatcagg  2580
ccaacacatc tgggagaaat tcctatcaca gtcacagctc tttcacccac tgcttctgat  2640
gctgtcaccc agatgatttt agtaaaggct gaaggaatag aaaaatcata ttcacaatcc  2700
atcttattag acttgactga caataggcta cagagtaccc tgaaaacttt gagtttctca  2760
tttcctccta atacagtgac tggcagtgaa agagttcaga tcactgcaat tggagatgtt  2820
cttggtcctt ccatcaatgg cttagcctca ttgattcgga tgccttatgg ctgtggtgaa  2880
cagaacatga taaattttgc tccaaatatt tacattttgg attatctgac taaaaagaaa  2940
caactgacag ataatttgaa agaaaaagct ctttcattta tgaggcaagg ttaccagaga  3000
gaacttctct atcagaggga agatggctct ttcagtgctt ttgggaatta tgacccttct  3060
gggagcactt ggttgtcagc ttttgtttta agatgtttcc ttgaagccga tccttacata  3120
gatattgatc agaatgtgtt acacagaaca tacacttggc ttaaaggaca tcagaaatcc  3180
aacggtgaat tttgggatcc aggaagagtg attcatagtg agcttcaagg tggcaataaa  3240
agtccagtaa cacttacagc ctatattgta acttctctcc tgggatatag aaagtatcag  3300
cctaacattg atgtgcaaga gtctatccat tttttggagt ctgaattcag tagaggaatt  3360
tcagacaatt atactctagc ccttataact tatgcattgt catcagtggg gagtcctaaa  3420
gcgaaggaag ctttgaatat gctgacttgg agagcagaac aagaaggtgg catgcaattc  3480
tgggtgtcat cagagtccaa actttctgac tcctggcagc cacgctccct ggatattgaa  3540
gttgcagcct atgcactgct ctcacacttc ttacaatttc agacttctga gggaatccca  3600
attatgaggt ggctaagcag gcaaagaaat agcttgggtg gttttgcatc tactcaggat  3660
accactgtgg ctttaaaggc tctgtctgaa tttgcagccc taatgaatac agaaaggaca  3720
aatatccagg tgaccgtgac ggggcctagc tcaccaagtc ctgtaaagtt tctgattgac  3780
acacacaacc gcttactcct tcagacagca gagcttgctg tggtacagcc aacggcagtt  3840
aatatttccg caaatggttt tggatttgct atttgtcagc tcaatgttgt atataatgtg  3900
aaggcttctg ggtcttctag aagacgaaga tctatccaaa atcaagaagc ctttgattta  3960
gatgttgctg taaaagaaaa taaagatgat ctcaatcatg tggatttgaa tgtgtgtaca  4020
agcttttcgg gcccgggtag gagtggcatg gctcttatgg aagttaacct attaagtggc  4080
tttatggtgc cttcagaagc aatttctctg agcgagacag tgaagaaagt ggaatatgat  4140
catggaaaac tcaacctcta tttagattct gtaaatgaaa cccagttttg tgttaatatt  4200
cctgctgtga gaaactttaa agtttcaaat acccaagatg cttcagtgtc catagtggat  4260
tactatgagc caaggagaca ggcggtgaga agttacaact ctgaagtgaa gctgtcctcc  4320
tgtgaccttt gcagtgatgt ccagggctgc cgtccttgtg aggatggagc ttcaggctcc  4380
catcatcact cttcagtcat ttttatttc tgtttcaagc ttctgtactt tatggaactt  4440
tggctgtga                                                    4449
```

```
SEQ ID NO: 21           moltype = DNA  length = 2273
FEATURE                 Location/Qualifiers
source                  1..2273
                        mol_type = genomic DNA
                        organism = Homo sapiens
SEQUENCE: 21
acacacccca cggtgcccgc gaacttcccc ggcagcggac tgtagcccag gcagacgccg  60
tcgagatgca gggcccaccg ctcctgaccg ccgcccacct cctctgcgtg tgcaccgccg  120
cgctggccgt ggctcccggg cctcggtttc tggtgacagc cccagggatc atcaggcccg  180
gaggaaatgt gactattggg gtggagcttc tggaacactg cccttcacag gtgactgtga  240
aggcggagct gctcaagaca gcatcaaacc tcactgtctc tgtcctggaa gcagaaggag  300
tctttgaaaa aggctctttt aagacactta ctcttccatc actacctctg aacagtgcag  360
atgagattta tgagctacgt gtaaccggac gtacccagga tgagatttta ttctctaata  420
gtacccgctt atcatttgag accaagagaa tatctgtctt cattcaaaca gacaaggcct  480
tatacaagcc aaagcaagaa gtgaagtttc gcattgttac actcttctca gattttaagc  540
cttacaaaac ctctttaaac attctcatta aggaccccaa atcaaatttg atccaacagt  600
ggttgtcaca acaaagtgat cttggagtca tttccaaaac ttttcagcta tcttcccatc  660
caatacttgg tgactggtct attcaagttc aagtgaatga ccagacatac tatcaatcat  720
ttcaggtttc agaatatgta ttaccaaaat ttgaagtgac tttgcagaca ccattatatt  780
gttctatgaa ttctaagcat ttaaatggta ccatcacggc aaagtataca tatgggaagc  840
cagtgaaagg agacgtaacg cttacatttt tacctttatc cttttgggga aagaagaaaa  900
atattacaaa aacatttaag ataaatggat ctgcaaactt ctcttttaat gatgaagaga  960
tgaaaaatgt aatggattct tcaaatggac tttctgaata cctggatcta tcttcccctg  1020
gaccagtaga aattttaacc acagtgacag aatcagttac aggtatttca agaaatgtaa  1080
gcactaatgt gttcttcaag caacatgatt acatcattga gtttttgat tatactactg  1140
tcttgaagcc atctctcaac ttcacagcca ctgtgaaggt aactcgtgct gatggcaacc  1200
aactgactct tgaagaaaga agaaataatg tagtcataac agtgacacag agaaactata  1260
ctgagtactg gagcggatct aacagtggaa atcagaaaat ggaagctgtt cagaaaataa  1320
attatactgt cccccaaagt ggaactttta agattgaatt cccaatcctg gaggattcca  1380
gtgagctaca gttgaaggcc tatttccttg gtagtaaaag tagcatggca gttcatagtc  1440
tgtttaagtc tcctagtaag acatacatcc aactaaaaac aagagatgaa aatataaagg  1500
tgggatcgcc ttttgagttg gtggttagtg gcaacaaacg attgaaggag ttaagctata  1560
tggtagtatc caggggacag ttggtggctg taggaaaaca aaattcaaca atgttctctt  1620
taacaccaga aaattcttgg actccaaaag cctgtgtaat tgtgtattat attgaagatg  1680
```

-continued

```
atggggaaat tataagtgat gttctaaaaa ttcctgttca gcttgttttt aaaaataaga  1740
taaagctata ttggagtaaa gtgaaagctg aaccatctga gaaagtctct cttaggatct  1800
ctgtgacaca gcctgactcc atagttggga ttgtagctgt tgacaaaagt gtgaatctga  1860
tgaatgcctc taatgatatt acaatggaaa atgtggtcca tgagttggaa ctttataaca  1920
caggatatta tttaggcatg ttcatgaatt cttttgcagt ctttcaggaa tgtggactct  1980
gggtattgac agatgcaaac ctcacgaagg attatattga tggtgtttat gacaatctct  2040
ttggtacaca ggaagcttta taaaatttca ttcacgaatc tcttatttg ggaagctgtt   2100
ttgcatatga gaagaacact gttgaaataa ggaactaaag ctttatatat tgatcaaggt  2160
gattctgaaa gttttaattt ttaatgttgt aatgttatgt tattgttaat tgtactttat  2220
tatgtattca atagaaaatc atgatttatt aataaaagct taaattctca tct         2273

SEQ ID NO: 22          moltype = DNA  length = 4688
FEATURE                Location/Qualifiers
source                 1..4688
                       mol_type = genomic DNA
                       organism = Homo sapiens
SEQUENCE: 22
gggactgtag cccaggcaga cgccgtcgag atgcagggcc caccgctcct gaccgccgcc  60
cacctcctct gcgtgtgcac cgccgcgctg gccgtggctc ccgggcctcg gtttctggtg  120
acagccccag ggatcatcag gcccggagga aatgtgacta ttggggtgga gcttctggaa  180
cactgccctt cacaggtgac tgtgaaggcg gagctgctca agacagcatc aaacctcact  240
gtctctgtcc tggaagcaga aggagtcttt gaaaaaggct cttttaagac acttactctt  300
ccatcactac ctctgaacag tgcagatgag atttatgagc tacgtgtaac cggacgtacc  360
caggatgaga ttttattctc taatagtacc cgcttatcat ttgagaccaa gagaatatct  420
gtcttcattc aaacagacaa ggccttatac aagccaaagc aagaagtgaa gtttcgcatt  480
gttacactct tctcagattt taagccttac aaaacctctt taaacattct cattaaggac  540
cccaaatcaa atttgatcca acagtggttg tcacaacaaa gtgatcttgg agtcatttcc  600
aaaacttttc agctatcttc ccatccaata cttggtgact ggtctattca agttcaagtg  660
aatgaccaga catattatca atcatttcag gtttcagaat atgtattacc aaaatttgaa  720
gtgactttgc agacaccatt atattgttct atgaattcta agcatttaaa tggtaccatc  780
acggcaaagt atacatatgg gaagccagtg aaaggagacg taacgcttac atttttacct  840
ttatcctttt ggggaaagaa gaaaaatatt acaaaaacat ttaagataaa tggatctgca  900
aacttctctt ttaatgatga agagatgaaa aatgtaatgg attcttcaaa tggactttct  960
gaatacctgg atctatcttc ccctggacca gtagaaattt taaccacagt gacagaatca  1020
gttacaggta tttcaagaaa tgtaagcact aatgtgttct tcaagcaaca tgattacatc  1080
attgagtttt ttgattatac cactgtcttg aagccatctc tcaacttcac agccactgtg  1140
aaggtaactc gtgctgatgg caaccaactg actcttgaag aaagaagaaa taatgtagtc  1200
ataacagtga cacagagaaa ctatactgag tactggagcg gatctaacag tggaaatcag  1260
aaaatggaag ctgttcagaa aataaattat actgtccccc aaagtggaac ttttaagatt  1320
gaattcccaa tcctggagga ttccagtgag ctacagttga aggcctattt ccttggtagt  1380
aaaagtagca tggcagttca tagtctgttt aagtctccta gtaagacata catccaacta  1440
aaaacaagag atgaaaatat aaaggtggga tcgccttttg agttggtggt tagtggcaac  1500
aaacgattga aggagttaag ctatatggta gtatccaggg gacagttggt ggctgtagga  1560
aaacaaaatt caacaatgtt ctctttaaca ccagaaaatt cttggactcc aaaagcctgt  1620
gtaattgtgt attatattga agatgatggg gaaattataa gtgatgttct aaaaattcct  1680
gttcagcttg tttttaaaaa taagataaag ctatattgga gtaaagtgaa agctgaacca  1740
tctgagaaag tctctcttag gatctctgtg acacagcctg actccatagt tgggattgta  1800
gctgttgaca aaagtgtgaa tctgatgaat gcctctaatg atattacaat ggaaaatgtg  1860
gtccatgagt tggaacttta taacacagga tattatttag gcatgttcat gaattctttt  1920
gcagtctttc aggaatgtgg actctgggta ttgacagatg caaacctcac gaaggattat  1980
attgatggtg tttatgacaa tgcagaatat gctgagaggt ttatggagga aaatgaagga  2040
catattgtag atattcatga cttttctttg ggtagcagtc cacatgtccg aaagcatttt  2100
ccagagactt ggatttggct agacaccaac atgggttcca ggatttacca agaatttgaa  2160
gtaactgtac ctgattctat cacttcttgg gtggctactg gttttgtgat ctctgaggac  2220
ctgggtcttg gactaacaac tactccagtg gagctccaag ccttccaacc atttttcatt  2280
tttttgaatc ttccctactc tgttatcaga ggtgaagaat ttgctttgga aataactata  2340
ttcaattatt tgaaagatgc cactgaggtt aaggtaatca ttgagaaaag tgacaaattt  2400
gatattctaa tgacttcaag tgaaataaat gccacaggcc accagcagac ccttctggtt  2460
cccagtgagg atggggcaac tgttcttttt cccatcaggc caacacatct gggagaaatt  2520
cctatcacag tcacagctct ttcacccact gcttctgatg ctatcaccca gatgatttta  2580
gtaaaggctg aaggaataga aaaatcatat tcacaatcca tcttattaga cttgactgac  2640
aataggctac agagtaccct gaaaactttg agtttctcat ttcctcctaa tacagtgact  2700
ggcagtgaaa gagttcagat cactgcaatt ggagatgttc ttggtccttc catcaatggc  2760
ttagcctcat tgattcggat gccttatggc tgtggtgaac agaacatgat aaattttgct  2820
ccaaatattt acattttgga ttatctgact aaaaagaaac aactgacaga taatttgaaa  2880
gaaaaagctc tttcatttat gaggcaaggt taccagagag aacttctcta tcagagggaa  2940
gatggctctt tcagtgcttt tgggaattat gacccttctg ggagcacttg gttgtcagct  3000
tttgttttaa gatgtttcct tgaagccgat ccttacatag atattgatca gaatgtgtta  3060
cacagaacat acacttggct taaaggacat cagaaatcca acggtgaatt ttgggatcca  3120
ggaagagtga ttcatagtga gcttcaaggt ggcaataaaa gtccagcaac acttacagcc  3180
tatattgtaa cttctctcct gggatataga aagtatcagc ctaacattga tgtgcaagag  3240
tctatccatt ttttggagtc tgaattcagt agaggaattt cagacaatta tactctagcc  3300
cttataactt atgcattgtc atcagtgggg agtcctaaag cgaaggaagc tttgaatatg  3360
ctgacttgga gagcagaaca agaaggtggc atgcaattct gggtgtcatc agagtccaaa  3420
ctttctgact cctggcagcc acgctccctg gatattgaag ttgcagccta tgcactgctc  3480
tcacacttct tacaatttca gacttctgag ggaatcccaa ttatgaggtg gctaagcagg  3540
caaagaaata gcttgggtgg ttttgcatct actcaggata ccactgtggc tttaaaggct  3600
ctgtctgaat ttgcagccct aatgaataca gaaaggacaa atatccaagt gaccgtgacg  3660
gggcctagct caccaagtcc tgtaaagttt ctgattgaca cacacaaccg cttactcctt  3720
```

-continued

```
cagacagcag agcttgctgt ggtacagcca atggcagtta atatttccgc aaatggtttt  3780
ggatttgcta tttgtcagct caatgttgta tataatgtga aggcttctgg gtcttctaga  3840
agacgaagat ctatccaaaa tcaagaagcc tttgatttag atgttgctgt aaaagaaaat  3900
aaagatgatc tcaatcatgt ggatttgaat gtgtgtacaa gcttttcggg cccgggtagg  3960
agtggcatgg ctcttatgga agttaaccta ttaagtggct ttatggtgcc ttcagaagca  4020
atttctctga gcgagacagt gaagaaagtg gaatatgatc atggaaaact caacctctat  4080
ttagattctg taaatgaaac ccagttttgt gttaatattc ctgctgtgag aaactttaaa  4140
gtttcaaata cccaagatgc ttcagtgtcc atagtggatt actatgagcc aaggagacag  4200
gcggtgagaa gttacaactc tgaagtgaag ctgtcctcct gtgacctttg cagtgatgtc  4260
cagggctgcc gtccttgtga ggatggagct tcaggctccc atcatcactc ttcagtcatt  4320
tttattttct gtttcaagct tctgtacttt atggaacttt ggctgtgatt tatttttaaa  4380
ggactctgtg taacactaac atttccagta gtcacatgtg attgttttgt tttcgtagaa  4440
gaatactgct tctattttga aaaaagagtt ttttttcttt ctatggggtt gcagggatgg  4500
tgtacaacag gtcctagcat gtatagctgc atagatttct tcacctgatc tttgtgtgga  4560
agatcagaat gaatgcagtt gtgtgtctat attttcccct ctcaaaatct tttagaattt  4620
ttttggaggt gtttgttttc tccagaataa aggtattact ttagaaaaca aaaaaaaaaa  4680
aaaaaaaa                                                            4688

SEQ ID NO: 23          moltype = DNA  length = 4369
FEATURE                Location/Qualifiers
source                 1..4369
                       mol_type = genomic DNA
                       organism = Homo sapiens
SEQUENCE: 23
tgtagcccag gcagacgccg tcgagatgca gggcccaccg ctcctgaccg ccgcccacct  60
cctctgcgtg tgcaccgccg cgctggccgt ggctcccggg cctcggtttc tggtgacagc  120
cccagggatc atcaggcccg gaggaaatgt gactattggg gtggagcttc tggaacactg  180
cccttcacag gtgactgtga aggcggagct gctcaagaca gcatcaaacc tcactgtctc  240
tgtcctggaa gcagaaggag tctttgaaaa aggctctttt aagacactta ctcttccatc  300
actacctctg aacagtgcag atgagattta tgagctacgt gtaaccggac gtacccagga  360
tgagatttta ttctctaata gtacccgctt atcatttgag accaagagaa tatctgtctt  420
cattcaaaca gacaaggcct tatacaagcc aaagcaagaa gtgaagtttc gcattgttac  480
actcttctca gattttaagc cttacaaaac ctctttaaac attctcatta aggaccccaa  540
atcaaatttg atccaacagt ggttgtcaca acaaagtgat cttggagtca tttccaaaac  600
ttttcagcta tcttcccatc caatacttgg tgactggtct attcaagttc aagtgaatga  660
ccagacatat tatcaatcat ttcaggtttc agaatatgta ttaccaaaat ttgaagtgac  720
tttgcagaca ccattatatt gttctatgaa ttctaagcat ttaaatggta ccatcacggc  780
aaagtataca tatgggaagc cagtgaaagg agacgtaacg cttacatttt tacctttatc  840
cttttgggga aagaagaaaa atattacaaa aacatttaag ataaatggat ctgcaaactt  900
ctcttttaat gatgaagaga tgaaaaatgt aatggattct tcaaatggac tttctgaata  960
cctggatcta tcttcccctg gaccagtaga aattttaacc acagtgacag aatcagttac  1020
aggtatttca agaaatgtaa gcactaatgt gttcttcaag caacatgatt acatcattga  1080
gtttttgat tatactactg tcttgaagcc atctctcaac ttcacagcca ctgtgaaggt  1140
aactcgtgct gatggcaacc aactgactct tgaagaaaga agaaataatg tagtcataac  1200
agtgacacag agaaactata ctgagtactg gagcggatct aacagtggaa atcagaaaat  1260
ggaagctgtt cagaaaataa attatactgt cccccaaagt ggaactttta agattgaatt  1320
cccaatcctg gaggattcca gtgagctaca gttgaaggcc tatttccttg gtagtaaaag  1380
tagcatggca gttcatagtc tgtttaagtc tcctagtaag acatacatcc aactaaaaac  1440
aagagatgaa aatataaagg tgggatcgcc ttttgagttg gtggttagtg gcaacaaacg  1500
attgaaggag ttaagctata tggtagtatc caggggacag ttggtggctg taggaaaaca  1560
aaattcaaca atgttctctt taacaccaga aaattcttgg actccaaaag cctgtgtaat  1620
tgtgtattat attgaagatg atggggaaat tataagtgat gttctaaaaa ttcctgttca  1680
gcttgttttt aaaaataaga taaagctata ttggagtaaa gtgaaagctg aaccatctga  1740
gaaagtctct cttaggatct ctgtgacaca gcctgactcc atagttggga ttgtagctgt  1800
tgacaaaagt gtgaatctga tgaatgcctc taatgatatt acaatggaaa atgtggtcca  1860
tgagttggaa ctttataaca caggatatta tttaggcatg ttcatgaatt cttttgcagt  1920
ctttcaggaa tgtggactct gggtattgac agatgcaaac ctcacgaagg attatattga  1980
tggtgtttat gacaatgcag aatatgctga gaggtttatg gaggaaaatg aaggacatat  2040
tgtagatatt catgactttt ctttgggtag cagtccacat gtccgaaagc attttccaga  2100
gacttggatt tggctagaca ccaacatggg ttccaggatt taccaagaat ttgaagtaac  2160
tgtacctgat tctatcactt cttgggtggc tactggtttt gtgatctctg aggacctggg  2220
tcttggacta acaactactc cagtggagct ccaagccttc caaccatttt tcattttttt  2280
gaatcttccc tactctgtta tcagaggtga agaatttgct ttggaaataa ctatattcaa  2340
ttatttgaaa gatgccactg aggttaaggt aatcattgag aaaagtgaca aatttgatat  2400
tctaatgact tcaagtgaaa taaatgccac aggccaccag cagacccttc tggttcccag  2460
tgaggatggg gcaactgttc tttttcccat caggccaaca catctgggag aaattcctat  2520
cacagtcaca gctctttcac ccactgcttc tgatgctatc acccagatga ttttagtaaa  2580
ggctgaagga atagaaaaat catattcaca atccatctta ttagacttga ctgacaatag  2640
gctacagagt accctgaaaa ctttgagttt ctcatttcct cctaatacag tgactggcag  2700
tgaaagagtt cagatcactg caattggaga tgttcttggt ccttccatca atggcttagc  2760
ctcattgatt cggatgcctt atggctgtgg tgaacagaac atgataaatt ttgctccaaa  2820
tatttacatt ttggattatc tgactaaaaa gaaacaactg acagataatt tgaaagaaaa  2880
agctctttca tttatgaggc aaggttacca gagagaactt ctctatcaga gggaagatgg  2940
ctctttcagt gcttttggga attatgaccc ttctgggagc acttggttgt cagcttttgt  3000
tttaagatgt ttccttgaag ccgatcctta catagatatt gatcagaatg tgttacacag  3060
aacatacact tggcttaaag gacatcagaa atccaacggt gaattttggg atccaggaag  3120
agtgattcat agtgagcttc aaggtggcaa taaaagtcca gtaacactta cagcctatat  3180
tgtaacttct ctcctgggat atagaaagta tcagcctaac attgatgtgc aagagtctat  3240
ccatttttg gagtctgaat tcagtagagg aatttcagac aattatactc tagcccttat  3300
```

```
aacttatgca ttgtcatcag tggggagtcc taaagcgaag gaagctttga atatgctgac  3360
ttggagagca gaacaagaag gtggcatgca attctgggtg tcatcagagt ccaaactttc  3420
tgactcctgg cagccacgct ccctggatat tgaagttgca gcctatgcac tgctctcaca  3480
cttcttacaa tttcagactt ctgagggaat cccaattatg aggtggctaa gcaggcaaag  3540
aaatagcttg ggtggttttg catctactca ggataccact gtggctttaa aggctctgtc  3600
tgaatttgca gccctaatga atacagaaag gacaaatatc caagtgaccg tgacggggcc  3660
tagctcacca agtcctcttg ctgtggtaca gccaacggca gttaatattt ccgcaaatgg  3720
ttttggattt gctatttgtc agctcaatgt tgtatataat gtgaaggctt ctgggtcttc  3780
tagaagacga agatctatcc aaaatcaaga agcctttgat ttagatgttg ctgtaaaaga  3840
aaataaagat gatctcaatc atgtggattt gaatgtgtgt acaagctttt cgggcccggg  3900
taggagtggc atggctctta tggaagttaa cctattaagt ggctttatgg tgccttcaga  3960
agcaatttct ctgagcgaga cagtgaagaa agtggaatat gatcatggaa aactcaacct  4020
ctatttagat tctgtaaatg aaacccagtt ttgtgttaat attcctgctg tgagaaactt  4080
taaagtttca aatacccaag atgcttcagt gtccatagtg gattactatg agccaaggag  4140
acaggcggtg agaagttaca actctgaagt gaagctgtcc tcctgtgacc tttgcagtga  4200
tgtccagggc tgccgtcctt gtgaggatgg agcttcaggc tcccatcatc actcttcagt  4260
catttttatt ttctgtttca agcttctgta ctttatggaa ctttggctgt gatttatttt  4320
taaaggactc tgtgtaacac taacatttcc agtagtcaca tgtgattgt             4369

SEQ ID NO: 24          moltype = DNA  length = 4237
FEATURE                Location/Qualifiers
source                 1..4237
                       mol_type = genomic DNA
                       organism = Homo sapiens
SEQUENCE: 24
gaggcagacg ccgtcgagat gcagggccca ccgctcctga ccgccgccca cctcctctgc  60
gtgtgcaccg ccgcgctggc cgtggctccc gggcctcggt ttctggtgac agccccaggg  120
atcatcaggc ccggaggaaa tgtgactatt ggggtggagc ttctggaaca ctgcccttca  180
caggtgactg tgaaggcgga gctgctcaag acagcatcaa acctcactgt ctctgtcctg  240
gaagcagaag gagtctttga aaaaggctct tttaagacac ttactcttcc atcagacccc  300
aaatcaaatt tgatccaaca gtggttgtca caacaaagtg atcttggagt catttccaaa  360
acttttcagc tatcttccca tccaatactt ggtgactggt ctattcaagt tcaagtgaat  420
gaccagacat actatcaatc atttcaggtt tcagaatatg tattaccaaa atttgaagtg  480
actttgcaga caccattata ttgttctatg aattctaagc atttaaatgg taccatcacg  540
gcaaagtata catatgggaa gccagtgaaa ggagacgtaa cgcttacatt tttaccttta  600
tccttttggg gaaagaagaa aaatattaca aaaacattta agataaatgg atctgcaaac  660
ttctctttta atgatgaaga gatgaaaaat gtaatggatt cttcaaatgg actttctgaa  720
tacctggatc tatcttcccc tggaccagta gaaattttaa ccacagtgac agaatcagtt  780
acaggtattt caagaaatgt aagcactaat gtgttcttca agcaacatga ttacatcatt  840
gagtttttg attatactac tgtcttgaag ccatctctca acttcacagc cactgtgaag  900
gtaactcgtg ctgatggcaa ccaactgact cttgaagaaa gaagaaataa tgtagtcata  960
acagtgacac agagaaacta tactgagtac tggagcggat ctaacagtgg aaatcagaaa  1020
atggaagctg ttcagaaaat aaattatact gtcccccaaa gtggaacttt taagattgaa  1080
ttcccaatcc tggaggattc cagtgagcta cagttgaagg cctatttcct tggtagtaaa  1140
agtagcatgg cagttcatag tctgtttaag tctcctagta agacatacat ccaactaaaa  1200
acaagagatg aaaatataaa ggtgggatcg ccttttgagt tggtggttag tggcaacaaa  1260
cgattgaagg agttaagcta tatggtagta tccaggggac agttggtggc tgtaggaaaa  1320
caaaattcaa caatgttctc tttaacacca gaaaattctt ggactccaaa agcctgtgta  1380
attgtgtatt atattgaaga tgatggggaa attataagtg atgttctaaa aattcctgtt  1440
cagcttgttt ttaaaaataa gataaagcta tattggagta aagtgaaagc tgaaccatct  1500
gagaaagtct ctcttaggat ctctgtgaca cagcctgact ccatagttgg gattgtagct  1560
gttgacaaaa gtgtgaatct gatgaatgcc tctaatgata ttacaatgga aaatgtggtc  1620
catgagttgg aactttataa cacaggatat tatttaggca tgttcatgaa ttcttttgca  1680
gtctttcagg aatgtggact ctgggtattg acagatgcaa acctcacgaa ggattatatt  1740
gatggtgttt atgacaatgc agaatatgct gagaggttta tggaggaaaa tgaaggacat  1800
attgtagata ttcatgactt ttctttgggt agcagtccac atgtccgaaa gcattttcca  1860
gagacttgga tttggctaga caccaacatg ggttacagga tttaccaaga atttgaagta  1920
actgtacctg attctatcac ttcttgggtg gctactggtt ttgtgatctc tgaggacctg  1980
ggtcttggac taacaactac tccagtggag ctccaagcct tccaaccatt tttcattttt  2040
ttgaatcttc cctactctgt tatcagaggt gaagaatttg ctttggaaat aactatattc  2100
aattatttga aagatgccac tgaggttaag gtaatcattg agaaaagtga caaatttgat  2160
attctaatga cttcaaatga aataaatgcc acaggccacc agcagaccct tctggttccc  2220
agtgaggatg gggcaactgt tctttttccc atcaggccaa cacatctggg agaaattcct  2280
atcacagtca cagctctttc acccactgct tctgatgctg tcacccagat gattttagta  2340
aaggctgaag gaatagaaaa atcatattca caatccatct tattagactt gactgacaat  2400
aggctacaga gtaccctgaa aactttgagt ttctcatttc ctcctaatac agtgactggc  2460
agtgaaagag ttcagatcac tgcaattgga gatgttcttg gtccttccat caatggctta  2520
gcctcattga ttcggatgcc ttatggctgt ggtgaacaga acatgataaa ttttgctcca  2580
aatatttaca ttttggatta tctgactaaa aagaaacaac tgacagataa tttgaaagaa  2640
aaagctcttt catttatgag gcaaggttac cagagagaac ttctctatca gagggaagat  2700
ggctctttca gtgcttttgg gaattatgac ccttctggga gcacttggtt gtcagccttt  2760
gttttaagat gtttccttga agccgatcct tacatagata ttgatcagaa tgtgttacac  2820
agaacataca cttggcttaa aggacatcag aaatccaacg gtgaattttg ggatccagga  2880
agagtgattc atagtgagct tcaaggtggc aataaaagtc cagtaacact tacagcctat  2940
attgtaactt ctctcctggg atatagaaag tatcagccta acattgatgt gcaagagtct  3000
atccattttt tggagtctga attcagtaga ggaatttcag acaattatac tctagccctt  3060
ataacttatg cattgtcatc agtggggagt cctaaagcga aggaagcttt gaatatgctg  3120
acttggagag cagaacaaga aggtggcatg caattctggg tgtcatcaga gtccaaactt  3180
tctgactcct ggcagccacg ctccctggat attgaagttg cagcctatgc actgctctca  3240
```

-continued

```
cacttcttac aatttcagac ttctgaggga atcccaatta tgaggtggct aagcaggcaa  3300
agaaatagct tgggtggttt tgcatctact caggatacca ctgtggcttt aaaggctctg  3360
tctgaatttg cagccctaat gaatacagaa aggacaaata tccaagtgac cgtgacgggg  3420
cctagctcac caagtcctgt aaagtttctg attgacacac acaaccgctt actccttcag  3480
acagcagagc ttgctgtggt acagccaatg gcagttaata tttccgcaaa tggttttgga  3540
tttgctattt gtcagctcaa tgttgtatat aatgtgaagg cttctgggtc ttctagaaga  3600
cgaagatcta tccaaaatca agaagccttt tgatttagat gttgctgtaa aagaaaataa  3660
agatgatctc aatcatgtgg atttgaatgt gtgtacaagc ttttcgggcc cgggtaggag  3720
tggcatggct cttatggaag ttaacctatt aagtggcttt atggtgcctt cagaagcaat  3780
ttctctgagc gagacagtga agaaagtgga atatgatcat ggaaaactca acctctattt  3840
agattctgta aatgaaaccc agttttgtgt taatattcct gctgtgagaa actttaaagt  3900
ttcaaatacc caagatgctt cagtgtccat agtggattac tatgagccaa ggagacaggc  3960
ggtgagaagt tacaactctg aagtgaagct gtcctcctgt gacctttgca gtgatgtcca  4020
gggctgccgt ccttgtgagg atggagcttc aggctcccat catcactctt cagtcatttt  4080
tattttctgt ttcaagcttc tgtactttat ggaactttgg ctgtgattta tttttaaagg  4140
actctgtgta acactaacat ttccagtagt cacatgtgat tgttttgttt tcgtagaaga  4200
atactgcttc tattttgaaa aaaaaaaaaa aaaaaca                           4237

SEQ ID NO: 25           moltype = DNA  length = 4338
FEATURE                 Location/Qualifiers
source                  1..4338
                        mol_type = genomic DNA
                        organism = Homo sapiens
SEQUENCE: 25
atgcagggcc caccgctcct gaccgccgcc cacctcctct gcgtgtgcac cgccgcgctg  60
gccgtggctc ccgggcctcg gtttctggtg acagccccag ggatcatcag gcccggagga  120
aatgtgacta ttggggtgga gcttctggaa cactgccctt cacaggtgac tgtgaaggcg  180
gagctgctca agacagcatc aaacctcact gtctctgtcc tggaagcaga aggagtcttt  240
gaaaaaggct cttttaagac acttactctt ccatcactac ctctgaacag tgcagatgag  300
atttatgagc tacgtgtaac cggacgtacc caggatgaga ttttattctc taatagtacc  360
cgcttatcat ttgagaccaa gagaatatct gtcttcattc aaacagacaa ggccttatac  420
aagccaaagc aagaagtgaa gtttcgcatt gttacactct tctcagattt taagccttac  480
aaaacctctt taaacattct cattaaggac cccaaatcaa atttgatcca acagtggttg  540
tcacaacaaa gtgatcttgg agtcatttcc aaaacttttc agctatcttc ccatccaata  600
cttggtgact ggtctattca agttcaagtg aatgaccaga catattatca atcatttcag  660
gtttcagaat atgtattacc aaaatttgaa gtgactttgc agacaccatt atattgttct  720
atgaattcta agcatttaaa tggtaccatc acggcaaagt atacatatgg gaagccagtg  780
aaaggagacg taacgcttac atttttacct ttatcctttt ggggaaagaa gaaaaatatt  840
acaaaaacat ttaagataaa tggatctgca aacttctctt ttaatgatga agagatgaaa  900
aatgtaatgg attcttcaaa tggactttct gaatacctgg atctatcttc ccctggacca  960
gtagaaattt taaccacagt gacagaatca gttacaggta tttcaagaaa tgtaagcact  1020
aatgtgttct tcaagcaaca tgattacatc attgagtttt ttgattatac tactgtcttg  1080
aagccatctc tcaacttcac agccactgtg aaggtaactc gtgctgatgg caaccaactg  1140
actcttgaag aaagaagaaa taatgtagtc ataacagtga cacagagaaa ctatactgag  1200
tactggagcg gatctaacag tggaaatcag aaaatggaag ctgttcagaa aataaattat  1260
actgtccccc aaagtggaac ttttaagatt gaattcccaa tcctggagga ttccagtgag  1320
ctacagttga aggcctattt ccttggtagt aaaagtagca tggcagttca tagtctgttt  1380
aagtctccta gtaagacata catccaacta aaaacaagag atgaaaatat aaaggtggga  1440
tcgccttttg agttggtggt tagtggcaac aaacgattga aggagttaag ctatatggta  1500
gtatccaggg gacagttggt ggctgtagga aaacaaaatt caacaatgtt ctctttaaca  1560
ccagaaaatt cttggactcc aaaagcctgt gtaattgtgt attatattga agatgatggg  1620
gaaattataa gtgatgttct aaaaattcct gttcagcttg tttttaaaaa taagataaag  1680
ctatattgga gtaaagtgaa agctgaacca tctgagaaag tctctcttag gatctctgtg  1740
acacagcctg actccatagt tgggattgta gctgttgaca aaagtgtgaa tctgatgaat  1800
gcctctaatg atattacaat ggaaaatgtg gtccatgagt tggaacttta taacacagga  1860
tattatttag gcatgttcat aaattctttt gcagtctttc aggaatgtgg actctgggta  1920
ttgacagatg caaacctcac gaaggattat attgatggtg tttatgacaa tgcagaatat  1980
gctgagaggt ttatggagga aaatgaagga catattgtag atattcatga cttttctttg  2040
ggtagcagtc cacatgtccg aaagcatttt ccagagactt ggatttggct agacaccaac  2100
atgggttcca ggatttacca agaatttgaa gtaactgtac ctgattctat cacttcttgg  2160
gtggctactg gttttgtgat ctctgaggac ctgggtcttg gactaacaac tactccagtg  2220
gagctccaag ccttccaacc atttttcatt tttttgaatc ttccctactc tgttatcaga  2280
ggtgaagaat ttgctttgga aataactata ttcaattatt tgaaagatgc cactgaggtt  2340
aaggtaatca ttgagaaaag tgacaaattt gatattctaa tgacttcaag tgaaataaat  2400
gccacaagcc accagcagac ccttctggtt cccagtgagg atggggcaac tgttcttttt  2460
cccatcaggc caacacatct gggagaaatt cctatcacag tcacagctct ttcacccact  2520
gcttctgatg ctatcaccca gatgatttta gtaaaggctg aaggaataga aaaatcatat  2580
tcacaatcca tcttattaga cttgactgac aataggctac agagtaccct gaaaactttg  2640
agtttctcat ttcctcctaa tacagtgact ggcagtgaaa gagttcagat cactgcaatt  2700
ggagatgttc ttggtccttc catcaatggc ttagcctcat tgattcggat gccttatggc  2760
tgtggtgaac agaacatgat aaattttgct ccaaatattt acattttgga ttatctgact  2820
aaaaagaaac aactgacaga taatttgaaa gaaaaagctc tttcatttat gaggcaaggt  2880
taccagagag aacttctcta tcagagggaa gatggctctt tcagtgcttt tgggaattat  2940
gacccttctg ggagcacttg gttgtcagct tttgttttaa gatgtttcct tgaagccgat  3000
ccttacatag atattgatca gaatgtgtta cacagaacat acacttggct taaaggacat  3060
cagaaatcca acggtgaatt ttgggatcca ggaagagtga ttcatagtga gcttcaaggt  3120
ggcaataaaa gtccagtaac acttacagcc tatattgtaa cttctctcct gggatataga  3180
aagtatcagc ctaacattga tgtgcaagag tctatccatt ttttggagtc tgaattcagt  3240
agaggaattt cagacaatta tactctagcc cttataactt atgcattgtc atcagtgggg  3300
```

-continued

```
agtcctaaag cgaaggaagc tttgaatatg ctgacttgga gagcagaaca agaaggtggc  3360
atgcaattct gggtgtcatc agagtccaaa ctttctgact cctggcagcc acgctccctg  3420
gatattgaag ttgcagccta tgcactgctc tcacacttct tacaatttca gacttctgag  3480
ggaatcccaa ttatgaggtg gctaagcagg caaagaaata gcttgggtgg ttttgcatct  3540
actcaggata ccactgtggc tttaaaggct ctgtctgaat ttgcagccct aatgaataca  3600
gaaaggacaa atatccaagt gaccgtgacg gggcctagct caccaagtcc tgtaaagttt  3660
ctgattgaca cacacaaccg cttactcctt cagacagcag agcttgctgt ggtacagcca  3720
acggcagtta atatttccgc aaatggtttt ggatttgcta tttgtcagct caatgttgta  3780
tataatgtga aggcttctgg gtcttctaga agacgaagat ctatccaaaa tcaagaagcc  3840
tttgatttag atgttgctgt aaaagaaaat aaagatgatc tcaatcatgt ggatttgaat  3900
gtgtgtacaa gcttttcggg cccgggtagg agtggcatgg ctcttatgga agttaaccta  3960
ttaagtggct ttatggtgcc ttcagaagca atttctctga gcgagacagt gaagaaagtg  4020
gaatatgatc atggaaaact caacctctat ttagattctg taaatgaaac ccagttttgt  4080
gttaatattc ctgctgtgag aaactttaaa gtttcaaata cccaagatgc ttcagtgtct  4140
atagtggatt actatgagcc aaggagacag gcggtgagaa gttacaactc tgaagtgaag  4200
ctgtcctcct gtgacctttg cagtgatgtc cagggctgcc gtccttgtga ggatggagct  4260
tcaggctccc atcatcactc ttcagtcatt tttatttttct gtttcaagct tctgtacttt  4320
atggaacttt ggctgtga                                                4338
```

```
SEQ ID NO: 26          moltype = DNA  length = 2938
FEATURE                Location/Qualifiers
source                 1..2938
                       mol_type = genomic DNA
                       organism = Homo sapiens
SEQUENCE: 26
gttgacaaaa gtgtgaatct gatgaatgcc tctaatgata ttacaatgga aaatgtggtc  60
catgagttgg aactttataa cacaggatat tatttaggca tgttcatgaa ttcttttgca  120
gtctttcagg aatgtggact ctgggtattg acagatgcaa acctcacgaa ggattatatt  180
gatggtgttt atgacaatgc agaatatgct gagaggttta tggaggaaaa tgaaggacat  240
attgtagata ttcatgactt ttctttgggt agcagtccac atgtccgaaa gcattttcca  300
gagacttgga tttggctaga caccaacatg ggttccagga tttaccaaga atttgaagta  360
actgtacctg attctatcac ttcttgggtg gctactggtt ttgtgatctc tgaggacctg  420
ggtcttggac taacaactac tccagtggag ctccaagcct tccaaccatt tttcattttt  480
ttgaatcttc cctactctgt tatcagaggt gaagaatttg ctttggaaat aactatattc  540
aattatttga aagatgccac tgaggttaag gtaatcattg agaaaagtga caaatttgat  600
attctaatga cttcaagtga aataaatgcc acaggccacc agcagaccct tctggttccc  660
agtgaggatg gggcaactgt tctttttccc atcaggccaa cacatctggg agaaattcct  720
atcacagtca cagctctttc acccactgct tctgatgcta tcacccagat gattttagta  780
aaggctgaag gaatagaaaa atcatattca caatccatct tattagactt gactgacaat  840
aggctacaga gtaccctgaa aactttgagt ttctcatttc ctcctaatac agtgactggc  900
agtgaaagag ttcagatcac tgcaattgga gatgttcttg gtccttccat caatggctta  960
gcctcattga ttcggatgcc ttatggctgt ggtgaacaga acatgataaa ttttgctcca  1020
aatatttaca ttttggatta tctgactaaa aagaaacaac tgacagataa tttgaaagaa  1080
aaagctcttt catttatgag gcaaggttac cagagagaac ttctctatca gagggaagat  1140
ggctctttca gtgcttttgg gaattatgac ccttctggga gcacttggtt gtcagctttt  1200
gttttaagat gtttccttga agccgatcct tacatagata ttgatcagaa tgtgttacac  1260
agaacataca cttggcttaa aggacatcag aaatccaacg gtgaattttg ggatccagga  1320
agagtgattc atagtgagct tcaaggtggc aataaaagtc cagtaacact tacagcctat  1380
attgtaactt ctctcctggg atatagaaag tatcagccta acattgatgt gcaagagtct  1440
atccattttt tggagtctga attcagtaga ggaatttcag acaattatac tctagccctt  1500
ataacttatg cattgtcatc agtggggagt cctaaagcga aggaagcttt gaatatgctg  1560
acttggagag cagaacaaga aggtggcatg caattctggg tgtcatcaga gtccaaactt  1620
tctgactcct ggcagccacg ctccctggat attgaagttg cagcctatgc actgctctca  1680
cacttcttac aatttcagac ttctgaggga atcccaatta tgaggtggct aagcaggcaa  1740
agaaatagct tgggtggttt tgcatctact caggatacca ctgtggcttt aaaggctctg  1800
tctgaatttg cagccctaat gaatacagaa aggacaaata tccaagtgac cgtgacgggg  1860
cctagctcac caagtcctgt aaagtttctg attgacacac acaaccgctt actccttcag  1920
acagcagagc ttgctgtggt acagccaacg gcagttaata tttccgcaaa tggttttgga  1980
tttgctattt gtcagctcaa tgttgtatat aatgtgaagg cttctgggtc ttctagaaga  2040
cgaagatcta tccaaaatca agaagccttt gatttagatg ttgctgtaaa agaaaataaa  2100
gatgatctca atcatgtgga tttgaatgtg tgtacaagct tttcgggccc gggtaggagt  2160
ggcatggctc ttatggaagt taacctatta agtggcttta tggtgccttc agaagcaatt  2220
tctctgagcg agacagtgaa gaaagtggaa tatgatcatg gaaaactcaa cctctattta  2280
gattctgtaa atgaaaccca gttttgtgtt aatattcctg ctgtgagaaa ctttaaagtt  2340
tcaaataccc aagatgcttc agtgtccata gtggattact atgagccaag gagacaggcg  2400
gtgagaagtt acaactctga agtgaagctg tcctcctgtg acctttgcag tgatgtccag  2460
ggctgccgtc cttgtgagga tggagcttca ggctcccatc atcactcttc agtcattttt  2520
attttctgtt tcaagcttct gtactttatg gaactttggc tgtgatttat ttttaaagga  2580
ctctgtgtaa cactaacatt tccagtagtc acatgtgatt gttttgtttt cgtagaagaa  2640
tactgcttct attttgaaaa aagagttttt tttctttcta tggggttgca gggatggtgt  2700
acaacaggtc ctagcatgta tagctgcata gatttcttca cctgatcttt gtgtggaaga  2760
tcagaatgaa tgcagttgtg tgtctatatt ttcccctctc aaaatctttt agaatttttt  2820
tggaggtgtt tgttttctcc agaataaagg tattacttta gaataaaaaa aaaaaaaaaa  2880
aaaaaaaaaa aaaaaaaaaa aaaaaaaaaa aaaaaaaaaa aaaaaaaaaa aaaaaaa    2938
```

```
SEQ ID NO: 27          moltype = DNA  length = 2843
FEATURE                Location/Qualifiers
source                 1..2843
                       mol_type = genomic DNA
```

```
                        organism = Homo sapiens
SEQUENCE: 27
ctgatgaatg cctctaatga tattacaatg gaaaatgtgg tccatgagtt ggaactttat  60
aacacaggat attatttagg catgttcatg aattcttttg cagtctttca ggaatgtgga  120
ctctgggtat tgacagatgc aaacctcacg aaggattata ttgatggtgt ttatgacaat  180
gcagaatatg ctgagaggtt tatggaggaa aatgaaggac atattgtaga tattcatgac  240
ttttctttgg gtagcagtcc acatgtccga aagcattttc cagagacttg gatttggcta  300
gacaccaaca tgggttccag gatttaccaa gaatttgaag taactgtacc tgattctatc  360
acttcttggg tggctactgg ttttgtgatc tctgaggacc tgggtcttgg actaacaact  420
actccagtgg agctccaagc cttccaacca tttttcattt ttttgaatct tccctactct  480
gttatcagag gtgaagaatt tgctttggaa ataactatat tcaattattt gaaagatgcc  540
actgaggtta aggtaatcat tgagaaaagt gacaaatttg atattctaat gacttcaagt  600
gaaataaatg ccacaggcca ccagcagacc cttctggttc ccagtgagga tggggcaact  660
gttctttttc ccatcaggcc aacacatctg ggagaaattc ctatcacagt cacagctctt  720
tcacccactg cttctgatgc tatcacccag atgattttag taaaggctga aggaatagaa  780
aaatcatatt cacaatccat cttattagac ttgactgaca ataggctaca gagtaccctg  840
aaaactttga gtttctcatt tcctcctaat acagtgactg gcagtgaaag agttcagatc  900
actgcaattg gagatgttct tggtccttcc atcaatggct tagcctcatt gattcggatg  960
ccttatggct gtggtgaaca gaacatgata aattttgctc caaatattta cattttggat  1020
tatctgacta aaaagaaaca actgacagat aatttgaaag aaaaagctct ttcatttatg  1080
aggcaaggtt accagagaga acttctctat cagagggaag atggctcttt cagtgctttt  1140
gggaattatg acccttctgg gagcacttgg ttgtcagctt ttgttttaag atgtttcctt  1200
gaagccgatc cttacataga tattgatcag aatgtgttac acagaacata cacttggctt  1260
aaaggacatc agaaatccaa cggtgaattt tgggatccag gaagagtgat tcatagtgag  1320
cttcaaggtg gcaataaaag tccagtaaca cttacagcct atattgtaac ttctctcctg  1380
ggatatagaa agtatcagcc taacattgat gtgcaagagt ctatccattt tttggagtct  1440
gaattcagta gaggaatttc agacaattat actctagccc ttataactta tgcattgtca  1500
tcagtgggga gtcctaaagc gaaggaagct ttgaatatgc tgacttggag agcagaacaa  1560
gaaggtggca tgcaattctg ggtgtcatca gagtccaaac tttctgactc ctggcagcca  1620
cgctccctgg atattgaagt tgcagcctat gcactgctct cacacttctt acaatttcag  1680
acttctgagg gaatcccaat tatgaggtgg ctaagcaggc aaagaaatag cttgggtggt  1740
tttgcatcta ctcaggatac cactgtggct ttaaaggctc tgtctgaatt tgcagcccta  1800
atgaatacag aaaggacaaa tatccaagtg accgtgacgg ggcctagctc accaagtcct  1860
gtaaagtttc tgattgacac acacaaccgc ttactccttc agacagcaga gcttgctgtg  1920
gtacagccaa cggcagttaa tatttccgca aatggttttg gatttgctat ttgtcagctc  1980
aatgttgtat ataatgtgaa ggcttctggg tcttctagaa gacgaagatc tatccaaaat  2040
caagaagcct ttgatttaga tgttgctgta aaagaaaata aagatgatct caatcatgtg  2100
gatttgaatg tgtgtacaag cttttcgggc ccgggtagga gtggcatggc tcttatggaa  2160
gttaacctat taagtggctt tatggtgcct tcagaagcaa tttctctgag cgagacagtg  2220
aagaaagtgg aatatgatca tggaaaactc aacctctatt tagattctgt aaatgaaacc  2280
cagttttgtg ttaatattcc tgctgtgaga aactttaaag tttcaaatac ccaagatgct  2340
tcagtgtcca tagtggatta ctatgagcca aggagacagg cggtgagaag ttacaactct  2400
gaagtgaagc tgtcctcctg tgacctttgc agtgatgtcc agggctgccg tccttgtgag  2460
aatggagctt caggctccca tcatcactct tcagtcattt ttattttctg tttcaagctt  2520
ctgtacttta tggaactttg gctgtgattt atttttaaag gactctgtgt aacactaaca  2580
tttccagtag tcacatgtga ttgttttgtt ttcgtagaag aatactgctt ctattttgaa  2640
aaaagagttt tttttctttc tatggggttg cagggatggt gtacaacagg tcctagcatg  2700
tatagctgca tagatttctt cacctgatct ttgtgtggaa gatcagaatg aatgcagttg  2760
tgtgtctata ttttcccctc tcaaaatctt ttagaatttt tttggaggtg tttgttttct  2820
ccagaataaa ggtattactt tag                                         2843

SEQ ID NO: 28           moltype = DNA  length = 8800
FEATURE                 Location/Qualifiers
source                  1..8800
                        mol_type = genomic DNA
                        organism = Homo sapiens
SEQUENCE: 28
agacgccgtc gagatgcagg gcccaccgct cctgaccgcc gcccacctcc tctgcgtgtg  60
caccgccgcg ctggccgtgg ctcccgggcc tcggtttctg gtgacagccc cagggatcat  120
caggcccgga ggaaatgtga ctattggggt ggagcttctg gaacactgcc cttcacaggt  180
gactgtgaag gcggagctgc tcaagacagc atcaaacctc actgtctctg tcctggaagc  240
agaaggagtc tttgaaaaag gctcttttaa gacacttact cttccatcag accccaaatc  300
aaatttgatc caacagtggt tgtcacaaca aagtgatctt ggagtcattt ccaaaacttt  360
tcagctatct tcccatccaa tacttggtga ctggtctatt caagttcaag tgaatgacca  420
gacatactat caatcatttc aggtttcaga atatgtatta ccaaaatttg aagtgacttt  480
gcagacacca ttatattgtt ctatgaattc taagcattta aatggtacca tcacggcaaa  540
gtatacatat gggaagccag tgaaaggaga cgtaacgctt acatttttac ctttatcctt  600
ttggggaaag aagaaaaata ttacaaaaac atttaagata aatggatctg caaacttctc  660
ttttaatgat gaagagatga aaaatgtaat ggattcttca aatggacttt ctgaatacct  720
ggatctatct tcccctggac cagtagaaat tttaaccaca gtgacagaat cagttacagg  780
tatttcaaga aatgtaagca ctaatgtgtt cttcaagcaa catgattaca tcattgagtt  840
ttttgattat actactgtct tgaagccatc tctcaacttc acagccactg tgaaggtaac  900
tcgtgctgat ggcaaccaac tgactcttga agaaagaaga aataatgtag tcataacagt  960
gacacagaga aactatactg agtactggag cggatctaac agtggaaatc agaaaatgga  1020
agctgttcag aaaataaatt atactgtccc ccaaagtgga acttttaaga ttgaattccc  1080
aatcctggag gattccagtg agctacagtt gaaggcctat ttccttggta gtaaaagtag  1140
catggcagtt catagtctgt ttaagtctcc tagtaagaca tacatccaac taaaaacaag  1200
agatgaaaat ataaaggtgg gatcgccttt tgagttggtg gttagtggca acaaacgatt  1260
gaaggagtta agctatatgg tagtatccag ggacagttg gtggctgtag gaaaacaaaa  1320
```

-continued

```
ttcaacaatg ttctctttaa caccagaaaa ttcttggact ccaaaagcct gtgtaattgt  1380
gtattatatt gaagatgatg gggaaattat aagtgatgtt ctaaaaattc ctgttcagct  1440
tgtttttaaa aataagataa agctatattg gagtaaagtg aaagctgaac catctgagaa  1500
agtctctctt aggatctctg tgacacagcc tgactccata gttgggattg tagctgttga  1560
caaaagtgtg aatctgatga atgcctctaa tgatattaca atggaaaatg tggtccatga  1620
gttggaactt tataacacag gatattattt aggcatgttc atgaattctt ttgcagtctt  1680
tcaggaatgt ggactctggg tattgacaga tgcaaacctc acgaaggatt atattgatgg  1740
tgtttatgac aatgcagaat atgctgagag gtttatggag gaaaatgaag gacatattgt  1800
agatattcat gacttttctt tgggtagcag tccacatgtc cgaaagcatt ttccagagac  1860
ttggatttgg ctagacacca acatgggtta caggatttac caagaatttg aagtaactgt  1920
acctgattct atcacttctt gggtggctac tggttttgtg atctctgagg acctgggtct  1980
tggactaaca actactccag tggagctcca agccttccaa ccatttttca ttttttgaa  2040
tcttccctac tctgttatca gaggtgaaga atttgctttg gaaataacta tattcaatta  2100
tttgaaagat gccactgagg ttaaggtaat cattgagaaa agtgacaaat ttgatattct  2160
aatgacttca aatgaaataa atgccacagg ccaccagcag acccttctgg ttcccagtga  2220
ggatggggca actgttcttt ttcccatcag gccaacacat ctgggagaaa ttcctatcac  2280
agtcacagct ctttcaccca ctgcttctga tgctgtcacc cagatgattt tagtaaaggc  2340
tgaaggaata gaaaaatcat attcacaatc catcttatta gacttgactg acaataggct  2400
acagagtacc ctgaaaactt tgagtttctc atttcctcct aatacagtga ctggcagtga  2460
aagagttcag atcactgcaa ttggagatgt tcttggtcct tccatcaatg gcttagcctc  2520
attgattcgg atgccttatg gctgtggtga acagaacatg ataaattttg ctccaaatat  2580
ttacatttttg gattatctga ctaaaaagaa acaactgaca gataatttga aagaaaaagc  2640
tctttcattt atgaggcaag gttaccagag agaacttctc tatcagaggg aagatggctc  2700
tttcagtgct tttgggaatt atgaccctc tgggagcact tggttgtcag cttttgtttt  2760
aagatgtttc cttgaagccg atccttacat agatattgat cagaatgtgt tacacagaac  2820
atacacttgg cttaaaggac atcagaaatc caacggtgaa ttttgggatc caggaagagt  2880
gattcatagt gagcttcaag gtggcaataa aagtccagta acacttacag cctatattgt  2940
aacttctctc ctgggatata gaaagtatca gcctaacatt gatgtgcaag agtctatcca  3000
ttttttggag tctgaattca gtagaggaat ttcagacaat tatactctag cccttataac  3060
ttatgcattg tcatcagtgg ggagtcctaa agcgaaggaa gctttgaata tgctgacttg  3120
gagagcagaa caagaaggtg gcatgcaatt ctgggtgtca tcagagtcca aactttctga  3180
ctcctggcag ccacgctccc tggatattga agttgcagcc tatgcactgc tctcacactt  3240
cttacaattt cagacttctg agggaatccc aattatgagg tggctaagca ggcaaagaaa  3300
tagcttgggt ggttttgcat ctactcagga taccactgtg gctttaaagg ctctgtctga  3360
atttgcagcc ctaatgaata cagaaaggac aaatatccaa gtgaccgtga cggggcctag  3420
ctcaccaagt cctgtaaagt ttctgattga cacacacaac cgcttactcc ttcagacagc  3480
agagcttgct gtggtacagc caacggcagt taatatttcc gcaaatggtt ttggatttgc  3540
tatttgtcag ctcaatgttg tatataatgt gaaggcttct gggtcttcta gaagacgaag  3600
atctatccaa aatcaagaag cctttgattt agatgttgct gtaaaagaaa ataaagatga  3660
tctcaatcat gtggatttga atgtgtgtac aagcttttcg ggcccgggta ggagtggcat  3720
ggctcttatg gaagttaacc tattaagtgg ctttatggtg ccttcagaag caatttctct  3780
gagcgagaca gtgaagaaag tggaatatga tcatggaaaa ctcaacctct atttagattc  3840
tgtaaatgaa acccagtttt gtgttaatat tcctgctgtg agaaacttta aagtttcaaa  3900
tacccaagat gcttcagtgt ccatagtgga ttactatgag ccaaggagac aggcggtgag  3960
aagttacaac tctgaagtga agctgtcctc ctgtgacctt tgcagtgatg tccagggctg  4020
ccgtccttgt gaggatggag cttcaggctc ccatcatcac tcttcagtca tttttatttt  4080
ctgtttcaag cttctgtact ttatggaact ttggctgtga tttattttta aaggactctg  4140
tgtaacacta acatttccag tagtcacatg tgattgtttt gttttcgtag aagaatactg  4200
cttctatttt gaaaaaagag ttttttttct ttctatgggg ttgcagggat ggtgtacaac  4260
aggtcctagc atgtatagct gcatagattt cttcacctga tctttgtgtg gaagatcaga  4320
atgaatgcag ttgtgtgtct atattttccc ctctcaaaat cttttagaat tttttggag  4380
gtgtttgttt tctccagaat aaaggtatta ctttagaata ggtattctcc tcattttgtg  4440
aaagaaatga acctagattc ttaagcatta ttacacatcc atgtttgctt aaagatggat  4500
ttccctggga atgggagaaa acagccagca ggaggagctt catctgttcc cttcccacct  4560
ccaacctagc cctactgccc accccacccc aacccacccc atgcccagtg gtctcagtag  4620
atacttctta actggaaatt ctttcttttc agaatctagg tggtgaattt tttttaagtg  4680
gcacggtctt tttctgcttg aaatctgatc acacccccca gccattgccc tccctctctt  4740
tttcctctgt agagaaatgt gaggggcagt acatttactg tgcttttcac accatctcag  4800
aggttgagga gcatactgaa aattgccctg gggggtgctg ggtgtgctgt ctccttccca  4860
catcctcagc cccacaccag ctctatttca ggggtgagag tcagagagca ctgcaatatg  4920
tgcttcatgg gatttcgatt cgaagatcct agaccaggga gacactgtga gccagggata  4980
caacaaaata ctaggtaagt cactgcagac cgacctccct gcagtttggg aaagaagctg  5040
ggtttgtgga gaatcagagc atcttgacat gactgctgac ctaaagatcc ctggcattgg  5100
ccagggatcc tgtggaacct cttctagttc aggggtgtga gcattagact gccagttgtc  5160
tagtgacatc tgatgcttgc tgtgaacttt taagatcccc gaatcctgag cacctcaatc  5220
tttaattgcc ctgtattccg aagggtaata taatttatct ggatggaaat tttaaagatg  5280
aatccccctt ttttcttttc ttctctcttt tctttccttc tccctttctt ctttgccttc  5340
taaatatact gaaatgattt agatatgtgt caacaattaa tgatctttta ttcaatctaa  5400
gaaatggttt agtttttctc tttagctcta tggcatttca ctcaagtgga caggggaaaa  5460
agtaattgcc atgggctcca aagaatttgc tttatgtttt tagctattta aaaataaatc  5520
catcaaaaat aaagtatgca aatgtatctt ttaaagttaa tttttaaaaa tgctcttatt  5580
ttagtgaatt ttcagaaatt atagtggaat ggatgctcat atattgctta tggatatttt  5640
ggataccaaa gtaggaataa ctgacattca gtattttaaa gctggcaaac ctgtacatag  5700
aaaatagatc cccagacagt ggtctatgaa gagggcagtt aagtatcaaa tacttaattt  5760
tcttgccttt ttttcttaag tggggaaaag tttctagatc tcttacacct ctgacacaat  5820
ctgttctaaa acaggcactt gtaatgttgg ggcctccttg taaacgtgtt tttgcccttt  5880
actctctggg agttctttaa aggtgaaatc atcttacaaa gaaattgggg gagggtcttg  5940
gcaaaggact ttcccctcct ctttcctggc ctgggaacct tatactgaca atcaatactt  6000
tatattttaa agtatataat ttatagttaa cttctagtgt aatatattag gaaacactag  6060
```

-continued

```
aatggaaagg ccattggaag acaggttgta tctttttttag accatatttc cttgtttaaa  6120
aactatcatt tgaatacttt tttggtgaag aactccatgt tttcaagtta aaggtcacct  6180
cgtaggccag gcgcagtggc tcatgcctgt aatcccagca ctctgggagg ctgaggcggg  6240
tgaatcacaa ggttaggagt ttgagaccag cctggccaat atggtgaaac cccgtcccta  6300
ctaaaaatac aaaatttagc caggcgtggt ggcatgcacc tgtagtccca cctactcggg  6360
aggctgaggc aggagaatca cttgaacctg agagacagag gttgcagtga gccgagatca  6420
cgccactgca ctccagcctg gggacagag tgagattctg tctcaaaaaa caaaaaacaa  6480
aaaagtcacc ttgtaactca tctcttttta ttgtaagttt attaaaaatg aagaggacaa  6540
caatgagaag gaacataaag ggttagctag cactgtctcc tggtgcatgg ggctgtgcag  6600
atgtcccggc cacttcttcc ttcatacttc ccttagagaa cttgctctgc tacaagcagt  6660
gggcttggac taaaagtgat taaaatacca caggcataag gagaaaagga gtatatgtag  6720
tagtaataat tactagtata aattatttc ttcacatgct atgagtaata atattaaaaa  6780
actcatttta ccattaagat tccttatgct gaagctcttc catttagaat actgtcaatg  6840
tcatttactg gtatgaacta aagtcccct tcttttccac tcactgggaa ccttagtaaa  6900
acaccagcat atcttacctc tctttctgac tggccgatgc ttccagagac tgaatgttgg  6960
gaaaacctag tagccaaaca attctaggac agaataacat ttttatattt ggttccacca  7020
tcttattaca tttagttata gttttaaaaa agaaattcaa gcccattaaa atatgtctgg  7080
tcaatgaaat gcttcctttt attgtgttgt gctattgtac tttgtttttc aaaacattgt  7140
aaaaatagta tctttggttt agtattttgg attatatatt ataatctgag gagtgttttg  7200
cttatgtaga atccagatat atttctgtta cctaggagat gttacttaca tatgtaatac  7260
tgtatcctgc acgtggaaat attcagaatt gtagatagca taactctccc tgctcctatt  7320
cttttgagcc taggtataat tttttttttt tttttagaaa aagacatatt tagctttaat  7380
ttctatttat gctaaacata tttataagta gtctgtcaat ataataccaa ctatttttat  7440
ttttacataa ttcaattatt tcatttgaca tgtctggcag actcaagaca ttaagtaaaa  7500
aattggaact atgattttc tttgtcattt tttaaaaaag aattatttta ttaacctgct  7560
ggcatataat ctggagttct tttcacaacc ttactttttc tgatttgctt tattgaatga  7620
ttgaatactc atttctttct aaaaatatgt tgtaaattct cccttggcaa gatttctccc  7680
tatgagggta gttattattt gagtctgcca agtggttacc atggggcaag gtgccatgat  7740
gtattcttgg gtgcattggt tttttgcgca ttgtaaattt aagacactta tagtaagtgg  7800
actcattcat agatgagttt cagaaccttt tacgttctcg gtagaggctt ctgtcggaca  7860
ggcagaagag tgtattcctc actttttttt ttgtcttcaa attccagtaa ggcatagcac  7920
ttttaagaaa ttagaatttt tctatcatct atgcaaatga tatttatgtt aatattaaat  7980
atcttatgtt acactgggag taatttgagg tgcaattatt tttattacta ctttgaatag  8040
aggaccatta tccttctttc ttcagaaaac taagaagtaa gtgtaacttt taaagtaagt  8100
atatatcagt gagagtaggc ttgttttaca actatttcta gccagtgagt tgtgttttca  8160
tgtctcatca aaagacaata ccacattgca tcattttaca aaatatgttg tcattttcat  8220
ttcagttgta acataggaaa atagatattt cctagatgat ttctgagttt cttactgcaa  8280
agaacagtta taaattggta tacatgtgtc tctgtaatag ggataatatt gatatatctg  8340
ttgctacata tttaagaatc attctatctt atgttgtctt gaggccaaga tttaccacgt  8400
ttgcccagtg tattgaattg gtggtagaag gtagttccat gttccatttg tagatcttta  8460
agattttatc tttgataact ttaatagaat gtggctcagt tctggtcctt caagcctgta  8520
tggtttggat tttcagtagg ggacagttga tgtggagtca atctctttgg tacacaggaa  8580
gctttataaa atttcattca cgaatctctt attttgggaa gctgttttgc atatgagaag  8640
aacactgttg aaataaggaa ctaaagcttt atatattgat caaggtgatt ctgaaagttt  8700
taatttttaa tgttgtaatg ttatgttatt gttaattgta ctttattatg tattcaatag  8760
aaaatcatga tttattaata aaagcttaaa ttctcatcta                          8800

SEQ ID NO: 29           moltype = DNA  length = 8980
FEATURE                 Location/Qualifiers
source                  1..8980
                        mol_type = genomic DNA
                        organism = Homo sapiens
SEQUENCE: 29
agacgccgtc gagatgcagg gcccaccgct cctgaccgcc gcccacctcc tctgcgtgtg  60
caccgccgcg ctggccgtgg ctcccgggcc tcggtttctg gtgacagccc cagggatcat  120
caggcccgga ggaaatgtga ctattggggt ggagcttctg gaacactgcc cttcacaggt  180
gactgtgaag gcggagctgc tcaagacagc atcaaacctc actgtctctg tcctggaagc  240
agaaggagtc tttgaaaaag gctcttttaa gacacttact cttccatcac tacctctgaa  300
cagtgcagat gagatttatg agctacgtgt aaccggacgt acccaggatg agattttatt  360
ctctaatagt acccgcttat catttgagac caagagaata tctgtcttca ttcaaacaga  420
caaggcctta tacaagccaa agcaagaagt gaagtttcgc attgttacac tcttctcaga  480
ttttaagcct tacaaaacct ctttaaacat tctcattaag gaccccaaat caaatttgat  540
ccaacagtgg ttgtcacaac aaagtgatct tggagtcatt tccaaaactt ttcagctatc  600
ttcccatcca atacttggtg actggtctat tcaagttcaa gtgaatgacc agacatacta  660
tcaatcattt caggtttcag aatatgtatt accaaaattt gaagtgactt tgcagacacc  720
attatattgt tctatgaatt ctaagcattt aaatggtacc atcacggcaa agtatacata  780
tgggaagcca gtgaaaggag acgtaacgct tacattttta cctttatcct tttggggaaa  840
gaagaaaaat attacaaaaa catttaagat aaatggatct gcaaacttct cttttaatga  900
tgaagagatg aaaaatgtaa tggattcttc aaatggactt tctgaatacc tggatctatc  960
ttcccctgga ccagtagaaa ttttaaccac agtgacagaa tcagttacag gtatttcaag  1020
aaatgtaagc actaatgtgt tcttcaagca acatgattac atcattgagt tttttgatta  1080
tactactgtc ttgaagccat ctctcaactt cacagccact gtgaaggtaa ctcgtgctga  1140
tggcaaccaa ctgactcttg aagaaagaag aaataatgta gtcataacag tgacacagag  1200
aaactatact gagtactgga gcggatctaa cagtggaaat cagaaaatgg aagctgttca  1260
gaaaataaat tatactgtcc cccaaagtgg aacttttaag attgaattcc caatcctgga  1320
ggattccagt gagctacagt tgaaggccta tttccttggt agtaaaagta gcatggcagt  1380
tcatagtctg tttaagtctc ctagtaagac atacatccaa ctaaaaacaa gagatgaaaa  1440
tataaaggtg ggatcgcctt ttgagttggt ggttagtggc aacaaacgat tgaaggagtt  1500
aagctatatg gtagtatcca ggggacagtt ggtggctgta ggaaaacaaa attcaacaat  1560
```

-continued

```
gttctcttta acaccagaaa attcttggac tccaaaagcc tgtgtaattg tgtattatat  1620
tgaagatgat ggggaaatta taagtgatgt tctaaaaatt cctgttcagc ttgtttttaa  1680
aaataagata aagctatatt ggagtaaagt gaaagctgaa ccatctgaga aagtctctct  1740
taggatctct gtgacacagc ctgactccat agttgggatt gtagctgttg acaaaagtgt  1800
gaatctgatg aatgcctcta atgatattac aatggaaaat gtggtccatg agttggaact  1860
ttataacaca ggatattatt taggcatgtt catgaattct tttgcagtct ttcaggaatg  1920
tggactctgg gtattgacag atgcaaacct cacgaaggat tatattgatg gtgtttatga  1980
caatgcagaa tatgctgaga ggtttatgga ggaaaatgaa ggacatattg tagatattca  2040
tgacttttct ttgggtagca gtccacatgt ccgaaagcat tttccagaga cttggatttg  2100
gctagacacc aacatgggtt acaggattta ccaagaattt gaagtaactg tacctgattc  2160
tatcacttct tgggtggcta ctggttttgt gatctctgag gacctgggtc ttggactaac  2220
aactactcca gtggagctcc aagccttcca accatttttc attttttttga atcttcccta  2280
ctctgttatc agaggtgaag aatttgcttt ggaaataact atattcaatt atttgaaaga  2340
tgccactgag gttaaggtaa tcattgagaa aagtgacaaa tttgatattc taatgacttc  2400
aaatgaaata aatgccacag gccaccagca gacccttctg gttcccagtg aggatggggc  2460
aactgttctt tttcccatca ggccaacaca tctgggagaa attcctatca cagtcacagc  2520
tctttcaccc actgcttctg atgctgtcac ccagatgatt ttagtaaagg ctgaaggaat  2580
agaaaaatca tattcacaat ccatcttatt agacttgact gacaataggc tacagagtac  2640
cctgaaaact ttgagtttct catttcctcc taatacagtg actggcagtg aaagagttca  2700
gatcactgca attggagatg ttcttggtcc ttccatcaat ggcttagcct cattgattcg  2760
gatgccttat ggctgtggtg aacagaacat gataaatttt gctccaaata tttacatttt  2820
ggattatctg actaaaaaga aacaactgac agataatttg aaagaaaaag ctctttcatt  2880
tatgaggcaa ggttaccaga gagaacttct ctatcagagg gaagatggct ctttcagtgc  2940
ttttgggaat tatgaccctt ctgggagcac ttggttgtca gcttttgttt taagatgttt  3000
ccttgaagcc gatccttaca tagatattga tcagaatgtg ttacacagaa catacacttg  3060
gcttaaagga catcagaaat ccaacggtga attttgggat ccaggaagag tgattcatag  3120
tgagcttcaa ggtggcaata aaagtccagt aacacttaca gcctatattg taacttctct  3180
cctgggatat agaaaagtatc agcctaacat tgatgtgcaa gagtctatcc atttttttgga  3240
gtctgaattc agtagaggaa tttcagacaa ttatactcta gcccttataa cttatgcatt  3300
gtcatcagtg gggagtccta aagcgaagga agctttgaat atgctgactt ggagagcaga  3360
acaagaaggt ggcatgcaat tctgggtgtc atcagagtcc aaactttctg actcctggca  3420
gccacgctcc ctggatattg aagttgcagc ctatgcactg ctctcacact tcttacaatt  3480
tcagacttct gagggaatcc caattatgag gtggctaagc aggcaaagaa atagcttggg  3540
tggttttgca tctactcagg ataccactgt ggctttaaag gctctgtctg aatttgcagc  3600
cctaatgaat acagaaagga caaatatcca agtgaccgtg acggggccta gctcaccaag  3660
tcctcttgct gtggtacagc caacggcagt taatatttcc gcaaatggtt ttggatttgc  3720
tatttgtcag ctcaatgttg tatataatgt gaaggcttct gggtcttcta gaagacgaag  3780
atctatccaa aatcaagaag cctttgattt agatgttgct gtaaaagaaa ataaagatga  3840
tctcaatcat gtggatttga atgtgtgtac aagcttttcg ggcccgggta ggagtggcat  3900
ggctcttatg gaagttaacc tattaagtgg ctttatggtg ccttcagaag caatttctct  3960
gagcgagaca gtgaagaaag tggaatatga tcatggaaaa ctcaacctct atttagattc  4020
tgtaaatgaa acccagtttt gtgttaatat tcctgctgtg agaaacttta aagtttcaaa  4080
tacccaagat gcttcagtgt ccatagtgga ttactatgag ccaaggagac aggcggtgag  4140
aagttacaac tctgaagtga agctgtcctc ctgtgacctt tgcagtgatg tccagggctg  4200
ccgtccttgt gaggatggag cttcaggctc ccatcatcac tcttcagtca tttttatttt  4260
ctgtttcaag cttctgtact ttatggaact ttggctgtga tttattttta aaggactctg  4320
tgtaacacta acatttccag tagtcacatg tgattgtttt gttttcgtag aagaatactg  4380
cttctatttt gaaaaaagag ttttttttct ttctatgggg ttgcagggat ggtgtacaac  4440
aggtcctagc atgtatagct gcatagattt cttcacctga tctttgtgtg gaagatcaga  4500
atgaatgcag ttgtgtgtct atattttccc ctctcaaaat cttttagaat ttttttggag  4560
gtgtttgttt tctccagaat aaaggtatta ctttagaata ggtattctcc tcattttgtg  4620
aaagaaatga acctagattc ttaagcatta ttacacatcc atgtttgctt aaagatggat  4680
ttccctggga atgggagaaa acagccagca ggaggagctt catctgttcc cttcccacct  4740
ccaacctagc cctactgccc accccacccc aacccacccc atgcccagtg gtctcagtag  4800
atacttctta actggaaatt ctttcttttc agaatctagg tggtgaattt tttttaagtg  4860
gcacggtctt tttctgcttg aaatctgatc acaccccccca gccattgccc tccctctctt  4920
tttcctctgt agagaaatgt gaggggcagt acatttactg tgcttttcac accatctcag  4980
aggttgagga gcatactgaa aattgccctg gggggtgctg ggtgtgctgt ctccttccca  5040
catcctcagc cccacaccag ctctatttca ggggtgagag tcagagagca ctgcaatatg  5100
tgcttcatgg gatttcgatt cgaagatcct agaccaggga gacactgtga gccagggata  5160
caacaaaata ctaggtaagt cactgcagac cgacctccct gcagtttggg aaagaagctg  5220
ggtttgtgga gaatcagagc atcttgacat gactgctgac ctaaagatcc ctggcattgg  5280
ccagggatcc tgtggaacct cttctagttc aggggtgtga gcattagact gccagttgtc  5340
tagtgacatc tgatgcttgc tgtgaacttt taagatcccc gaatcctgag cacctcaatc  5400
tttaattgcc ctgtattccg aagggtaata taatttatct ggatggaaat tttaaagatg  5460
aatccccctt ttttctttttc ttctctcttt tctttccttc tccctttctt ctttgccttc  5520
taaatatact gaaatgattt agatatgtgt caacaattaa tgatctttta ttcaatctaa  5580
gaaatggttt agtttttctc tttagctcta tggcatttca ctcaagtgga caggggaaaa  5640
agtaattgcc atgggctcca aagaatttgc tttatgtttt tagctattta aaaataaatc  5700
catcaaaaat atgggtatgca aatgtatctt ttaaagttaa tttttaaaaa tgctcttatt  5760
ttagtgaatt ttcagaaatt atagtggaat ggatgctcat atattgctta tggatatttt  5820
ggataccaaa gtaggaataa ctgacattca gtattttaaa gctggcaaac ctgtacatag  5880
aaaatagatc cccagacagt ggtctatgaa gagggcagtt aagtatcaaa tacttaattt  5940
tcttgccttt ttttcttaag tggggaaaag tttctagatc tcttacacct ctgacacaat  6000
ctgttctaaa acaggcactt gtaatgttgg ggcctccttg taaacgtgtt tttgcccttt  6060
actctctggg agttctttaa aggtgaaatc atcttacaaa gaaattgggg gagggtcttg  6120
gcaaaggact ttcccctcct ctttcctggc ctgggaacct tatactgaca atcaatactt  6180
tatattttaa agtatataat ttatagttaa cttctagtgt aatatattag gaaacactag  6240
aatggaaagg ccattggaag acaggttgta tctttttttag accatatttc cttgtttaaa  6300
```

-continued

```
aactatcatt tgaatacttt tttggtgaag aactccatgt tttcaagtta aaggtcacct  6360
cgtaggccag gcgcagtggc tcatgcctgt aatcccagca ctctgggagg ctgaggcggg  6420
tgaatcacaa ggttaggagt ttgagaccag cctggccaat atggtgaaac cccgtcccta  6480
ctaaaaatac aaaatttagc caggcgtggt ggcatgcacc tgtagtccca cctactcggg  6540
aggctgaggc aggagaatca cttgaacctg agagacagag gttgcagtga gccgagatca  6600
cgccactgca ctccagcctg gggacagag tgagattctg tctcaaaaaa caaaaaacaa  6660
aaaagtcacc ttgtaactca tctcttttta ttgtaagttt attaaaaatg aagaggacaa  6720
caatgagaag gaacataaag ggttagctag cactgtctcc tggtgcatgg ggctgtgcag  6780
atgtcccggc cacttcttcc ttcatacttc ccttagagaa cttgctctgc tacaagcagt  6840
gggcttggac taaaagtgat taaaatacca caggcataag gagaaaagga gtatatgtag  6900
tagtaataat tactagtata aattattttc ttcacatgct atgagtaata atattaaaaa  6960
actcatttta ccattaagat tccttatgct gaagctcttc catttagaat actgtcaatg  7020
tcatttactg gtatgaacta aagtcccccct tcttttccac tcactgggaa ccttagtaaa  7080
acaccagcat atcttacctc tctttctgac tggccgatgc ttccagagac tgaatgttgg  7140
gaaaacctag tagccaaaca attctaggac agaataacat ttttatattt ggttccacca  7200
tcttattaca tttagttata gttttaaaaa agaaattcaa gcccattaaa atatgtctgg  7260
tcaatgaaat gcttcctttt attgtgttgt gctattgtac tttgtttttc aaaacattgt  7320
aaaaatagta tctttggttt agtattttgg attatatatt ataatctgag gagtgttttg  7380
cttatgtaga atccagatat atttctgtta cctaggagat gttacttaca tatgtaatac  7440
tgtatcctgc acgtggaaat attcagaatt gtagatagca taactctccc tgctcctatt  7500
cttttgagcc taggtataat tttttttttt tttttagaaa aagacatatt tagctttaat  7560
ttctatttat gctaaacata tttataagta gtctgtcaat ataataccaa ctatttttat  7620
ttttacataa ttcaattatt tcatttgaca tgtctggcag actcaagaca ttaagtaaaa  7680
aattggaact atgattttc tttgtcattt tttaaaaaag aattatttta ttaacctgct  7740
ggcatataat ctggagttct tttcacaacc ttacttttc tgatttgctt tattgaatga  7800
ttgaatactc atttctttct aaaaatatgt tgtaaattct cccttggcaa gatttctccc  7860
tatgagggta gttattattt gagtctgcca agtggttacc atggggcaag gtgccatgat  7920
gtattcttgg gtgcattggt tttttgcgca ttgtaaattt aagacactta tagtaagtgg  7980
actcattcat agatgagttt cagaaccttt tacgttctcg gtagaggctt ctgtcggaca  8040
ggcagaagag tgtattcctc actttttttt ttgtcttcaa attccagtaa ggcatagcac  8100
ttttaagaaa ttagaatttt tctatcatct atgcaaatga tatttatgtt aatattaaat  8160
atcttatgtt acactgggag taatttgagg tgcaattatt tttattacta ctttgaatag  8220
aggaccatta tccttctttc ttcagaaaac taagaagtaa gtgtaacttt taaagtaagt  8280
atatatcagt gagagtaggc ttgttttaca actatttcta gccagtgagt tgtgtttca  8340
tgtctcatca aaagacaata ccacattgca tcattttaca aaatatgttg tcattttcat  8400
ttcagttgta acataggaaa atagatattt cctagatgat ttctgagttt cttactgcaa  8460
agaacagtta taaattggta tacatgtgtc tctgtaatag ggataatatt gatatatctg  8520
ttgctacata tttaagaatc attctatctt atgttgtctt gaggccaaga tttaccacgt  8580
ttgcccagtg tattgaattg gtggtagaag gtagttccat gttccatttg tagatcttta  8640
agattttatc tttgataact ttaatagaat gtggctcagt tctggtcctt caagcctgta  8700
tggtttggat tttcagtagg ggacagttga tgtggagtca atctctttgg tacacaggaa  8760
gctttataaa atttcattca cgaatctctt attttgggaa gctgttttgc atatgagaag  8820
aacactgttg aaataaggaa ctaaagcttt atatattgat caaggtgatt ctgaaagttt  8880
taatttttaa tgttgtaatg ttatgttatt gttaattgta ctttattatg tattcaatag  8940
aaaatcatga tttattaata aaagcttaaa ttctcatcta                         8980

SEQ ID NO: 30          moltype = AA  length = 1428
FEATURE                Location/Qualifiers
source                 1..1428
                       mol_type = protein
                       organism = Homo sapiens
SEQUENCE: 30
MQGPPLLTAA HLLCVCTAAL AVAPGPRFLV TAPGIIRPGG NVTIGVELLE HCPSQVTVKA  60
ELLKTASNLT VSVLEAEGVF EKGSFKTLTL PSLPLNSADE IYELRVTGRT QDEILFSNST  120
RLSFETKRIS VFIQTDKALY KPKQEVKFRI VTLFSDFKPY KTSLNILIKD PKSNLIQQWL  180
SQQSDLGVIS KTFQLSSHPI LGDWSIQVQV NDQTYYQSFQ VSEYVLPKFE VTLQTPLYCS  240
MNSKHLNGTI TAKYTYGKPV KGDVTLTFLP LSFWGKKKNI TKTFKINGSA NFSFNDEEMK  300
NVMDSSNGLS EYLDLSSPGP VEILTTVTES VTGISRNVST NVFFKQHDYI IEFFDYTTVL  360
KPSLNFTATV KVTRADGNQL TLEERRNNVV ITVTQRNYTE YWSGSNSGNQ KMEAVQKINY  420
TVPQSGTFKI EFPILEDSSE LQLKAYFLGS KSSMAVHSLF KSPSKTYIQL KTRDENIKVG  480
SPFELVVSGN KRLKELSYMV VSRGQLVAVG KQNSTMFSLT PENSWTPKAC VIVYYIEDDG  540
EIISDVLKIP VQLVFKNKIK LYWSKVKAEP SEKVSLRISV TQPDSIVGIV AVDKSVNLMN  600
ASNDITMENV VHELELYNTG YYLGMFMNSF AVFQECGLWV LTDANLTKDY IDGVYDNAEY  660
AERFMEENEG HIVDIHDFSL GSSPHVRKHF PETWIWLDTN MGYRIYQEFE VTVPDSITSW  720
VATGFVISED LGLGLTTTPV ELQAFQPFFI FLNLPYSVIR GEEFALEITI FNYLKDATEV  780
KVIIEKSDKF DILMTSNEIN ATGHQQTLLV PSEDGATVLF PIRPTHLGEI PITVTALSPT  840
ASDAVTQMIL VKAEGIEKSY SQSILLDLTD NRLQSTLKTL SFSFPPNTVT GSERVQITAI  900
GDVLGPSING LASLIRMPYG CGEQNMINFA PNIYILDYLT KKKQLTDNLK EKALSFMRQG  960
YQRELLYQRE DGSFSAFGNY DPSGSTWLSA FVLRCFLEAD PYIDIDQNVL HRTYTWLKGH  1020
QKSNGEFWDP GRVIHSELQG GNKSPVTLTA YIVTSLLGYR KYQPNIDVQE SIHFLESEFS  1080
RGISDNYTLA LITYALSSVG SPKAKEALNM LTWRAEQEGG MQFWVSSESK LSDSWQPRSL  1140
DIEVAAYALL SHFLQFQTSE GIPIMRWLSR QRNSLGGFAS TQDTTVALKA LSEFAALMNT  1200
ERTNIQVTVT GPSSPSPLAV VQPTAVNISA NGFGFAICQL NVVYNVKASG SSRRRRSIQN  1260
QEAFDLDVAV KENKDDLNHV DLNVCTSFSG PGRSGMALME VNLLSGFMVP SEAISLSETV  1320
KKVEYDHGKL NLYLDSVNET QFCVNIPAVR NFKVSNTQDA SVSIVDYYEP RRQAVRSYNS  1380
EVKLSSCDLC SDVQGCRPCE DGASGSHHHS SVIFIFCFKL LYFMELWL                1428

SEQ ID NO: 31          moltype = AA  length = 1368
FEATURE                Location/Qualifiers
```

-continued

```
source                  1..1368
                        mol_type = protein
                        organism = Homo sapiens
SEQUENCE: 31
MQGPPLLTAA HLLCVCTAAL AVAPGPRFLV TAPGIIRPGG NVTIGVELLE HCPSQVTVKA  60
ELLKTASNLT VSVLEAEGVF EKGSFKTLTL PSDPKSNLIQ QWLSQQSDLG VISKTFQLSS  120
HPILGDWSIQ VQVNDQTYYQ SFQVSEYVLP KFEVTLQTPL YCSMNSKHLN GTITAKYTYG  180
KPVKGDVTLT FLPLSFWGKK KNITKTFKIN GSANFSFNDE EMKNVMDSSN GLSEYLDLSS  240
PGPVEILTTV TESVTGISRN VSTNVFFKQH DYIIEFFDYT TVLKPSLNFT ATVKVTRADG  300
NQLTLEERRN NVVITVTQRN YTEYWSGSNS GNQKMEAVQK INYTVPQSGT FKIEFPILED  360
SSELQLKAYF LGSKSSMAVH SLFKSPSKTY IQLKTRDENI KVGSPFELVV SGNKRLKELS  420
YMVVSRGQLV AVGKQNSTMF SLTPENSWTP KACVIVYYIE DDGEIISDVL KIPVQLVFKN  480
KIKLYWSKVK AEPSEKVSLR ISVTQPDSIV GIVAVDKSVN LMNASNDITM ENVVHELELY  540
NTGYYLGMFM NSFAVFQECG LWVLTDANLT KDYIDGVYDN AEYAERFMEE NEGHIVDIHD  600
FSLGSSPHVR KHFPETWIWL DTNMGYRIYQ EFEVTVPDSI TSWVATGFVI SEDLGLGLTT  660
TPVELQAFQP FFIFLNLPYS VIRGEEFALE ITIFNYLKDA TEVKVIIEKS DKFDILMTSN  720
EINATGHQQT LLVPSEDGAT VLFPIRPTHL GEIPITVTAL SPTASDAVTQ MILVKAEGIE  780
KSYSQSILLD LTDNRLQSTL KTLSFSFPPN TVTGSERVQI TAIGDVLGPS INGLASLIRM  840
PYGCGEQNMI NFAPNIYILD YLTKKKQLTD NLKEKALSFM RQGYQRELLY QREDGSFSAF  900
GNYDPSGSTW LSAFVLRCFL EADPYIDIDQ NVLHRTYTWL KGHQKSNGEF WDPGRVIHSE  960
LQGGNKSPVT LTAYIVTSLL GYRKYQPNID VQESIHFLES EFSRGISDNY TLALITYALS  1020
SVGSPKAKEA LNMLTWRAEQ EGGMQFWVSS ESKLSDSWQP RSLDIEVAAY ALLSHFLQFQ  1080
TSEGIPIMRW LSRQRNSLGG FASTQDTTVA LKALSEFAAL MNTERTNIQV TVTGPSSPSP  1140
VKFLIDTHNR LLLQTAELAV VQPTAVNISA NGFGFAICQL NVVYNVKASG SSRRRRSIQN  1200
QEAFDLDVAV KENKDDLNHV DLNVCTSFSG PGRSGMALME VNLLSGFMVP SEAISLSETV  1260
KKVEYDHGKL NLYLDSVNET QFCVNIPAVR NFKVSNTQDA SVSIVDYYEP RRQAVRSYNS  1320
EVKLSSCDLC SDVQGCRPCE DGASGSHHHS SVIFIFCFKL LYFMELWL          1368

SEQ ID NO: 32           moltype = AA  length = 1445
FEATURE                 Location/Qualifiers
source                  1..1445
                        mol_type = protein
                        organism = Homo sapiens
SEQUENCE: 32
MQGPPLLTAA HLLCVCTAAL AVAPGPRFLV TAPGIIRPGG NVTIGVELLE HCPSQVTVKA  60
ELLKTASNLT VSVLEAEGVF EKGSFKTLTL PSLPLNSADE IYELRVTGRT QDEILFSNST  120
RLSFETKRIS VFIQTDKALY KPKQEVKFRI VTLFSDFKPY KTSLNILIKD PKSNLIQQWL  180
SQQSDLGVIS KTFQLSSHPI LGDWSIQVQV NDQTYYQSFQ VSEYVLPKFE VTLQTPLYCS  240
MNSKHLNGTI TAKYTYGKPV KGDVTLTFLP LSFWGKKKNI TKTFKINGSA NFSFNDEEMK  300
NVMDSSNGLS EYLDLSSPGP VEILTTVTES VTGISRNVST NVFFKQHDYI IEFFDYTTVL  360
KPSLNFTATV KVTRADGNQL TLEERRNNVV ITVTQRNYTE YWSGSNSGNQ KMEAVQKINY  420
TVPQSGTFKI EFPILEDSSE LQLKAYFLGS KSSMAVHSLF KSPSKTYIQL KTRDENIKVG  480
SPFELVVSGN KRLKELSYMV VSRGQLVAVG KQNSTMFSLT PENSWTPKAC VIVYYIEDDG  540
EIISDVLKIP VQLVFKNKIK LYWSKVKAEP SEKVSLRISV TQPDSIVGIV AVDKSVNLMN  600
ASNDITMENV VHELELYNTG YYLGMFMNSF AVFQECGLWV LTDANLTKDY IDGVYDNAEY  660
AERFMEENEG HIVDIHDFSL GSSPHVRKHF PETWIWLDTN MGYRIYQEFE VTVPDSITSW  720
VATGFVISED LGLGLTTTPV ELQAFQPFFI FLNLPYSVIR GEEFALEITI FNYLKDATEV  780
KVIIEKSDKF DILMTSNEIN ATGHQQTLLV PSEDGATVLF PIRPTHLGEI PITVTALSPT  840
ASDAVTQMIL VKAEGIEKSY SQSILLDLTD NRLQSTLKTL SFSFPPNTVT GSERVQITAI  900
GDVLGPSING LASLIRMPYG CGEQNMINFA PNIYILDYLT KKKQLTDNLK EKALSFMRQG  960
YQRELLYQRE DGSFSAFGNY DPSGSTWLSA FVLRCFLEAD PYIDIDQNVL HRTYTWLKGH  1020
QKSNGEFWDP GRVIHSELQG GNKSPVTLTA YIVTSLLGYR KYQPNIDVQE SIHFLESEFS  1080
RGISDNYTLA LITYALSSVG SPKAKEALNM LTWRAEQEGG MQFWVSSESK LSDSWQPRSL  1140
DIEVAAYALL SHFLQFQTSE GIPIMRWLSR QRNSLGGFAS TQDTTVALKA LSEFAALMNT  1200
ERTNIQVTVT GPSSPSPVKF LIDTHNRLLL QTAELAVVQP TAVNISANGF GFAICQLNVV  1260
YNVKASGSSR RRRSIQNQEA FDLDVAVKEN KDDLNHVDLN VCTSFSGPGR SGMALMEVNL  1320
LSGFMVPSEA ISLSETVKKV EYDHGKLNLY LDSVNETQFC VNIPAVRNFK VSNTQDASVS  1380
IVDYYEPRRQ AVRSYNSEVK LSSCDLCSDV QGCRPCEDGA SGSHHHSSVI FIFCFKLLYF  1440
MELWL                                                            1445

SEQ ID NO: 33           moltype = AA  length = 665
FEATURE                 Location/Qualifiers
source                  1..665
                        mol_type = protein
                        organism = Homo sapiens
SEQUENCE: 33
MQGPPLLTAA HLLCVCTAAL AVAPGPRFLV TAPGIIRPGG NVTIGVELLE HCPSQVTVKA  60
ELLKTASNLT VSVLEAEGVF EKGSFKTLTL PSLPLNSADE IYELRVTGRT QDEILFSNST  120
RLSFETKRIS VFIQTDKALY KPKQEVKFRI VTLFSDFKPY KTSLNILIKD PKSNLIQQWL  180
SQQSDLGVIS KTFQLSSHPI LGDWSIQVQV NDQTYYQSFQ VSEYVLPKFE VTLQTPLYCS  240
MNSKHLNGTI TAKYTYGKPV KGDVTLTFLP LSFWGKKKNI TKTFKINGSA NFSFNDEEMK  300
NVMDSSNGLS EYLDLSSPGP VEILTTVTES VTGISRNVST NVFFKQHDYI IEFFDYTTVL  360
KPSLNFTATV KVTRADGNQL TLEERRNNVV ITVTQRNYTE YWSGSNSGNQ KMEAVQKINY  420
TVPQSGTFKI EFPILEDSSE LQLKAYFLGS KSSMAVHSLF KSPSKTYIQL KTRDENIKVG  480
SPFELVVSGN KRLKELSYMV VSRGQLVAVG KQNSTMFSLT PENSWTPKAC VIVYYIEDDG  540
EIISDVLKIP VQLVFKNKIK LYWSKVKAEP SEKVSLRISV TQPDSIVGIV AVDKSVNLMN  600
ASNDITMENV VHELELYNTG YYLGMFMNSF AVFQECGLWV LTDANLTKDY IDGVYDNLFG  660
TQEAL                                                            665
```

-continued

```
SEQ ID NO: 34          moltype = AA  length = 1374
FEATURE                Location/Qualifiers
source                 1..1374
                       mol_type = protein
                       organism = Homo sapiens
SEQUENCE: 34
EADAVEMQGP PLLTAAHLLC VCTAALAVAP GPRFLVTAPG IIRPGGNVTI GVELLEHCPS  60
QVTVKAELLK TASNLTVSVL EAEGVFEKGS FKTLTLPSDP KSNLIQQWLS QQSDLGVISK  120
TFQLSSHPIL GDWSIQVQVN DQTYYQSFQV SEYVLPKFEV TLQTPLYCSM NSKHLNGTIT  180
AKYTYGKPVK GDVTLTFLPL SFWGKKKNIT KTFKINGSAN FSFNDEEMKN VMDSSNGLSE  240
YLDLSSPGPV EILTTVTESV TGISRNVSTN VFFKQHDYII EFFDYTTVLK PSLNFTATVK  300
VTRADGNQLT LEERRNNVVI TVTQRNYTEY WSGSNSGNQK MEAVQKINYT VPQSGTFKIE  360
FPILEDSSEL QLKAYFLGSK SSMAVHSLFK SPSKTYIQLK TRDENIKVGS PFELVVSGNK  420
RLKELSYMVV SRGQLVAVGK QNSTMFSLTP ENSWTPKACV IVYYIEDDGE IISDVLKIPV  480
QLVFKNKIKL YWSKVKAEPS EKVSLRISVT QPDSIVGIVA VDKSVNLMNA SNDITMENVV  540
HELELYNTGY YLGMFMNSFA VFQECGLWVL TDANLTKDYI DGVYDNAEYA ERFMEENEGH  600
IVDIHDFSLG SSPHVRKHFP ETWIWLDTNM GYRIYQEFEV TVPDSITSWV ATGFVISEDL  660
GLGLTTTPVE LQAFQPFFIF LNLPYSVIRG EEFALEITIF NYLKDATEVK VIIEKSDKFD  720
ILMTSNEINA TGHQQTLLVP SEDGATVLFP IRPTHLGEIP ITVTALSPTA SDAVTQMILV  780
KAEGIEKSYS QSILLDLTDN RLQSTLKTLS FSFPPNTVTG SERVQITAIG DVLGPSINGL  840
ASLIRMPYGC GEQNMINFAP NIYILDYLTK KKQLTDNLKE KALSFMRQGY QRELLYQRED  900
GSFSAFGNYD PSGSTWLSAF VLRCFLEADP YIDIDQNVLH RTYTWLKGHQ KSNGEFWDPG  960
RVIHSELQGG NKSPVTLTAY IVTSLLGYRK YQPNIDVQES IHFLESEFSR GISDNYTLAL  1020
ITYALSSVGS PKAKEALNML TWRAEQEGGM QFWVSSESKL SDSWQPRSLD IEVAAYALLS  1080
HFLQFQTSEG IPIMRWLSRQ RNSLGGFAST QDTTVALKAL SEFAALMNTE RTNIQVTVTG  1140
PSSPSPVKFL IDTHNRLLLQ TAELAVVQPM AVNISANGFG FAICQLNVVY NVKASGSSRR  1200
RRSIQNQEAF DLDVAVKENK DDLNHVDLNV CTSFSGPGRS GMALMEVNLL SGFMVPSEAI  1260
SLSETVKKVE YDHGKLNLYL DSVNETQFCV NIPAVRNFKV SNTQDASVSI VDYYEPRRQA  1320
VRSYNSEVKL SSCDLCSDVQ GCRPCEDGAS GSHHHSSVIF IFCFKLLYFM ELWL        1374

SEQ ID NO: 35          moltype = AA  length = 854
FEATURE                Location/Qualifiers
source                 1..854
                       mol_type = protein
                       organism = Homo sapiens
SEQUENCE: 35
VDKSVNLMNA SNDITMENVV HELELYNTGY YLGMFMNSFA VFQECGLWVL TDANLTKDYI  60
DGVYDNAEYA ERFMEENEGH IVDIHDFSLG SSPHVRKHFP ETWIWLDTNM GSRIYQEFEV  120
TVPDSITSWV ATGFVISEDL GLGLTTTPVE LQAFQPFFIF LNLPYSVIRG EEFALEITIF  180
NYLKDATEVK VIIEKSDKFD ILMTSSEINA TGHQQTLLVP SEDGATVLFP IRPTHLGEIP  240
ITVTALSPTA SDAITQMILV KAEGIEKSYS QSILLDLTDN RLQSTLKTLS FSFPPNTVTG  300
SERVQITAIG DVLGPSINGL ASLIRMPYGC GEQNMINFAP NIYILDYLTK KKQLTDNLKE  360
KALSFMRQGY QRELLYQRED GSFSAFGNYD PSGSTWLSAF VLRCFLEADP YIDIDQNVLH  420
RTYTWLKGHQ KSNGEFWDPG RVIHSELQGG NKSPVTLTAY IVTSLLGYRK YQPNIDVQES  480
IHFLESEFSR GISDNYTLAL ITYALSSVGS PKAKEALNML TWRAEQEGGM QFWVSSESKL  540
SDSWQPRSLD IEVAAYALLS HFLQFQTSEG IPIMRWLSRQ RNSLGGFAST QDTTVALKAL  600
SEFAALMNTE RTNIQVTVTG PSSPSPVKFL IDTHNRLLLQ TAELAVVQPT AVNISANGFG  660
FAICQLNVVY NVKASGSSRR RRSIQNQEAF DLDVAVKENK DDLNHVDLNV CTSFSGPGRS  720
GMALMEVNLL SGFMVPSEAI SLSETVKKVE YDHGKLNLYL DSVNETQFCV NIPAVRNFKV  780
SNTQDASVSI VDYYEPRRQA VRSYNSEVKL SSCDLCSDVQ GCRPCEDGAS GSHHHSSVIF  840
IFCFKLLYFM ELWL                                                    854

SEQ ID NO: 36          moltype = AA  length = 847
FEATURE                Location/Qualifiers
source                 1..847
                       mol_type = protein
                       organism = Homo sapiens
SEQUENCE: 36
MNASNDITME NVVHELELYN TGYYLGMFMN SFAVFQECGL WVLTDANLTK DYIDGVYDNA  60
EYAERFMEEN EGHIVDIHDF SLGSSPHVRK HFPETWIWLD TNMGSRIYQE FEVTVPDSIT  120
SWVATGFVIS EDLGLGLTTT PVELQAFQPF FIFLNLPYSV IRGEEFALEI TIFNYLKDAT  180
EVKVIIEKSD KFDILMTSSE INATGHQQTL LVPSEDGATV LFPIRPTHLG EIPITVTALS  240
PTASDAITQM ILVKAEGIEK SYSQSILLDL TDNRLQSTLK TLSFSFPPNT VTGSERVQIT  300
AIGDVLGPSI NGLASLIRMP YGCGEQNMIN FAPNIYILDY LTKKKQLTDN LKEKALSFMR  360
QGYQRELLYQ REDGSFSAFG NYDPSGSTWL SAFVLRCFLE ADPYIDIDQN VLHRTYTWLK  420
GHQKSNGEFW DPGRVIHSEL QGGNKSPVTL TAYIVTSLLG YRKYQPNIDV QESIHFLESE  480
FSRGISDNYT LALITYALSS VGSPKAKEAL NMLTWRAEQE GGMQFWVSSE SKLSDSWQPR  540
SLDIEVAAYA LLSHFLQFQT SEGIPIMRWL SRQRNSLGGF ASTQDTTVAL KALSEFAALM  600
NTERTNIQVT VTGPSSPSPV KFLIDTHNRL LLQTAELAVV QPTAVNISAN GFGFAICQLN  660
VVYNVKASGS SRRRRSIQNQ EAFDLDVAVK ENKDDLNHVD LNVCTSFSGP GRSGMALMEV  720
NLLSGFMVPS EAISLSETVK KVEYDHGKLN LYLDSVNETQ FCVNIPAVRN FKVSNTQDAS  780
VSIVDYYEPR RQAVRSYNSE VKLSSCDLCS DVQGCRPCEN GASGSHHHSS VIFIFCFKLL  840
YFMELWL                                                            847

SEQ ID NO: 37          moltype = DNA  length = 21
FEATURE                Location/Qualifiers
misc_feature           1..21
                       note = Synthetic sequence; gRNA Recognition Sequence
source                 1..21
```

```
                        mol_type = other DNA
                        organism = synthetic construct
SEQUENCE: 37
gcctccaagt cctgtctcaa t                                              21

SEQ ID NO: 38           moltype = DNA  length = 21
FEATURE                 Location/Qualifiers
misc_feature            1..21
                        note = Synthetic sequence; gRNA Recognition Sequence
source                  1..21
                        mol_type = other DNA
                        organism = synthetic construct
SEQUENCE: 38
ggtaccatca cggcaaagta t                                              21

SEQ ID NO: 39           moltype = DNA  length = 21
FEATURE                 Location/Qualifiers
misc_feature            1..21
                        note = Synthetic sequence; gRNA Recognition Sequence
source                  1..21
                        mol_type = other DNA
                        organism = synthetic construct
SEQUENCE: 39
gtaccatcac ggcaaagtat a                                              21

SEQ ID NO: 40           moltype = DNA  length = 21
FEATURE                 Location/Qualifiers
misc_feature            1..21
                        note = Synthetic sequence; gRNA Recognition Sequence
source                  1..21
                        mol_type = other DNA
                        organism = synthetic construct
SEQUENCE: 40
gctacagttg aaggcctatt t                                              21

SEQ ID NO: 41           moltype = DNA  length = 21
FEATURE                 Location/Qualifiers
misc_feature            1..21
                        note = Synthetic sequence; gRNA Recognition Sequence
source                  1..21
                        mol_type = other DNA
                        organism = synthetic construct
SEQUENCE: 41
gattgaagga gttaagctat a                                              21

SEQ ID NO: 42           moltype = DNA  length = 21
FEATURE                 Location/Qualifiers
misc_feature            1..21
                        note = Synthetic sequence; gRNA Recognition Sequence
source                  1..21
                        mol_type = other DNA
                        organism = synthetic construct
SEQUENCE: 42
ggtcttggac taacaactac t                                              21

SEQ ID NO: 43           moltype = DNA  length = 21
FEATURE                 Location/Qualifiers
misc_feature            1..21
                        note = Synthetic sequence; gRNA Recognition Sequence
source                  1..21
                        mol_type = other DNA
                        organism = synthetic construct
SEQUENCE: 43
gaaagatgcc actgaggtta a                                              21

SEQ ID NO: 44           moltype = DNA  length = 21
FEATURE                 Location/Qualifiers
misc_feature            1..21
                        note = Synthetic sequence; gRNA Recognition Sequence
source                  1..21
                        mol_type = other DNA
                        organism = synthetic construct
SEQUENCE: 44
gcatctactc aggataccac t                                              21

SEQ ID NO: 45           moltype = DNA  length = 21
FEATURE                 Location/Qualifiers
misc_feature            1..21
                        note = Synthetic sequence; gRNA Recognition Sequence
```

```
source                1..21
                      mol_type = other DNA
                      organism = synthetic construct
SEQUENCE: 45
ggtacagcca acggcagtta a                                          21

SEQ ID NO: 46         moltype = DNA  length = 21
FEATURE               Location/Qualifiers
misc_feature          1..21
                      note = Synthetic sequence; gRNA Recognition Sequence
source                1..21
                      mol_type = other DNA
                      organism = synthetic construct
SEQUENCE: 46
ggctcttatg gaagttaacc t                                          21

SEQ ID NO: 47         moltype = DNA  length = 21
FEATURE               Location/Qualifiers
misc_feature          1..21
                      note = Synthetic sequence; gRNA Recognition Sequence
source                1..21
                      mol_type = other DNA
                      organism = synthetic construct
SEQUENCE: 47
gacaggcggt gagaagttac a                                          21

SEQ ID NO: 48         moltype = DNA  length = 21
FEATURE               Location/Qualifiers
misc_feature          1..21
                      note = Synthetic sequence; gRNA Recognition Sequence
source                1..21
                      mol_type = other DNA
                      organism = synthetic construct
SEQUENCE: 48
gcccagtggt ctcagtagat a                                          21

SEQ ID NO: 49         moltype = DNA  length = 19
FEATURE               Location/Qualifiers
misc_feature          1..19
                      note = Synthetic sequence; gRNA Recognition Sequence
source                1..19
                      mol_type = other DNA
                      organism = synthetic construct
SEQUENCE: 49
gccgatcctt acatagata                                             19

SEQ ID NO: 50         moltype = DNA  length = 19
FEATURE               Location/Qualifiers
misc_feature          1..19
                      note = Synthetic sequence; gRNA Recognition Sequence
source                1..19
                      mol_type = other DNA
                      organism = synthetic construct
SEQUENCE: 50
cctagattct taagcatta                                             19

SEQ ID NO: 51         moltype = DNA  length = 19
FEATURE               Location/Qualifiers
misc_feature          1..19
                      note = Synthetic sequence; gRNA Recognition Sequence
source                1..19
                      mol_type = other DNA
                      organism = synthetic construct
SEQUENCE: 51
aagcctgtgt aattgtgta                                             19

SEQ ID NO: 52         moltype = DNA  length = 19
FEATURE               Location/Qualifiers
misc_feature          1..19
                      note = Synthetic sequence; gRNA Recognition Sequence
source                1..19
                      mol_type = other DNA
                      organism = synthetic construct
SEQUENCE: 52
agagttcaga tcactgcaa                                             19

SEQ ID NO: 53         moltype = DNA  length = 19
FEATURE               Location/Qualifiers
misc_feature          1..19
```

-continued

```
                      note = Synthetic sequence; gRNA Recognition Sequence
source                1..19
                      mol_type = other DNA
                      organism = synthetic construct
SEQUENCE: 53
aggagacgta acgcttaca                                             19

SEQ ID NO: 54         moltype = DNA  length = 19
FEATURE               Location/Qualifiers
misc_feature          1..19
                      note = Synthetic sequence; gRNA Recognition Sequence
source                1..19
                      mol_type = other DNA
                      organism = synthetic construct
SEQUENCE: 54
tgtaagcact aatgtgttc                                             19

SEQ ID NO: 55         moltype = DNA  length = 19
FEATURE               Location/Qualifiers
misc_feature          1..19
                      note = Synthetic sequence; gRNA Recognition Sequence
source                1..19
                      mol_type = other DNA
                      organism = synthetic construct
SEQUENCE: 55
tgcagaatat gctgagagg                                             19

SEQ ID NO: 56         moltype = DNA  length = 19
FEATURE               Location/Qualifiers
misc_feature          1..19
                      note = Synthetic sequence; gRNA Recognition Sequence
source                1..19
                      mol_type = other DNA
                      organism = synthetic construct
SEQUENCE: 56
actaagaagt aagtgtaac                                             19

SEQ ID NO: 57         moltype = DNA  length = 19
FEATURE               Location/Qualifiers
misc_feature          1..19
                      note = Synthetic sequence; gRNA Recognition Sequence
source                1..19
                      mol_type = other DNA
                      organism = synthetic construct
SEQUENCE: 57
tgcagaatat gctgagagg                                             19

SEQ ID NO: 58         moltype = DNA  length = 19
FEATURE               Location/Qualifiers
misc_feature          1..19
                      note = Synthetic sequence; gRNA Recognition Sequence
source                1..19
                      mol_type = other DNA
                      organism = synthetic construct
SEQUENCE: 58
ttggagatgt tcttggtcc                                             19
```

METHODS OF TREATING DECREASED BONE MINERAL DENSITY WITH CLUSTER OF DIFFERENTIATION 109 (CD109) INHIBITORS

REFERENCE TO SEQUENCE LISTING

This application includes a Sequence Listing filed electronically as an XML file named 381203985SEQ, created on Nov. 13, 2023, with a size of 363,730 bytes. The Sequence Listing is incorporated herein by reference.

FIELD

The present disclosure relates generally to the treatment of subjects having decreased bone mineral density with Cluster of Differentiation 109 (CD109) inhibitors, and methods of identifying subjects having an increased risk of developing decreased bone mineral density.

BACKGROUND

Degenerative conditions of the bone can make individuals susceptible to bone fractures, bone pain, and other complications. Two significant degenerative conditions of the bone are osteopenia and osteoporosis. Decreased bone mineral density (osteopenia) is a condition of the bone that is less severe than osteoporosis and is characterized by a reduction in bone mass due to the loss of bone at a rate greater than new bone growth.

Osteopenia manifests in bone having a mineral density lower than normal peak bone mineral density, but not as low as found in osteoporosis. Osteopenia can arise from a decrease in muscle activity, which may occur as the result of a bone fracture, bed rest, fracture immobilization, joint reconstruction, arthritis, and the like. Osteoporosis is a disease characterized by a gradual bone weakening due to demineralization of the bone and/or problems with its architecture. Osteoporosis manifests in bones by making them more susceptible to breaking. Hormone deficiencies related to menopause in women, and hormone deficiencies due to aging in both sexes contribute to degenerative conditions of the bone. In addition, insufficient dietary uptake of minerals essential to bone growth and maintenance are potential causes of bone loss. Genetic influences on osteoporosis have also been reported (Morris et al., Nature Genet., 2019, 51, 258-266).

The effects of osteopenia can be slowed, stopped, and even reversed by reproducing some of the effects of muscle use on the bone. This typically involves some application or simulation of the effects of mechanical stress on the bone. Compounds for the treatment of osteopenia or osteoporosis include pharmaceutical preparations that induce bone growth or retard bone demineralization, or mineral complexes that supplement the diet in an effort to replenish lost bone minerals. Low levels of estrogen in women, and low levels of androgen in men are the primary hormonal deficiencies that cause osteoporosis in the respective sexes. Other hormones such as the thyroid hormones, progesterone, and testosterone contribute to bone health. As such, the aforementioned hormonal compounds have been developed synthetically, or extracted from non-mammalian sources, and compounded into therapies for treating osteoporosis. Mineral supplement preparations containing iodine, zinc, manganese, boron, strontium, vitamin D3, calcium, magnesium, vitamin K, phosphorous, and copper have also been used to supplement insufficient dietary uptake of such minerals. However, long-term hormonal therapies have undesirable side effects such as increased cancer risk. In addition, it is uncertain if many of the mineral and hormonal supplements proposed can actually reduce the risk of fracture. Moreover, therapies using many synthetic or non-mammalian hormones have additional undesirable side effects, such as an increased risk of cardiovascular disorders, neurological disorders, or the exacerbation of pre-existing conditions.

Cluster Of Differentiation 109 (CD109) is a member of alpha2-macroglobulin/complement (AMCOM) family of thioester containing proteins. This glycosyl phosphatidylinositol (GPI)-linked glycoprotein localizes to the surface of platelets, activated T-cells, and endothelial cells. In addition, CD109 is expressed in hematopoietic cell lineages and some epithelial cells. CD109 protein binds to and negatively regulates signaling by transforming growth factor beta (TGF-β) in keratinocytes, and also associates with TGF-βRI and TGF-βRII. Moreover, CR109 could function as protease inhibitors like most members of AMCOM family.

SUMMARY

The present disclosure provides methods of treating a subject having decreased bone mineral density or at risk of developing decreased bone mineral density, the methods comprising administering a CD109 inhibitor to the subject.

The present disclosure also provides methods of treating a subject having osteopenia or at risk of developing osteopenia, the methods comprising administering a CD109 inhibitor to the subject.

The present disclosure also provides methods of treating a subject having Type I osteoporosis or at risk of developing Type I osteoporosis, the methods comprising administering a CD109 inhibitor to the subject.

The present disclosure also provides methods of treating a subject having Type II osteoporosis or at risk of developing Type II osteoporosis, the methods comprising administering a CD109 to the subject.

The present disclosure also provides methods of treating a subject having secondary osteoporosis or at risk of developing secondary osteoporosis, the methods comprising administering a CD109 inhibitor to the subject.

The present disclosure also provides methods of treating a subject with a therapeutic agent that treats or inhibits decreased bone mineral density, wherein the subject has decreased bone mineral density or is at risk of developing decreased bone mineral density, the methods comprising the steps of: determining whether the subject has a CD109 missense variant nucleic acid molecule encoding a CD109 predicted loss-of-function polypeptide by: obtaining or having obtained a biological sample from the subject; and performing or having performed a sequence analysis on the biological sample to determine if the subject has a genotype comprising the CD109 missense variant nucleic acid molecule encoding a CD109 predicted loss-of-function polypeptide; and: i) administering or continuing to administer the therapeutic agent that treats or inhibits decreased bone mineral density in a standard dosage amount to a subject that is CD109 reference, and/or administering a CD109 inhibitor to the subject; ii) administering or continuing to administer the therapeutic agent that treats or inhibits decreased bone mineral density in an amount that is the same as or less than a standard dosage amount to a subject that is heterozygous for the CD109 missense variant nucleic acid molecule, and/or administering a CD109 inhibitor to the subject; or iii) administering or continuing to administer the therapeutic agent that treats or inhibits decreased bone mineral density in an amount that is the same as or less than a standard dosage amount to a subject that is homozygous for the CD109 missense variant nucleic acid molecule; wherein the presence of a genotype having the CD109 missense variant nucleic acid molecule encoding the CD109 predicted loss-of-function polypeptide indicates the subject has a decreased risk of developing decreased bone mineral density.

The present disclosure also provides methods of identifying a subject having an increased risk of developing decreased bone mineral density, the methods comprising: determining or having determined the presence or absence of a CD109 missense variant nucleic acid molecule encoding a CD109 predicted loss-of-function polypeptide in a biological sample obtained from the subject; when the subject is CD109 reference, then the subject has an increased risk of developing decreased bone mineral density; and when the subject is heterozygous or homozygous for the CD109 missense variant nucleic acid molecule encoding the CD109 predicted loss-of-function polypeptide, then the subject has a decreased risk of developing decreased bone mineral density.

The present disclosure also provides therapeutic agents that treat or inhibit decreased bone mineral density for use in the treatment of decreased bone mineral density in a subject having: a CD109 missense variant genomic nucleic acid molecule encoding a CD109 predicted loss-of-function polypeptide; a CD109 missense variant mRNA molecule encoding a CD109 predicted loss-of-function polypeptide; or a CD109 missense variant cDNA molecule encoding a CD109 predicted loss-of-function polypeptide.

The present disclosure also provides CD109 inhibitors for use in the treatment of decreased bone mineral density in a subject that: a) is reference for a CD109 genomic nucleic acid molecule, a CD109 mRNA molecule, or a CD109 cDNA molecule; or b) is heterozygous for: i) a CD109 missense variant genomic nucleic acid molecule encoding a CD109 predicted loss-of-function polypeptide; ii) a CD109 missense variant mRNA molecule encoding a CD109 predicted loss-of-function polypeptide; or iii) a CD109 missense variant cDNA molecule encoding a CD109 predicted loss-of-function polypeptide.

DESCRIPTION

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, the term "about" means the numerical value can vary by ±10% and remain within the scope of the disclosed embodiments.

As used herein, the term "comprising" may be replaced with "consisting" or "consisting essentially of" in particular embodiments as desired.

As used herein, the term "isolated", in regard to a nucleic acid molecule or a polypeptide, means that the nucleic acid molecule or polypeptide is in a condition other than its native environment, such as apart from blood and/or animal tissue. In some embodiments, an isolated nucleic acid molecule or polypeptide is substantially free of other nucleic acid molecules or other polypeptides, particularly other nucleic acid molecules or polypeptides of animal origin. In some embodiments, the nucleic acid molecule or polypeptide can be in a highly purified form, i.e., greater than 95% pure or greater than 99% pure. When used in this context, the term "isolated" does not exclude the presence of the same nucleic acid molecule or polypeptide in alternative physical forms, such as dimers or Alternately phosphorylated or derivatized forms.

As used herein, the terms "nucleic acid", "nucleic acid molecule", "nucleic acid sequence", "polynucleotide", or "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates. In some embodiments, the subject is a human. In some embodiments, the human is a patient under the care of a physician.

It has been observed in accordance with the present disclosure that CD109 missense variant nucleic acid molecules encoding a CD109 predicted loss-of-function polypeptide (whether these variations are homozygous or heterozygous in a particular subject) associate with a decreased risk of developing decreased bone mineral density. The details or directionality of CD109's involvement in bone mineral density is unclear. The data presented herein is the first to show that rare, nonsynonymous/loss-of-unction variants in CD109 are associated with a decreased risk of developing decreased bone mineral density. Therefore, subjects that are CD109 reference or heterozygous for CD109 missense variant nucleic acid molecules encoding CD109 predicted loss-of-function polypeptides may be treated with a CD109 inhibitor such that decreased bone mineral density is inhibited, the symptoms thereof are reduced, and/or development of symptoms is repressed. It is also believed that such subjects having decreased bone mineral density may further be treated with therapeutic agents that treat or inhibit decreased bone mineral density.

For purposes of the present disclosure, any particular subject, such as a human, can be categorized as having one of three CD109 genotypes: i) CD109 reference; ii) heterozygous for a CD109 missense variant nucleic acid molecule encoding a CD109 predicted loss-of-function polypeptide; or iii) homozygous for a CD109 missense variant nucleic acid molecules encoding a CD109 predicted loss-of-function polypeptide. A subject is CD109 reference when the subject does not have a copy of a CD109 missense variant nucleic acid molecules encoding a CD109 predicted loss-of-function polypeptide. A subject is heterozygous for a CD109 missense variant nucleic acid molecules encoding a CD109 predicted loss-of-function polypeptide when the subject has a single copy of a CD109 missense variant nucleic acid molecule encoding a CD109 predicted loss-of-function polypeptide. A CD109 missense variant nucleic acid molecule encoding a CD109 predicted loss-of-function polypeptide is any nucleic acid molecule (such as, a genomic nucleic acid molecule, an mRNA molecule, or a cDNA molecule) encoding a variant CD109 polypeptide having a partial loss-of-function, a complete loss-of-function, a predicted partial loss-of-function, or a predicted complete loss-of-function. A subject who has a CD109 polypeptide having a partial loss-of-function (or predicted partial loss-of-function) is hypomorphic for CD109. A subject is homozygous for a CD109 missense variant nucleic acid molecule encoding a CD109 predicted loss-of-function polypeptide when the subject has two copies (same or different) of a CD109 missense variant nucleic acid molecules encoding a CD109 predicted loss-of-function polypeptide.

For subjects that are genotyped or determined to be CD109 reference, such subjects have an increased risk of developing decreased bone mineral density, such as osteopenia, Type I osteoporosis, Type II osteoporosis, and/or secondary osteoporosis. For subjects that are genotyped or determined to be either CD109 reference or heterozygous for a CD109 missense variant nucleic acid molecules encoding a CD109 predicted loss-of-function polypeptide, such subjects or subjects can be treated with a CD109 inhibitor.

In any of the embodiments described herein, the CD109 missense variant nucleic acid molecules encoding a CD109 predicted loss-of-function polypeptide can be any nucleic acid molecule (such as, for example, genomic nucleic acid molecule, mRNA molecule, or cDNA molecule) encoding a CD109 variant polypeptide having a partial loss-of-function, a complete loss-of-function, a predicted partial loss-of-function, or a predicted complete loss-of-function. In some embodiments, the CD109 missense variant nucleic acid molecules encoding a CD109 predicted loss-of-function polypeptide is associated with a reduced in vitro response to CD109 ligands compared with reference CD109. In some embodiments, the CD109 missense variant nucleic acid molecules encoding a CD109 predicted loss-of-function polypeptide is a CD109 variant that results or is predicted to result in a premature truncation of a CD109 polypeptide compared to the human reference genome sequence. In some embodiments, the CD109 missense variant nucleic acid molecules encoding a CD109 predicted loss-of-function polypeptide is a variant that is predicted to be damaging by in vitro prediction algorithms such as Polyphen, SIFT, or similar algorithms. In some embodiments, the CD109 missense variant nucleic acid molecules encoding a CD109 predicted loss-of-function polypeptide is a variant that causes or is predicted to cause a nonsynonymous amino-acid substitution in CD109 and whose allele frequency is less than 1/100 alleles in the population from which the subject is selected. In some embodiments, the CD109 missense variant nucleic acid molecules encoding a CD109 predicted loss-of-function polypeptide is any rare missense variant (allele frequency<0.1%; or 1 in 1,000 alleles), or any splice-site, stop-gain, start-loss, stop-loss, frameshift, or in-frame indel, or other frameshift CD109 variant.

In any of the embodiments described herein, the CD109 predicted loss-of-function polypeptide can be any CD109 polypeptide having a partial loss-of-function, a complete loss-of-function, a predicted partial loss-of-function, or a predicted complete loss-of-function.

In any of the embodiments described herein, the CD109 missense variant nucleic acid molecules encoding a CD109 predicted loss-of-function polypeptide can include variations at positions of chromosome 6 using the nucleotide sequence of the CD109 reference genomic nucleic acid molecule (SEQ ID NO:1; ENSG00000156535.15 chr6:73,695,785-73,828,316 in the GRCh38/hg38 human genome assembly) as a reference sequence.

Numerous genetic variants in CD109 exist which cause subsequent changes in the CD109 polypeptide sequence including, but not limited to: 6:73730573:A:G, 6:73823473:GA:G (p.Ser1394fs, p.Ser1317fs, p. Ser1377fs), 6:73763607:C:A (p.Phe343Leu, p. Phe266Leu, p. Phe343Leu), 6:73803256:G:T (p.Gly972Val, p. Gly895Val, p. Gly972Val), 6:73818486:T:C (p.Val1337Ala, p. Val1260Ala, p. Val1320Ala), 6:73787379:G:A (p.Gly828Glu, p. Gly751Glu, p. Gly828Glu), 6:73771510:A:G (p.Ile586Val, p. Ile509Val, p. Ile586Val), 6:73806987:A:T (p.His1035Leu, p. His958Leu, p. His1035Leu), 6:73758991:A:G (p.Met241Val, p. Met164Val, p. Met241Val), 6:73823456:A:G 6:73762778:A:C (p.Glu298Ala, p. Glu221Ala, p. Glu298Ala), 6:73763660:A:G (p.Lys361Arg, p. Lys284Arg, p. Lys361Arg), 6:73730573:A:G (p.Lys169Arg, p. Lys169Arg), 6:73806956:G:A (p.Gly1025Ser, p. Gly948Ser, p. Gly1025Ser), 6:73792628:G:C (p.Asp902His, p. Asp825His, p. Asp902His), 6:73806926:A:T (p.Thr1015Ser, p. Thr938Ser, p. Thr1015Ser), 6:73771576:G:A (p.Glu608Lys, p. Glu531Lys, p. Glu608Lys), 6:73815026:C:T (p.Arg1272*, p. Arg1195*, p. Arg1255*), 6:73765952:G:A (p.Gly377Asp, p. Gly300Asp, p. Gly377Asp).

Any one or more (i.e., any combination) of the CD109 missense variant nucleic acid molecules encoding a CD109 predicted loss-of-function polypeptide can be used within any of the methods described herein to determine whether a subject has an increased risk of developing decreased bone mineral density. The combinations of particular variants can form a mask used for statistical analysis of the particular correlation of CD109 and increased risk of developing decreased bone mineral density.

In any of the embodiments described herein, the decreased bone mineral density is osteopenia, Type I osteoporosis, Type II osteoporosis, and/or secondary osteoporosis. In some embodiments, the decreased bone mineral density is osteopenia. In some embodiments, the decreased bone mineral density is Type I osteoporosis. In some embodiments, the decreased bone mineral density is Type II osteoporosis. In some embodiments, the decreased bone mineral density is secondary osteoporosis.

Symptoms of a decreased bone mineral density include, but are not limited to, increased bone fragility (manifesting as bone fracture as a result of a mild to moderate trauma), reduced bone density, localized bone pain and weakness in an area of a broken bone, loss of height or change in posture, such as stooping over, high levels of serum calcium or alkaline phosphatase on a blood test, vitamin D deficiency, and joint or muscle aches, or any combination thereof.

The present disclosure provides methods of treating a subject having decreased bone mineral density or at risk of developing decreased bone mineral density, the methods comprising administering a CD109 inhibitor to the subject.

The present disclosure also provides methods of treating a subject having osteopenia or at risk of developing osteopenia, the methods comprising administering a CD109 inhibitor to the subject.

The present disclosure also provides methods of treating a subject having Type 1 osteoporosis or at risk of developing Type I osteoporosis, the methods comprising administering a CD109 inhibitor to the subject.

The present disclosure also provides methods of treating a subject having Type II osteoporosis or at risk of developing Type II osteoporosis, the methods comprising administering a CD109 to the subject.

The present disclosure also provides methods of treating a subject having secondary osteoporosis or at risk of developing secondary osteoporosis, the methods comprising administering a CD109 inhibitor to the subject.

In some embodiments, the CD109 inhibitor comprises an inhibitory nucleic acid molecule. Examples of inhibitory nucleic acid molecules include, but are not limited to, antisense nucleic acid molecules, small interfering RNAs (siRNAs), and short hairpin RNAs (shRNAs). Such inhibitory nucleic acid molecules can be designed to target any region of a CD109 nucleic acid molecule. In some embodiments, the antisense RNA, siRNA, or shRNA hybridizes to a sequence within a CD109 genomic nucleic acid molecule or mRNA molecule and decreases expression of the CD109 polypeptide in a cell in the subject. In some embodiments, the CD109 inhibitor comprises an antisense molecule that hybridizes to a CD109 genomic nucleic acid molecule or mRNA molecule and decreases expression of the CD109 polypeptide in a cell in the subject. In some embodiments, the CD109 inhibitor comprises an siRNA that hybridizes to a CD109 genomic nucleic acid molecule or mRNA molecule and decreases expression of the CD109 polypeptide in a cell in the subject. In some embodiments, the CD109 inhibitor comprises an shRNA that hybridizes to a CD109 genomic nucleic acid molecule or mRNA molecule and decreases expression of the CD109 polypeptide in a cell in the subject.

The inhibitory nucleic acid molecules can comprise RNA, DNA, or both RNA and DNA. The inhibitory nucleic acid molecules can also be linked or fused to a heterologous nucleic acid sequence, such as in a vector, or a heterologous label. For example, the inhibitory nucleic acid molecules can be within a vector or as an exogenous donor sequence comprising the inhibitory nucleic acid molecule and a heterologous nucleic acid sequence. The inhibitory nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The inhibitory nucleic acid molecules can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The inhibitory nucleic acid molecules can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (such as, for example, 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, 3-deazaguanine, and 3-deazaadenine.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, $—O[(CH_2)_nO]_mCH_3$, $—O(CH_2)_nOCH_3$, $—O(CH_2)_nNH_2$, $—O(CH_2)_nCH_3$, $—O(CH_2)_n—ONH_2$, and $—O(CH_2)_nON[(CH_2)_nCH_3)]_2$, where n and m, independently, are from 1 to about 10. Other modifications at the 2' position include, but are not limited to, $C_{1-10}$alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as $CH_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included. Nucleotide substitutes also include peptide nucleic acids (PNAs).

In some embodiments, the antisense nucleic acid molecules are gapmers, whereby the first one to seven nucleotides at the 5' and 3' ends each have 2'-methoxyethyl (2'-MOE) modifications. In some embodiments, the first five nucleotides at the 5' and 3' ends each have 2'-MOE modifications. In some embodiments, the first one to seven nucleotides at the 5' and 3' ends are RNA nucleotides. In some embodiments, the first five nucleotides at the 5' and 3' ends are RNA nucleotides. In some embodiments, each of the backbone linkages between the nucleotides is a phosphorothioate linkage.

In some embodiments, the siRNA molecules have termini modifications. In some embodiments, the 5' end of the antisense strand is phosphorylated. In some embodiments, 5'-phosphate analogs that cannot be hydrolyzed, such as 5'-(E)-vinyl-phosphonate are used.

In some embodiments, the siRNA molecules have backbone modifications. In some embodiments, the modified phosphodiester groups that link consecutive ribose nucleosides have been shown to enhance the stability and in vivo bioavailability of siRNAs The non-ester groups (—OH, =O) of the phosphodiester linkage can be replaced with sulfur, boron, or acetate to give phosphorothioate, boranophosphate, and phosphonoacetate linkages. In addition, substituting the phosphodiester group with a phosphotriester can facilitate cellular uptake of siRNAs and retention on serum components by eliminating their negative charge. In some embodiments, the siRNA molecules have sugar modifications. In some embodiments, the sugars are deprotonated (reaction catalyzed by exo- and endonucleases) whereby the 2'-hydroxyl can act as a nucleophile and attack the adjacent phosphorous in the phosphodiester bond. Such alternatives include 2'-O-methyl, 2'-O-methoxyethyl, and 2'-fluoro modifications.

In some embodiments, the siRNA molecules have base modifications. In some embodiments, the bases can be substituted with modified bases such as pseudouridine, 5'-methylcytidine, N6-methyladenosine, inosine, and N7-methylguanosine.

In some embodiments, the siRNA molecules are conjugated to lipids. Lipids can be conjugated to the 5' or 3' termini of siRNA to improve their in vivo bioavailability by allowing them to associate with serum lipoproteins. Representative lipids include, but are not limited to, cholesterol and vitamin E, and fatty acids, such as palmitate and tocopherol.

In some embodiments, a representative siRNA has the following formula:

mN*mN*/i2FN/mN/i2FN/mN/i2FN/mN/i2FN/mN/i2FN/mN/i2FN/mN/i2FN/mN/i2FN/*mN*/32FN/ Sense:

/52FN/*/i2FN/*mN/i2FN/mN/i2FN/mN/i2FN/mN/i2FN/mN/i2FN/mN/i2FN/mN/i2FN/mN/i2FN/mN*N*N Antisense:

wherein: "N" is the base; "2F" is a 2'-F modification; "m" is a 2'-O-methyl modification, "I" is an internal base; and "*" is a phosphorothioate backbone linkage.

The present disclosure also provides vectors comprising any one or more of the inhibitory nucleic acid molecules. In some embodiments, the vectors comprise any one or more of the inhibitory nucleic acid molecules and a heterologous nucleic acid. The vectors can be viral or nonviral vectors capable of transporting a nucleic acid molecule. In some embodiments, the vector is a plasmid or cosmid (such as, for example, a circular double-stranded DNA into which additional DNA segments can be ligated). In some embodiments, the vector is a viral vector, wherein additional DNA segments can be ligated into the viral genome. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and other expression vectors known in the art.

The present disclosure also provides compositions comprising any one or more of the inhibitory nucleic acid molecules. In some embodiments, the composition is a pharmaceutical composition. In some embodiments, the compositions comprise a carrier and/or excipient. Examples of carriers include, but are not limited to, poly(lactic acid) (PLA) microspheres, poly(D,L-lactic-coglycolic-acid) (PLGA) microspheres, liposomes, micelles, inverse micelles, lipid cochleates, and lipid microtubules. A carrier may comprise a buffered salt solution such as PBS, HBSS, etc.

In some embodiments, the CD109 inhibitor is or comprises LY294002, which is a PI3K inhibitor that suppresses CD109 expression.

In some embodiments, the CD109 inhibitor comprises a nuclease agent that induces one or more nicks or double-strand breaks at a recognition sequence(s) or a DNA-binding protein that binds to a recognition sequence within a CD109 genomic nucleic acid molecule. The recognition sequence can be located within a coding region of the CD109 gene, or within regulatory regions that influence the expression of the gene. A recognition sequence of the DNA-binding protein or nuclease agent can be located in an intron, an exon, a promoter, an enhancer, a regulatory region, or any non-protein coding region. The recognition sequence can include or be proximate to the start codon of the CD109 gene. For example, the recognition sequence can be located about 10, about 20, about 30, about 40, about 50, about 100, about 200, about 300, about 400, about 500, or about 1,000 nucleotides from the start codon. As another example, two or more nuclease agents can be used, each targeting a nuclease recognition sequence including or proximate to the start codon. As another example, two nuclease agents can be used, one targeting a nuclease recognition sequence including or proximate to the start codon, and one targeting a nuclease recognition sequence including or proximate to the stop codon, wherein cleavage by the nuclease agents can result in deletion of the coding region between the two nuclease recognition sequences. Any nuclease agent that induces a nick or double-strand break into a desired recognition sequence can be used in the methods and compositions disclosed herein. Any DNA-binding protein that binds to a desired recognition sequence can be used in the methods and compositions disclosed herein.

Suitable nuclease agents and DNA-binding proteins for use herein include, but are not limited to, zinc finger protein or zinc finger nuclease (ZFN) pair, Transcription Activator-Like Effector (TALE) protein or Transcription Activator-Like Effector Nuclease (TALEN), or Clustered Regularly Interspersed Short Palindromic Repeats (CRISPR)/CRISPR-associated (Cas) systems. The length of the recognition sequence can vary, and includes, for example, recognition sequences that are about 30-36 bp for a zinc finger protein or ZFN pair, about 15-18 bp for each ZFN, about 36 bp for a TALE protein or TALEN, and about 20 bp for a CRISPR/Cas guide RNA.

In some embodiments, CRISPR/Cas systems can be used to modify a CD109 genomic nucleic acid molecule within a cell. The methods and compositions disclosed herein can employ CRISPR-Cas systems by utilizing CRISPR complexes (comprising a guide RNA (gRNA) complexed with a Cas protein) for site-directed cleavage of CD109 nucleic acid molecules.

Cas proteins generally comprise at least one RNA recognition or binding domain that can interact with gRNAs. Cas proteins can also comprise nuclease domains (such as, for example, DNase or RNase domains), DNA binding domains, helicase domains, protein-protein interaction domains, dimerization domains, and other domains. Suitable Cas proteins include, for example, a wild type Cas9 protein and a wild type Cpf1 protein (such as, for example, FnCpf1). A Cas protein can have full cleavage activity to create a double-strand break in a CD109 genomic nucleic acid molecule or it can be a nickase that creates a single-strand break in a CD109 genomic nucleic acid molecule. Additional examples of Cas proteins include, but are not limited to, Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof. Cas proteins can also be operably linked to heterologous polypeptides as fusion proteins. For example, a Cas protein can be fused to a cleavage domain, an epigenetic modification domain, a transcriptional activation domain, or a transcriptional repressor domain. Cas proteins can be provided in any form. For example, a Cas protein can be provided in the form of a protein, such as a Cas protein complexed with a gRNA. Alternately, a Cas protein can be provided in the form of a nucleic acid molecule encoding the Cas protein, such as an RNA or DNA.

In some embodiments, targeted genetic modifications of CD109 genomic nucleic acid molecules can be generated by contacting a cell with a Cas protein and one or more gRNAs that hybridize to one or more gRNA recognition sequences within a target genomic locus in the CD109 genomic nucleic acid molecule. For example, a gRNA recognition sequence can be located within a region of SEQ ID NO:1. The gRNA recognition sequence can include or be proximate to the start codon of a CD109 genomic nucleic acid molecule or the stop codon of a CD109 genomic nucleic acid molecule. For example, the gRNA recognition sequence can be located from about 10, from about 20, from about 30, from about 40, from about 50, from about 100, from about 200, from about 300, from about 400, from about 500, or from about 1,000 nucleotides of the start codon or the stop codon.

The gRNA recognition sequences within a target genomic locus in a CD109 genomic nucleic acid molecule are located near a Protospacer Adjacent Motif (PAM) sequence, which is a 2-6 base pair DNA sequence immediately following the DNA sequence targeted by the Cas9 nuclease. The canonical PAM is the sequence 5'-NGG-3' where "N" is any nucleobase followed by two guanine ("G") nucleobases. gRNAs can transport Cas9 to anywhere in the genome for gene editing, but no editing can occur at any site other than one at which Cas9 recognizes PAM. In addition, 5'-NGA-3' can be a highly efficient non-canonical PAM for human cells. Generally, the PAM is about 2-6 nucleotides downstream of the DNA sequence targeted by the gRNA. The PAM can flank the gRNA recognition sequence. In some embodiments, the gRNA recognition sequence can be flanked on the 3' end by the PAM. In some embodiments, the gRNA recognition sequence can be flanked on the 5' end by the PAM. For example, the cleavage site of Cas proteins can be about 1 to about 10, about 2 to about 5 base pairs, or three base pairs upstream or downstream of the PAM sequence. In some embodiments (such as when Cas9 from *S. pyogenes* or a closely related Cas9 is used), the PAM sequence of the non-complementary strand can be 5'-NGG-3', where N is any DNA nucleotide and is immediately 3' of the gRNA recognition sequence of the non-complementary strand of the target DNA. As such, the PAM sequence of the complementary strand would be 5'-CCN-3', where N is any DNA nucleotide and is immediately 5' of the gRNA recognition sequence of the complementary strand of the target DNA.

A gRNA is an RNA molecule that binds to a Cas protein and targets the Cas protein to a specific location within a CD109 genomic nucleic acid molecule. An exemplary gRNA is a gRNA effective to direct a Cas enzyme to bind to or cleave a CD109 genomic nucleic acid molecule, wherein the gRNA comprises a DNA-targeting segment that hybridizes to a gRNA recognition sequence within the CD109 genomic nucleic acid molecule. Exemplary gRNAs comprise a DNA-targeting segment that hybridizes to a gRNA recognition sequence present within a CD109 genomic nucleic acid molecule that includes or is proximate to the start codon or the stop codon. For example, a gRNA can be selected such that it hybridizes to a gRNA recognition sequence that is located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of the start codon or located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of the stop codon. Suitable gRNAs can comprise from about 17 to about 25 nucleotides, from about 17 to about 23 nucleotides, from about 18 to about 22 nucleotides, or from about 19 to about 21 nucleotides. In some embodiments, the gRNAs can comprise 20 nucleotides.

Examples of suitable gRNA recognition sequences located within the human CD109 reference gene are set forth in Table 1 as SEQ ID NOs:37-58.

TABLE 1

| Guide RNA Recognition Sequences Near CD109 | | |
|---|---|---|
| Strand | gRNA Recognition Sequence | SEQ ID NO: |
| + | GCCTCCAAGTCCTGTCTCAAT | 37 |
| + | GGTACCATCACGGCAAAGTAT | 38 |
| + | GTACCATCACGGCAAAGTATA | 39 |
| + | GCTACAGTTGAAGGCCTATTT | 40 |
| + | GATTGAAGGAGTTAAGCTATA | 41 |
| + | GGTCTTGGACTAACAACTACT | 42 |
| + | GAAAGATGCCACTGAGGTTAA | 43 |
| + | GCATCTACTCAGGATACCACT | 44 |
| + | GGTACAGCCAACGGCAGTTAA | 45 |
| + | GGCTCTTATGGAAGTTAACCT | 46 |
| + | GACAGGCGGTGAGAAGTTACA | 47 |
| + | GCCCAGTGGTCTCAGTAGATA | 48 |
| + | GCCGATCCTTACATAGATA | 49 |
| + | CCTAGATTCTTAAGCATTA | 50 |
| + | AAGCCTGTGTAATTGTGTA | 51 |
| + | AGAGTTCAGATCACTGCAA | 52 |
| + | AGGAGACGTAACGCTTACA | 53 |
| + | TGTAAGCACTAATGTGTTC | 54 |
| + | CTGTACCTGATTCTATCAC | 55 |
| + | ACTAAGAAGTAAGTGTAAC | 56 |
| + | TGCAGAATATGCTGAGAGG | 57 |
| = | TTGGAGATGTTCTTGGTCC | 58 |

The Cas protein and the gRNA form a complex, and the Cas protein cleaves the target CD109 genomic nucleic acid molecule. The Cas protein can cleave the nucleic acid molecule at a site within or outside of the nucleic acid sequence present in the target CD109 genomic nucleic acid molecule to which the DNA-targeting segment of a gRNA will bind. For example, formation of a CRISPR complex (comprising a gRNA hybridized to a gRNA recognition sequence and complexed with a Cas protein) can result in cleavage of one or both strands in or near (such as, for example, within 1, 2, 3, 4, 5, 6, 7, 8, 9, 10, 20, 50, or more base pairs from) the nucleic acid sequence present in the CD109 genomic nucleic acid molecule to which a DNA-targeting segment of a gRNA will bind.

Such methods can result, for example, in a CD109 genomic nucleic acid molecule in which a region of SEQ ID NO:1 is disrupted, the start codon is disrupted, the stop codon is disrupted, or the coding sequence is disrupted or deleted. Optionally, the cell can be further contacted with one or more additional gRNAs that hybridize to additional gRNA recognition sequences within the target genomic locus in the CD109 genomic nucleic acid molecule. By contacting the cell with one or more additional gRNAs (such as, for example, a second gRNA that hybridizes to a second gRNA recognition sequence), cleavage by the Cas protein can create two or more double-strand breaks or two or more single-strand breaks.

In some embodiments, the methods of treatment further comprise detecting the presence or absence of a CD109 missense variant nucleic acid molecule encoding a CD109 predicted loss-of-function polypeptide in a biological sample from the subject. As used throughout the present disclosure, a "CD109 missense variant nucleic acid molecule encoding a CD109 predicted loss-of-function polypeptide" is any CD109 nucleic acid molecule (such as, for example, genomic nucleic acid molecule, mRNA molecule, or cDNA molecule) encoding a CD109 polypeptide having a partial loss-of-function, a complete loss-of-function, a predicted partial loss-of-function, or a predicted complete loss-of-function.

The present disclosure also provides methods of treating a subject with a therapeutic agent that treats or inhibits decreased bone mineral density, wherein the subject has decreased bone mineral density or is at risk of developing decreased bone mineral density. In some embodiments, the subject has decreased bone mineral density. In some embodiments, the subject is at risk of developing decreased bone mineral density. In some embodiments, the methods comprise determining whether the subject has a CD109 missense variant nucleic acid molecule encoding a CD109 predicted loss-of-function polypeptide by obtaining or having obtained a biological sample from the subject, and performing or having performed a sequence analysis on the biological sample to determine if the subject has a genotype comprising the CD109 missense variant nucleic acid molecule encoding a CD109 predicted loss-of-function polypeptide. In some embodiments, the methods further comprise administering or continuing to administer the therapeutic agent that treats or inhibits decreased bone mineral density in a standard dosage amount to a subject that is CD109 reference, and/or administering a CD109 inhibitor to the subject. In some embodiments, the methods further comprise administering or continuing to administer the therapeutic agent that treats or inhibits decreased bone mineral density in an amount that is the same as or less than a standard dosage amount to a subject that is heterozygous for the CD109 missense variant nucleic acid molecule, and/or administering a CD109 inhibitor to the subject. In some embodiments, the methods further comprise administering or continuing to administer the therapeutic agent that treats or inhibits decreased bone mineral density in an amount that is the same as or less than a standard dosage amount to a subject that is homozygous for the CD109 missense variant nucleic acid molecule. The presence of a genotype having the CD109 missense variant nucleic acid molecule encoding the CD109 predicted loss-of-function polypeptide indicates the subject has a decreased risk of developing decreased bone mineral density. In some embodiments, the subject is CD109 reference. In some embodiments, the subject is heterozygous for a CD109 missense variant nucleic acid molecule encoding a CD109 predicted loss-of-function polypeptide.

For subjects that are genotyped or determined to be either CD109 reference or heterozygous for a CD109 missense variant nucleic acid molecule encoding a CD109 predicted loss-of-function polypeptide, such subjects can be treated with a CD109 inhibitor, as described herein.

Detecting the presence or absence of a CD109 missense variant nucleic acid molecule encoding a CD109 predicted loss-of-function polypeptide in a biological sample from a subject and/or determining whether a subject has a CD109 missense variant nucleic acid molecule encoding a CD109 predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, when the subject is CD109 reference, the subject is administered a therapeutic agent that treats or inhibits decreased bone mineral density in a standard dosage amount. In some embodiments, when the subject is heterozygous for a CD109 missense variant nucleic acid molecule encoding a CD109 predicted loss-of-function polypeptide, the subject is administered a therapeutic agent that treats or inhibits decreased bone mineral density in a dosage amount that is the same as or less than a standard dosage amount.

In some embodiments, the treatment methods further comprise detecting the presence or absence of a CD109 predicted loss-of-function polypeptide in a biological sample from the subject. In some embodiments, when the subject does not have a CD109 predicted loss-of-function polypeptide, the subject is administered a therapeutic agent that treats or inhibits decreased bone mineral density in a standard dosage amount. In some embodiments, when the subject has a CD109 predicted loss-of-function polypeptide, the subject is administered a therapeutic agent that treats or inhibits decreased bone mineral density in a dosage amount that is the same as or less than a standard dosage amount.

The present disclosure also provides methods of treating a subject with a therapeutic agent that treats or inhibits decreased bone mineral density, wherein the subject has decreased bone mineral density or is at risk of developing decreased bone mineral density. In some embodiments, the subject has decreased bone mineral density. In some embodiments, the subject is at risk of developing decreased bone mineral density. In some embodiments, the method comprises determining whether the subject has a CD109 predicted loss-of-function polypeptide by obtaining or having obtained a biological sample from the subject, and performing or having performed an assay on the biological sample to determine if the subject has a CD109 predicted loss-of-function polypeptide. When the subject does not have a CD109 predicted loss-of-function polypeptide, the therapeutic agent that treats or inhibits decreased bone mineral density is administered or continued to be administered to the subject in a standard dosage amount, and/or a CD109 inhibitor is administered to the subject. When the subject has a CD109 predicted loss-of-function polypeptide, the therapeutic agent that treats or inhibits decreased bone mineral density is administered or continued to be administered to the subject in an amount that is the same as or less than a standard dosage amount, and/or a CD109 inhibitor is administered to the subject. The presence of a CD109 predicted loss-of-function polypeptide indicates the subject has a decreased risk of developing decreased bone mineral density. In some embodiments, the subject has a CD109 predicted loss-of-function polypeptide. In some embodiments, the subject does not have a CD109 predicted loss-of-function polypeptide.

Detecting the presence or absence of a CD109 predicted loss-of-function polypeptide in a biological sample from a subject and/or determining whether a subject has a CD109 predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the polypeptide can be present within a cell obtained from the subject.

Examples of therapeutic agents that treat or inhibit decreased bone mineral density include, but are not limited to: calcium and vitamin D supplementation (vitamin D2, vitamin D3, and cholecalciferol), bisphosphonate medications, such as FOSAMAX®, (alendronate), BONIVA® (ibandronate), RECLAST® (zoledronate), ACTONEL® (risedronate), MIACALCIN®, FORTICAL®, and CALCIMAR® (calcitonin), FORTEO® (teriparatide), PROLIA® (denosumab), hormone replacement therapy with estrogen and progesterone as well as EVISTA® (raloxifene), and EVENITY® (romosozumab). In some embodiments, the therapeutic agent that treats or inhibits decreased bone mineral density is vitamin D2, vitamin D3, cholecalciferol, alendronate, ibandronate, zoledronate, risedronate, calcitonin, teriparatide, denosumab, or raloxifene. In some embodiments, the therapeutic agent that treats or inhibits decreased bone mineral density is vitamin D2. In some embodiments, the therapeutic agent that treats or inhibits decreased bone mineral density is vitamin D3. In some embodiments, the therapeutic agent that treats or inhibits decreased bone mineral density is cholecalciferol. In some embodiments, the therapeutic agent that treats or inhibits decreased bone mineral density is alendronate. In some embodiments, the therapeutic agent that treats or inhibits decreased bone mineral density is ibandronate. In some embodiments, the therapeutic agent that treats or inhibits decreased bone mineral density is zoledronate. In some embodiments, the therapeutic agent that treats or inhibits decreased bone mineral density is risedronate. In some embodiments, the therapeutic agent that treats or inhibits decreased bone mineral density is calcitonin. In some embodiments, the therapeutic agent that treats or inhibits decreased bone mineral density is teriparatide. In some embodiments, the therapeutic agent that treats or inhibits decreased bone mineral density is denosumab. In some embodiments, the therapeutic agent that treats or inhibits decreased bone mineral density is raloxifene.

In some embodiments, the dose of the therapeutic agents that treat or inhibit decreased bone mineral density can be decreased by about 10%, by about 20%, by about 30%, by about 40%, by about 50%, by about 60%, by about 70%, by about 80%, or by about 90% for subjects that are heterozygous for a CD109 missense variant nucleic acid molecule encoding a CD109 predicted loss-of-function polypeptide (i.e., a less than the standard dosage amount) compared to subjects that are CD109 reference (who may receive a standard dosage amount). In some embodiments, the dose of the therapeutic agents that treat or inhibit decreased bone mineral density can be decreased by about 10%, by about 20%, by about 30%, by about 40%, or by about 50%. In addition, the subjects that are heterozygous for a CD109 missense variant nucleic acid molecule encoding a CD109 predicted loss-of-function polypeptide can be administered less frequently compared to subjects that are CD109 reference.

In some embodiments, the dose of the therapeutic agents that treat or inhibit decreased bone mineral density can be decreased by about 10%, by about 20%, by about 30%, by about 40%, by about 50%, for subjects that are homozygous for a CD109 missense variant nucleic acid molecule encoding a CD109 predicted loss-of-function polypeptide compared to subjects that are heterozygous for a CD109 missense variant nucleic acid molecule encoding a CD109 predicted loss-of-function polypeptide. In some embodiments, the dose of the therapeutic agents that treat or inhibit decreased bone mineral density can be decreased by about 10%, by about 20%, by about 30%, by about 40%, or by about 50%. In addition, the dose of therapeutic agents that treat or inhibit decreased bone mineral density in subjects that are homozygous for a CD109 missense variant nucleic acid molecule encoding a CD109 predicted loss-of-function polypeptide can be administered less frequently compared to subjects that are heterozygous for a CD109 missense variant nucleic acid molecule encoding a CD109 predicted loss-of-function polypeptide.

Administration of the therapeutic agents that treat or inhibit decreased bone mineral density and/or CD109 inhibitors can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a subject can receive therapy for a prolonged period of time such as, for example, 6 months, 1 year, or more.

Administration of the therapeutic agents that treat or inhibit decreased bone mineral density and/or CD109 inhibitors can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in decreased bone mineral density, a decrease/reduction in the severity of decreased bone mineral density (such as, for example, a reduction or inhibition of development of decreased bone mineral density), a decrease/reduction in symptoms and decreased bone mineral density-related effects, delaying the onset of symptoms and decreased bone mineral density-related effects, reducing the severity of symptoms of decreased bone mineral density-related effects, reducing the number of symptoms and decreased bone mineral density-related effects, reducing the latency of symptoms and decreased bone mineral density-related effects, an amelioration of symptoms and decreased bone mineral density-related effects, reducing secondary symptoms, reducing secondary infections, preventing relapse to decreased bone mineral density, decreasing the number or frequency of relapse episodes, increasing latency between symptomatic episodes, increasing time to sustained progression, speeding recovery, or increasing efficacy of or decreasing resistance to alternative therapeutics, and/or an increased survival time of the affected host animal, following administration of the agent or composition comprising the agent. A prophylactic effect may comprise a complete or partial avoidance/inhibition or a delay of decreased bone mineral density development/progression (such as, for example, a complete or partial avoidance/inhibition or a delay), and an increased survival time of the affected host animal, following administration of a therapeutic protocol. Treatment of decreased bone mineral density encompasses the treatment of a subject already diagnosed as having any form of decreased bone mineral density at any clinical stage or manifestation, the delay of the onset or evolution or aggravation or deterioration of the symptoms or signs of decreased bone mineral density, and/or preventing and/or reducing the severity of decreased bone mineral density.

The present disclosure also provides methods of identifying a subject having an increased risk of developing decreased bone mineral density. In some embodiments, the method comprises determining or having determined in a biological sample obtained from the subject the presence or absence of a CD109 missense variant nucleic acid molecule (such as a genomic nucleic acid molecule, mRNA molecule, and/or cDNA molecule) encoding a CD109 predicted loss-of-function polypeptide encoding a CD109 polypeptide. When the subject lacks a CD109 missense variant nucleic acid molecule encoding a CD109 predicted loss-of-function polypeptide (i.e., the subject is genotypically categorized as a CD109 reference), then the subject has an increased risk of developing decreased bone mineral density. When the subject has a CD109 missense variant nucleic acid molecule encoding a CD109 predicted loss-of-function polypeptide (i.e., the subject is heterozygous or homozygous for a CD109 missense variant nucleic acid molecule encoding a CD109 predicted loss-of-function polypeptide), then the subject has a decreased risk of developing decreased bone mineral density.

Having a single copy of a CD109 missense variant nucleic acid molecule encoding a CD109 predicted loss-of-function polypeptide is more protective of a subject from developing decreased bone mineral density than having no copies of a CD109 missense variant nucleic acid molecule encoding a CD109 predicted loss-of-function polypeptide. Without intending to be limited to any particular theory or mechanism of action, it is believed that a single copy of a CD109 missense variant nucleic acid molecule encoding a CD109 predicted loss-of-function polypeptide (i.e., heterozygous for a CD109 missense variant nucleic acid molecule encoding a CD109 predicted loss-of-function polypeptide) is protective of a subject from developing decreased bone mineral density, and it is also believed that having two copies of a CD109 missense variant nucleic acid molecule encoding a CD109 predicted loss-of-function polypeptide (i.e., homozygous for a CD109 missense variant nucleic acid molecule encoding a CD109 predicted loss-of-function polypeptide) may be more protective of a subject from developing decreased bone mineral density, relative to a subject with a single copy. Thus, in some embodiments, a single copy of a CD109 missense variant nucleic acid molecule encoding a CD109 predicted loss-of-function polypeptide may not be completely protective, but instead, may be partially or incompletely protective of a subject from developing decreased bone mineral density. While not desiring to be bound by any particular theory, there may be additional factors or molecules involved in the development of decreased bone mineral density that are still present in a subject having a single copy of a CD109 missense variant nucleic acid molecule encoding a CD109 predicted loss-offunction polypeptide, thus resulting in less than complete protection from the development of decreased bone mineral density.

Determining whether a subject has a CD109 missense variant nucleic acid molecule encoding a CD109 predicted loss-of-function polypeptide in a biological sample from a subject and/or determining whether a subject has a CD109 missense variant nucleic acid molecule encoding a CD109 predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, when a subject is identified as having an increased risk of developing decreased bone mineral density, the subject is treated with a therapeutic agent that treats or inhibits decreased bone mineral density, and/or a CD109 inhibitor, as described herein. For example, when the subject is CD109 reference, and therefore has an increased risk of developing decreased bone mineral density, the subject is administered a CD109 inhibitor. In some embodiments, such a subject is also administered a therapeutic agent that treats or inhibits decreased bone mineral density. In some embodiments, when the subject is heterozygous for a CD109 missense variant nucleic acid molecule encoding a CD109 predicted loss-of-function polypeptide, the subject is administered the therapeutic agent that treats or inhibits decreased bone mineral density in a dosage amount that is the same as or less than a standard dosage amount, and is also administered a CD109 inhibitor. In some embodiments, such a subject is also administered a therapeutic agent that treats or inhibits decreased bone mineral density. In some embodiments, when the subject is homozygous for a CD109 missense variant nucleic acid molecule encoding a CD109 predicted loss-of-function polypeptide, the subject is administered the therapeutic agent that treats or inhibits decreased bone mineral density in a dosage amount that is the same as or less than a standard dosage amount. In some embodiments, the subject is CD109 reference. In some embodiments, the subject is heterozygous for a CD109 missense variant nucleic acid molecule encoding a CD109 predicted loss-of-function polypeptide. In some embodiments, the subject is homozygous for a CD109 missense variant nucleic acid molecule encoding a CD109 predicted loss-of-function polypeptide.

In some embodiments, any of the methods described herein can further comprise determining the subject's gene burden of having a CD109 missense variant nucleic acid molecule encoding a CD109 predicted loss-of-function polypeptide, and/or a CD109 predicted loss-of-function variant polypeptide associated with a decreased risk of developing decreased bone mineral density. The gene burden is the aggregate of all variants in the CD109 gene, which can be carried out in an association analysis with decreased bone mineral density. In some embodiments, the subject is homozygous for one or more CD109 missense variant nucleic acid molecules encoding a CD109 predicted loss-of-function polypeptide associated with a decreased risk of developing decreased bone mineral density. In some embodiments, the subject is heterozygous for one or more CD109 missense variant nucleic acid molecules encoding a CD109 predicted loss-of-function polypeptide associated with a decreased risk of developing decreased bone mineral density. The result of the association analysis suggests that CD109 missense variant nucleic acid molecules encoding a CD109 predicted loss-of-function polypeptide are associated with decreased risk of developing decreased bone mineral density. When the subject has a lower gene burden, the subject is at a higher risk of developing decreased bone mineral density and the subject is administered or continued to be administered the therapeutic agent that treats or inhibits decreased bone mineral density in a standard dosage amount. When the subject has a greater gene burden, the subject is at a lower risk of developing decreased bone mineral density and the subject is administered or continued to be administered the therapeutic agent that treats or inhibits decreased bone mineral density in an amount that is the same as or less than the standard dosage amount. The greater the gene burden, the lower the risk of developing decreased bone mineral density.

The CD109 missense variant nucleic acid molecule encoding a CD109 predicted loss-of-function polypeptide, and/or a CD109 predicted loss-of-function variant polypeptide used for determining the subject's gene burden include, but are not limited to 6:73730573:A:G, 6:73823473:GA:G (p.Ser1394fs, p.Ser1317fs, p. Ser1377fs), 6:73763607:C:A (p.Phe343Leu, p. Phe266Leu, p. Phe343Leu), 6:73803256:G:T (p.Gly972Val, p. Gly895Val, p. Gly972Val), 6:73818486:T:C (p.Val1337Ala, p. Val1260Ala, p. Val1320Ala), 6:73787379:G:A (p.Gly828Glu, p. Gly751Glu, p. Gly828Glu), 6:73771510:A:G (p.Ile586Val, p. Ile509Val, p. Ile586Val), 6:73806987:A:T (p.His1035Leu, p. His958Leu, p. His1035Leu), 6:73758991:A:G (p.Met241Val, p. Met164Val, p. Met241Val), 6:73823456:A:G 6:73762778:A:C (p.Glu298Ala, p. Glu221Ala, p. Glu298Ala), 6:73763660:A:G (p.Lys361Arg, p. Lys284Arg, p. Lys361Arg), 6:73730573:A:G (p.Lys169Arg, p. Lys169Arg), 6:73806956:G:A (p.Gly1025Ser, p. Gly948Ser, p. Gly1025Ser), 6:73792628:G:C (p.Asp902His, p. Asp825His, p. Asp902His), 6:73806926:A:T (p.Thr1015Ser, p. Thr938Ser, p. Thr1015Ser), 6:73771576:G:A (p.Glu608Lys, p. Glu531Lys, p. Glu608Lys), 6:73815026:C:T (p.Arg1272*, p. Arg1195*, p. Arg1255*), 6:73765952:G:A (p.Gly377Asp, p. Gly300Asp, p. Gly377Asp).

In some embodiments, the subject's gene burden of having any one or more CD109 missense variant nucleic acid molecules encoding a CD109 predicted loss-of-function polypeptide represents a weighted sum of a plurality of any of the CD109 missense variant nucleic acid molecules encoding a CD109 predicted loss-of-function polypeptide. In some embodiments, the gene burden is calculated using at least about 2, at least about 3, at least about 4, at least about 5, at least about 10, at least about 20, at least about 30, at least about 40, at least about 50, at least about 60, at least about 70, at least about 80, at least about 100, at least about 120, at least about 150, at least about 200, at least about 250, at least about 300, at least about 400, at least about 500, at least about 1,000, at least about 10,000, at least about 100,000, or at least about or more than 1,000,000 genetic variants present in or around (up to 10 Mb) the CD109 gene where the genetic burden is the number of alleles multiplied by the association estimate with decreased bone mineral density or related outcome for each allele (e.g., a weighted burden score). This can include any genetic variants, regardless of their genomic annotation, in proximity to the CD109 gene (up to 10 Mb around the gene) that show a non-zero association with decreased bone mineral density-related traits in a genetic association analysis. In some embodiments, when the subject has a gene burden above a desired threshold score, the subject has a decreased risk of developing decreased bone mineral density. In some embodiments, when the subject has an gene burden below a desired threshold score, the subject has an increased risk of developing decreased bone mineral density.

In some embodiments, the gene burden may be divided into quintiles, e.g., top quintile, intermediate quintile, and bottom quintile, wherein the top quintile of gene burden corresponds to the lowest risk group and the bottom quintile of gene burden corresponds to the highest risk group. In some embodiments, a subject having a greater gene burden comprises the highest weighted gene burdens, including, but not limited to the top 10%, top 20%, top 30%, top 40%, or top 50% of gene burdens from a subject population. In some embodiments, the genetic variants comprise the genetic variants having association with decreased bone mineral density in the top 10%, top 20%, top 30%, top 40%, or top 50% of p-value range for the association. In some embodiments, each of the identified genetic variants comprise the genetic variants having association with decreased bone mineral density with p-value of no more than about $10^{-2}$, about $10^{-3}$, about $10^{-4}$, about $10^{-1}$, about $10^{-6}$, about $10^{-7}$, about $10^{-8}$, about $10^{-9}$, about $10^{-10}$, about $10^{-11}$, about $10^{-12}$, about $10^{-13}$, about $10^{-14}$, about or $10^{-15}$. In some embodiments, the identified genetic variants comprise the genetic variants having association with decreased bone mineral density with p-value of less than $5\times10^{-8}$. In some embodiments, the identified genetic variants comprise genetic variants having association with decreased bone mineral density in high-risk subjects as compared to the rest of the reference population with odds ratio (OR) about 1.5 or greater, about 1.75 or greater, about 2.0 or greater, or about 2.25 or greater for the top 20% of the distribution; or about 1.5 or greater, about 1.75 or greater, about 2.0 or greater, about 2.25 or greater, about 2.5 or greater, or about 2.75 or greater. In some embodiments, the odds ratio (OR) may range from about 1.0 to about 1.5, from about 1.5 to about 2.0, from about 2.0 to about 2.5, from about 2.5 to about 3.0, from about 3.0 to about 3.5, from about 3.5 to about 4.0, from about 4.0 to about 4.5, from about 4.5 to about 5.0, from about 5.0 to about 5.5, from about 5.5 to about 6.0, from about 6.0 to about 6.5, from about 6.5 to about 7.0, or greater than 7.0. In some embodiments, high-risk subjects comprise subjects having gene burdens in the bottom decile, quintile, or tertile in a reference population. The threshold of the gene burden is determined on the basis of the nature of the intended practical application and the risk difference that would be considered meaningful for that practical application.

In some embodiments, when a subject is identified as having an increased risk of developing decreased bone mineral density, the subject is treated with a therapeutic agent that treats or inhibits decreased bone mineral density, and/or a CD109 inhibitor, as described herein. For example, when the subject is CD109 reference, and therefore has an increased risk of developing decreased bone mineral density, the subject is administered a CD109 inhibitor. In some embodiments, such a subject is administered a therapeutic agent that treats or inhibits decreased bone mineral density. In some embodiments, when the subject is heterozygous for a CD109 missense variant nucleic acid molecule encoding a CD109 predicted loss-of-function polypeptide, the subject is administered the therapeutic agent that treats or inhibits decreased bone mineral density in a dosage amount that is the same as or less than a standard dosage amount, and is also administered a CD109 inhibitor. In some embodiments, the subject is CD109 reference. In some embodiments, the subject is heterozygous for a CD109 missense variant nucleic acid molecule encoding a CD109 predicted loss-of-function polypeptide. Furthermore, when the subject has a lower gene burden for having a CD109 missense variant nucleic acid molecule encoding a CD109 predicted loss-of-function polypeptide, and therefore has an increased risk of developing decreased bone mineral density, the subject is administered a therapeutic agent that treats or inhibits decreased bone mineral density. In some embodiments, when the subject has a lower gene burden for having a CD109 missense variant nucleic acid molecule encoding a CD109 predicted loss-of-function polypeptide, the subject is administered the therapeutic agent that treats or inhibits decreased bone mineral density in a dosage amount that is the same as or greater than the standard dosage amount administered to a subject who has a greater gene burden for having a CD109 missense variant nucleic acid molecule encoding a CD139 predicted loss-of-function polypeptide.

CD109 variants that can be used in the gene burden analysis include any one or more, or any combination, of the following (the Variant column indicates the chromosome, physical genomic position in base pairs, reference allele, and alternative allele for each variant, according to build 38 of the Human Genome sequence by the Human Genome Reference Consortium; coding DNA and protein changes are provided according to the Human Genome Variation Society nomenclature, and refer to three CD109 transcripts annotated in the in the Ensembl database (URL: world wide at "useast.ensembl.org/index.html"); annotations on these three transcripts are reported in the table in the following order: ENST00000287097:ENST00000422508:ENST00000437994):

| Variant | Coding DNA change | Protein change |
|---|---|---|
| 6:73696217:T:C | c.2T > C:c.2T > C:c.2T > C | p.Met1?:p.Met1?:p.Met1? |
| 6:73696249:C:T | c.34C > T:c.34C > T:c.34C > T | p.Leu12Phe:p.Leu12Phe:p.Leu12Phe |
| 6:73696250:T:G | c.35T > G:c.35T > G:c.35T > G | p.Leu12Arg:p.Leu12Arg:p.Leu12Arg |
| 6:73696250:TC:T | c.37delC:c.37delC:c.37delC | p.Leu13fs:p.Leu13fs:p.Leu13fs |
| 6:73697404:C:CG | c.81dupG:c.81dupG:c.81dupG | p.Phe28fs:p.Phe28fs:p.Phe28fs |
| 6:73697413:G:GT | c.89dupT:c.89dupT:c.89dupT | p.Thr31fs:p.Thr31fs:p.Thr31fs |
| 6:73697434:A:G | c.109A > G:c.109A > G:c.109A > G | p.Arg37Gly:p.Arg37Gly:p.Arg37Gly |
| 6:73697459:G:T | c.134G > T:c.134G > T:c.134G > T | p.Gly45Val:p.Gly45Val:p.Gly45Val |
| 6:73697504:C:T | c.179C > T:c.179C > T:c.179C > T | p.Ala60Val:p.Ala60Val:p.Ala60Val |
| 6:73697506:G:T | c.181G > T:c.181G > T:c.181G > T | p.Glu61*:p.Glu61*:p.Glu61* |
| 6:73697515:A:T | c.190A > T:c.190A > T:c.190A > T | p.Lys64*:p.Lys64*:p.Lys64* |
| 6:73697534:CTG:C | c.211_212delGT:c.211_212delGT:c.211_212delGT | p.Val71fs:p.Val71fs:p.Val71fs |
| 6:73723265:C:T | c.262C > T:c.262C > T:c.262C > T | p.Leu88Phe:p.Leu88Phe:p.Leu88Phe |
| 6:73723278:C:G | c.275C > G:c.275C > G:c.275C > G | p.Ser92*:p.Ser92*:p.Ser92* |
| 6:73730377:C:G | c.310C > G:c.310C > G | p.Leu104Val:p.Leu104Val |
| 6:73730398:C:T | c.331C > T:c.331C > T | p.Gln111*:p.Gln111* |
| 6:73730430:CT:C | c.365delT:c.365delT | p.Leu122fs:p.Leu122fs |

-continued

| Variant | Coding DNA change | Protein change |
|---|---|---|
| 6:73730456:C:CT | c.390dupT:c.390dupT | p.Val131fs:p.Val131fs |
| 6:73730474:A:G | c.407A > G:c.407A > G | p.Asp136Gly:p.Asp136Gly |
| 6:73730475:C:G | c.408C > G:c.408C > G | p.Asp136Glu:p.Asp136Glu |
| 6:73730512:C:T | c.445C > T:c.445C > T | p.Arg149Cys:p.Arg149Cys |
| 6:73730513:G:A | c.446G > A:c.446G > A | p.Arg149His:p.Arg149His |
| 6:73730513:G:T | c.446G > T:c.446G > T | p.Arg149Leu:p.Arg149Leu |
| 6:73730528:T:TA | c.461_462insA:c.461_462insA | p.Phe154fs:p.Phe154fs |
| 6:73736444:C:G | c.569C > G:c.338C > G:c.569C > G | p.Ser190Cys:p.Ser113Cys:p.Ser190Cys |
| 6:73736450:CT:C | c.579delT:c.348delT:c.579delT | p.Gln194fs:p.Gln117fs:p.Gln194fs |
| 6:73736460:A:AT | c.586dupT:c.355dupT:c.586dupT | p.Ser196fs:p.Ser119fs:p.Ser196fs |
| 6:73736462:C:G | c.587C > G:c.356C > G:c.587C > G | p.Ser196Cys:p.Ser119Cys:p.Ser196Cys |
| 6:73736471:C:T | c.596C > T:c.365C > T:c.596C > T | p.Pro199Leu:p.Pro122Leu:p.Pro199Leu |
| 6:73736491:A:G | c.616A > G:c.385A > G:c.616A > G | p.Ile206Val:p.Ile129Val:p.Ile206Val |
| 6:73756670:G:A | c.661G > A:c.430G > A:c.661G > A | p.Val221Ile:p.Val144Ile:p.Val221Ile |
| 6:73756683:G:T | c.673 + 1G > T:c.442 + 1G > T:c.673 + 1G > T | |
| 6:73758949:C:T | c.679C > T:c.448C > T:c.679C > T | p.Pro227Ser:p.Pro150Ser:p.Pro227Ser |
| 6:73758966:T:TTG | c.697_698insGT:c.466_467insGT:c.697_698insGT | p.Leu233fs:p.Leu156fs:p.Leu233fs |
| 6:73759007:TA:T | c.740delA:c.509delA:c.740delA | p.Asn247fs:p.Asn170fs:p.Asn247fs |
| 6:73759013:G:A | c.743G > A:c.512G > A:c.743G > A | p.Gly248Asp:p.Gly171Asp:p.Gly248Asp |
| 6:73759024:G:T | c.754G > T:c.523G > T:c.754G > T | p.Ala252Ser:p.Ala175Ser:p.Ala252Ser |
| 6:73759025:C:A | c.755C > A:c.524C > A:c.755C > A | p.Ala252Glu:p.Ala175Glu:p.Ala252Glu |
| 6:73759026:AAAGT:A | c.757_758 + 2delAAGT:c.526_527 + 2delAAGT:c.757_758 + 2delAAGT | p.Lys253fs:p.Lys176fs:p.Lys253fs |
| 6:73759029:G:T | c.758 + 1G > T:c.527 + 1G > T:c.758 + 1G > T | |
| 6:73762393:TG:T | c.771delG:c.540delG:c.771delG | p.Lys258fs:p.Lys181fs:p.Lys258fs |
| 6:73762396:GA:G | c.773delA:c.542delA:c.773delA | p.Lys258fs:p.Lys181fs:p.Lys258fs |
| 6:73762400:C:T | c.775C > T:c.544C > T:c.775C > T | p.Pro259Ser:p.Pro182Ser:p.Pro259Ser |
| 6:73762403:G:A | c.778G > A:c.547G > A:c.778G > A | p.Val260Met:p.Val183Met:p.Val260Met |
| 6:73762409:G:A | c.784G > A:c.553G > A:c.784G > A | p.Gly262Arg:p.Gly185Arg:p.Gly262Arg |
| 6:73762479:AG:A | c.844delG:c.613delG:c.844delG | p.Thr283fs:p.Thr206fs:p.Thr283fs |
| 6:73762481:G:A | c.855 + 1G > A:c.624 + 1G > A:c.855 + 1G > A | |
| 6:73762796:AT:A | c.913delT:c.682delT:c.913delT | p.Ser305fs:p.Ser228fs:p.Ser305fs |
| 6:73762870:GA:G | c.987delA:c.756delA:c.987delA | p.Glu329fs:p.Glu252fs:p.Glu329fs |
| 6:73762882:G:A | c.997G > A:c.766G > A:c.997G > A | p.Gly333Ser:p.Gly256Ser:p.Gly333Ser |
| 6:73762882:G:T | c.997G > T:c.766G > T:c.997G > T | p.Gly333Cys:p.Gly256Cys:p.Gly333Cys |
| 6:73763574:AG:A | c.998-1delG:c.767-ldelG:c.998-1delG | |
| 6:73763575:G:A | c.998-1G > A:c.767-1G > A:c.998-1G > A | |
| 6:73763575:G:C | c.998-1G > C:c.767-1G > C:c.998-1G > C | |
| 6:73763576:G:A | c.998G > A:c.767G > A:c.998G > A | p.Gly333Asp:p.Gly256Asp:p.Gly333Asp |
| 6:73763624:A:T | c.1046A > T:c.815A > T:c.1046A > T | p.Tyr349Phe:p.Tyr272Phe:p.Tyr349Phe |
| 6:73763629:A:AT | c.1053dupT:c.822dupT:c.1053dupT | p.Glu352fs:p.Glu275fs:p.Glu352fs |
| 6:73763662:C:A | c.1084C > A:c.853C > A:c.1084C > A | p.Pro362Thr:p.Pro285Thr:p.Pro362Thr |
| 6:73763664:ATC:A | c.1091_1092delTC:c.860_861delTC:c.1091_1092delTC | p.Leu364fs:p.Leu287fs:p.Leu364fs |
| 6:73763666:C:A | c.1088C > A:c.857C > A:c.1088C > A | p.Ser363Tyr:p.Ser286Tyr:p.Ser363Tyr |
| 6:73765929:G:T | c.1108-1G > T:c.877-1G > T:c.1108-1G > T | |
| 6:73765949:A:G | c.1127A > G:c.896A > G:c.1127A > G | p.Asp376Gly:p.Asp299Gly:p.Asp376Gly |
| 6:73765957:C:T | c.1135C > T:c.904C > T:c.1135C > T | p.Gln379*:p.Gln302*:p.Gln379* |
| 6:73765969:G:T | c.1147G > T:c.916G > T:c.1147G > T | p.Glu383*:p.Glu306*:p.Glu383* |
| 6:73766146:C:T | c.1324C > T:c.1093C > T:c.1324C > T | p.Gln442*:p.Gln365*:p.Gln442* |
| 6:73766155:G:A | c.1332 + 1G > A:c.1101 + 1G > A:c.1332 + 1G > A | |
| 6:73766825:T:C | c.1399T > C:c.1168T > C:c.1399T > C | p.Tyr467His:p.Tyr390His:p.Tyr467His |
| 6:73766830:C:G | c.1404C > G:c.1173C > G:c.1404C > G | p.Ile468Met:p.Ile391Met:p.Ile468Met |
| 6:73766841:CAA:C | c.1416_1417delAA:c.1185_1186delAA:c.1416_1417delAA | p.Asp474fs:p.Asp397fs:p.Asp474fs |
| 6:73766861:G:A | c.1434 + 1G > A:c.1203 + 1G > A:c.1434 + 1G > A | |
| 6:73766946:A:G | c.1435-2A > G:c.1204-2A > G:c.1435-2A > G | |
| 6:73766951:G:A | c.1438G > A:c.1207G > A:c.1438G > A | p.Gly480Arg:p.Gly403Arg:p.Gly480Arg |
| 6:73766987:C:T | c.1474C > T:c.1243C > T:c.1474C > T | p.Arg492*:p.Arg415*:p.Arg492* |
| 6:73767006:A:C | c.1493A > C:c.1262A > C:c.1493A > C | p.Tyr498Ser:p.Tyr421Ser:p.Tyr498Ser |
| 6:73767006:A:G | c.1493A > G:c.1262A > G:c.1493A > G | p.Tyr498Cys:p.Tyr421Cys:p.Tyr498Cys |
| 6:73767012:T:C | c.1497 + 2T > C:c.1266 + 2T > C:c.1497 + 2T > C | |
| 6:73768070:C:T | c.1513C > T:c.1282C > T:c.1513C > T | p.Gln505*:p.Gln428*:p.Gln505* |
| 6:73768071:A:C | c.1514A > C:c.1283A > C:c.1514A > C | p.Gln505Pro:p.Gln428Pro:p.Gln505Pro |
| 6:73768110:C:CT | c.1556dupT:c.1325dupT:c.1556dupT | p.Leu519fs:p.Leu442fs:p.Leu519fs |
| 6:73768136:C:T | c.1579C > T:c.1348C > T:c.1579C > T | p.Pro527Ser:p.Pro450Ser:p.Pro527Ser |
| 6:73768137:C:T | c.1580C > T:c.1349C > T:c.1580C > T | p.Pro527Leu:p.Pro450Leu:p.Pro527Leu |
| 6:73768146:G:A | c.1589G > A:c.1358G > A:c.1589G > A | p.Cys530Tyr:p.Cys453Tyr:p.Cys530Tyr |
| 6:73768176:G:C | c.1619G > C:c.1388G > C:c.1619G > C | p.Gly540Ala:p.Gly463Ala:p.Gly540Ala |
| 6:73768176:G:T | c.1619G > T:c.1388G > T:c.1619G > T | p.Gly540Val:p.Gly463Val:p.Gly540Val |
| 6:73768178:G:A | c.1621G > A:c.1390G > A:c.1621G > A | p.Glu541Lys:p.Glu464Lys:p.Glu541Lys |
| 6:73768190:G:A | c.1633G > A:c.1402G > A:c.1633G > A | p.Asp545Asn:p.Asp468Asn:p.Asp545Asn |
| 6:73768197:T:TA | c.1645dupA:c.1414dupA:c.1645dupA | p.Ile549fs:p.Ile472fs:p.Ile549fs |
| 6:73768206:C:G | c.1649C > Gx.1418C > G:c.1649C > G | p.Pro550Arg:p.Pro473Arg:p.Pro550Arg |
| 6:73768232:G:C | c.1674 + 1G > C:c.1443 + 1G > C:c.1674 + 1G > C | |
| 6:73771427:A:G | c.1675-2A > G:c.1444-2A > G:c.1675-2A > G | |
| 6:73771428:G:T | c.1675-1G > T:c.1444-1G > T:c.1675-1G > T | |
| 6:73771463:C:T | c.1709C > T:c.1478C > T:c.1709C > T | p.Pro570Leu:p.Pro493Leu:p.Pro570Leu |
| 6:73771481:T:C | c.1727T > C:c.1496T > C:c.1727T > C | p.Leu576Pro:p.Leu499Pro:p.Leu576Pro |

-continued

| Variant | Coding DNA change | Protein change |
|---|---|---|
| 6:73771502:C:T | c.1748C > T:c.1517C > T:c.1748C > T | p.Pro583Leu:p.Pro506Leu:p.Pro583Leu |
| 6:73771508:C:T | c.1754C > T:c.1523C > T:c.1754C > T | p.Ser585Phe:p.Ser508Phe:p.Ser585Phe |
| 6:73771526:C:G | c.1772C > G:c.1541C > G:c.1772C > G | p.Ala591Gly:p.Ala514Gly:p.Ala591Gly |
| 6:73771538:G:A | c.1784G > A:c.1553G > A:c.1784G > A | p.Ser595Asn:p.Ser518Asn: p.Ser595Asn |
| 6:73771564:G:T | c.1810G > T:c.1579G > T:c.1810G > T | p.Asp604Tyr:p.Asp527Tyr:p.Asp604Tyr |
| 6:73780421:TA:T | c.1828-2delA:c.1597-2delA:c.1828-2delA | |
| 6:73780423:G:T | c.1828-1G > T:c.1597-1G > T:c.1828-1G > T | |
| 6:73780425:TG:T | c.1831delG:c.1600delG:c.1831delG | p.Val611fs:p.Val534fs:p.Val611fs |
| 6:73780447:TA:T | c.1853delA:c.1622delA:c.1853delA | p.Asn618fs:p.Asn541fs:p.Asn618fs |
| 6:73780458:ATTAT:A | c.1866_1869delTTTA:c.1635_1638delTTTA: c.1866_1869delTTTA | p.Tyr622fs:p.Tyr545fs:p.Tyr622fs |
| 6:73780492:C:CT | c.1899dupT:c.1668dupT:c.1899dupT | p.Gln634fs:p.Gln557fs:p.Gln634fs |
| 6:73781262:T:C | c.1906T > C:c.1675T > C:c.1906T > C | p.Cys636Arg:p.Cys559Arg:p.Cys636Arg |
| 6:73781268:C:T | c.1912C > T:c.1681C > T:c.1912C > T | p.Leu638Phe:p.Leu561Phe:p.Leu638Phe |
| 6:73781269:T:A | c.1913T > A:c.1682T > A:c.1913T > A | p.Leu638His:p.Leu561His:p.Leu638His |
| 6:73781273:G:A | c.1917G > A:c.1686G > A:c.1917G > A | p.Trp639*:p.Trp562*:p.Trp639* |
| 6:73781320:G:A | c.1963 + 1G > A:c.1732 + 1G > A:c.1963 + 1G > A | |
| 6:73781320:GT:G | c.1963 + 2delT:c.1732 + 2delT:c.1963 + 2delT | |
| 6:73782612:A:C | c.1964-2A > C:c.1733-2A > C:c.1964-2A > C | |
| 6:73782612:AG:A | c.1964-1delG:c.1733-1delG:c.1964-1delG | |
| 6:73782618:CAA:C | c.1969_1970delAA:c.1738_1739delAA: c.1969_1970delAA | p.Asn657fs:p.Asn580fs:p.Asn657fs |
| 6:73782625:G:T | c.1975G > T:c.1744G > T:c.1975G > T | p.Glu659*:p.Glu582*:p.Glu659* |
| 6:73782696:C:CA | c.2047dupA:c.1816dupA:c.2047dupA | p.Ser683fs:p.Ser606fs:p.Ser683fs |
| 6:73782709:C:G | c.2059C > G:c.1828C > G:c.2059C > G | p.Arg687Gly:p.Arg610Gly:p.Arg687Gly |
| 6:73782709:C:T | c.2059C > T:c.1828C > T:c.2059C > T | p.Arg687*:p.Arg610*:p.Arg687* |
| 6:73782716:A:AT | c.2070dupT:c.1839dupT:c.2070dupT | p.Pro691fs:p.Pro614fs:p.Pro691fs |
| 6:73782718:T:C | c.2068T > C:c.1837T > C:c.2068T > C | p.Phe690Leu:p.Phe613Leu:p.Phe690Leu |
| 6:73783720:C:T | c.2119C > T:c.1888C > T:c.2119C > T | p.Gln707*:p.Gln630*:p.Gln707* |
| 6:73783723:G:T | c.2122G > T:c.1891G > T:c.2122G > T | p.Glu708*:p.Glu631*:p.Glu708* |
| 6:73783760:G:A | c.2159G > A:c.1928G > A:c.2159G > A | p.Trp720*:p.Trp643*:p.Trp720* |
| 6:73783761:G:C | c.2160G > C:c.1929G > C:c.2160G > C | p.Trp720Cys:p.Trp643Cys:p.Trp720Cys |
| 6:73783761:G:T | c.2160G > T:c.1929G > T:c.2160G > T | p.Trp720Cys:p.Trp643Cys:p.Trp720Cys |
| 6:73783765:G:T | c.2164G > T:c.1933G > T:c.2164G > T | p.Ala722Ser:p.Ala645Ser:p.Ala722Ser |
| 6:73783771:G:T | c.2170G > T:c.1939G > T:c.2170G > T | p.Gly724Cys:p.Gly647Cys:p.Gly724Cys |
| 6:73783772:GT:G | c.2175delT:c.1944delT:c.2175delT | p.Phe725fs:p.Phe648fs:p.Phe725fs |
| 6:73783783:T:C | c.2182T > C:c.1951T > C:c.2182T > C | p.Ser728Pro:p.Ser651Pro:p.Ser728Pro |
| 6:73783784:C:CT | c.2184dupT:c.1953dupT:c.2184dupT | p.Glu729fs:p.Glu652fs:p.Glu729fs |
| 6:73783795:6:C | c.2194G > C:c.1963G > C:c.2194G > C | p.Gly732Arg:p.Gly655Arg:p.Gly732Arg |
| 6:73783796:G:A | c.2195G > A:c.1964G > A:c.2195G > A | p.Gly732Asp:p.Gly655Asp:p.Gly732Asp |
| 6:73783810:AC:A | c.2210delC:c.1979delC:c.2210delC | p.Thr737fs:p.Thr660fs:p.Thr737fs |
| 6:73783817:C:T | c.2216C > T:c.1985C > T:c.2216C > T | p.Pro739Leu:p.Pro662Leu:p.Pro739Leu |
| 6:73785363:G:A | c.2224-1G > A:c.1993-1G > A:c.2224-1G > A | |
| 6:73785364:C:A | c.2224C > A:c.1993C > A:c.2224C > A | p.Leu742Ile:p.Leu665Ile:p.Leu742Ile |
| 6:73785364:CT:C | c.2225delT:c.1994delT:c.2225delT | p.Leu742fs:p.Leu665fs:p.Leu742fs |
| 6:73785365:T:C | c.2225T > C:c.1994T > C:c.2225T > C | p.Leu742Pro:p.Leu665Pro:p.Leu742Pro |
| 6:73785382:T:C | c.2242T > C:c.2011T > C:c.2242T > C | p.Phe748Leu:p.Phe671Leu:p.Phe748Leu |
| 6:73785385:T:C | c.2245T > C:c.2014T > C:c.2245T > C | p.Phe749Leu:p.Phe672Leu:p.Phe749Leu |
| 6:73785408:C:A | c.2268C > A:c.2037C > A:c.2268C > A | p.Tyr756*:p.Tyr679*:p.Tyr756* |
| 6:73785408:C:G | c.2268C > G:c.2037C > G:c.2268C > G | p.Tyr756*:p.Tyr679*:p.Tyr756* |
| 6:73785410:C:G | c.2270C > G:c.2039C > G:c.2270C > G | p.Ser757Cys:p.Ser680Cys:p.Ser757Cys |
| 6:73785419:G:A | c.2279G > A:c.2048G > A:c.2279G > A | p.Arg760Lys:p.Arg683Lys:p.Arg760Lys |
| 6:73785454:A:T | c.2314A > T:c.2083A > T:c.2314A > T | p.Asn772Tyr:p.Asn695Tyr:p.Asn772Tyr |
| 6:73785458:A:G | c.2318A > G:c.2087A > G:c.2318A > G | p.Tyr773Cys:p.Tyr696Cys:p.Tyr773Cys |
| 6:73787237:A:T | c.2341A > T:c.2110A > T:c.2341A > T | p.Lys781*:p.Lys704*:p.Lys781* |
| 6:73787241:T:A | c.2345T > A:c.2114T > A:c.2345T > A | p.Val782Glu:p.Val705Glu:p.Val782Glu |
| 6:73787264:T:G | c.2368T > G:c.2137T > G:c.2368T > G | p.Phe790Val:p.Phe713Val:p.Phe790Val |
| 6:73787271:T:G | c.2375T > G:c.2144T > G:c.2375T > G | p.Ile792Ser:p.Ile715Ser:p.Ile792Ser |
| 6:73787330:A:T | c.2434A > T:c.2203A > T:c.2434A > T | p.Ser812Cys:p.Ser735Cys:p.Ser812Cys |
| 6:73787338:TG:T | c.2446delG:c.2215delG:c.2446delG | p.Ala816fs:p.Ala739fs:p.Ala816fs |
| 6:73787366:C:T | c.2470C > T:c.2239C > T:c.2470C > T | p.Pro824Ser:p.Pro747Ser:p.Pro824Ser |
| 6:73787378:G:T | c.2482G > T:c.2251G > T:c.2482G > T | p.Gly828*:p.Gly751*:p.Gly828* |
| 6:73787379:G:A | c.2483G > A:c.2252G > A:c.2483G > A | p.Gly828Glu:p.Gly751Glu:p.Gly828Glu |
| 6:73787394:C:T | c.2498C > T:c.2267C > T:c.2498C > T | p.Thr833Ile:p.Thr756Ile:p.Thr833Ile |
| 6:73787447:G:A | c.2551G > A:c.2320G > A:c.2551G > A | p.Val851Ile:p.Val774Ile:p.Val851Ile |
| 6:73787448:T:TA | c.2555dupA:c.2324dupA:c.2555dupA | p.Ala853fs:p.Ala776fs:p.Ala853fs |
| 6:73787452:G:T | c.2556G > T:c.2325G > T:c.2556G > T | p.Lys852Asn:p.Lys775Asn:p.Lys852Asn |
| 6:73788469:C:G | c.2558C > G:c.2327C > G:c.2558C > G | p.Ala853Gly:p.Ala776Gly:p.Ala853Gly |
| 6:73788503:CT:C | c.2594delT:c.2363delT:c.2594delT | p.Leu865fs:p.Leu788fs:p.Leu865fs |
| 6:73788564:C:T | c.2653C > T:c.2422C > T:c.2653C > T | p.Pro885Ser:p.Pro808Ser:p.Pro885Ser |
| 6:73788565:C:T | c.2654C > T:c.2423C > T:c.2654C > T | p.Pro885Leu:p.Pro808Leu:p.Pro885Leu |
| 6:73788582:G:A | c.2671G > A:c.2440G > A:c.2671G > A | p.Gly891Ser:p.Gly814Ser:p.Gly891Ser |
| 6:73788588:G:T | c.2677G > T:c.2446G > T:c.2677G > T | p.Glu893*:p.Glu816*:p.Glu893* |
| 6:73788601:T:TC | c.2691dupC:c.2460dupC:c.2691dupC | p.Thr898fs:p.Thr821fs:p.Thr898fs |
| 6:73792622:CCAGGAG:C | c.2702-3_2704delCAGGAG:c.2471-3_2473delCAGGAG:c.2702-3_2704delCAGGAG | p.Gly901del:p.Gly824del:p.Gly901del |

-continued

| Variant | Coding DNA change | Protein change |
|---|---|---|
| 6:73792628:G:C | c.2704G > C:c.2473G > C:c.2704G > C | p.Asp902His:p.Asp825His:p.Asp902His |
| 6:73792629:A:T | c.2705A > T:c.2474A > T:c.2705A > T | p.Asp902Val:p.Asp825Val:p.Asp902Val |
| 6:73792637:G:T | c.2713G > T:c.2482G > T:c.2713G > T | p.Gly905Cys:p.Gly828Cys:p.Gly905Cys |
| 6:73792686:G:T | c.2762G > T:c.2531G > T:c.2762G > T | p.Cys921Phe:p.Cys844Phe:p.Cys921Phe |
| 6:73792688:G:A | c.2764G > A:c.2533G > A:c.2764G > A | p.Gly922Ser:p.Gly845Ser:p.Gly922Ser |
| 6:73792703:A:C | c.2779A > C:c.2548A > C:c.2779A > C | p.Ile927Leu:p.Ile850Leu:p.Ile927Leu |
| 6:73792712:G:T | c.2788G > T:c.2557G > T:c.2788G > T | p.Ala930Ser:p.Ala853Ser:p.Ala930Ser |
| 6:73792718:A:G | c.2794A > G:c.2563A > G:c.2794A > G | p.Asn932Asp:p.Asn855Asp:p.Asn932Asp |
| 6:73792736:T:A | c.2812T > A:c.2581T > A:c.2812T > A | p.Tyr938Asn:p.Tyr861Asn:p.Tyr938Asn |
| 6:73792754:C:T | c.2830C > T:c.2599C > T:c.2830C > T | p.Gln944*:p.Gln867*:p.Gln944* |
| 6:73792775:G:GA | c.2856dupA:c.2625dupA:c.2856dupA | p.Ala953fs:p.Ala876fs:p.Ala953fs |
| 6:73792780:A:C | c.2856A > C:c.2625A > C:c.2856A > C | p.Lys952Asn:p.Lys875Asn:p.Lys952Asn |
| 6:73792782:C:A | c.2858C > A:c.2627C > A:c.2858C > A | p.Ala953Asp:p.Ala876Asp:p.Ala953Asp |
| 6:73792784:C:CT | c.2863dupT:c.2632dupT:c.2863dupT | p.Ser955fs:p.Ser878fs:p.Ser955fs |
| 6:73792799:C:T | c.2875C > T:c.2644C > T:c.2875C > T | p.Gln959*:p.Gln882*:p.Gln959* |
| 6:73792802:G:A | c.2878G > A:c.2647G > A:c.2878G > A | p.Gly960Ser:p.Gly883Ser:p.Gly960Ser |
| 6:73803231:G:A | c.2890G > A:c.2659G > A:c.2890G > A | p.Glu964Lys:p.Glu887Lys:p.Glu964Lys |
| 6:73803253:A:G | c.2912A > G:c.2681A > G:c.2912A > G | p.Asp971Gly:p.Asp894Gly:p.Asp971Gly |
| 6:73803256:G:A | c.2915G > A:c.2684G > A:c.2915G > A | p.Gly972Asp:p.Gly895Asp:p.Gly972Asp |
| 6:73803256:G:T | c.2915G > T:c.2684G > T:c.2915G > T | p.Gly972Val:p.Gly895Val:p.Gly972Val |
| 6:73803264:A:G | c.2923A > G:c.2692A > G:c.2923A > G | p.Ser975Gly:p.Ser898Gly:p.Ser975Gly |
| 6:73803298:C:T | c.2957C > T:c.2726C > T:c.2957C > T | p.Thr986Ile:p.Thr909Ile:p.Thr986Ile |
| 6:73803301:G:A | c.2960G > A:c.2729G > A:c.2960G > A | p.Trp987*:p.Trp910*:p.Trp987* |
| 6:73806844:G:T | c.2961G > T:c.2730G > T:c.2961G > T | p.Trp987Cys:p.Trp910Cys:p.Trp987Cys |
| 6:73806855:T:C | c.2972T > C:c.2741T > C:c.2972T > C | p.Phe991Ser:p.Phe914Ser:p.Phe991Ser |
| 6:73806870:T:G | c.2987T > G:c.2756T > G:c.2987T > G | p.Phe996Cys:p.Phe919Cys:p.Phe996Cys |
| 6:73806897:T:C | c.3014T > C:c.2783T > C:c.3014T > C | p.Ile1005Thr:p.Ile928Thr:p.Ile1005Thr |
| 6:73806902:C:T | c.3019C > T:c.2788C > T:c.3019C > T | p.Gln1007*:p.Gln930*:p.Gln1007* |
| 6:73806908:G:A | c.3025G > A:c.2794G > A:c.3025G > A | p.Val1009Met:p.Val932Met:p.Val1009Met |
| 6:73806921:C:CAT | c.3040_3041dupTA:c.2809_2810dupTA: c.3040_3041dupTA | p.Trp1016fs:p.Trp939fs:p.Trp1016fs |
| 6:73806956:G:A | c.3073G > A:c.2842G > A:c.3073G > A | p.Gly1025Ser:p.Gly948Ser:p.Gly1025Ser |
| 6:73806956:G:C | c.3073G > C:c.2842G > C:c.3073G > C | p.Gly1025Arg:p.Gly948Arg:p.Gly1025Arg |
| 6:73806981:T:A | c.3098T > A:c.2867T > A:c.3098T > A | p.Val1033Glu:p.Val956Glu:p.Val1033Glu |
| 6:73806984:T:G | c.3101T > G:c.2870T > G:c.3101T > G | p.Ile1034Ser:p.Ile957Ser:p.Ile1034Ser |
| 6:73806987:A:T | c.3104A > T:c.2873A > T:c.3104A > T | p.His1035Leu:p.His958Leu:p.His1035Leu |
| 6:73807002:G:A | c.3119G > A:c.2888G > A:c.3119G > A | p.Gly1040Asp:p.Gly963Asp:p.Gly1040Asp |
| 6:73807005:G:A | c.3122G > A:c.2891G > A:c.3122G > A | p.Gly1041Asp:p.Gly964Asp:p.Gly1041Asp |
| 6:73807029:C:G | c.3146C > G:c.2915C > G:c.3146C > G | p.Thr1049Arg:p.Thr972Arg:p.Thr1049Arg |
| 6:73807034:T:A | c.3151T > A:c.2920T > A:c.3151T > A | p.Tyr1051Asn:p.Tyr974Asn:p.Tyr1051Asn |
| 6:73807035:A:G | c.3152A > G:c.2921A > G:c.3152A > G | p.Tyr1051Cys:p.Tyr974Cys:p.Tyr1051Cys |
| 6:73807035:A:T | c.3152A > T:c.2921A > T:c.3152A > T | p.Tyr1051Phe:p.Tyr974Phe:p.Tyr1051Phe |
| 6:73808113:T:G | c.3220T > G:c.2989T > G:c.3220T > G | p.Phe1074Val:p.Phe997Val:p.Phe1074Val |
| 6:73808146:G:A | c.3253G > A:c.3022G > A:c.3253G > A | p.Asp1085Asn:p.Asp1008Asn:p.Asp1085Asn |
| 6:73808153:A:T | c.3260A > T:c.3029A > T:c.3260A > T | p.Tyr1087Phe:p.Tyr1010Phe:p.Tyr1087Phe |
| 6:73808156:C:T | c.3263C > T:c.3032C > T:c.3263C > T | p.Thr1088Ile:p.Thr1011Ile:p.Thr1088Ile |
| 6:73808159:T:C | c.3266T > C:c.3035T > C:c.3266T > C | p.Leu1089Pro:p.Leu1012Pro:p.Leu1089Pro |
| 6:73808176:G:T | c.3283G > T:c.3052G > T:c.3283G > T | p.Ala1095Ser:p.Ala1018Ser:p.Ala1095Ser |
| 6:73808244:AGAAGGTAAT:A | c.3352_3355 + 5delGAAGGTAAT:c.3121_3124 + 5delGAAGGTAAT:c.3352_3355 + 5delGAAGGTAAT | p.Glu1118fs:p.Glu1041fs:p.Glu1118fs |
| 6:73808245:GA:G | c.3354delA:c.3123delA:c.3354delA | p.Gly1119fs:p.Gly1042fs:p.Gly1119fs |
| 6:73809981:CA:C | c.3356-2delA:c.3125-2delA:c.3356-2delA | |
| 6:73809992:C:T | c.3364C > T:c.3133C > T:c.3364C > T | p.Gln112*:p.Gln1045*:p.Gln1122* |
| 6:73809995:T:A | c.3367T > A:c.3136T > A:c.3367T > A | p.Phe1123Ile:p.Phe1046Ile:p.Phe1123Ile |
| 6:73810034:C:A | c.3406C > A:c.3175C > A:c.3406C > A | p.Gln1136Lys:p.Gln1059Lys:p.Gln1136Lys |
| 6:73810044:C:T | c.3416C > T:c.3185C > T:c.3416C > T | p.Ser1139Phe:p.Ser1062Phe:p.Ser1139Phe |
| 6:73810054:T:G | c.3426T > G:c.3195T > G:c.3426T > G | p.Ile1142Met:p.Ile1065Met:p.Ile1142Met |
| 6:73810089:T:TA | c.3462dupA:c.3231dupA:c.3462dupA | p.Gln1155fs:p.Gln1078fs:p.Gln1155fs |
| 6:73810106:G:A | c.3478G > A:c.3247G > A:c.3478G > A | p.Glu1160Lys:p.Glu1083Lys:p.Glu1160Lys |
| 6:73810143:G:T | c.3515G > T:c.3284G > T:c.3515G > T | p.Arg1172Ile:p.Arg1095Ile:p.Arg1172Ile |
| 6:73810154:G:A | c.3526G > A:c.3295G > A:c.3526G > A | p.Gly1176Ser:p.Gly1099Ser:p.Gly1176Ser |
| 6:73810155:G:A | c.3527G > A:c.3296G > A:c.3527G > A | p.Gly1176Asp:p.Gly1099Asp:p.Gly1176Asp |
| 6:73810155:G:C | c.3527G > C:c.3296G > C:c.3527G > C | p.Gly1176Ala:p.Gly1099Ala:p.Gly1176Ala |
| 6:73810155:G:T | c.3527G > T:c.3296G > T:c.3527G > T | p.Gly1176Val:p.Gly1099Val:p.Gly1176Val |
| 6:73810157:G:T | c.3529G > T:c.3298G > T:c.3529G > T | p.Gly1177Cys:p.Gly1100Cys:p.Gly1177Cys |
| 6:73810158:G:A | c.3530G > A:c.3299G > A:c.3530G > A | p.Gly1177Asp:p.Gly1100Asp:p.Gly1177Asp |
| 6:73810172:C:T | c.3544C > T:c.3313C > T:c.3544C > T | p.Gln1182*:p.Gln1105*:p.Gln1182* |
| 6:73810990:A:G | c.3547-2A > G:c.3316-2A > G:c.3547-2A > G | |
| 6:73810993:A:C | c.3548A > C:c.3317A > C:c.3548A > C | p.Asp1183Ala:p.Asp1106Ala:p.Asp1183Ala |
| 6:73811013:G:C | c.3568G > C:c.3337G > C:c.3568G > C | p.Ala1190Pro:p.Ala1113Pro:p.Ala1190Pro |
| 6:73811013:G:T | c.3568G > T:c.3337G > T:c.3568G > T | p.Ala1190Ser:p.Ala1113Ser:p.Ala1190Ser |
| 6:73811029:C:A | c.3584C > A:c.3353C > A:c.3584C > A | p.Ala1195Glu:p.Ala1118Glu:p.Ala1195Glu |
| 6:73811051:GA:G | c.3607delA:c.3376delA:c.3607delA | p.Thr1203fs:p.Thr1126fs:p.Thr1203fs |
| 6:73811110:T:C | c.3665T > C:c.3434T > C | p.Ile1222Thr:p.Ile1145Thr |
| 6:73811120:CA:C | c.3677delA:c.3446delA | p.Asn1226fs:p.Asn1149fs |
| 6:73811121:A:T | c.3676A > T:c.3445A > T | p.Asn1226Tyr:p.Asn1149Tyr |
| 6:73812271:G:A | c.3768 + 1G > A:c.3537 + 1G > A:c.3717 + 1G > A | |

-continued

| Variant | Coding DNA change | Protein change |
|---|---|---|
| 6:73812271:G:C | c.3768 + 1G > C:c.3537 + 1G > C:c.3717 + 1G > C | |
| 6:73812271:G:T | c.3768 + 1G > T:c.3537 + 1G > T:c.3717 + 1G > T | |
| 6:73812272:T:A | c.3768 + 2T > A:c.3537 + 2T > A:c.3717 + 2T > A | |
| 6:73814990:GTA:G | c.3783_3784delTA:c.3552_3553delTA:c.3732_3733delTA | p.Tyr1261fs:p.Tyr1184fs:p.Tyr1244fs |
| 6:73814994:A:G | c.3782A > G:c.3551A > G:c.3731A > G | p.Tyr1261Cys:p.Tyr1184Cys:p.Tyr1244Cys |
| 6:73815026:C:T | c.3814C > T:c.3583C > T:c.3763C > T | p.Arg1272*:p.Arg1195*:p.Arg1255* |
| 6:73815098:CAT:C | c.3887_3888delAT:c.3656_3657delAT:c.3836_3837delAT | p.His1296fs:p.His1219fs:p.His1279fs |
| 6:73815113:G:A | c.3901G > A:c.3670G > A:c.3850G > A | p.Val1301Met:p.Val1224Met:p.Val1284Met |
| 6:73815117:G:A | c.3905G > A:c.3674G > A:c.3854G > A | p.Cys1302Tyr:p.Cys1225Tyr:p.Cys1285Tyr |
| 6:73818386:A:G | c.3912-2A > G:c.3681-2A > G:c.3861-2A > G | |
| 6:73818413:A:G | c.3937A > G:c.3706A > G:c.3886A > G | p.Met1313Val:p.Met1236Val:p.Met1296Val |
| 6:73818415:G:C | c.3939G > C:c.3708G > C:c.3888G > C | p.Met1313Ile:p.Met1236Ile:p.Met1296Ile |
| 6:73818417:C:A | c.3941C > A:c.3710C > A:c.3890C > A | p.Ala1314Asp:p.Ala1237Asp:p.Ala1297Asp |
| 6:73818423:T:G | c.3947T > G:c.3716T > G:c.3896T > G | p.Met1316Arg:p.Met1239Arg:p.Met1299Arg |
| 6:73818425:G:A | c.3949G > A:c.3718G > A:c.3898G > A | p.Glu1317Lys:p.Glu1240Lys:p.Glu1300Lys |
| 6:73818443:G:T | c.3967G > T:c.3736G > T:c.3916G > T | p.Gly1323Cys:p.Gly1246Cys:p.Gly1306Cys |
| 6:73818450:TG:T | c.3976delG:c.3745delG:c.3925delG | p.Val1326fs:p.Val1249fs:p.Val1309fs |
| 6:73818456:CT:C | c.3982delT:c.3751delT:c.3931delT | p.Ser1328fs:p.Ser1251fs:p.Ser1311fs |
| 6:73818479:G:T | c.4003G > T:c.3772G > T:c.3952G > T | p.Glu1335*:p.Glu1258*:p.Glu1318* |
| 6:73820459:A:G | c.4060-2A > G:c.3829-2A > G:c.4009-2A > G | |
| 6:73820480:G:C | c.4079G > C:c.3848G > C:c.4028G > C | p.Cys1360Ser:p.Cys1283Ser:p.Cys1343Ser |
| 6:73820528:A:T | c.4127A > T:c.3896A > T:c.4076A > T | p.Asp1376Val:p.Asp1299Val:p.Asp1359Val |
| 6:73820537:T:C | c.4136T > C:c.3905T > C:c.4085T > C | p.Val1379Ala:p.Val1302Ala:p.Val1362Ala |
| 6:73820549:A:C | c.4148A > C:c.3917A > C:c.4097A > C | p.Asp1383Ala:p.Asp1306Ala:p.Asp1366Ala |
| 6:73820549:A:G | c.4148A > G:c.3917A > G:c.4097A > G | p.Asp1383Gly:p.Asp1306Gly:p.Asp1366Gly |
| 6:73820549:AT:A | c.4150delT:c.3919delT:c.4099delT | p.Tyr1384fs:p.Tyr1307fs:p.Tyr1367fs |
| 6:73823456:A:G | c.4163-2A > G:c.3932-2A > G:c.4112-2A > G | |
| 6:73823473:GA:G | c.4180delA:c.3949delA:c.4129delA | p.Ser1394fs:p.Ser1317fs:p.Ser1377fs |
| 6:73823481:A:G | c.4186A > G:c.3955A > G:c.4135A > G | p.Asn1396Asp:p.Asn1319Asp:p.Asn1379Asp |
| 6:73823485:C:G | c.4190C > G:c.3959C > G:c.4139C > G | p.Ser1397Cys:p.Ser1320Cys:p.Ser1380Cys |
| 6:73823530:GC:G | c.4236delC:c.4005delC:c.4185delC | p.Cys1413fs:p.Cys1336fs:p.Cys1396fs |
| 6:73823534:C:A | c.4239C > A:c.4008C > A:c.4188C > A | p.Cys1413*:p.Cys1336*:p.Cys1396* |
| 6:73823583:A:AT | c.4293dupT:c.4062dupT:c.4242dupT | p.Ile1432fs:p.Ile1355fs:p.Ile1415fs |
| 6:73823592:TTC:T | c.4299_4300delCT:c.4068_4069delCT:c.4248_4249delCT | p.Phe1433fs:p.Phe1356fs:p.Phe1416fs |
| 6:73823612:C:A | c.4317C > A:c.4086C > A:c.4266C > A | p.Tyr1439*:p.Tyr1362*:p.Tyr1422* |

The present disclosure also provides methods of detecting the presence or absence of a CD109 missense variant nucleic acid molecule (i.e., a genomic nucleic acid molecule, an mRNA molecule, or a cDNA molecule produced from an mRNA molecule) encoding a CD109 predicted loss-of-function polypeptide in a biological sample from a subject. It is understood that gene sequences within a population and mRNA molecules encoded by such genes can vary due to polymorphisms such as single-nucleotide polymorphisms. The sequences provided herein for the CD109 variant genomic nucleic acid molecule, CD109 variant mRNA molecule, and CD109 variant cDNA molecule are only exemplary sequences. Other sequences for the CD109 variant genomic nucleic acid molecule, variant mRNA molecule, and variant cDNA molecule are also possible.

The biological sample can be derived from any cell, tissue, or biological fluid from the subject. The biological sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The biological sample used in the methods disclosed herein can vary based on the assay format, nature of the detection method, and the tissues, cells, or extracts that are used as the sample. A biological sample can be processed differently depending on the assay being employed. For example, when detecting any CD109 missense variant nucleic acid molecule encoding a CD109 predicted loss-of-function polypeptide, preliminary processing designed to isolate or enrich the biological sample for the genomic DNA can be employed. A variety of techniques may be used for this purpose. When detecting the level of any CD109 variant mRNA molecule, different techniques can be used enrich the biological sample with mRNA molecules. Various methods to detect the presence or level of an mRNA molecule or the presence of a particular variant genomic DNA locus can be used.

In some embodiments, detecting a CD109 missense variant nucleic acid molecule encoding a CD109 predicted loss-of-function polypeptide in a subject comprises performing a sequence analysis on a biological sample obtained from the subject to determine whether a CD109 genomic nucleic acid molecule in the biological sample, and/or a CD109 mRNA molecule in the biological sample, and/or a CD109 cDNA molecule produced from an mRNA molecule in the biological sample, comprises one or more variations that cause a loss-of-function (partial or complete) or are predicted to cause a loss-of-function (partial or complete).

In some embodiments, the methods of detecting the presence or absence of a CD109 missense variant nucleic acid molecule encoding a CD109 predicted loss-of-function polypeptide (such as, for example, a genomic nucleic acid molecule, an mRNA molecule, and/or a cDNA molecule produced from an mRNA molecule) in a subject, comprise performing an assay on a biological sample obtained from the subject. The assay determines whether a nucleic acid molecule in the biological sample comprises a particular nucleotide sequence.

In some embodiments, the biological sample comprises a cell or cell lysate. Such methods can further comprise, for example, obtaining a biological sample from the subject comprising a CD109 genomic nucleic acid molecule or mRNA molecule, and if mRNA, optionally reverse transcribing the mRNA into cDNA. Such assays can comprise, for example determining the identity of these positions of the particular CD109 nucleic acid molecule. In some embodiments, the method is an in vitro method.

In some embodiments, the determining step, detecting step, or sequence analysis comprises sequencing at least a portion of the nucleotide sequence of the CD109 genomic nucleic acid molecule, the CD109 mRNA molecule, or the CD109 cDNA molecule in the biological sample, wherein the sequenced portion comprises one or more variations that cause a loss-of-function (partial or complete) or are predicted to cause a loss-of-function (partial or complete).

In some embodiments, the assay comprises sequencing the entire nucleic acid molecule. In some embodiments, only a CD109 genomic nucleic acid molecule is analyzed. In some embodiments, only a CD109 mRNA is analyzed. In some embodiments, only a CD109 cDNA obtained from CD109 mRNA is analyzed.

Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the nucleic acid molecule in the sample is mRNA and the mRNA is reverse-transcribed into a cDNA prior to the amplifying step. In some embodiments, the nucleic acid molecule is present within a cell obtained from the subject.

In some embodiments, the assay comprises contacting the biological sample with a primer or probe, such as an alteration-specific primer or alteration-specific probe, that specifically hybridizes to a CD109 variant genomic sequence, variant mRNA sequence, or variant cDNA sequence and not the corresponding CD109 reference sequence under stringent conditions, and determining whether hybridization has occurred.

In some embodiments, the determining step, detecting step, or sequence analysis comprises: a) amplifying at least a portion of the nucleic acid molecule that encodes the CD109 polypeptide; b) labeling the amplified nucleic acid molecule with a detectable label; c) contacting the labeled nucleic acid molecule with a support comprising an alteration-specific probe; and d) detecting the detectable label.

In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify a polynucleotide comprising a CD109 variant genomic nucleic acid molecule, variant mRNA molecule, or variant cDNA molecule. The hybridization conditions or reaction conditions can be determined by the operator to achieve this result. The nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Probes and primers can have about 80%, about 85%, about 90%, about 91%, about 92%, about 93%, about 94%, about 95%, about 96%, about 97%, about 98%, about 99%, or 100% sequence identity or complementarity with the nucleotide sequence of the target nucleic acid molecule.

Illustrative examples of nucleic acid sequencing techniques include, but are not limited to, chain terminator (Sanger) sequencing and dye terminator sequencing. Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. In some embodiments, a polynucleotide primer or probe under stringent conditions will hybridize to its target nucleotide sequence to a detectably greater degree than to other nucleotide sequences by at least 2-fold. In some embodiments, a polynucleotide primer or probe under stringent conditions will hybridize to its target nucleotide sequence to a detectably greater degree than to other nucleotide sequences by at least 3-fold. In some embodiments, a polynucleotide primer or probe under stringent conditions will hybridize to its target nucleotide sequence to a detectably greater degree than to other nucleotide sequences by at least 4-fold. In some embodiments, a polynucleotide primer or probe under stringent conditions will hybridize to its target nucleotide sequence to a detectably greater degree than to other nucleotide sequences by over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2×SSC at 50° C., are known or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M $Na^+$ ion, typically about 0.01 to 1.0 M $Na^+$ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 200, at least about 300, at least about 400, at least about 500, at least about 600, at least about 700, at least about 800, at least about 900, at least about 1000, at least about 2000, at least about 3000, at least about 4000, or at least about 5000 nucleotides. In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides. In some embodiments, the isolated nucleic acid molecules comprise or consist of at least about 18 nucleotides. In some embodiments, the isolated nucleic acid molecules comprise or consists of at least about 15 nucleotides. In some embodiments, the isolated nucleic acid molecules consist of or comprise from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides. In some embodiments, the isolated nucleic acid molecules consist of or comprise from about 18 to about 30 nucleotides. In some embodiments, the isolated nucleic acid molecules comprise or consist of at least about 15 nucleotides to at least about 35 nucleotides.

In some embodiments, such isolated nucleic acid molecules hybridize to CD109 missense variant nucleic acid molecules (such as genomic nucleic acid molecules, mRNA molecules, and/or cDNA molecules) under stringent conditions. Such nucleic acid molecules can be used, for example, as probes, primers, alteration-specific probes, or alteration-specific primers as described or exemplified herein, and include, without limitation primers, probes, antisense RNAs, shRNAs, and siRNAs, each of which is described in more detail elsewhere herein, and can be used in any of the methods described herein.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to CD109 missense variant genomic nucleic acid molecules, CD109 missense variant mRNA molecules, and/or CD109 missense variant cDNA molecules. In some embodiments, the isolated nucleic acid molecules consist of or comprise from about 15 to about 100 nucleotides, or from about 15 to about 35 nucleotides. In some embodiments, the isolated nucleic acid molecules consist of or comprise from about 15 to about 100 nucleotides. In some embodiments, the isolated nucleic acid molecules consist of or comprise from about 15 to about 35 nucleotides.

In some embodiments, the alteration-specific probes and alteration-specific primers comprise DNA. In some embodiments, the alteration-specific probes and alteration-specific primers comprise RNA.

In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers specifically hybridize to any of the nucleic acid molecules disclosed herein under stringent conditions.

In some embodiments, the primers, including alteration-specific primers, can be used in second generation sequencing or high throughput sequencing. In some instances, the primers, including alteration-specific primers, can be modified. In particular, the primers can comprise various modifications that are used at different steps of, for example, Massive Parallel Signature Sequencing (MPSS), Polony sequencing, and 454 Pyrosequencing. Modified primers can be used at several steps of the process, including biotinylated primers in the cloning step and fluorescently labeled primers used at the bead loading step and detection step. Polony sequencing is generally performed using a paired-end tags library wherein each molecule of DNA template is about 135 bp in length. Biotinylated primers are used at the bead loading step and emulsion PCR. Fluorescently labeled degenerate nonamer oligonucleotides are used at the detection step. An adaptor can contain a 5'-biotin tag for immobilization of the DNA library onto streptavidin-coated beads.

The probes and primers described herein can be used to detect a nucleotide variation within any of the CD109 variant missense genomic nucleic acid molecules, CD109 missense variant mRNA molecules, and/or CD109 missense variant cDNA molecules disclosed herein. The primers described herein can be used to amplify CD109 missense variant genomic nucleic acid molecules, CD109 missense variant mRNA molecules, or CD109 missense variant cDNA molecules, or a fragment thereof.

In the context of the disclosure "specifically hybridizes" means that the probe or primer (such as, for example, the alteration-specific probe or alteration-specific primer) does not hybridize to a nucleic acid sequence encoding a CD109 reference genomic nucleic acid molecule, a CD109 reference mRNA molecule, and/or a CD109 reference cDNA molecule.

In some embodiments, the probes (such as, for example, an alteration-specific probe) comprise a label. In some embodiments, the label is a fluorescent label, a radiolabel, or biotin.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern. A form for a solid-state substrate is a microtiter dish, such as a standard 96-well type. In some embodiments, a multiwell glass slide can be employed that normally contains one array per well.

The nucleotide sequence of a CD109 reference genomic nucleic acid molecule is set forth in SEQ ID NO:1 (ENSG00000156535.15 chr6:73,695,785-73,828,316 in the GRCh38/hg38 human genome assembly).

The nucleotide sequence of a CD109 reference mRNA molecule is set forth in SEQ ID NO:2. The nucleotide sequence of another CD109 reference mRNA molecule is set forth in SEQ ID NO:3. The nucleotide sequence of another CD109 reference mRNA molecule is set forth in SEQ ID NO:4. The nucleotide sequence of another CD109 reference mRNA molecule is set forth in SEQ ID NO:5. The nucleotide sequence of another CD109 reference mRNA molecule is set forth in SEQ ID NO:6. The nucleotide sequence of another CD109 reference mRNA molecule is set forth in SEQ ID NO:7. The nucleotide sequence of another CD109 reference mRNA molecule is set forth in SEQ ID NO:8. The nucleotide sequence of another CD109 reference mRNA molecule is set forth in SEQ ID NO:9. The nucleotide sequence of another CD109 reference mRNA molecule is set forth in SEQ ID NO:10. The nucleotide sequence of another CD109 reference mRNA molecule is set forth in SEQ ID NO:11. The nucleotide sequence of another CD109 reference mRNA molecule is set forth in SEQ ID NO:12. The nucleotide sequence of another CD109 reference mRNA molecule is set forth in SEQ ID NO:13. The nucleotide sequence of another CD109 reference mRNA molecule is set forth in SEQ ID NO:14. The nucleotide sequence of another CD109 reference mRNA molecule is set forth in SEQ ID NO:15. The nucleotide sequence of another CD109 reference mRNA molecule is set forth in SEQ ID NO:16.

The nucleotide sequence of a CD109 reference cDNA molecule is set forth in SEQ ID NO:17. The nucleotide sequence of another CD109 reference cDNA molecule is set forth in SEQ ID NO:18. The nucleotide sequence of another CD109 reference cDNA molecule is set forth in SEQ ID NO:19. The nucleotide sequence of another CD109 reference cDNA molecule is set forth in SEQ ID NO:20. The nucleotide sequence of another CD109 reference cDNA molecule is set forth in SEQ ID NO:21. The nucleotide sequence of another CD109 reference cDNA molecule is set forth in SEQ ID NO:22. The nucleotide sequence of another CD109 reference cDNA molecule is set forth in SEQ ID NO:23. The nucleotide sequence of another CD109 reference cDNA molecule is set forth in SEQ ID NO:24. The nucleotide sequence of another CD109 reference cDNA molecule is set forth in SEQ ID NO:25. The nucleotide sequence of another CD109 reference cDNA molecule is set forth in SEQ ID NO:26. The nucleotide sequence of another CD109 reference cDNA molecule is set forth in SEQ ID NO:27. The nucleotide sequence of another CD109 reference cDNA molecule is set forth in SEQ ID NO:28. The nucleotide sequence of another CD109 reference cDNA molecule is set forth in SEQ ID NO:29.

The amino acid sequence of a CD109 reference polypeptide is set forth in SEQ ID NO:30, and is 1,428 amino acids in length. The nucleotide sequence of another CD109 reference polypeptide is set forth in SEQ ID NO:31, and is 1,368 amino acids in length. The nucleotide sequence of another CD109 reference polypeptide is set forth in SEQ ID NO:32, and is 1,445 amino acids in length. The nucleotide sequence of another CD109 reference polypeptide is set forth in SEQ ID NO:33, and is 665 amino acids in length. The nucleotide sequence of another CD109 reference polypeptide is set forth in SEQ ID NO:34, and is 1,374 amino acids in length. The nucleotide sequence of another CD109 reference polypeptide is set forth in SEQ ID NO:35, and is 854 amino acids in length. The nucleotide sequence of another CD109 reference polypeptide is set forth in SEQ ID NO:36, and is 847 amino acids in length.

The genomic nucleic acid molecules, mRNA molecules, and cDNA molecules can be from any organism. For example, the genomic nucleic acid molecules, mRNA molecules, and cDNA molecules can be human or an ortholog from another organism, such as a non-human mammal, a rodent, a mouse, or a rat. It is understood that gene sequences within a population can vary due to polymorphisms such as single-nucleotide polymorphisms. The examples provided herein are only exemplary sequences. Other sequences are also possible.

Also provided herein are functional polynucleotides that can interact with the disclosed nucleic acid molecules. Examples of functional polynucleotides include, but are not limited to, antisense molecules, aptamers, ribozymes, triplex forming molecules, and external guide sequences. The functional polynucleotides can act as effectors, inhibitors, modulators, and stimulators of a specific activity possessed by a target molecule, or the functional polynucleotides can possess a de novo activity independent of any other molecules.

The isolated nucleic acid molecules disclosed herein can comprise RNA, DNA, or both RNA and DNA. The isolated nucleic acid molecules can also be linked or fused to a heterologous nucleic acid sequence, such as in a vector, or a heterologous label. For example, the isolated nucleic acid molecules disclosed herein can be within a vector or as an exogenous donor sequence comprising the isolated nucleic acid molecule and a heterologous nucleic acid sequence. The isolated nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×his or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

Percent identity (or percent complementarity) between particular stretches of nucleotide sequences within nucleic acid molecules or amino acid sequences within polypeptides can be determined routinely using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Herein, if reference is made to percent sequence identity, the higher percentages of sequence identity are preferred over the lower ones.

As used herein, the phrase "corresponding to" or grammatical variations thereof when used in the context of the numbering of a particular nucleotide or nucleotide sequence or position refers to the numbering of a specified reference sequence when the particular nucleotide or nucleotide sequence is compared to a reference sequence (such as, for example, SEQ ID NO:1). In other words, the residue (such as, for example, nucleotide or amino acid) number or residue (such as, for example, nucleotide or amino acid) position of a particular polymer is designated with respect to the reference sequence rather than by the actual numerical position of the residue within the particular nucleotide or nucleotide sequence. For example, a particular nucleotide sequence can be aligned to a reference sequence by introducing gaps to optimize residue matches between the two sequences. In these cases, although the gaps are present, the numbering of the residue in the particular nucleotide or nucleotide sequence is made with respect to the reference sequence to which it has been aligned.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequence follows the standard convention of beginning at the amino terminus of the sequence and proceeding forward (i.e., from left to right in each line) to the carboxy terminus.

The present disclosure also provides therapeutic agents that treat or inhibit decreased bone mineral density for use in the treatment of decreased bone mineral density in a subject having: a CD109 missense variant genomic nucleic acid molecule encoding a CD109 predicted loss-of-function polypeptide; a CD109 missense variant mRNA molecule encoding a CD109 predicted loss-of-function polypeptide; or a CD109 missense variant cDNA molecule encoding a CD109 predicted loss-of-function polypeptide. Any of the therapeutic agents that treat or inhibit decreased bone mineral density described herein can be used in these methods. The subject can have or have a risk of developing decreased bone mineral density, osteopenia, Type I osteoporosis, Type II osteoporosis, or secondary osteoporosis.

The present disclosure also provides uses of therapeutic agents that treat or inhibit decreased bone mineral density for use in the preparation of a medicament for treating decreased bone mineral density in a subject having: a CD109 missense variant genomic nucleic acid molecule encoding a CD109 predicted loss-of-function polypeptide; a CD109 missense variant mRNA molecule encoding a CD109 predicted loss-of-function polypeptide; or a CD109 missense variant cDNA molecule encoding a CD109 predicted loss-of-function polypeptide. Any of the therapeutic agents that treat or inhibit decreased bone mineral density described herein can be used in these methods. The subject can have or have a risk of developing decreased bone mineral density, osteopenia, Type I osteoporosis, Type II osteoporosis, or secondary osteoporosis.

The present disclosure also provides CD109 inhibitors for use in the treatment of decreased bone mineral density in a subject that: a) is reference for a CD109 genomic nucleic acid molecule, a CD109 mRNA molecule, or a CD109 cDNA molecule; or b) is heterozygous for: i) a CD109 missense variant genomic nucleic acid molecule encoding a CD109 predicted loss-of-function polypeptide; ii) a CD109 missense variant mRNA molecule encoding a CD109 predicted loss-of-function polypeptide; or iii) a CD109 missense variant cDNA molecule encoding a CD109 predicted loss-of-function polypeptide. Any of the CD109 inhibitors described herein can be used in these methods. The subject can have or have a risk of developing decreased bone mineral density, osteopenia, Type I osteoporosis, Type II osteoporosis, or secondary osteoporosis.

The present disclosure also provides uses of CD109 inhibitors in the preparation of a medicament for treating decreased bone mineral density in a subject that: a) is reference for a CD109 genomic nucleic acid molecule, a CD109 mRNA molecule, or a CD109 cDNA molecule; or b) is heterozygous for: i) a CD109 missense variant genomic nucleic acid molecule encoding a CD109 predicted loss-of-function polypeptide; ii) a CD109 missense variant mRNA molecule encoding a CD109 predicted loss-of-function polypeptide; or iii) a CD109 missense variant cDNA molecule encoding a CD109 predicted loss-of-function polypeptide. Any of the CD109 inhibitors described herein can be used in these methods. The subject can have or have a risk of developing decreased bone mineral density, osteopenia, Type I osteoporosis, Type II osteoporosis, or secondary osteoporosis.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

General Methodology

UK Biobank Cohort Description

Genetic associations were examined in the United Kingdom (UK) Biobank (UKB). The UKB is a population-based cohort of individuals aged between 40 to 69 years and recruited via 22 testing centers in the UK between 2006-

2010. Genetic and phenotypic information from close to 300,000 European-ancestry participants in UKB were used.

Phenotype Definition

Data pertaining to quantitative ultrasound of the heel were extracted from UKB. eBMD trait values (in g/cm$^2$) were derived using a combination of speed of sound (SOS) and bone ultrasound attenuation (BUA; eBMD=0.002592×(BUA+SOS)−3.687). Sex-specific quality control measures were implemented for SOS (Subjects were excluded if SOS≤1,450 or 1,700 m/s for men, ≤1,455 or ≥1,700 m/s for women), BUA (exclude if BUA 27 or 138 dB/MHz for men, ≤22 or ≥138 dB/MHz for women), and eBMD (exclude if ≤0.18 or ≥1.06 g/cm$^2$ for men, ≤0.12 or ≥1.025 g/cm$^2$ for women). Phenotypic values for eBMD were first transformed using rank-based inverse normal transformation, applied within each ancestry group and separately in men and women, and adjusted for fine-mapped common genetic variants associated with eBMD.

Genotype Data

High coverage whole exome sequencing was performed as previously described (Dewey et al., Science, 2016, 354, aaf6814; and Van Hout et al., Nature, 2020, 586, 749-756) and as summarized below. A modified version of the xGen design available from Integrated DNA Technologies (IDT) was used for target sequence capture of the exome. A unique 10 bp barcode (IDT) was added to each DNA fragment during library preparation to facilitate multiplexed exome capture and sequencing. Equal amounts of sample were pooled prior to exome capture. Sequencing was performed using 75 bp paired-end reads on Illumina NovaSeq instruments. Sequencing had a coverage depth (i.e., number of sequence-reads covering each nucleotide in the target areas of the genome) sufficient to provide greater than 20× coverage over 90% of targeted bases in 99% of IDT samples. Data processing steps included sample de-multiplexing using Illumina software, alignment to the GRCh38 Human Genome reference sequence including generation of binary alignment and mapping files (BAM), processing of BAM files (e.g., marking of duplicate reads and other read mapping evaluations). Variant calling was performed using the GLNexus system (Lin et al., 2018, bioRxiv: 343970). Variant mapping and annotation were based on the GRCh38 Human Genome reference sequence and Ensembl v85 gene definitions using the snpEff software. The snpEff predictions that involve protein-coding transcripts with an annotated start and stop were then combined into a single functional impact prediction by selecting the most deleterious functional effect class for each gene. The hierarchy (from most to least deleterious) for these annotations was frameshift, stop-gain, stop-loss, splice acceptor, splice donor, stop-lost, in-frame indel, missense, other annotations. Predicted LoF genetic variants included: a) insertions or deletions resulting in a frameshift, b) insertions, deletions or single nucleotide variants resulting in the introduction of a premature stop codon or in the loss of the transcription start site or stop site, and c) variants in donor or acceptor splice sites. Missense variants were classified for likely functional impact according to the number of in silico prediction algorithms that predicted deleteriousness using SIFT (Vaser et al., Nature Protocols, 2016, 11, 1-9), Polyphen2_HDIV and Polyphen2_HVAR (Adzhubei et al., Nat. Methods, 2010, 7, 248-249), LRT (Chun et al., Genome Res., 2009, 19, 1553-1561) and MutationTaster (Schwarz et al., Nat. Methods, 2010, 7, 575-576). For each gene, the alternative allele frequency (AAF) and functional annotation of each variant determined inclusion into 7 gene burden exposures: 1) pLOF variants with AAF<1%; 2) pLOF or missense variants predicted deleterious by 5/5 algorithms with AAF<1%; 3) pLOF or missense variants predicted deleterious by 5/5 algorithms with AAF<0.1%; 4) pLOF or missense variants predicted deleterious by at least 1/5 algorithms with AAF<1%; 5) pLOF or missense variants predicted deleterious by at least 1/5 algorithms with AAF<0.1%; 6) pLOF or any missense with AAF<1%; 7) pLOF or any missense variants with AAF<0.1%.

Association Analysis of Gene Burden of Rare pLOF and Missense Variation in CD109

Association between the burden of rare predicted loss-of-function or missense variants in CD109 and eBMD was examined by fitting a linear regression model, including adjustment for a polygenic score that approximates a genomic kinship matrix, using REGENIE v1.0 (Mbatchou et al., Nature Genetics, 2021). Analyses were adjusted for age, age$^2$, sex, age-by-sex and age$^2$-by-sex interaction terms, experimental batch-related covariates, ten common variant-derived principal components, and twenty rare variant-derived principal components. Association analyses were performed using single variants, and using gene burden tests. In gene burden tests, all individuals are labelled as heterozygotes if they carry one or more qualifying rare variant (as described above based on frequency and functional annotation) and as homozygotes if they carry any qualifying variant in the homozygous state. This "composite genotype" is then used to test for association.

Effector Index for eBMD Causal Genes

Effector Index, a novel machine-learning algorithm, has been described elsewhere in the literature (Forgetta et al., bioRxiv: 2021, 2020.2006.2028.171561). Training data were generated by performing GWAS analysis for eleven diseases and traits (type 2 diabetes, low density lipoprotein cholesterol level, adult height, calcium level, hypothyroidism, triglyceride level, glucose level, red blood cell count systolic blood pressure, diastolic blood pressure and direct bilirubin level). Fine-mapping was performed for each GWAS dataset, and genomic annotations were used as features to predict positive control genes at fine-mapped GWAS loci, using a gradient boosted trees algorithm (XGBoost). This trained algorithm was then tested on fine-mapped and annotated eBMD associations data at the CD109 locus to test the probability that the CD109 gene is the gene at this locus that influences eBMD.

Mendelian Randomization Analysis of Circulating CD109

Two-sample Mendelian randomization (MR) was used to examine the association between genetically-predicted circulating CD109 and eBMD. This approach uses common genetic variants associated with CD109 protein concentration (termed protein quantitative trait loci, or pQTLs) as instrumental variables. The lead CD109 cis-pQTL was identified in two previously published studies performed in the INTERVAL (N=3,301) and AGES (N=3,200) cohorts (Sun et al., Nature, 2018, 558, 73-79; and Emilsson et al., Science, 2018, eaaq1327). The pQTL-outcome associations for this analysis were extracted from a previously published GWAS of eBMD in UKB, and the TwoSampleMR R package was used to perform MR analysis using the Wald ratio method. Colocalization analyses were performed to interrogate the influence of confounding by linkage disequilibrium. This entailed assessing the whether the genetic association signal for CD109 protein concentration is likely to share the same causal variant with the eBMD genetic association signal at CD109. These colocalization analyses were implemented using two previously published algorithms, Coloc (Giambartolomei et al., PLOS Genetics, 2014, 10, e1004383) and eCAVIAR (Hormozdiari et al., Am. J. Hum. Genet., 2016, 99, 1245-1260).

Example 1: Loss-of-Function of CD109 is Associated with Higher Estimated Bone Mineral Density Whole exome sequencing of 278,807 European-ancestry individuals in the UK Biobank (UKB) was performed to identify predicted loss-of-function (pLoF) and missense genetic variants in each gene in the genome. The association of each sequenced gene and genetic variant in UKB with estimated bone mineral density (eBMD, measured using ultrasound of the heel) was examined. eBMD is a commonly-used biomarker of bone density and strength, and is highly correlated with bone mineral density as measured using dual-energy X-ray absorptiometry (DXA) technology. Lower levels of bone density are strongly associated with a higher risk of osteoporotic fractures.

The exome-wide analysis in UKB found that the burden of rare (alternative allele frequency [AAF]<1%) pLoF variants in the CD109 gene is associated with 0.18 standard deviation units higher eBMD (P-value=$1.20\times10^{-09}$, meeting a Bonferroni-corrected, exome-wide statistical significance threshold of P<$3.6\times10^{-7}$ (corrected for 20,000 genes and seven variant aggregation models)) (Table 2; estimates of association pertain to the burden of CD109 pLoF variants with AAF<1%, and were derived in UKB).

TABLE 2

Association of rare pLOF variants in CD109 with higher eBMD.

| Beta, per allele, SD units of eBMD (95% CI) | Beta, per allele, g/cm² units of eBMD (95% CI) | P-value | Genotype counts, RR\|RA\|AA genotypes | AAF |
|---|---|---|---|---|
| 0.18 (0.12, 0.24) | 0.022 (0.015, 0.029) | $1.20 \times 10^{-09}$ | 277945\|862\|0 | 0.0015 |

Genotype counts indicates the number of individuals in each of three genotype categories: RR indicates individuals carrying no rare pLoF variants in CD109; RA indicates individuals carrying a rare pLoF variant in a single CD109 allele; AA indicates individuals carrying rare pLoF variants in both CD109 alleles. AAF indicates the alternative allele frequency of pLoF variants included in this analysis. g/cm², grams per centimeter squared; SD, standard deviation; CI, confidence interval.

The association of CD109 variants with higher eBMD was also significant when examining the gene burden of rare pLoF or predicted-damaging missense variants in CD109 (Table 3; estimates of association pertain to the burden of CD109 pLoF or predicted-damaging missense variants with AAF<1% or <0.1% and were derived in UKB (see Genotype Data below for description of in silico algorithms used to identify predicted damaging missense variants)). These genetic data suggest that loss-of-function of CD109 leads to a higher eBMD in humans.

TABLE 3

Association of rare pLOF or missense variants in CD109 with higher eBMD

| Genetic exposure | Beta, per allele, SD units of eBMD (95% CI) | Beta, per allele, g/cm² units of eBMD (95% CI) | P-value | Genotype counts, RR\|RA\|AA genotypes | AAF |
|---|---|---|---|---|---|
| pLoF or damaging missense variants, AAF <1% | 0.07 (0.04, 0.09) | 0.008 (0.005, 0.011) | $7.0 \times 10^{-08}$ | 273953\|4846\|8 | 0.0087 |
| pLoF or damaging missense variants, AAF <0.1% | 0.11 (0.08, 0.15) | 0.014 (0.009, 0.018) | $3.2 \times 10^{-09}$ | 276693\|2114\|0 | 0.0038 |

Genotype counts indicates the number of individuals in each of three genotype categories: RR indicates individuals carrying no rare pLoF variants in CD109; RA indicates individuals carrying a rare pLoF or damaging missense variant in a single CD109 allele; AA indicates individuals carrying rare pLoF variants or damaging missense variants in both CD109 alleles. AAF, alternative allele frequency of variants included in this analysis. $g/cm^2$, grams per centimeter squared; SD, standard deviation; CI, confidence interval.

Example 2: Variants Associated with Lower CD109 Protein Concentration in Blood are Also Associated with Higher eBMD Using Mendelian randomization, it was discovered that lower circulating CD109 protein (encoded by the CD109 gene) due to common genetic variants in the CD109 locus was associated with higher eBMD (Table 4; the lead cis protein quantitative trait locus (pQTL) for CD109 was obtained in two independent cohorts: INTERVAL and AGES. A two-sample Mendelian randomization analysis was performed using eBMD GWAS data from UKB as the outcome dataset). This relationship was further supported by a colocalization analysis, performed using two distinct algorithms (Coloc and eCAVIAR; Coloc posterior probability of H3=0.042, Coloc posterior probability of H4=0.958; eCAV/AR CLPP C1=0.024, CLPP C2=0.002). These results provide complementary evidence for the results reported in Table 2, which showed that loss-of-function of CD109 is associated with a higher eBMD. Several individual rare pLoF and missense variants in CD109 showed nominal evidence of association with eBMD in UKB (P-value for association<0.05; Table 4).

TABLE 4

Mendelian randomization analysis supports a causal influence of circulating CD109 concentration on eBMD

| pQTL source | PQTL | Effect on eBMD, in SD units, per SD unit decrease in circulating CD109 concentration | P-value |
|---|---|---|---|
| INTERVAL | rs6903575 | 0.056 (SE = 0.004) | $6.4 \times 10^{-37}$ |
| AGES | rs6909201 | 0.043 (SE = 0.003) | $3.2 \times 10^{-09}$ |

pQTL, protein quantitative trait locus; SD, standard deviation; SE, standard error.

Example 3: Machine-Learning Algorithm Applied to Common Genetic Variation at CD109 Identifies Further Evidence Implicating CD109 as the Causal Gene Mediating the Association with eBMD A machine-learning algorithm (Effector Index) was applied to eBMD genome-wide association data and strong evidence was observed to suggest that CD109 is the causal gene mediating the eBMD GWAS association in this genomic region (Effector index=0.96, which indicates that the probability that CD109 is the causal gene at this locus is high).

What is claimed is:

1. A method of treating a subject having decreased bone mineral density, an osteopenia, Type I osteoporosis, Type II osteoporosis, or secondary osteoporosis or at risk of developing decreased bone mineral density, an osteopenia, Type I osteoporosis, Type II osteoporosis, or secondary osteoporosis the method comprising administering a Cluster of Differentiation 109 (CD109) inhibitor to the subject, wherein the CD109 inhibitor comprises:

a) LY294002; or b) a Cas protein and guide RNA (gRNA) that hybridizes to a gRNA recognition sequence within a CD109 genomic nucleic acid molecule.

2. The method according to claim 1, further comprising detecting the presence or absence of a CD109 missense variant nucleic acid molecule encoding a CD109 predicted loss-of-function polypeptide in a biological sample from the subject.

3. The method according to claim 2, further comprising administering a therapeutic agent that treats or inhibits decreased bone mineral density in a standard dosage amount to a subject wherein the CD109 missense variant nucleic acid molecule is absent from the biological sample.

4. The method according to claim 2, further comprising administering a therapeutic agent that treats or inhibits decreased bone mineral density in a dosage amount that is the same as or less than a standard dosage amount to a subject that is heterozygous for the CD109 missense variant nucleic acid molecule.

5. The method according to claim 2, wherein the CD109 predicted missense variant nucleic acid molecule is a splice-site variant, a stop-gain variant, a start-loss variant, a stop-loss variant, a frameshift variant, or an in-frame indel variant, or a variant that encodes a truncated CD109 predicted loss-of-function polypeptide.

6. The method according to claim 2, wherein the CD109 predicted loss-of-function variant nucleic acid molecule is 6:73730573: A: G, 6:73823473: GA: G, 6:73763607:C: A, 6:73803256:G: T, 6:73818486: T: C, 6:73787379:G: A, 6:73771510: A: G, 6:73806987:A: T, 6:73758991: A: G, 6:73823456: A: G 6:73762778: A: C, 6:73763660: A: G, 6:73730573: A: G, 6:73806956:G: A, 6:73792628: G: C, 6:73806926: A: T, 6:73771576:G: A, 6:73815026:C: T, 6:73765952:G: A, or an mRNA molecule produced therefrom, or a cDNA molecule produced from the mRNA molecule.

7. The method according to claim 5, wherein the CD109 missense variant nucleic acid molecule encodes a truncated CD109 predicted loss-of-function polypeptide.

8. A method of treating a subject with a therapeutic agent that treats or inhibits decreased bone mineral density, wherein the subject has decreased bone mineral density or is at risk of developing decreased bone mineral density, the method comprising the steps of:

determining whether the subject has a Cluster of Differentiation 109 (CD109) missense variant nucleic acid molecule encoding a CD109 predicted loss-of-function polypeptide by:

obtaining or having obtained a biological sample from the subject; and performing or having performed a sequence analysis on the biological sample to determine if the subject has a genotype comprising the CD109 missense variant nucleic acid molecule; and administering or continuing to administer the therapeutic agent that treats or inhibits decreased bone mineral density in a standard dosage amount to a subject that is CD109 reference, and/or administering a CD109 inhibitor to the subject;

administering or continuing to administer the therapeutic agent that treats or inhibits decreased bone mineral density in an amount that is the same as or less than a standard dosage amount to a subject that is heterozygous for the CD109 missense variant nucleic acid molecule, and/or administering a CD109 inhibitor to the subject; or administering or continuing to administer the therapeutic agent that treats or inhibits decreased bone mineral density in an amount that is the same as or less than a standard dosage amount to a subject that is homozygous for the CD109 missense variant nucleic acid molecule;

wherein the presence of a genotype having the CD109 missense variant nucleic acid molecule encoding the CD109 predicted loss-of-function polypeptide indicates the subject has a decreased risk of developing decreased bone mineral density; and wherein the CD109 inhibitor comprises a) LY294002, or b) a Cas protein and guide RNA (gRNA) that hybridizes to a gRNA recognition sequence within a CD109 genomic nucleic acid molecule.

9. The method according to claim 8, wherein the subject is CD109 reference, and the subject is administered or continued to be administered the therapeutic agent that treats or inhibits decreased bone mineral density in a standard dosage amount, and is administered a CD109 inhibitor.

10. The method according to claim 8, wherein the subject is heterozygous for a CD109 missense variant nucleic acid molecule, and the subject is administered or continued to be administered the therapeutic agent that treats or inhibits decreased bone mineral density in an amount that is the same as or less than a standard dosage amount, and is administered a CD109 inhibitor.

11. The method according to claim 8, wherein the CD109 missense variant nucleic acid molecule is a splice-site variant, a stop-gain variant, a start-loss variant, a stop-loss variant, a frameshift variant, or an in-frame indel variant, or a variant that encodes a truncated CD109 predicted loss-of-function polypeptide.

12. The method according to claim 8, wherein the CD109 predicted loss-of-function variant nucleic acid molecule is 6:73730573: A: G, 6:73823473: GA: G, 6:73763607:C: A, 6:73803256:G: T, 6:73818486:T: C, 6:73787379:G: A, 6:73771510: A: G, 6:73806987:A: T, 6:73758991: A: G, 6:73823456: A: G 6:73762778: A: C, 6:73763660: A: G, 6:73730573: A: G, 6:73806956:G: A, 6:73792628: G: C, 6:73806926: A: T, 6:73771576:G: A, 6:73815026:C: T, 6:73765952:G: A, or an mRNA molecule produced therefrom, or a cDNA molecule produced from the mRNA molecule.

13. The method according to claim 8, wherein the CD109 missense variant nucleic acid molecule encodes a truncated CD109 predicted loss-of-function polypeptide.

14. The method according to claim 8, wherein the decreased bone mineral density is an osteopenia, Type I osteoporosis, Type II osteoporosis, or secondary osteoporosis.

15. The method according to claim 8, wherein the therapeutic agent is chosen from alendronate, ibandronate, zoledronate, risedronate, calcitonin, teriparatide, denosumab, estrogen and progesterone, raloxifene, or any combination thereof.

16. The method according to claim 1, wherein the Cas protein is Cas9 or Cpf1.

17. The method according to claim 16, wherein the gRNA recognition sequence is located within SEQ ID NO:1.

18. The method according to claim 16, wherein a Protospacer Adjacent Motif (PAM) sequence is about 2 to about 6 nucleotides downstream of the gRNA recognition sequence.

19. The method according to claim 16, wherein the gRNA comprises from about 17 to about 23 nucleotides.

20. The method according to claim 16, wherein the gRNA recognition sequence comprises a nucleotide sequence according to any one of SEQ ID NOs: 37-58.

21. The method according to claim 8, wherein the Cas protein is Cas9 or Cpf1.

22. The method according to claim 21, wherein the gRNA recognition sequence is located within SEQ ID NO:1.

23. The method according to claim 21, wherein a Protospacer Adjacent Motif (PAM) sequence is about 2 to about 6 nucleotides downstream of the gRNA recognition sequence.

24. The method according to claim 21, wherein the gRNA comprises from about 17 to about 23 nucleotides.

25. The method according to claim 21, wherein the gRNA recognition sequence comprises a nucleotide sequence according to any one of SEQ ID NOs: 37-58.

* * * * *